(12) United States Patent
Jin et al.

(10) Patent No.: US 9,414,588 B2
(45) Date of Patent: Aug. 16, 2016

(54) HERBICIDE COMPOSITION

(71) Applicant: SUMITOMO CHEMICAL COMPANY, LIMITED, Tokyo (JP)

(72) Inventors: Yoshinobu Jin, Kasai (JP); Yoshimi Fujino, Kasai (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 14/440,650

(22) PCT Filed: Oct. 31, 2013

(86) PCT No.: PCT/JP2013/080170
§ 371 (c)(1),
(2) Date: May 5, 2015

(87) PCT Pub. No.: WO2014/073624
PCT Pub. Date: May 15, 2014

(65) Prior Publication Data
US 2015/0289505 A1    Oct. 15, 2015

(30) Foreign Application Priority Data

Nov. 8, 2012    (JP) ................. 2012-246170

(51) Int. Cl.
| | | |
|---|---|---|
| A01N 35/06 | (2006.01) |
| A01N 39/00 | (2006.01) |
| A01N 41/02 | (2006.01) |
| A01N 41/10 | (2006.01) |
| A01N 43/08 | (2006.01) |
| A01N 43/10 | (2006.01) |
| A01N 43/40 | (2006.01) |
| A01N 43/54 | (2006.01) |
| A01N 43/56 | (2006.01) |
| A01N 43/647 | (2006.01) |
| A01N 43/42 | (2006.01) |
| A01N 25/32 | (2006.01) |
| A01N 47/06 | (2006.01) |
| C07C 317/24 | (2006.01) |
| C07C 323/22 | (2006.01) |
| C07C 323/36 | (2006.01) |
| C07C 323/42 | (2006.01) |
| C07D 213/70 | (2006.01) |
| C07D 213/76 | (2006.01) |

(Continued)

(52) U.S. Cl.
CPC ............... *A01N 35/06* (2013.01); *A01N 39/00* (2013.01); *A01N 41/02* (2013.01); *A01N 41/10* (2013.01); *A01N 43/08* (2013.01); *A01N 43/10* (2013.01); *A01N 43/40* (2013.01); *A01N 43/54* (2013.01); *A01N 43/56* (2013.01); *A01N 43/647* (2013.01); *A01N 47/06* (2013.01); *C07C 317/24* (2013.01); *C07C 323/22* (2013.01); *C07C 323/36* (2013.01); *C07C 323/42* (2013.01); *C07D 213/70* (2013.01); *C07D 213/76* (2013.01); *C07D 239/38* (2013.01); *C07D 249/06* (2013.01); *C07D 307/64* (2013.01); *C07C 2101/02* (2013.01); *C07C 2101/16* (2013.01)

(58) Field of Classification Search
CPC ....... A01N 35/06; A01N 39/00; A01N 41/02; A01N 41/10; A01N 43/08; A01N 43/40; A01N 43/54; A01N 43/56; A01N 43/647; A01N 47/06
See application file for complete search history.

(56) References Cited

U.S. PATENT DOCUMENTS 9,101,140 B2 * 8/2015 Nakashima ........... C07C 49/747
2010/0173774 A1   7/2010 Muehlebach et al.
(Continued)

FOREIGN PATENT DOCUMENTS

JP    2010-520867 A    6/2010
JP    2012-505848 A    3/2012
(Continued)

OTHER PUBLICATIONS

International Preliminary Report on Patentability and English translation of the Written Opinion of the International Searching Authority (Forms PCT/IB/373 and PCT/ISA/237), dated May 12, 2015, for International Application No. PCT/JP2013/080170.
(Continued)

*Primary Examiner* — John Pak
(74) *Attorney, Agent, or Firm* — Birch, Stewart, Kolasch & Birch, LLP

(57) ABSTRACT

There is provided a herbicidal composition containing a cyclohexanone compound represented by Formula (I) and at least one compound selected from Group A.

Formula (I)

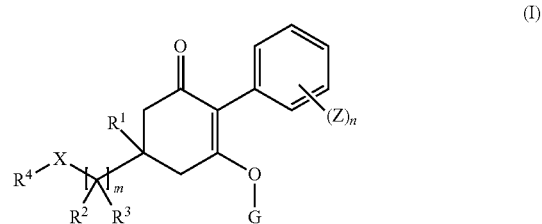

Group A: consisting of benoxacor, cloquintocet-mexyl, cyometrinil, dichlormid, fenchlorazole-ethyl, fenclorim, flurazole, furilazole, mefenpyr-diethyl, oxabetrinil, isoxadifen-ethyl, cyprosulfamide, fluxofenim, 1,8-naphthalic anhydride, and AD-67.

6 Claims, No Drawings

(51) Int. Cl.
*C07D 239/38* (2006.01)
*C07D 249/06* (2006.01)
*C07D 307/64* (2006.01)

(56) References Cited

U.S. PATENT DOCUMENTS

| | | |
|---|---|---|
| 2011/0275515 A1 | 11/2011 | Whittingham et al. |
| 2012/0035053 A1 | 2/2012 | Mathews et al. |
| 2014/0228219 A1 | 8/2014 | Nakashima et al. |

FOREIGN PATENT DOCUMENTS

| | | |
|---|---|---|
| JP | 2012-515190 A | 7/2012 |
| JP | 2014-94903 A | 5/2014 |
| JP | 2014-94904 A | 5/2014 |
| JP | 2014-94905 A | 5/2014 |
| JP | 2014-94906 A | 5/2014 |
| JP | 2014-94907 A | 5/2014 |
| JP | 2014-94908 A | 5/2014 |
| JP | 2014-94909 A | 5/2014 |
| WO | WO 2008/110308 A2 | 9/2008 |
| WO | WO 2010/081689 A2 | 7/2010 |
| WO | WO 2012/165648 A1 | 12/2012 |

OTHER PUBLICATIONS

Chinese Office Action and Search Report, dated Nov. 3, 2015, for Chinese Application No. 201380056157.X, with a partial English translation.

The Pesticide Manual, Fifteenth Edition, British Crop Production Council, 2009, ISBN: 978-1-901396-18-8 (two pages—cover and copyright pages).

International Search Report, issued in PCT/JP2013/080170, dated Dec. 17, 2013.

European Patent Office Communication and extended search report issued in the corresponding European Patent Application No. 13853225.4 on May 17, 2016.

\* cited by examiner

HERBICIDE COMPOSITION

TECHNICAL FIELD

The present invention relates to a herbicidal composition, etc.

BACKGROUND ART

Currently, a great number of herbicides are sold and used. (for example, refer to Non-Patent Literature 1)

CITATION LIST

Non-Patent Literature

[Non-Patent Literature 1] The Pesticide Manual, Fifteenth Edition (2009), British Crop Production Council (ISBN: 978-1-901396-18-8)

SUMMARY OF INVENTION

An object of the invention is to provide a herbicidal composition having an excellent weed-controlling effect.

The present inventors have found that a herbicidal composition containing a cyclohexanone compound represented by the following Formula (I) and a specific compound has an excellent weed-controlling effect.

That is, the invention is as follows.

[1] A herbicidal composition comprising a cyclohexanone compound represented by Formula (I) and at least one compound selected from the following Group A;

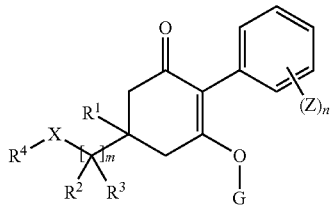

(I)

in the formula, m represents 1, 2, or 3, n represents an integer of 1 to 5,

X represents $CH_2$, O, $NR^9$, S, S(O), or $S(O)_2$, $R^1$ represents hydrogen or a methyl group, $R^2$ and $R^3$ each independently represent hydrogen, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl) $C_{3-8}$ cycloalkyl group, a ($C_{3-8}$ cycloalkyl) $C_{1-6}$ alkyl group, a ($C_{3-8}$ cycloalkyl) $C_{3-8}$ cycloalkyl group, a ($C_{3-8}$ halocycloalkyl) $C_{1-6}$ alkyl group, a {($C_{1-6}$ alkyl) $C_{3-6}$ cycloalkyl} $C_{1-6}$ alkyl group, or $R^2$ and $R^3$ are bonded to form a $C_{2-5}$ alkylene chain, or $R^2$ and $R^3$ together represent a $C_{1-3}$ alkylidene group optionally having a halogen, and when m is 2 or 3, two or three $R^2$'s are the same or different, and two or three $R^3$'s are the same or different, $R^4$ represents a $C_{6-10}$ aryl group or a 5- or 6-membered heteroaryl group, wherein the $C_{6-10}$ aryl group and the 5- or 6-membered heteroaryl group optionally have one or more substituents selected from the group consisting of a halogen, a cyano group, a nitro group, an amino group, a ($C_{1-6}$ alkyl) amino group, a ($C_{1-6}$ alkyl) ($C_{1-6}$ alkyl) amino group, a benzoylamino group, an aminocarbonyl group, a ($C_{1-6}$ alkyl)aminocarbonyl group, a ($C_{1-6}$ alkyl) ($C_{1-6}$ alkyl)aminocarbonyl group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group, a $C_{6-10}$ aryl group, a $C_{6-10}$ aryloxy group, a $C_{1-6}$ alkylsulfinyl group, a $C_{1-6}$ alkylsulfonyl group, a hydroxyl group, a ($C_{1-6}$ alkyl) carbonyl group, a hydroxycarbonyl group, a ($C_{1-6}$ alkoxy)carbonyl group, and a ($C_{6-10}$ aryl) $C_{1-6}$ alkoxy group, and when two or more substituents are present, the substituents are the same or different, and wherein the ($C_{1-6}$ alkyl) amino group, the ($C_{1-6}$ alkyl) ($C_{1-6}$ alkyl)amino group, the benzoylamino group, the ($C_{1-6}$ alkyl) aminocarbonyl group, the ($C_{1-6}$ alkyl) ($C_{1-6}$ alkyl) amino carbonyl group, the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy) carbonyl group, and the ($C_{6-10}$ aryl) $C_{1-6}$ alkoxy group optionally have one or more halogens or $C_{1-3}$ haloalkyl groups, and when two or more halogens or $C_{1-3}$ haloalkyl groups are present, the halogens or $C_{1-3}$ haloalkyl groups are the same or different, G represents hydrogen or any one group of the following formulae:

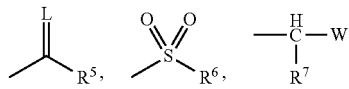

in the formulae,

L represents oxygen or sulfur, $R^5$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl) $C_{1-6}$ alkoxy group, a ($C_{1-6}$ alkyl) ($C_{1-6}$ alkylamino group, a ($C_{3-6}$ alkenyl) ($C_{3-6}$ alkenyl) amino group, a ($C_{1-6}$ alkyl) ($C_{6-10}$ aryl) amino group, or a 5- or 6-membered heteroaryl group, wherein all of these optionally have one or more halogens, and when two or more halogens are present, the halogens are the same or different, and wherein all of the $C_{3-8}$ cycloalkyl group, the $C_{6-10}$ aryl group, an aryl moiety of the ($C_{6-10}$ aryl) $C_{1-6}$ alkyl group, the $C_{3-8}$ cycloalkoxy group, the $C_{6-10}$ aryloxy group, an aryl moiety of the ($C_{6-10}$ aryl) $C_{1-6}$ alkoxy group, an aryl moiety of a ($C_{1-5}$ alkyl) ($C_{6-10}$ aryl)amino group, and the 5- or 6-membered heteroaryl group optionally have one or more $C_{1-6}$ alkyl groups, and when two or more $C_{1-6}$ alkyl groups are present, the alkyl groups are the same or different, $R^6$ represents a $C_{1-6}$ alkyl group, a $C_{6-10}$ aryl group, or a ($C_{1-6}$ alkyl) ($C_{1-6}$ alkyl) amino group, wherein all of these optionally have one or more halogens, and when two or more halogens are present, the halogens are the same or different, and wherein the $C_{6-10}$ aryl group optionally has one or more $C_{1-6}$ alkyl groups, and when two or more $C_{1-6}$ alkyl groups are present, the $C_{1-6}$ alkyl groups are the same or different, $R^7$ represents hydrogen or a $C_{1-6}$ alkyl group, W represents a $C_{1-6}$ alkoxy group, a $C_{1-6}$ alkylthio group, a $C_{1-6}$ alkylsulfinyl group, or a $C_{1-6}$ alkylsulfonyl group, wherein all of these optionally have one or more halogens, and when two or more halogens are present, the halogens are the same or different, $R^9$ represents hydrogen, a $C_{1-6}$ alkyl group, a $C_{6-10}$ aryl group, a $C_{6-10}$ arylthio group, a $C_{6-10}$ arylsulfinyl group, or a $C_{6-10}$ arylsulfonyl group, wherein the $C_{1-6}$ alkyl group optionally has one or more halogens, and when two or more halogens are present, the halogens are the same or different, and wherein the $C_{6-10}$ aryl group, the $C_{6-10}$ arylthio group, the $C_{6-10}$ arylsulfinyl group, and the $C_{6-10}$ arylsulfonyl group optionally have one or more substituents selected from the group consisting of a halogen, a cyano group, a nitro group, and an amino group, Z represents a halogen, a cyano group, a nitro group, a $C_{1-6}$ alkyl group, a $C_{2-6}$ alkenyl group, a $C_{2-6}$ alkynyl group, a $C_{1-6}$ alkoxy group, a ($C_{1-6}$ alkyl) carbonyl group, a $C_{1-6}$ alkylthio group, a $C_{6-10}$ aryloxy group, a 5- or 6-membered heteroaryloxy group, a $C_{3-8}$ cycloalkyl group, a $C_{6-10}$ aryl group, or a 5- or 6-membered heteroaryl group, wherein the $C_{1-6}$ alkyl group, the $C_{2-6}$ alkenyl group, the $C_{2-6}$ alkynyl group, the $C_{1-6}$ alkoxy group, the ($C_{1-6}$ alkyl) carbonyl group, and the $C_{1-6}$ alkylthio group optionally have one or more halogens, and when two or more halogens are present, the halogens are the same or different, and wherein the $C_{6-10}$ aryl group, the 5- or 6-membered heteroaryl group, the $C_{6-10}$ aryloxy group, and the 5- or 6-membered heteroaryloxy group optionally have one or more substituents selected from the group consisting of a halogen, a $C_{1-6}$ alkyl group, and $C_{1-6}$ haloalkyl group, and when two or more substituents are present, the substituents are the same or different, and wherein the $C_{3-8}$ cycloalkyl group optionally has one or more substituents selected from the group consisting of a halogen and a $C_{1-6}$ alkyl group, and when two or more substituents are present, the substituents are the same or different, and when n represents an integer of equal to or greater than 2, Z's are the same or different, Group A: consisting of benoxacor, cloquintocet-mexyl, cyometrinil, dichlormid, fenchlorazole-ethyl, fenclorim, flurazole, furilazole, mefenpyr-diethyl, oxabetrinil, isoxadifen-ethyl, cyprosulfamide, fluxofenim, 1,8-naphthalic anhydride, and AD-67.

[2] The herbicidal composition according to [1], wherein
n is an integer of 1 to 3,
$R^1$ is hydrogen,
$R^2$ and $R^3$ each independently are hydrogen, a $C_{1-3}$ alkyl group, or $R^2$ and $R^3$ are bonded to form a $C_{2-5}$ alkylene chain, and when m is 2 or 3, two or three $R^2$'s are the same or different, and two or three $R^3$'s are the same or different, $R^4$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group, wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and the 2-thiazolyl group optionally have one or more substituents selected from the group consisting of a halogen, a $C_{1-3}$ alkyl group, a hydroxyl group, a ($C_{1-3}$ alkyl) carbonyl group, a ($C_{1-3}$ alkoxy)carbonyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group, and a $C_{1-3}$ haloalkoxy group, and when two or more substituents are present, the substituents are the same or different, and wherein the 1,2,3-triazolyl group and the 1-pyrazolyl group optionally have one or more substituents selected from the group consisting of a $C_{1-3}$ alkyl group and a $C_{6-10}$ aryl group, the $C_{1-3}$ alkyl group and the $C_{6-10}$ aryl group optionally have one or more halogens or one or more $C_{1-3}$ haloalkyl groups, and when two or more halogens or two or more $C_{1-3}$ haloalkyl groups are present, the halogens or the $C_{1-3}$ haloalkyl groups are the same or different, G is hydrogen or any one group of the following formulae:

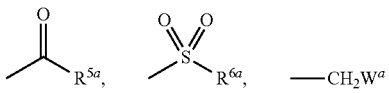

in the formulae,
$R^{5a}$ represents a $C_{1-6}$ alkyl group, a $C_{1-6}$ alkoxy group, a $C_{3-6}$ alkenyloxy group, or a $C_{6-10}$ aryloxy group,
$R^{6a}$ represents a $C_{1-6}$ alkyl group, and
$W^a$ represents a $C_{1-3}$ alkoxy group,
$R^9$ is hydrogen, a $C_{1-6}$ alkyl group, or a $C_{6-10}$ arylsulfonyl group, wherein the $C_{1-6}$ alkyl group optionally has one or more halogens, and when two or more halogens are present, the halogens are the same or different, and the $C_{6-10}$ arylsulfonyl group optionally has one or more substituents selected from the group consisting of a halogen and a nitro group, and when two or more substituents are present, the substituents are the same or different, Z is a halogen, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group, or a 5- or 6-membered heteroaryloxy group, wherein the $C_{1-3}$ alkyl group, the $C_{2-6}$ alkenyl group, the $C_{2-6}$ alkynyl group, the $C_{2-3}$ alkoxy group, the phenyl group, and the 5- or 6-membered heteroaryloxy group optionally have one or more halogens, and when two or more halogens are present, the halogens may be the same or different.

[3] The herbicidal composition according to [2] in which $R^2$ and $R^3$ each independently are hydrogen, a methyl group, an ethyl group, or $R^2$ and $R^3$ are bonded to form an ethylene chain, wherein two $R^2$'s may be the same or different, and two $R^3$'s may be the same or different, $R^4$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group, wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and 2-thiazolyl group have one or more substituents selected from the group consisting of chlorine, bromine, iodine, fluorine, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group, and a trifluoromethyl group, and wherein the 1,2,3-triazolyl group and 1-pyrazolyl group optionally have one or more substituents selected from the group consisting of a methyl group and a phenyl group, and wherein the phenyl group optionally has one or more substituents selected from the group consisting of chlorine, bromine, iodine, fluorine, and a trifluoromethyl group, G is hydrogen, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group, or an ethoxymethyl group, $R^9$ is hydrogen, a 2-nitrophenylsulfonyl group, or a methyl group, and Z represents a methyl group, an ethyl group, a phenyl group, a vinyl group, a cyclopropyl group, a nitro group, fluorine, chlorine, bromine, a methoxy group, a trifluoromethyl group, a 5-trifluoromethyl-2-chloropyridyloxy group, or an ethynyl group.

[4] The herbicidal composition according to any one of [1] to [3] in which G is hydrogen.

[5] A herbicide comprising the herbicidal composition according to any one of [1] to [4].

[6] A method for controlling weeds, comprising applying effective amounts of a cyclohexanone compound represented by Formula (I) and at least one compound selected from the Group A below to weeds or soil where weeds grow.

Formula (I)

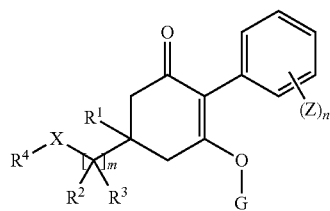

(I)

in the formula, m, n, X, $R^1$, $R^2$, $R^3$, $R^4$, G, and Z each have the same definition as that in [1].

Group A is the same group as defined in [1].

[7] Use of a herbicidal composition containing a compound represented by Formula (I) and at least one compound selected from among Group A, for controlling weeds.

Formula (I)

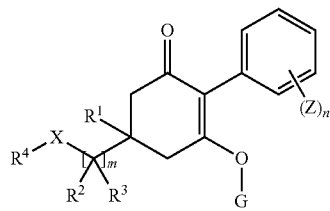

(I)

in the formula, m, n, X, $R^1$, $R^2$, $R^3$, $R^4$, G, and Z each have the same definition as defined in [1].

Group A is the same group as defined in [1].

DESCRIPTION OF EMBODIMENTS

A herbicidal composition (hereinafter, referred to as the herbicidal composition according to the invention) of the invention represented by Formula (I):

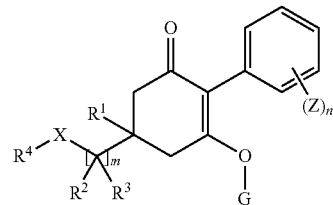

(I)

in the formula, m, n, X, $R^1$, $R^2$, $R^3$, $R^4$, G, and Z each have the same definition as that in [1].

Group A is the same group as that in [1].

Substituents of the cyclohexanone compound represented by Formula (I) which is an effective component of the composition of the invention will be described.

The $C_{1-6}$ alkyl group means an alkyl group having 1 to 6 carbon atoms, and examples thereof include, for example, a methyl group, an ethyl group, an n-propyl group, an isopropyl group, an n-butyl group, an isobutyl group, a sec-butyl group, a tert-butyl group, an n-pentyl group, a sec-pentyl group, an isopentyl group, a neopentyl group, an n-hexyl group, and an isohexyl group.

The $C_{1-6}$ haloalkyl group means a $C_{1-6}$ alkyl group substituted with a halogen such as fluorine, chlorine, bromine, or iodine, and examples thereof include, for example, a trifluoromethyl group, a chloromethyl group, a 2,2,2-trichloroethyl group, a 2,2,2-trifluoroethyl group, and a 2,2,2-trifluoro-1,1-dichloroethyl group.

The $C_{3-8}$ cycloalkyl group means a cycloalkyl group having 3 to 8 carbon atoms, and examples thereof include, for example, a cyclopropyl group, a cyclopentyl group, and a cyclohexyl group.

The $C_{3-8}$ halocycloalkyl group means a cycloalkyl group having 3 to 8 carbon atoms substituted with a halogen such as fluorine, chlorine, bromine, or iodine, and examples thereof include, for example, a 2-chlorocyclopropyl group and a 4,4-difluorocyclohexyl group.

The ($C_{1-6}$ alkyl) $C_{3-8}$ cycloalkyl group means a cycloalkyl group having 3 to 8 carbon atoms substituted with an alkyl group having 1 to 6 carbon atoms, and examples thereof include, for example, an ethylcyclopropyl group, an isobutylcyclopropyl group, a 3-methylcyclopentyl group, and a 4-methylcyclohexyl group.

The ($C_{3-8}$ cycloalkyl) $C_{1-6}$ alkyl group means an alkyl group having 1 to 6 carbon atoms substituted with a cycloalkyl group having 3 to 8 carbon atoms, and examples thereof include, for example, a cyclopropylmethyl group and a cyclopentylmethyl group.

The ($C_{3-8}$ cycloalkyl) $C_{3-8}$ cycloalkyl group means a cycloalkyl group having 3 to 8 carbon atoms substituted with a cycloalkyl group having 3 to 8 carbon atoms, and examples thereof include, for example, a 2-cyclopropylcyclopropyl group and a 3-cyclopropylcyclopentyl group.

The ($C_{3-8}$ halocycloalkyl) $C_{1-6}$ alkyl group means an alkyl group having 1 to 6 carbon atoms substituted with a cycloalkyl group which has 3 to 8 carbon atoms and substituted with a halogen such as fluorine, chlorine, bromine, or iodine, and examples thereof include, for example, a 2-chlorocyclopropylmethyl group and a 3-chlorocyclopentylethyl group.

The {($C_{1-6}$ alkyl) $C_{3-8}$ cycloalkyl} $C_{1-6}$ alkyl group means an alkyl group having 1 to 6 carbon atoms substituted with a cycloalkyl group which has 3 to 8 carbon atoms substituted with an alkyl group having 1 to 6 carbon atoms, and examples thereof include, for example, a 2-methylcyclopropylmethyl group and a 3-methylcyclopentylmethyl group.

The $C_{2-5}$ alkylene chain means an alkylene chain having 2 to 5 carbon atoms, and examples thereof include, for example, an ethylene chain, a propylene chain (trimethylene chain), a butylene chain (tetramethylene chain), and a pentylene chain (pentamethylene chain).

When $R^2$ and $R^3$ are bonded to form an alkylene having 2 to 6 carbon atoms, $R^2$ and $R^3$ represent a cycloalkyl group having 3 to 6 carbon atoms, together with the carbon to which $R^2$ and $R^3$ are bonded. For example, when ethylene is formed by bonding of $R^2$ and $R^3$, $R^2$ and $R^3$ represent cyclopropyl, together with the carbon to which $R^2$ and $R^3$ are bonded.

When $R^{2b}$ and $R^{3b}$ are bonded to form an alkylene having 2 to 6 carbon atoms, $R^{2b}$ and $R^{3b}$ represent a cycloalkyl group having 3 to 6 carbon atoms, together with the carbon to which $R^{2b}$ and $R^{3b}$ are bonded. For example, when ethylene is formed by bonding of $R^{2b}$ and $R^{3b}$, $R^{2b}$ and $R^{3b}$ represent cyclopropyl, together with the carbon to which $R^{2b}$ and $R^{3b}$ are bonded.

The $C_{1-3}$ alkylidene group means an alkylidene group having 1 to 3 carbon atoms, and examples thereof include, for example, methylidene, ethylidene, and isopropylidene.

Examples of the halogen include, for example, fluorine, chlorine, bromine, and iodine.

The $C_{2-6}$ alkenyl group means an alkenyl group having 2 to 6 carbon atoms, and examples thereof include, for example, a vinyl group, an allyl group, a 1-buten-3-yl group, and a 3-buten-1-yl group.

The $C_{2-6}$ alkynyl group means an alkynyl group having 2 to 6 carbon atoms, and examples thereof include, for example, an ethynyl group, a propargyl group, and a 2-butynyl group.

The $C_{1-6}$ alkoxy group means an alkoxy group having 1 to 6 carbon atoms, and examples thereof include, for example, a methoxy group, an ethoxy group, an n-propyloxy group, an isopropyloxy group, an n-butoxy group, an isobutoxy group, a sec-butoxy group, a tert-butoxy group, an n-pentyloxy group, a sec-pentyloxy group, an isopentyloxy group, a neopentyloxy group, an n-hexyloxy group, and an isohexyloxy group.

The $C_{1-6}$ alkylthio group means an alkylthio group having 1 to 6 carbon atoms, and examples thereof include, for example, a methylthio group, an ethylthio group, and an isopropylthio group.

The $C_{3-6}$ alkenyloxy group means an alkenyloxy group having 3 to 6 carbon atoms, and examples thereof include, for example, an allyloxy group and a 2-butenyloxy group.

The $C_{3-6}$ alkynyloxy group means an alkynyloxy group having 3 to 6 carbon atoms, and examples thereof include, for example, a propargyloxy group and a 2-butynyloxy group.

The ($C_{6-10}$ aryl) $C_{1-6}$ alkoxy group means an alkoxy group having 1 to 6 carbon atoms substituted with an aryl group having 6 to 10 carbon atoms, and examples thereof include, for example, a benzyloxy group and a phenethyloxy group.

The ($C_{5-10}$ aryl) $C_{1-6}$ alkyl group means an alkyl group having 1 to 6 carbon atoms substituted with an aryl group having 6 to 10 carbon atoms, and examples thereof include, for example, a benzyl group and a phenethyl group.

The $C_{3-8}$ cycloalkoxy group means a cycloalkoxy group having 3 to 8 carbon atoms, and examples thereof include, for example, a cyclopropyloxy group, a cyclopentyloxy group, and a cyclohexyloxy group.

The ($C_{1-6}$ alkyl) ($C_{1-6}$ alkyl) amino group means an amino group substituted with the same or different two alkyl groups having 1 to 6 carbon atoms, and examples thereof include, for example, a dimethylamino group, a diethylamino group, and an ethylmethylamino group.

The ($C_{3-6}$ alkenyl) ($C_{3-6}$ alkenyl) amino group means an amino group substituted with the same or different two alkenyl groups having 3 to 6 carbon atoms, and examples thereof include, for example, a diallylamino group and a di(3-butenyl) amino group.

The ($C_{1-6}$ alkyl) ($C_{6-10}$ aryl) amino group means an amino group which was substituted with an alkyl group having 1 to 6 carbon atoms and a $C_{6-10}$ aryl group, and examples thereof include, for example, a methylphenylamino group and an ethylphenylamino group.

The $C_{1-6}$ alkylsulfinyl group means an alkylsulfinyl group having 1 to 6 carbon atoms, and examples thereof include, for example, a methylsulfinyl group, an ethylsulfinyl group, and an isopropylsulfinyl group.

The $C_{1-6}$ alkylsulfonyl group means an alkylsulfonyl group having 1 to 6 carbon atoms, and examples thereof include, for example, a methylsulfonyl group, an ethylsulfonyl group, and an isopropylsulfonyl group.

The $C_{6-10}$ aryl group means an aryl group having 6 to 10 carbon atoms, and examples thereof include, for example, a phenyl group and a naphthyl group.

The 5- or 6-membered heteroaryl group means an aromatic 5- or 6-membered heterocyclic group containing 1 to 3 heteroatoms selected from nitrogen, oxygen, and sulfur, and examples thereof include, for example, a 2-pyridyl group, a 4-pyridyl group, a 3-furyl group, a pyrimidinyl group, a 3-thienyl group, and a 1-pyrazolyl group.

The $C_{6-10}$ aryloxy group means an aryloxy group having 6 to 10 carbon atoms, and examples thereof include, for example, a phenoxy group and a naphthyloxy group.

The 5- or 6-membered heteroaryloxy group means an aromatic 5- or 6-membered heterocyclic oxy group, containing 1 to 3 heteroatoms selected from nitrogen, oxygen, and sulfur, and examples thereof include, for example, a 2-pyridyloxy group and a 3-pyridyloxy group.

The ($C_{1-6}$ alkoxy)carbonyl group means a carbonyl group substituted with an alkoxy group having 1 to 6 carbon atoms, and examples thereof include, for example, a methoxycarbonyl group and an ethoxycarbonyl group.

The ($C_{1-6}$ alkyl) amino group means an amino group substituted with an alkyl group having 1 to 6 carbon atoms, and examples thereof include, for example, a monomethylamino group and a monoethylamino group.

The ($C_{1-6}$ alkyl)aminocarbonyl group means an aminocarbonyl group substituted with an alkyl group having 1 to 6 carbon atoms, and examples thereof include, for example, a monomethylaminocarbonyl group and a monoethylaminocarbonyl group.

The ($C_{1-6}$ alkyl) ($C_{1-6}$ alkyl)aminocarbonyl group means an aminocarbonyl group substituted with the same or different two alkyl groups having 1 to 6 carbon atoms, and examples thereof include, for example, a dimethylaminocarbonyl group, a diethylaminocarbonyl group, and an ethylmethylaminocarbonyl group.

The ($C_{1-6}$ alkyl)carbonyl group means a carbonyl group substituted with an alkyl group having 1 to 6 carbon atoms, and examples thereof include, for example, a methylcarbonyl group, an ethylcarbonyl group, and an isopropylcarbonyl group.

The $C_{6-10}$ arylthio group means an arylthio group having 6 to 10 carbon atoms, and examples thereof include, for example, a phenylthio group and a naphthylthio group.

The $C_{1-3}$ alkyl group means an alkyl group having 1 to 3 carbon atoms, and examples thereof include, for example, a methyl group, an ethyl group, an n-propyl group, and an isopropyl group.

The $C_{1-3}$ alkoxy group means an alkoxy group having 1 to 3 carbon atoms, and examples thereof include, for example, a methoxy group, an ethoxy group, an n-propyloxy group, and an isopropyloxy group.

The $C_{1-3}$ haloalkyl group means a $C_{1-3}$ alkyl group substituted with a halogen such as fluorine, chlorine, bromine, or iodine, and examples thereof include, for example, a trifluoromethyl group, a chloromethyl group, a 2,2,2-trichloroethyl group, a 2,2,2-trifluoroethyl group, and a 2,2,2-trifluoro-1,1-dichloroethyl group.

The $C_{1-3}$ haloalkoxy group means an alkoxy group having 1 to 3 carbon atoms substituted with a halogen such as fluorine, chlorine, bromine, or iodine, and examples thereof include, for example, a trifluoromethoxy group, a 2,2,2-trichloroethoxy group, a 3,3-difluoropropyloxy group, and a 2,2,2-trifluoroethoxy group.

The $C_{1-3}$ haloalkylthio group means a $C_{1-3}$ alkylthio group substituted with a halogen such as fluorine, chlorine, bromine, or iodine, and examples thereof include, for example, a trifluoromethylthio group, a chloromethylthio group, a 2,2,2-trichloroethylthio group, a 2,2,2-trifluoroethylthio group, and a 2,2,2-trifluoro-1,1-dichloroethylthio group.

In the present compound, although the cyclohexanone compound represented by Formula (I) takes the form of an agriculturally acceptable salt with an inorganic base or an organic base in some cases, the cyclohexanone compound having the salt form is also included in the invention. Examples of the salt include, for example, salts produced by mixing inorganic bases (for example, hydroxide, carbonate, bicarbonate, acetate, and hydride of alkali metals (lithium, sodium, potassium, etc.), hydroxide or hydride of alkaline earth metals (magnesium, calcium, barium, etc.), and ammonia), organic bases (for example, dimethylamine, triethylamine, piperazine, pyrrolidine, piperidine, 2-phenylethylamine, benzylamine, ethanolamine, diethanolamine, pyridine, collidine, etc.), metal alkoxides (for example, sodium methoxide, potassium tert-butoxide, magnesium methoxide, etc.), etc.

In the case where the present compound has one or more asymmetric centers, two or more stereoisomers (for example, enantiomers, diastereomers, etc.) are present in the compound. The present compound embraces a mixture of all of these stereoisomers or any two or more of the stereoisomers.

In addition, in the case where the present compound has geometrical isomerism due to a double bond, etc., two or more geometrical isomers (for example, each isomer of E/Z or trans/cis, each isomer of S-trans/S-cis, etc.) are present in the compound. A mixture formed of all of these geometrical isomers or any two or more geometrical isomers among these is contained in the present compound.

Examples of the cyclohexanone compound represented by Formula (I), which is an effective component of the herbicidal composition according to the invention include, for example, compounds described below.

A compound in which m is 2;

A compound in which n is 3;

A compound in which m is 2, and n is 3;

A compound in which X is S;

A compound in which $R^2$ is hydrogen;

A compound in which $R^3$ is hydrogen;

A compound in which the moiety represented by

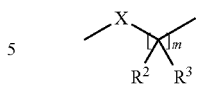

in Formula (I) is —S—CH$_2$CH$_2$—, —S—CH$_2$CH(CH$_3$)—, —S—CH(CH$_3$)CH$_2$—, —O—CH$_2$CH$_2$—, —CH$_2$—CH$_2$CH$_2$—, —S(O)—CH$_2$CH$_2$—, —S(O)—CH$_2$CH(CH$_3$)—, —S(O)$_2$—CH$_2$CH$_2$—, —S(O)$_2$—CH$_2$CH(CH$_3$)—, —S—CH$_2$C(CH$_3$)$_2$—, —S—CH$_2$C(cyclopropyl)-, —S—CH$_2$CH(C$_2$H$_5$)—, —S—CH$_2$—, —S—CH$_2$CH$_2$CH$_2$—, —N(CH$_3$)—CH$_2$CH(CH$_3$)—, or —N(CH$_3$)—CH$_2$CH$_2$—;

A compound in which $R^4$ is a phenyl group, a 2-pyridyl group, a 3-pyridyl group, a 4-pyridyl group, a 2-pyrimidinyl group, a 2-pyrazinyl group, a 3-pyridazinyl group, or a 3-furyl group;

A compound in which Z is a phenyl group or a $C_{1-6}$ alkyl group which may have a halogen; and A compound in which m is 1, 2, or 3, n is an integer of 1, 2, or 3, X is CH$_2$, O, S, S(O), S(O)$_2$, or N(CH$_3$), $R^1$ is hydrogen, $R^2$ and $R^3$ each independently are hydrogen or a $C_{1-6}$ alkyl group, or $R^2$ and $R^3$ are bonded to form a C2-6 alkenylene chain, $R^4$ represents a $C_{6-10}$ aryl group or a 5- or 6-membered heteroaryl group, wherein the $C_{6-10}$ aryl group and the 5- or 6-membered heteroaryl group may have one or more substituents selected from the group consisting of a halogen, a cyano group, a nitro group, a pentafluorothio group, a $C_{1-6}$ alkyl group, and a $C_{1-6}$ alkoxy group, and when two or more substituents are present, the substituents may be the same or different, and wherein the $C_{1-6}$ alkyl group and the $C_{1-6}$ alkoxy group optionally have one or more halogens, G is hydrogen or any one group of the following formulae:

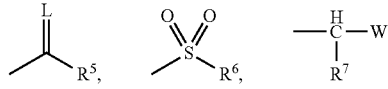

in the formulae,

L is oxygen, $R^5$ is a $C_{1-6}$ alkyl group, a $C_{1-6}$ alkoxy group, a $C_{3-6}$ alkenyloxy group, or a $C_{6-10}$ aryloxy group, $R^6$ is a $C_{1-6}$ alkyl group, $R^7$ is hydrogen, and W is a $C_{1-6}$ alkoxy group, Z is a halogen, a phenyl group, a $C_{1-6}$ alkyl group, a $C_{2-6}$ alkenyl group, a $C_{2-6}$ alkynyl group, or a 6-membered heteroaryloxy group, wherein the phenyl group and the 6-membered heteroaryloxy group may have one or more substituents selected from the group consisting of a halogen and a $C_{1-6}$ haloalkyl group, and when two or more substituents are present, the substituents may be the same or different.

The present compound A is known as a safener, and is a compound described in The Pesticide Manual, Fifteenth Edition (2009), British Crop Production Council (ISBN: 978-1-901396-18-8), or a compound specified by a CAS number.

TABLE 1

| Effective component name | Entry No.of Pesticide Manual or CAS No. |
|---|---|
| Benoxacor | 70 |
| Cloquintocet-mexyl | 174 |
| Cyometrinil | 1054 |
| Cyprosulfamide | CAS221667-31-8 |
| Dichlormid | 249 |
| Fenchlorazole-ethyl | 1148 |
| Fenchlorim | 356 |
| Flurazole | 1185 |
| Furilazole | 439 |
| Fluxofenim | 424 |
| Isoxadifen-ethyl | 509 |
| Mefenpyr-diethyl | 542 |
| Oxabetrinil | 636 |
| 1,8-Naphthalic anhydride | 1279 |
| AD67 | 13 |

Cyprosulfamide is a known compound, and can be produced by, for example, the method described in U.S. Pat. No. 6,251,827.

Benoxacor, cloquintocet-mexyl, cyometrinil, dichlormid, fenchlorazole-ethyl, fenclorim, flurazole, furilazole, mefenpyr-diethyl, oxabetrinil, isoxadifen-ethyl, fluxofenim, 1,8-naphthalic anhydride, and AD-67 are known compounds, and these are commercially available. In addition, the above compounds can be produced according to the references described in The Pesticide Manual, Fifteenth Edition (2009), British Crop Production Council (ISBN: 978-1-901396-18-8).

Examples of the herbicidal composition according to the invention include, for example, the following compositions.

[Aspect 1]

A herbicidal composition containing a compound of Formula (I), wherein n is 1 to 3, and at least one compound selected from Group A;

A herbicidal composition containing a compound of Formula (I) wherein m is 1 or 2, and n is 3 in and cloquintocet-mexyl, mefenpyr-diethyl, or fenchlorazole-ethyl;

A herbicidal composition containing a compound of Formula (I), wherein X is $CH_2$, O, S, S(O), $S(O)_2$, N(H), or $N(CH_3)$, and cloquintocet-mexyl, mefenpyr-diethyl, or fenchlorazole-ethyl;

A herbicidal composition containing a compound of Formula (I), wherein $R^2$ is hydrogen or a $C_{1-3}$ alkyl group, and cloquintocet-mexyl, mefenpyr-diethyl, or fenchlorazole-ethyl;

A herbicidal composition containing a compound of Formula (I), wherein $R^3$ is hydrogen or a $C_{1-3}$ alkyl group, and cloquintocet-mexyl, mefenpyr-diethyl, or fenchlorazole-ethyl;

A herbicidal composition containing a compound of Formula (I), wherein the moiety represented by

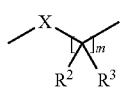

is —S—$CH_2CH_2$—, —S—$CH_2CH(CH_3)$—, —S—CH($CH_3$)$CH_2$—, —O—$CH_2CH_2$—, —$CH_2$—$CH_2$—, —$CH_2$—$CH_2CH_2$—, —S(O)—$CH_2CH_2$—, —S(O)—$CH_2CH(CH_3)$—, —$S(O)_2$—$CH_2CH_2$—, —$S(O)_2$—$CH_2CH(CH_3)$—, —S—$CH_2C(CH_3)_2$—, —S—$CH_2C$(cyclopropyl)-, —S—$CH_2CH(C_2H_5)$—, —S—$CH_2$—, —S—$CH_2CH_2CH_2$—, —$N(CH_3)$—$CH_2CH(CH_3)$—, or —$N(CH_3)$—$CH_2CH_2$—, and cloquintocet-mexyl, mefenpyr-diethyl, or fenchlorazole-ethyl;

A herbicidal composition containing a compound of Formula (I), wherein $R^4$ is a phenyl group, a 2-pyridyl group, a 3-pyridyl group, a 4-pyridyl group, a 2-pyrimidinyl group, a 2-pyrazinyl group, a 3-pyridazinyl group, or a 3-furyl group, and cloquintocet-mexyl, mefenpyr-diethyl, or fenchlorazole-ethyl;

A herbicidal composition containing a compound of Formula (I), wherein Z is a halogen, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group, or a 5- or 6-membered heteroaryloxy group, and cloquintocet-mexyl, mefenpyr-diethyl, or fenchlorazole-ethyl; and A herbicidal composition containing a cyclohexanone compound of Formula (I), wherein
n is 1 to 3,
X is $CH_2$, O, S, S(O), $S(O)_2$, N(H), or $N(CH_3)$,
$R^2$ is hydrogen or a $C_{1-3}$ alkyl group,
$R^3$ is hydrogen or a $C_{1-3}$ alkyl group,
the moiety represented by

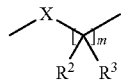

is —S—$CH_2CH_2$—, —S—$CH_2CH(CH_3)$—, —S—CH($CH_3$)$CH_2$—, —O—$CH_2CH_2$—, —$CH_2$—$CH_2$—, —$CH_2$—$CH_2CH_2$—, —S(O)—$CH_2CH_2$—, —S(O)—$CH_2CH(CH_3)$—, —$S(O)_2$—$CH_2CH_2$—, —$S(O)_2$—$CH_2CH(CH_3)$—, —S—$CH_2C(CH_3)_2$—, —S—$CH_2C$(cyclopropyl)-S—$CH_2CH(C_2H_5)$—S—$CH_2$—, —S—$CH_2CH_2CH_2$—, —$N(CH_3)$—$CH_2CH(CH_3)$—, or —$N(CH_3)$—$CH_2CH_2$—,
$R^4$ is a phenyl group, a 2-pyridyl group, a 3-pyridyl group, a 4-pyridyl group, a 2-pyrimidinyl group, a 2-pyrazinyl group, a 3-pyridazinyl group, or a 3-furyl group, and Z is a halogen, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group, or a 5- or 6-membered heteroaryloxy group; and cloquintocet-mexyl, mefenpyr-diethyl, or fenchlorazole-ethyl.

[Aspect 2]

A herbicidal composition containing a cyclohexanone compound of Formula (I), wherein
n is any integer of 1 to 3,
$R^1$ is hydrogen,
$R^2$ and $R^3$ each independently are hydrogen, a $C_{1-3}$ alkyl group, or $R^2$ and $R^3$ are combined to form a $C_{2-5}$ alkylene chain wherein when m is 2 or 3, two or three $R^2$'s may be the same or different, and two or three $R^3$'s may be the same or different,
$R^4$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group,
wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and the 2-thiazolyl group may have one or more substituents selected from the group consisting of a halogen, a $C_{1-3}$ alkyl group, a hydroxyl group, a ($C_{1-3}$ alkyl) carbonyl group, a ($C_{1-3}$ alkoxy)carbonyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group, and a $C_{1-3}$ haloalkoxy group, and when two or more substituents are present, the substituents may be the same or different, and wherein the 1,2,3-triazolyl group and the 1-pyrazolyl group may have one or more substituents selected from the group consisting of a $C_{1-3}$ alkyl group and a $C_{6-10}$ aryl group, the $C_{1-3}$ alkyl group and the $C_{6-10}$ aryl group may have one or more halogens or one or more $C_{1-3}$ haloalkyl groups, and when two or more halogens or two or more $C_{1-3}$ haloalkyl groups are present, the halogens or the $C_{1-3}$ haloalkyl groups may be the same or different, G is hydrogen or any one group of the following formulae:

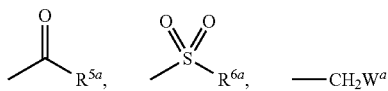

in the formulae, $R^{5a}$ represents a $C_{1-6}$ alkyl group, a $C_{6-10}$ aryl group, a $C_{1-6}$ alkoxy group, a $C_{3-6}$ alkenyl group, a $C_{3-6}$ alkynyloxy group, or a $C_{6-10}$ aryloxy group, $R^{6a}$ represents a $C_{1-6}$ alkyl group, and $W^{a}$ represents a $C_{1-3}$ alkoxy group, $R^{9}$ is hydrogen, a $C_{1-6}$ alkyl group, or a $C_{6-10}$ arylsulfonyl group, wherein the $C_{1-6}$ alkyl group may have one or more halogens, and when two or more halogens are present, the halogens may be the same or different, and wherein the $C_{6-10}$ arylsulfonyl group may have one or more substituents selected from the group consisting of a halogen and a nitro group, and when two or more substituents are present, the substituents may be the same or different, and Z is a halogen, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group, or a 5- or 6-membered heteroaryloxy group, wherein the $C_{1-3}$ alkyl group, the $C_{2-6}$ alkenyl group, the $C_{2-6}$ alkynyl group, the $C_{1-3}$ alkoxy group, the phenyl group, or the 5- or 6-membered heteroaryloxy group may have one or more halogens, and when two or more halogens are present, the halogens may be the same or different; and cloquintocet-mexyl.

[Aspect 3]

A herbicidal composition containing a cyclohexanone compound of Formula (I), wherein n is any integer of 1 to 3, $R^{1}$ is hydrogen, $R^{2}$ and $R^{3}$ each independently are hydrogen, a $C_{1-3}$ alkyl group, or $R^{2}$ and $R^{3}$ are bonded to form a $C_{2-5}$ alkylene chain, and wherein when m is 2 or 3, two or three $R^{2}$'s may be the same or different, and two or three $R^{3}$'s may be the same or different, $R^{4}$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group, wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and the 2-thiazolyl group may have one or more substituents selected from the group consisting of a halogen, a $C_{1-3}$ alkyl group, a hydroxyl group, a ($C_{1-3}$ alkyl)carbonyl group, a ($C_{1-3}$ alkoxy)carbonyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group, and a $C_{1-3}$ haloalkoxy group, and when two or more substituents are present, the substituents may be the same or different, and wherein the 1,2,3-triazolyl group and the 1-pyrazolyl group may have one or more substituents selected from the group consisting of a $C_{1-3}$ alkyl group and a $C_{6-10}$ aryl group, the $C_{1-3}$ alkyl group and the $C_{6-10}$ aryl group may have one or more halogens or one or more $C_{1-3}$ haloalkyl groups, and when two or more halogens or two or more $C_{1-3}$ haloalkyl groups are present, the halogens or the $C_{1-3}$ haloalkyl groups may be the same or different, G is hydrogen or any one group of the following formulae:

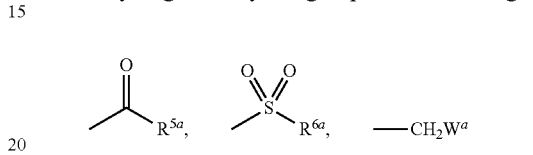

in the formulae, $R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group, or a $C_{6-10}$ aryloxy group, $R^{6a}$ represents a $C_{1-6}$ alkyl group, and $W^{a}$ represents a $C_{1-3}$ alkoxy group.}, $R^{9}$ is hydrogen, a $C_{1-6}$ alkyl group, or a $C_{6-10}$ arylsulfonyl group, wherein the $C_{1-6}$ alkyl group may have one or more halogens, and when two or more halogens are present, the halogens may be the same or different, and the $C_{6-10}$ arylsulfonyl group may have one or more substituents selected from the group consisting of a halogen and a nitro group, and when two or more substituents are present, the substituents may be the same or different, and Z is a halogen, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group, or a 5- or 6-membered heteroaryloxy group, wherein the $C_{1-3}$ alkyl group, the $C_{2-6}$ alkenyl group, the $C_{2-6}$ alkynyl group, the $C_{1-3}$ alkoxy group, the phenyl group, or the 5- or 6-membered heteroaryloxy group may have one or more halogens, and when two or more halogens are present, the halogens may be the same or different; and mefenpyr-diethyl.

[Aspect 4]

A herbicidal composition containing a cyclohexanone compound of Formula (I), wherein n is any integer of 1 to 3, $R^{1}$ is hydrogen, $R^{2}$ and $R^{3}$ each independently are hydrogen, a $C_{1-3}$ alkyl group, or $R^{2}$ and $R^{3}$ are bonded to form a $C_{2-5}$ alkylene chain, wherein when m is 2 or 3, two or three $R^{2}$'s may be the same or different, and two or three $R^{3}$'s may be the same or different, $R^{4}$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group, wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and the 2-thiazolyl group may have one or more substituents selected from the group consisting of a halogen, a $C_{1-3}$ alkyl group, a hydroxyl group, a ($C_{1-3}$ alkyl)

carbonyl group, a ($C_{1-3}$ alkoxy)carbonyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group, and a $C_{1-3}$ haloalkoxy group, and when two or more substituents are present, the substituents may be the same or different, and wherein the 1,2,3-triazolyl group and the 1-pyrazolyl group may have one or more substituents selected from the group consisting of a $C_{1-3}$ alkyl group and a $C_{6-10}$ aryl group, the $C_{1-3}$ alkyl group and the $C_{6-10}$ aryl group may have one or more halogens or one or more $C_{1-3}$ haloalkyl groups, and when two or more halogens or two or more $C_{1-3}$ haloalkyl groups are present, the halogens or the $C_{1-3}$ haloalkyl groups may be the same or different, G is hydrogen or any one group of the following formulae:

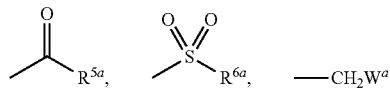

in the formulae, $R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group, or a $C_{6-10}$ aryloxy group, $R^{6a}$ represents a $C_{1-6}$ alkyl group, and $W^a$ represents a $C_{1-3}$ alkoxy group, $R^9$ is hydrogen, a $C_{1-6}$ alkyl group, or a $C_{6-10}$ arylsulfonyl group, wherein the $C_{1-6}$ alkyl group may have one or more halogens, and when two or more halogens are present, the halogens may be the same or different, and the $C_{6-10}$ arylsulfonyl group may have one or more substituents selected from the group consisting of a halogen and a nitro group, and when two or more substituents are present, the substituents may be the same or different, and Z is a halogen, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group, or a 5- or 6-membered heteroaryloxy group, wherein the $C_{1-3}$ alkyl group, the $C_{2-6}$ alkenyl group, the $C_{2-6}$ alkynyl group, the $C_{1-3}$ alkoxy group, the phenyl group, or the 5- or 6-membered heteroaryloxy group may have one or more halogens, and when two or more halogens are present, the halogens may be the same or different; and fenchlorazole-ethyl.

[Aspect 5]

A herbicidal composition containing a cyclohexanone compound of Formula (I), wherein $R^2$ and $R^3$ each independently are hydrogen, a methyl group, an ethyl group, or $R^2$ and $R^3$ are bonded to form an ethylene chain, wherein two $R^2$'s may be the same or different, and two $R^3$'s may be the same or different, $R^4$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group, wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and 2-thiazolyl group may have one or more substituents selected from the group consisting of chlorine, bromine, iodine, fluorine, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group, and a trifluoromethyl group, and wherein the 1,2,3-triazolyl group and 1-pyrazolyl group may have one or more substituents selected from the group consisting of a methyl group and a phenyl group, wherein the phenyl group may have one or more substituents selected from the group consisting of chlorine, bromine, iodine, fluorine, and a trifluoromethyl group, G is hydrogen, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group, or an ethoxymethyl group, $R^9$ is hydrogen, a 2-nitrophenylsulfonyl group, or a methyl group, and Z is a methyl group, an ethyl group, a phenyl group, a vinyl group, a cyclopropyl group, a nitro group, fluorine, chlorine, bromine, a methoxy group, a trifluoromethyl group, a 5-trifluoromethyl-2-chloropyridyloxy group, or an ethynyl group; and cloquintocet-mexyl.

[Aspect 6]

A herbicidal composition containing a cyclohexanone compound of Formula (I), wherein $R^2$ and $R^3$ each independently are hydrogen, a methyl group, an ethyl group, or $R^2$ and $R^3$ are bonded to form an ethylene chain, two $R^2$'s may be the same or different, and two $R^3$'s may be the same or different, $R^4$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group, wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and 2-thiazolyl group may have one or more substituents selected from the group consisting of chlorine, bromine, iodine, fluorine, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group, and a trifluoromethyl group, and wherein the 1,2,3-triazolyl group and 1-pyrazolyl group may have one or more substituents selected from the group consisting of a methyl group and a phenyl group, and wherein the phenyl group may have one or more substituents selected from the group consisting of chlorine, bromine, iodine, fluorine, and a trifluoromethyl group, G is hydrogen, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group, or an ethoxymethyl group, $R^9$ is hydrogen, a 2-nitrophenylsulfonyl group, or a methyl group, and Z is a methyl group, an ethyl group, a phenyl group, a vinyl group, a cyclopropyl group, a nitro group, fluorine, chlorine, bromine, a methoxy group, a trifluoromethyl group, a 5-trifluoromethyl-2-chloropyridyl group, or an ethynyl group; and mefenpyr-diethyl.

[Aspect 7]

A herbicidal composition containing a cyclohexanone compound of Formula (I), wherein $R^2$ and $R^3$ each independently are hydrogen, a methyl group, an ethyl group, or $R^2$ and $R^3$ are bonded to form an ethylene chain, wherein two $R^2$'s may be the same or different, and two $R^3$'s may be the same or different, $R^4$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group, wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and 2-thiazolyl group may have one or more substituents selected from the group consisting of chlorine, bromine, iodine, fluorine, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group, and a trifluoromethyl group, and wherein the 1,2,3-triazolyl group and 1-pyrazolyl group may have one or more substituents selected from the group consisting of a methyl group and a phenyl group, wherein the phenyl group may have one or more substituents selected from the group consisting of chlorine, bromine, iodine, fluorine, and a trifluoromethyl group, G is hydrogen, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group, or an ethoxymethyl group, $R^9$ is hydrogen, a 2-nitrophenylsulfonyl group, or a methyl group, and Z is a methyl group, an ethyl group, a phenyl group, a vinyl group, a cyclopropyl group, a nitro group, fluorine, chlorine, bromine, a methoxy group, a trifluoromethyl group, a 5-trifluoromethyl-2-chloropyridyloxy group, or an ethynyl group; and fenchlorazole-ethyl.

[Aspect 8]

A herbicidal composition containing a cyclohexanone compound of Formula (I), wherein $R^2$ and $R^3$ each independently are hydrogen or a methyl group, wherein two $R^2$'s may be the same or different, and two $R^3$'s may be the same or different, $R^4$ is a phenyl group or a 2-pyridyl group, wherein the phenyl group and the 2-pyridyl group may have one or more substituents selected from the group consisting of chlorine, bromine, iodine, fluorine, a methyl group, an ethyl group, an isopropyl group, a t-butyl group, a pentafluoroethyl group, a heptafluoroisopropyl group, and a trifluoromethyl group), G is hydrogen, X is O, S, or S(O), and Z is a methyl group, an ethyl group, or a phenyl group; and cloquintocet-mexyl.

[Aspect 9]

A herbicidal composition containing a cyclohexanone compound of Formula (I), wherein $R^2$ and $R^3$ each independently are hydrogen or a methyl group, and two $R^2$'s may be the same or different, and two $R^3$'s may be the same or different, $R^4$ is a phenyl group or a 2-pyridyl group, wherein the phenyl group and the 2-pyridyl group may have one or more substituents selected from the group consisting of chlorine, bromine, iodine, fluorine, a methyl group, an ethyl group, an isopropyl group, a t-butyl group, a pentafluoroethyl group, a heptafluoroisopropyl group, and a trifluoromethyl group, G is hydrogen, X is O, S, or S(O), and Z is a methyl group, an ethyl group, or a phenyl group; and mefenpyr-diethyl.

[Aspect 10]

A herbicidal composition containing a cyclohexanone compound of Formula (I), wherein $R^2$ and $R^3$ each independently are hydrogen or a methyl group, wherein two $R^2$'s may be the same or different, and two $R^3$'s may be the same or different, $R^4$ is a phenyl group or a 2-pyridyl group, wherein the phenyl group and the 2-pyridyl group may have one or more substituents selected from the group consisting of chlorine, bromine, iodine, fluorine, a methyl group, an ethyl group, an isopropyl group, a t-butyl group, a pentafluoroethyl group, a heptafluoroisopropyl group, and a trifluoromethyl group, G is hydrogen, X is O, S, or S(O), and Z is a methyl group, an ethyl group, or a phenyl group; and fenchlorazole-ethyl.

The herbicidal composition according to the invention has a herbicidal activity against a wide variety of weeds, and may effectively control a wide variety of weeds in crop fields, vegetable fields, on arboricultural land, or non-agricultural land where usual tillage cultivation or no-tillage cultivation are performed.

Examples of the control target of the herbicidal composition according to the invention include, for example, the following.

Weeds such as crabgrass (*Digitaria ciliaris*), goosegrass (*Eleusine indica*), green foxtail (*Setaria viridis*), giant foxtail (*Setaria faberi*), golden bristlegrass (*Setaria glauca*), barnyardgrass (*Echinochloa crus-galli*), redtop (*Agrostis alba*), fall panicum (*Panicum dichotomiflorum*), Texas panicum (*Panicum texanum*), broadleaf signalgrass (*Brachiaria platyphylla*), Alexandergrass (*Brachiaria plantaginea*), Surinamgrass (*Brachiaria decumbens*), Johnsongrass (*Sorghum halepense*), shattercane (*Andropogon sorghum*), bermudagrass (*Cynodon dactylon*), wild oat (*Avena fatua*), Italian ryegrass (*Lolium multiflorum*), black glass (*Alopecurus myosuroides*), downy brome (*Bromustectorum*), poverty brome (*Bromus sterilis*), lesser canarygrass (*Phalaris minor*), loose silky bentgrass (*Apera spica-venti*), annual bluegrass (*Poa annua*), quackgrass (*Agropyron repens*), rice flatsedge (*Cyperus iria*), nut grass (*Cyperus rotundus*), yellow nutsedge (*Cyperus esculentus*), purslane (*Portulaca oleracea*), rough pigweed (*Amaranthus retroflexus*), smooth amaranth (*Amaranthus hybridus*), Palmer amaranth (*Amaranthus palmeri*), waterhemp (*Amaranthus rudis*), Velvetleaf (*Abutilon theophrasti*), prickly mallow (*Sida spinosa*), black bindweed (*Fallopia convolvulus*), green smartweed (*Polygonum scabrum*), Pennsylvania smartweed (*Persicaria pensylvanica*), peachwort (*Persicaria vulgaris*), yellow dock (*Rumex crispus*), broadleaf dock (*Rumex obtusifolius*), Japanese knotweed (*Fallopia japonica*), lamb's quarter (*Chenopodium album*), summer cypress (*Kochia scoparia*), Persicaria longiseta (*Polygonum longisetum*), black nightshade (*Solanum nigrum*), Jimsonweed (*Datura stramonium*), common morning glory (*Ipomoea purpurea*), ivyleaf morningglory (*Ipomoea hederacea*), entireleaf morningglory (*Ipomoea hederacea* var. *integriuscula*), pitted morningglory (*Ipomoea lacunosa*), field bindweed (*Convolvulus arvensis*), red deadnettle (*Lamium purpureum*), henbit deadnettle (*Lamium amplexicaule*), common cocklebur (*Xanthium pensylvanicum*), common sunflower (*Helianthus annuus*), scentless chamomile (*Matricaria perforata* or *inodora*), chamomile (*Matricaria chamomilla*), corn marigold (*Chrysanthemum*

*segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*), hairy fleabane (*Conyza bonariensis*), hemp sesbania (*Sesbania exalta*), sicklepod (*Cassia obtusifolia*), Florida beggar weed (*Desmodium tortuosum*), white clover (*Trifolium repens*), kudzu vine (*Pueraria lobata*), narrowleaf vetch (*Vicia angustifolia*), Asiatic dayflower (*Commelina communis*), Benghal dayflower (*Commelina benghalensis*), cleaver (*Galium aparine*), common chickweed (*Stellaria media*), wild radish (*Raphanus raphanistrum*), wild mustard (*Sinapis arvensis*), shepherd's purse (*Capsella bursa-pastoris*), Persian speedwell (*Veronica persica*), ivy-leaved speedwell (*Veronica hederifolia*), field pansy (*Viola arvensis*), wild pansy (*Viola tricolor*), common poppy (*Papaver rhoeas*), true forget-me-not (*Myosotis scorpioides*), Common milkweed (*Asclepias syriaca*), sun spurge (*Euphorbia helioscopia*), eyebane (*Chamaesyce nutans*), Carolina geranium (*Geranium carolinianum*), pin clover (*Erodium cicutarium*), horsetail (*Equisetum arvense*), Japanese cutgrass (*Leersia japonica*), late watergrass (*Echinochloa oryzicola*), hime-tainubie (*Echinochloa crus-galli* var. *formosensis*), Chinese sprangletop (*Leptochloa chinensis*), smallflower flatsedge (*Cyperus difformis*), grass-like fimbristylis (*Fimbristylis miliacea*), needle spikerush (*Eleocharis acicularis*), rock bulrush (*Scirpus juncoides*), Taiwan-yamai (*Scirpus wallichii*), tidalmarsh flatsedge (*Cyperus serotinus*), water chestnut (*Eleocharis kuroguwai*), sea clubrush (*Bolboschoenus koshevnikovii*), shizui (*Schoenoplectus nipponicus*), oval-leaved monochoria (*Monochoria vaginalis*), common falsepimpernel (*Lindernia procumbens*), horsefly's eye (*Dopatrium junceum*), indian toothcup (*Rotala indica*), many-flowered ammannia (*Ammannia multiflora*), three stamen waterwort (*Elatine triandra*), water primrose (*Ludwigia epilobioides*), threeleaf arrowhead (*Sagittaria pygmaea*), waterplantain (*Alisma canaliculatum*), arrowhead (*Sagittaria trifolia*), roundleaf pondweed (*Potamogeton distinctus*), Japanese parsley (*Oenanthe javanica*), spring water-starwort (*Callitriche palustris*), Japanese falsepimpernel (*Lindernia micrantha*), low falsepimpernel (*Lindernia dubia*), false daisy (*Eclipta prostrata*), marsh dewflower (*Murdannia keisak*), knotgrass (*Paspalum distichum*), rice cutglass (*Leersia oryzoides*), etc. Aquatic plants such as alligatorweed (*Alternanthera philoxeroides*), frog's-bit (*Limnobium spongia*), water fern (*Salvinia* genus), water lettuce (*Pistiastratiotes*), water pennywort (*Hydrocotyle* genus), filamentous algae (*Pithophora* genus, *Cladophora* genus), rigid hornwort (*Ceratophyllum demersum*), duckweed (*Lemna* genus), fanwort (*Cabomba caroliniana*), hydrilla (*Hydrilla verticillata*), Southern naiad (*Najas guadalupensis*), pondweeds (*Potamogeton crispus, Potamogeton illinoensis, Potamogeton pectinatus*, etc.), water meal (*Wolffia* genus), watermilfoils (*Myriophyllum spicatum, Myriophyllum heterophyllum*, etc.), water hyacinth (*Eichhornia crassipes*), etc. Mosses, liverworts, and hornworts. Cyanobacteria. Ferns. Suckers of perennial crops (pomaceous fruits, stone fruits, berries, nuts, citrus, hops, grapes, etc.).

The herbicide of the invention (hereinafter, referred to as the herbicide according to the invention) contains the herbicidal composition according to the invention. The herbicide according to the invention is used as a herbicide in agricultural land or non-agricultural land such as a field, a paddy field, a lawn, or an orchard. In agricultural land where the following "plants" are cultivated, the herbicide according to the invention may control weeds in the agricultural land. "Plants":

Crops: corn, rice, wheat, barley, rye, sorghum, cotton, soybean, peanut, buckwheat, sugar beet, rapeseed, sunflower, sugarcane, tobacco, hop, etc.

Vegetables:

Solanaceae vegetables (eggplant, tomato, green pepper, red pepper, potato, etc.), Cucurbitaceae vegetables(cucumber, squash, zucchini, watermelon, melon, oriental melon, etc.), Cruciferae vegetables (radish, turnip, horseradish, kohlrabi, chinese cabbage, cabbage, mustard, broccoli, cauliflower, etc.), Compositae vegetables (burdock, edible chrysanthemum, artichoke, lettuce, etc.), Liliceae vegetables (green onion, onion, garlic, asparagus, etc.), Apiaceae vegetables (carrot, parsley, celery, and parsnip), Chenopodiaceae vegetables (spinach, chard, etc.), Lamiaceae vegetables (Japanese basil, mint, basil, etc.), Leguminosae crops (pea, common bean, azuki bean, broad bean, chickpea, etc.), strawberry, sweet potato, Japanese yam, taro, konjac, ginger, okra, etc.

Fruit trees: pomaceous fruits (apple, pear, European pear, Chinese quince, quince, etc.), stone fruits (peach, plum, nectarine, Japanese apricot, cherry, apricot, prune, etc.), citrus (Citrus unshiu, orange, lemon, lime, grapefruit, etc.), nuts (chestnut, walnut, hazelnut, almond, pistachio, cashew nut, macadamia nut, etc.), berries (blueberry, cranberry, blackberry, raspberry, etc.), grape, persimmon, olive, loquat, banana, coffee, date palm, coconut palm, oil palm, etc.

Trees other than fruit trees: tea, a mulberry tree, flowering trees (*azalea, camellia, hydrangea, sasanqua*, Japanese star anise, cherry tree, tulip tree, crape myrtle, fragrant olive, etc.), roadside trees (ash, birch, dogwood, eucalyptus, gingko, lilac, maple, oak, poplar, *cercis, liquidambar*, plane, Japanese zelkova, Japanese arborvitae, fir, southern Japanese hemlock, juniper, pine, spruce, yew, elm, buckeye, etc.), sweet viburnum, yew plum pine, Japanese cedar, Japanese cypress, croton, Japanese spindle tree, Japanese photinia, etc.

Others: flowers and ornamental plants (rose, carnation, *chrysanthemum*, Russell prairie gentian, *gypsophila, gerbera*, marigold, *salvia, petunia, verbena*, tulip, aster, gentian, lily, pansy, cyclamen, orchid, lily of the valley, lavender, stock, ornamental cabbage, *primula*, poinsettia, *gladiolus, cattleya*, daisy, *cymbidium, begonia*, etc.), biofuel plants (*jatropha*, safflower, camelinas, switchgrass, *miscanthus, Arundo donax*, ambari hemp, cassava, withy, etc.), foliage plants, etc.

The above "plants", also embrace genetically modified crops.

The herbicide according to the invention contains the herbicidal composition according to the invention, that is, the present compound and the compound A. An inert carrier and adjuvants for formulation such as a surfactant, a sticking agent, a dispersant, and a stabilizer are generally further added to the herbicide according to the invention, and the herbicide according to the invention is formulated as a wettable powder, water dispersible granules, a suspension concentrate, granules, a dry flowable, an emulsifiable concentrate, an aqueous liquid formulation, an oil solution, an aerosol, or microcapsules, etc. In the herbicide according to the invention, the total weight of the present compound and the compound A is usually 0.1% to 800%.

Examples of the inert carrier include, for example, a solid carrier and a liquid carrier.

Examples of the solid carrier include, for example, fine powder or particulate matters of clays (for example, kaolin, diatomaceous earth, synthesized hydrous silicon oxide, fubasami clay, bentonite, and Japanese acid clay), talcs, and other inorganic minerals (for example, sericite, quartz powder, sulfur powder, activated carbon, calcium carbonate, and hydrated silica), and examples of the liquid carrier include, for example, water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutylnitrile), ethers (for example, dioxane and diisopropyl ether), acid amides (for example, N,N-dimethylformamide and dimethylacetamide), halogenated hydrocarbons (for example, dichloroethane, trichloroethylene, and carbon tetrachloride), etc.

Examples of the surfactant include, for example, alkylsulfuric esters, alkylsulfonate, alkylarylsulfonate, alkylaryl ethers and polyoxyethylene compounds thereof, polyoxyethylene glycol ethers, polyhydric alcohol esters, sugar alcohol derivatives, etc.

Examples of other adjuvants for formulation include, for example, a sticking agent or a dispersant, and specific examples thereof include, for example, casein, gelatin, polysaccharides (for example, starch, gum arabic, cellulose derivatives, and alginic acid), lignin derivatives, bentonite, sugars, synthesized water-soluble polymers (for example, polyvinyl alcohol, polyvinyl pyrrolidone, and polyacrylic acids), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oil, mineral oil, fatty acids or esters thereof, etc.

When spraying the solution obtained by diluting the herbicide according to the invention with water, an adjuvant may be added to the spray liquid. Examples of the adjuvant capable of being added include, for example, surfactants (non-ionic surfactants such as fatty acid alkyl ester, alkyl polyoxyethylene ether, etc. and ionic surfactant such as alkylbenzene sulfonate, dialkyldimethyl ammonium salt, etc.), crop oil, vegitative oil, crop oil concentrate, methylated seed oil, an organic silicon-based spreading agent, liquid fertilizer (ammonium sulfate, urea ammonium nitrate, etc.), etc. These adjuvants may be used alone or two or more adjuvants may be used in combination.

A method for controlling weeds using the herbicidal composition according to the invention includes a method for applying effective amounts of the present compound and the compound A to weeds or soil where the weeds grow. Examples of the application method of the herbicide according to the invention include, for example, a method in which weeds are foliage-treated with the herbicide according to the invention, a method in which the surface of soil for growth of weeds is treated with the herbicide according to the invention, and a method in which soil for growth of weeds is mixing-treated with the herbicide according to the invention. In the method for controlling weeds of the invention, the total amount of the present compound and the compound A per an area of 10000 m$^2$ in which weeds are controlled is usually 1 g to 5000 g, preferably 1 g to 3000 g, and more preferably 1 g to 500 g.

In the case where the compound A in the herbicidal composition according to the invention is benoxacor, the mixing proportion between the present compound and the benoxacor is within a range from 1:0.001 to 1:30, and preferably within a range from 1:0.002 to 1:20 in a weight ratio.

In the case where the compound A in the herbicidal composition according to the invention is cloquintocet-mexyl, the mixing proportion between the present compound and the cloquintocet-mexyl is within a range from 1:0.001 to 1:30, more preferably within a range from 1:0.002 to 1:20, and still more preferably within a range from 1:0.05 to 1:2 in a weight ratio.

In the case where the compound A in the herbicidal composition according to the invention is cyometrinil, the mixing proportion between the present compound and the cyometrinil is within a range from 1:0.001 to 1:30, and preferably within a range from 1:0.002 to 1:20 in a weight ratio.

In the case where the compound A in the herbicidal composition according to the invention is dichlormid, the mixing proportion between the present compound and the dichlormid is within a range from 1:0.001 to 1:30, and preferably within a range from 1:0.002 to 1:20 in a weight ratio.

In the case where the compound A in the herbicidal composition according to the invention is fenchlorazole-ethyl, the mixing proportion between the present compound and the fenchlorazole-ethyl is within a range from 1:0.001 to 1:30, and preferably within a range from 1:0.002 to 1:20 in a weight ratio.

In the case where the compound A in the herbicidal composition according to the invention is fenclorim, the mixing proportion between the present compound and the fenclorim is within a range from 1:0.001 to 1:30, and preferably within a range from 1:0.002 to 1:20 in a weight ratio.

In the case where the compound A in the herbicidal composition according to the invention is flurazole, the mixing proportion between the present compound and the flurazole is within a range from 1:0.001 to 1:30, and preferably within a range from 1:0.002 to 1:20 in a weight ratio.

In the case where the compound A in the herbicidal composition according to the invention is furilazole, the mixing proportion between the present compound and the furilazole is within a range from 1:0.001 to 1:30, and preferably within a range from 1:0.002 to 1:20 in a weight ratio.

In the case where the compound A in the herbicidal composition according to the invention is mefenpyr-diethyl, the mixing proportion between the present compound and the mefenpyr-diethyl is within a range from 1:0.001 to 1:30, more preferably within a range from 1:0.002 to 1:20, and still more preferably within a range from 1:0.01 to 1:5 in a weight ratio.

In the case where the compound A in the herbicidal composition according to the invention is oxabetrinil, the mixing proportion between the present compound and the oxabetrinil is within a range from 1:0.001 to 1:30, and preferably within a range from 1:0.002 to 1:20 in a weight ratio.

In the case where the compound A in the herbicidal composition according to the invention is isoxadifen, the mixing proportion between the present compound and the isoxadifen is within a range from 1:0.001 to 1:30, and preferably within a range from 1:0.002 to 1:20 in a weight ratio.

In the case where the compound A in the herbicidal composition according to the invention is cyprosulfamide, the mixing proportion between the present compound and the cyprosulfamide is within a range from 1:0.001 to 1:30, and preferably within a range from 1:0.002 to 1:20 in a weight ratio.

In the case where the compound A in the herbicidal composition according to the invention is fluxofenim, the mixing proportion between the present compound and the fluxofenim is within a range from 1:0.001 to 1:30, and preferably within a range from 1:0.002 to 1:20 in a weight ratio.

In the case where the compound A in the herbicidal composition according to the invention is 1,8-naphthalic anhydride, the mixing proportion between the present compound and the 1,8-naphthalic anhydride is within a range from 1:0.001 to 1:30, and preferably within a range from 1:0.002 to 1:20 in a weight ratio.

In the case where the compound A in the herbicidal composition according to the invention is AD-67, the mixing proportion between the present compound and the AD-67 is within a range from 1:0.001 to 1:30, and preferably within a range from 1:0.002 to 1:20 in a weight ratio.

After formulating each of the effective components, the herbicide according to the invention may also be produced by mixing these.

The herbicide according to the invention may also be used in mixture or in combination with an insecticide, an acaricide, a nematicide, a fungicide, a plant-growth regulator, a fertilizer, or a soil conditioner.

The present compound used in the herbicidal composition according to the invention can be produced according to, for example, the following method.

Production Method 1

Among the present compounds, the compound of Formula (1a) in which G is hydrogen can be produced by a reaction of the compound represented by Formula (2) with the compound represented by Formula (3) in the presence of a base.

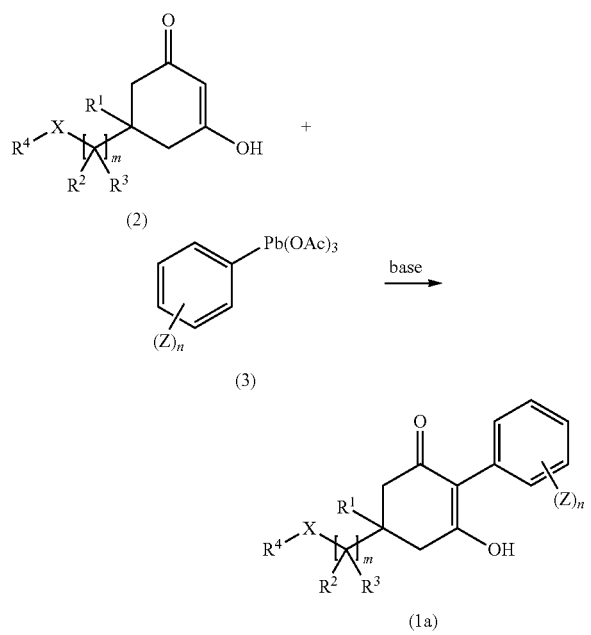

In the formula, $R^1$, $R^2$, $R^3$, $R^4$, X, n, m, and Z each have the same definition as described above.

This reaction is usually performed in a solvent. Examples of the usable solvent include, for example, aromatic hydrocarbons such as benzene, toluene, and xylene; ethers such as diethyl ether, diisopropyl ether, dioxane, tetrahydrofuran, and dimethoxyethane; halogenated hydrocarbons such as dichloromethane, chloroform, and 1,2-dichloroethane; amides such as dimethylformamide and dimethylacetamide; sulfones such as sulfolane; and mixture of the solvents.

Examples of the base used in this reaction include, for example, organic bases such as triethylamine, tripropylamine, pyridine, dimethylaminopyridine, and 1,8-diazabicyclo[5.4.0]-7-undecene. The amount of the base is usually 1 molar equivalent to 10 molar equivalents, and preferably 2 molar equivalents to 5 molar equivalents with respect to the compound represented by Formula (2). The amount of the compound represented by Formula (3) used in this reaction is usually 1 molar equivalent to 3 molar equivalents with respect to the compound represented by Formula (2).

The reaction temperature of this reaction is usually −60° C. to 180° C., and preferably −10° C. to 100° C. The reaction time of this reaction is usually 10 minutes to 30 hours.

The completion of this reaction may be confirmed by sampling a portion of the reaction mixture and using analysis means such as thin-layer chromatography or high-performance liquid chromatography. After this reaction is completed, for example, operations in which the reaction mixture is acidified by adding acid, mixed with water, and extracted with an organic solvent, and the obtained organic layer is dried and concentrated are performed, whereby the compound represented by Formula (1a) can be obtained.

Production Method 2

Among the present compounds, the compound of Formula (1b), wherein G is a group other than hydrogen can be produced from the compound represented by Formula (1a) and a compound represented by Formula $G^1$-$X^1$.

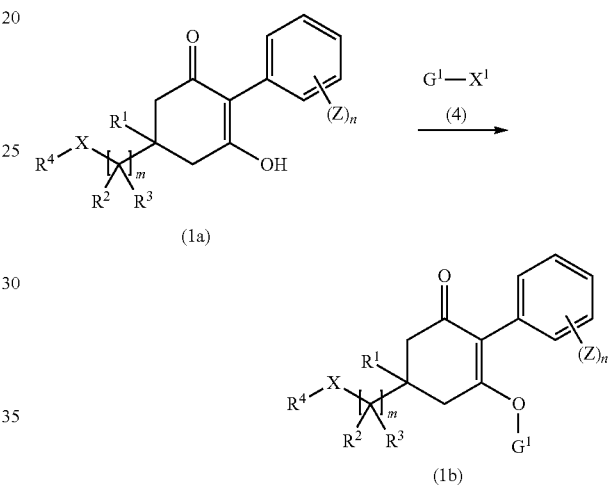

In the formula, $G^1$ represents any one group represented by the following formulae:

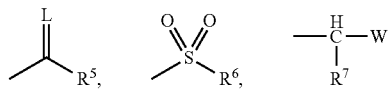

in the formulae, L, $R^5$, $R^6$, $R^7$, and W each have the same definition as described above, $X^1$ represents a halogen (for example, chlorine, bromine, or iodine), a $C_{1-3}$ alkylsulfonyloxy group which may be substituted with a halogen (for example, a methylsulfonyloxy group or a trifluoromethylsulfonyloxy group), or a group represented by Formula $OG^1$, wherein when $G^1$ is a group represented by the following formula:

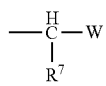

$X^1$ is a halogen or a $C_{1-3}$ alkylsulfonyloxy group which may be substituted with a halogen), and $R^1$, $R^2$, $R^3$, $R^4$, X, n, m, and Z each have the same definition as described above.]

This reaction may be performed in a solvent. Examples of the usable solvent include, for example, aromatic hydrocarbons such as benzene and toluene; ethers such as diethylether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethyl sulfoxide; sulfones such as sulfolane; and mixture of these solvents.

Examples of the compound represented by Formula (4) used in this reaction include, for example, halides of carboxylic acid such as acetyl chloride, propionyl chloride, isobutyryl chloride, pivaloyl chloride, benzoyl chloride, and cyclohexanecarboxylic acid chloride; anhydrides of carboxylic acid such as acetic anhydride and trifluoroacetic anhydride; halides of carbonic acid half ester such as methyl chloroformate, ethyl chloroformate, and phenyl chloroformate; halides of carbamic acid such as dimethylcarbamoyl chloride; halides of sulfonic acid such as methanesulfonyl chloride and p-toluenesulfonyl chloride; anhydrides of sulfonic acid such as methanesulfonic anhydride and trifluoromethanesulfonic anhydride; and alkyl halogenoalkyl ether such as chloromethyl methyl ether and ethyl chloromethyl ether. The amount of the compound represented by Formula (4) used in this reaction is usually equal to or greater than 1 molar equivalent, and preferably 1 molar equivalent to 3 molar equivalents with respect to the compound represented by Formula (1a).

This reaction is usually performed in the presence of a base. Examples of the base used in this reaction include, for example, organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, and sodium hydride. The amount of the base is usually 0.5 molar equivalents to 10 molar equivalents, and preferably 1 molar equivalent to 5 molar equivalents with respect to the compound represented by Formula (1a).

The reaction temperature of this reaction is usually −30° C. to 180° C., and preferably −10° C. to 50° C. The reaction time of this reaction is usually 10 minutes to 30 hours.

The completion of this reaction can be confirmed by sampling a portion of the reaction mixture and using analysis means such as thin-layer chromatography or high-performance liquid chromatography. After this reaction is completed, for example, operations in which the reaction mixture is mixed with water, and extracted with an organic solvent, and the obtained organic layer is dried and concentrated are performed, whereby the compound represented by Formula (1b) can be obtained.

The compound represented by Formula (4) may be a known compound, or can be produced from a known compound.

Production Method 3

Among the present compounds, a compound in which X is S(O) can be produced by oxidizing a compound in which X is S. In the case where an alkylthio group, an alkylsulfinyl group, a haloalkylthio group and/or a haloalkylsulfinyl group are included in a portion other than X of the compound represented by Formula (1c), these groups are also oxidized in some cases.

In the formula, $R^1$, $R^2$, $R^3$, $R^4$, G, n, m, and Z each have the same definition as described above.

An oxidant is used in the reaction. Examples of the oxidant include, for example, hydrogen peroxide; peracids such as peracetic acid, perbenzoic acid, and m-chloroperbenzoic acid; sodium metaperiodate, ozone, selenium dioxide, chromic acid, dinitrogen tetraoxide, acetyl nitrate, iodine, bromine, N-bromosuccinimide, and iodosylbenzene. The oxidant is used in an amount of 0.8 moles to 1.2 moles in general with respect to 1 mole of the compound represented by Formula (1c).

This reaction is performed in a solvent. Examples of the solvent used in the reaction include, for example, saturated hydrocarbons such as hexane, heptane, octane, and cyclohexane; aromatic hydrocarbons such as benzene, toluene, xylene, chlorobenzene, and dichlorobenzene; halogenated saturated hydrocarbons such as dichloromethane, chloroform, 1,2-dichloroethane, and carbon tetrachloride; alcohols such as methanol, ethanol, and propanol; nitriles such as acetonitrile; amides such as dimethyl formamide and dimethyl acetamide; sulfones such as sulfolane; organic acids such as acetic acid and propionic acid; water, and mixtures of these.

The reaction temperature of this reaction is usually −50° C. to 100° C., and preferably 0° C. to 50° C. The reaction time of this reaction is usually 10 minutes to 10 hours. The completion of the reaction may be confirmed by analyzing a portion of the reaction mixture by thin-layer chromatography or high-performance liquid chromatography. After the reaction is completed, for example, operations in which the reaction mixture is mixed with water, and extracted with an organic solvent, and the obtained organic layer is dried and concentrated are performed, whereby the compound represented by Formula (1d) can be obtained.

Production Method 4

Among the present compounds, a compound in which X is $SO_2$ can be produced by oxidizing a compound in which X is S or a compound in which X is SO. In the case where an alkylthio group, an alkylsulfinyl group, a haloalkylthio group and/or a haloalkylsulfinyl group are included in a group other than X of the compound represented by Formula (1e), these groups are also oxidized in some cases.

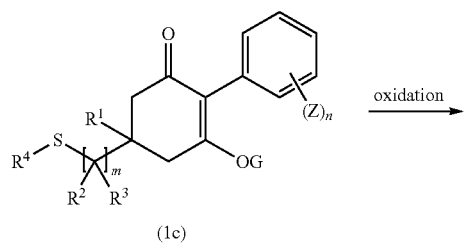

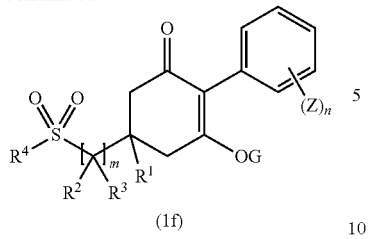

(1f)

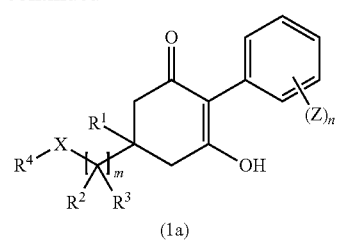

(1a)

In the formula, r represents 0 or 1, and $R^1$, $R^2$, $R^3$, $R^4$, G, n, m, and Z each have the same definition as described above.

An oxidant is used in the reaction. Examples of the oxidant include, for example, hydrogen peroxide; peracids such as peracetic acid, perbenzoic acid, and m-chloroperbenzoic acid; sodium metaperiodate, ozone, selenium dioxide, chromic acid, dinitrogen tetraoxide, acetyl nitrate, iodine, bromine, N-bromosuccinimide, iodosylbenzene, the combination of hydrogen peroxide and a tungsten catalyst, the combination of hydrogen peroxide and a vanadium catalyst, and potassium permanganate. In the case where the compound in which r is 0 represented by Formula (1e) is used, the amount of the oxidant is usually 2 moles to 10 moles, and preferably 2 moles to 4 moles with respect to 1 mole of the compound. In addition, in the case where the compound in which r is 1 represented by Formula (1e) is used, the amount of the oxidant is usually 1 mole to 10 moles, and preferably 1 mole to 3 moles with respect to 1 mole of the compound.

This reaction is performed in a solvent. Examples of the solvent used in the reaction include, for example, saturated hydrocarbons such as hexane, heptane, octane, and cyclohexane; aromatic hydrocarbons such as benzene, toluene, xylene, chlorobenzene, and dichlorobenzene; halogenated saturated hydrocarbons such as dichloromethane, chloroform, 1,2-dichloroethane, and carbon tetrachloride; alcohols such as methanol, ethanol, and propanol; nitriles such as acetonitrile; amides such as dimethyl formamide and dimethyl acetamide; sulfones such as sulfolane; organic acids such as acetic acid and propionic acid; water, and mixtures of these.

The reaction temperature of the reaction is usually 0° C. to 200° C., and preferably 20° C. to 150° C. The reaction time of the reaction is usually 30 minutes to 10 hours. The completion of the reaction may be confirmed by analyzing a portion of the reaction mixture by thin-layer chromatography or high-performance liquid chromatography. After the reaction is completed, for example, operations in which the reaction mixture is mixed with water, and extracted with an organic solvent, and the obtained organic layer is dried and concentrated are performed, whereby the compound represented by Formula (1f) can be obtained.

Production Method 5

Among the present compounds, the compound in which G is hydrogen represented by Formula (1a) can be produced by a reaction of the compound represented by Formula (2) with the compound represented by Formula (31) in the presence of a base.

In the formula, $R^1$, $R^2$, $R^3$, $R^4$, X, n, m, and Z each have the same definition as described above.

The reaction is usually performed in a solvent. Examples of the usable solvent include, for example, aromatic hydrocarbons such as benzene, toluene, and xylene; ethers such as diethyl ether, diisopropyl ether, dioxane, tetrahydrofuran, and dimethoxyethane; halogenated hydrocarbons such as dichloromethane, chloroform, and 1,2-dichloroethane; amides such as dimethylformamide and dimethylacetamide; sulfones such as sulfolane; and mixture of the solvents.

Examples of the base used in the reaction include, for example, organic bases such as triethylamine, tripropylamine, pyridine, dimethylaminopyridine, and 1,8-diazabicyclo[5.4.0]-7-undecene. The amount of the base is usually 1 mole to 10 moles, and preferably 1 mole to 5 moles with respect to 1 mole of the compound represented by Formula (2). The amount of the compound represented by Formula (31) used in this reaction is usually 1 mole to 3 moles with respect to 1 mole of the compound represented by Formula (2).

The reaction temperature of the reaction is usually −60° C. to 180° C., and preferably −10° C. to 100° C. The reaction time of the reaction is usually 10 minutes to 30 hours.

The completion of the reaction may be confirmed by analyzing a portion of the reaction mixture by thin-layer chromatography or high-performance liquid chromatography. After the reaction is completed, for example, operations in which after acid is added to the reaction mixture, the resultant product is mixed with water and extracted with an organic solvent, and the obtained organic layer is dried and concentrated are performed, whereby the compound represented by Formula (1a) may be obtained.

Production Method 6

Among the present compounds, the compound represented by Formula (1g) can be produced by a reaction of the compound represented by Formula (22) with the compound represented by Formula (21) in the presence of phosphine.

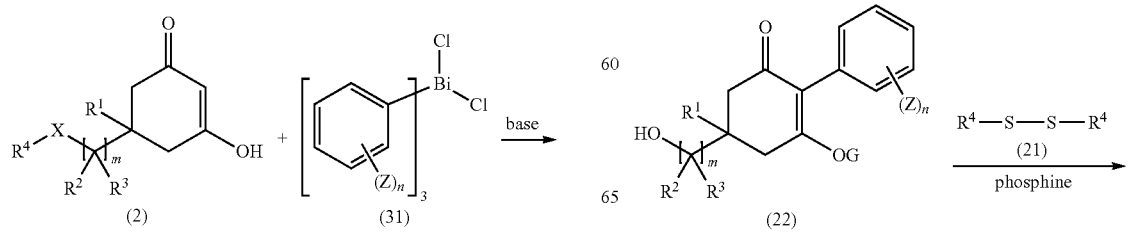

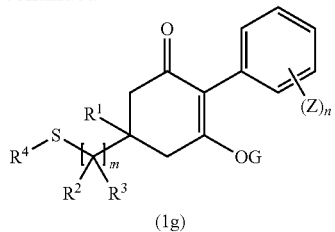

(1g)

In the formula, $G^3$ represents a group represented by the following formula:

In the formula, L and $R^5$ each have the same definition as described above, $G^4$ represents hydrogen or a group represented by the following formula:

In the formula, L and $R^5$ each have the same definition as described above.), $R^1$, $R^2$, $R^3$, $R^4$, n, m, and Z each have the same definition as described above.

The reaction is usually performed in a solvent. Examples of the solvent include, for example, ethers such as diethylether, diisopropylether, dioxane, tetrahydrofuran, and dimethoxyethane; halogenated hydrocarbons such as dichloromethane, chloroform, and 1,2-dichloroethane; and mixtures of these.

Examples of the phosphine include, for example, tri-n-butylphosphine and triphenylphosphine. The amount of the phosphine is usually equal to or greater than 1 molar equivalent, and preferably 1 molar equivalent to 3 molar equivalents with respect to the compound represented by Formula (22). The amount of the compound represented by Formula (21) used in this reaction is usually equal to or greater than 1 molar equivalent, and preferably 1 molar equivalent to 3 molar equivalents with respect to the compound represented by Formula (22).

The reaction temperature of the reaction is usually –60° C. to 180° C., and preferably –10° C. to 100° C. The reaction time of the reaction is usually 10 minutes to 30 hours.

The completion of the reaction may be confirmed by analyzing a portion of the reaction mixture by thin-layer chromatography or high-performance liquid chromatography. After the reaction is completed, for example, operations in which after acid is added to the reaction mixture, the resultant product is mixed with water and extracted with an organic solvent, and the obtained organic layer is dried and concentrated are performed, whereby the compound represented by Formula (1g) can be obtained.

Production Method 7

Among the present compounds, the compound represented by Formula (1g) can be produced by a reaction of the compound represented by Formula (34) with the compound represented by Formula (10).

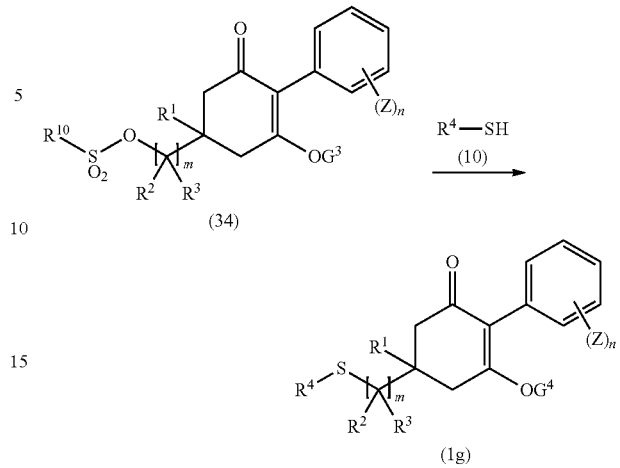

In the formula, $R^{10}$ represents a $C_{1-6}$ alkyl group or a $C_{6-10}$ aryl group, wherein the $C_{1-6}$ alkyl group and the $C_{6-10}$ aryl group may have one or more halogens, and when two or more halogens are present, the halogens may be the same or different, and the $C_{6-10}$ aryl group which may have one or more $C_{1-6}$ alkyl group, and when two or more $C_{1-6}$ alkyl groups are present, the alkyl groups may be the same or different, and $R^1$, $R^2$, $R^3$, $R^4$, n, m, Z, $G^3$, and $G^4$ each have the same definition as described above.

The reaction is usually performed in a solvent. Examples of the solvent include, for example, ethers such as diethylether, diisopropylether, 1,4-dioxane, tetrahydrofuran, and dimethoxyethane; halogenated hydrocarbons such as dichloromethane, chloroform, and 1,2-dichloroethane; amides such as dimethyl formamide and dimethyl acetamide; and mixtures of these. The amount of the compound represented by Formula (10) used in this reaction is usually equal to or greater than 1 molar equivalent, and preferably 1 molar equivalent to 5 molar equivalents with respect to the compound represented by Formula (34).

The reaction temperature of the reaction is usually –60° C. to 180° C., and preferably –10° C. to 100° C. The reaction time of the reaction is usually 10 minutes to 30 hours.

The completion of the reaction may be confirmed by analyzing a portion of the reaction mixture by thin-layer chromatography or high-performance liquid chromatography. After the reaction is completed, for example, operations in which after acid is added to the reaction mixture, the resultant product is mixed with water and extracted with an organic solvent, and the obtained organic layer is dried and concentrated are performed, whereby the compound represented by Formula (1g) can be obtained.

Production Method 8

Among the present compounds, the compound represented by Formula (1h) can be produced by hydrolyzing the compound represented by Formula (1g) in the presence of a base.

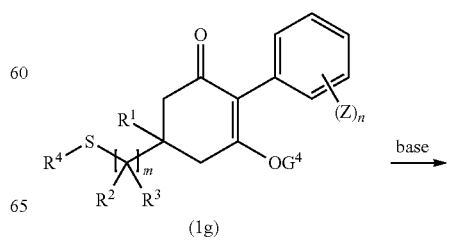

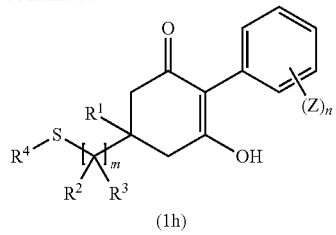

In the formula, $R^1$, $R^2$, $R^3$, $R^4$, n, m, Z, and $G^4$ each have the same definition as described above.

The reaction is usually performed in a solvent. Examples of the solvent include, for example, ethers such as diethylether, diisopropylether, dioxane, tetrahydrofuran, and dimethoxyethane; alcohols such as methanol and ethanol; amides such as dimethyl formamide and dimethyl acetamide; and mixtures of these.

Examples of the base used in the reaction include, for example, lithium hydroxide, sodium hydroxide, potassium hydroxide, sodium methoxide, and sodium ethoxide. The amount of the base is usually 1 mole to 10 moles, and preferably 1 mole to 5 moles with respect to 1 mole of the compound represented by Formula (1g).

The reaction temperature of the reaction is usually $-60°$ C. to $180°$ C., and preferably $-10°$ C. to $100°$ C. The reaction time of the reaction is usually 10 minutes to 30 hours.

The completion of the reaction may be confirmed by analyzing a portion of the reaction mixture by thin-layer chromatography or high-performance liquid chromatography. After the reaction is completed, for example, operations in which after acid is added to the reaction mixture, the resultant product is mixed with water and extracted with an organic solvent, and the obtained organic layer is dried and concentrated are performed, whereby the compound represented by Formula (1h) can be obtained.

Production Method 9

Among the present compounds, the compound represented by Formula (1i) can be produced by a reaction of the compound represented by Formula (35) with the compound represented by Formula (11) in the presence of copper sulfate and sodium ascorbate.

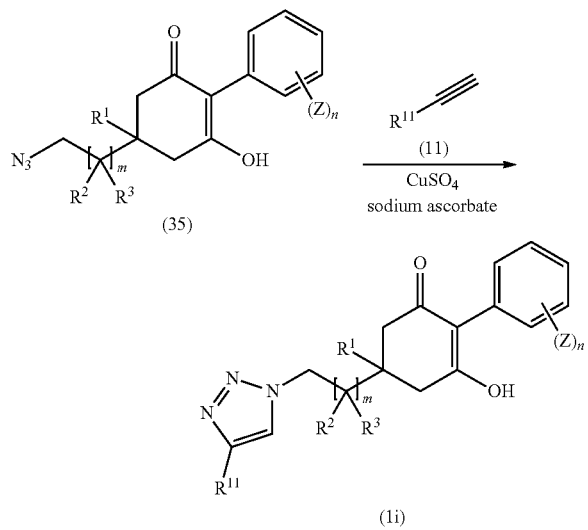

In the formula, $R^{11}$ represents a $C_{6-10}$ aryl group, wherein the $C_{6-10}$ aryl group may have one or more halogens or one or more $C_{1-3}$ haloalkyl groups, and when two or more halogens or two or more $C_{1-3}$ haloalkyl groups are present, the halogens or the $C_{1-3}$ haloalkyl groups may be the same or different, and $R^1$, $R^2$, $R^3$, n, m, and Z each have the same definition as described above.]

The reaction is usually performed in a solvent. Examples of the solvent include, for example, nitriles such as acetonitrile; amides such as dimethylformamide; sulfoxides such as dimethyl sulfoxide; and mixtures of these. The amount of the compound represented by Formula (11) used in this reaction is usually 1 molar equivalent to 10 molar equivalents, and preferably 1 molar equivalent to 3 molar equivalents with respect to the compound represented by Formula (35). The amount of the copper sulfate used in this reaction is usually 0.02 molar equivalents to 0.2 molar equivalents with respect to the compound represented by Formula (35). The amount of the sodium ascorbate used in this reaction is usually 0.05 molar equivalents to 0.5 molar equivalents with respect to the compound represented by Formula (35).

The reaction temperature of the reaction is usually $20°$ C. to $100°$ C. The reaction time of the reaction is usually 10 minutes to 30 hours.

The completion of the reaction can be confirmed by analyzing a portion of the reaction mixture by thin-layer chromatography or high-performance liquid chromatography. After the reaction is completed, for example, operations in which after acid is added to the reaction mixture, the resultant product is mixed with water and extracted with an organic solvent, and the obtained organic layer is dried and concentrated are performed, whereby the compound represented by Formula (1i) can be obtained.

Respective compounds produced by Production Methods 1 to 9 described above may also be isolated or purified by other known means, for example, methods such as concentration, concentration under reduced pressure, extraction, transfer dissolution, crystallization, recrystallization, and chromatography in some cases.

Reference Production Example 1

The compound represented by Formula (3) can be produced by a reaction of the compound represented by Formula (5) with lead tetraacetate in the presence of a base, for example, according to the method described in Marie-Luise Huber and John T. Pinhey, Journal of Chemical Society Perkin Transion 1 (1990) 721.

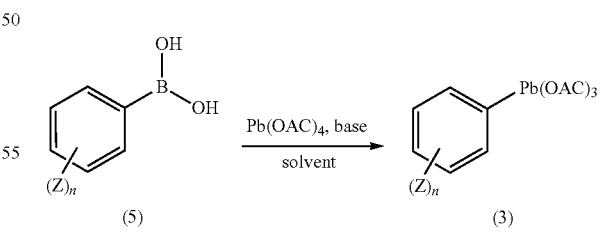

In the formula, Z and n each have the same definition as described above.

The compound represented by Formula (5) may be a known compound, or can be produced from a known compound. For example, the compound can be produced according to the method described in Japanese Unexamined Patent Application Publication No. 2008-133252 or a method based on this.

Reference Production Example 2

The compound represented by Formula (2) can be produced by, for example, the following reaction scheme.

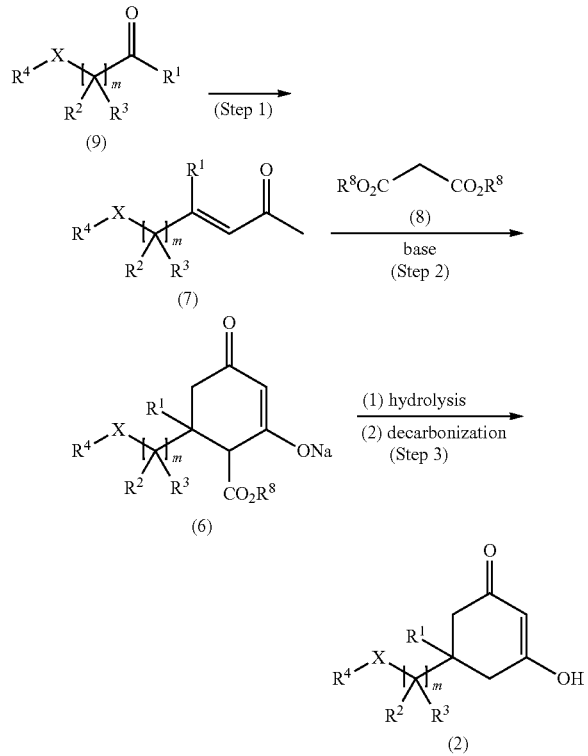

In the formula, $R^8$ represents a $C_{1-3}$ alkyl group; and X, m, $R^1$, $R^2$, $R^3$, $R^4$, and n each have the same definition as described above.

The compound represented by Formula (2) can be produced according to, for example, the method described in Japanese Unexamined Patent Application Publication No. 63-146856.

In Step 1, the compound represented by Formula (7) can be produced by a Wittig reaction of the compound represented by Formula (9) with 1-triphenylphosphoranylidene-2-propanone.

In Step 2, the compound represented by Formula (6) can be produced by a reaction of the compound represented by Formula (7) with the compound represented by Formula (8) under a basic condition. Among the present compounds represented by Formula (8), dimethyl malonate or diethyl malonate is preferable. This reaction is performed in a suitable solvent, for example, tetrahydrofuran, methanol, ethanol, or toluene.

In Step 3, the compound represented by Formula (2) can be produced by hydrolyzing the compound represented by Formula (6) and by decarbonizing the resultant product.

The compound represented by Formula (9) may be a known compound, or can be produced from a known compound, and can be produced according to, for example, the method described in Tetrahedron letter 28 (1987) 2893-2894, Tetrahedron letter 47 (2006) 5869-5873, Tetrahedron 42 (1986) 6071-6095, Japanese Unexamined Patent Application Publication No. 63-146856, or methods based on these.

Reference Production Example 3

The compound represented by Formula (31) can be produced by, for example, the following method.

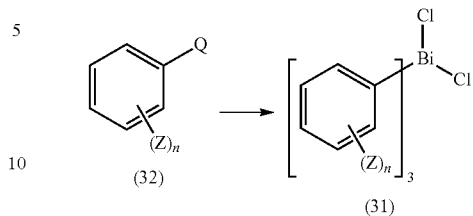

[In the formula, Q represents a halogen, and Z and n each have the same definition as described above.]

The compound represented by Formula (31) can be produced from the compound represented by Formula (32) according to, for example, the method described in Bull. Chem. Soc. Jpn., 65, 3504-3506 (1992).

The compound represented by Formula (32) may be a known compound, or can be produced from a known compound, and can be produced according to, for example, the method described in WO2010102761 or WO2006084663, or methods based on these.

Reference Production Example 4

The compound represented by Formula (22) can be produced by, for example, the following method.

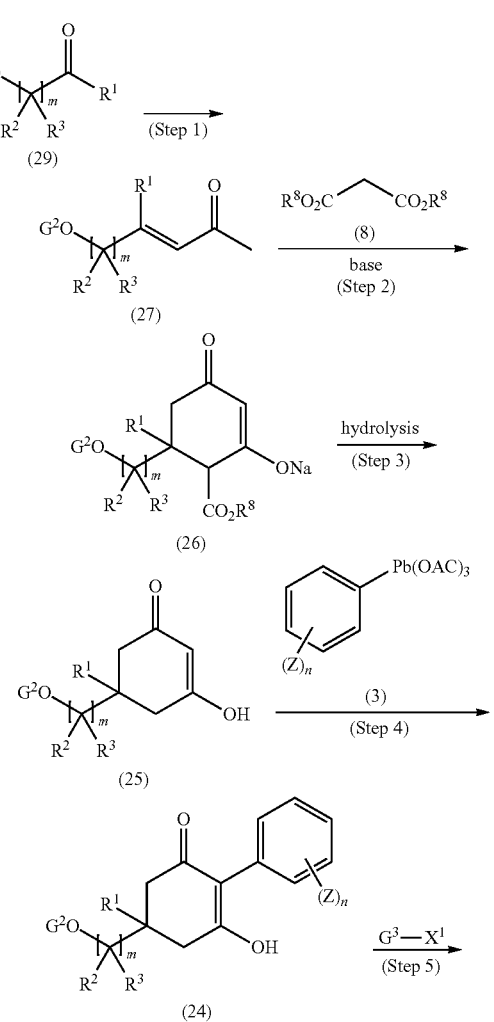

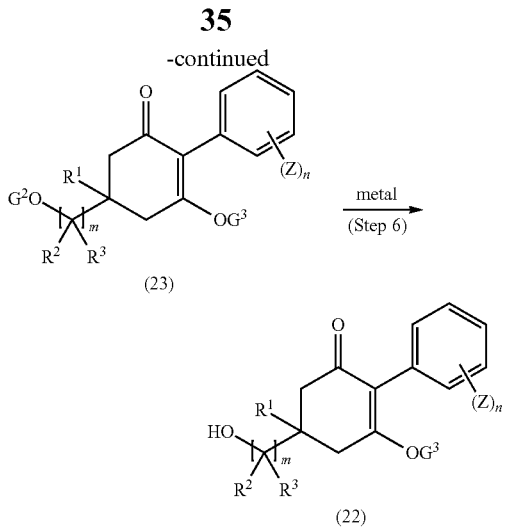

In the formula, $G^2$ represents a benzyl group or a paramethoxybenzyl group, and $G^3$, m, $R^1$, $R^2$, $R^3$, $R^8$, Z, and n each have the same definition as described above.

The compound represented by Formula (25) can be produced according to, for example, the method described in Japanese Unexamined Patent Application Publication No. 63-146856.

Step 1

The compound represented by Formula (27) can be produced by a Wittig reaction of the compound represented by Formula (29) with 1-triphenylphosphoranylidene-2-propanone.

Step 2

The compound represented by Formula (26) can be produced by a reaction of the compound represented by Formula (27) with the compound represented by Formula (8) under a basic condition.

Examples of the compound represented by Formula (8) include, for example, dimethyl malonate and diethyl malonate. Examples of the solvent used in the reaction include, for example, tetrahydrofuran, methanol, ethanol, and toluene.

Step 3

The compound represented by Formula (25) can be produced by hydrolyzing the compound represented by Formula (26) and decarbonizing the resultant product.

Step 4

The compound represented by Formula (24) can be produced by a reaction of the compound represented by Formula (25) with the compound represented by Formula (3) in the presence of a base.

The reaction is usually performed in a solvent.

Examples of the solvent include, for example, aromatic hydrocarbons such as benzene, toluene, and xylene; ethers such as diethyl ether, diisopropyl ether, dioxane, tetrahydrofuran, and dimethoxyethane; halogenated hydrocarbons such as dichloromethane, chloroform, and 1,2-dichloroethane; amides such as dimethylformamide and dimethylacetamide; sulfones such as sulfolane; and mixtures of these.

Examples of the base used in the reaction include, for example, organic bases such as triethylamine, tripropylamine, pyridine, dimethylaminopyridine, and 1,8-diazabicyclo[5.4.0]-7-undecene. The amount of the base is usually 1 mole to 10 moles, and preferably 2 moles to 5 moles with respect to 1 mole of the compound represented by Formula (25). The amount of the compound represented by Formula (3) used in this reaction is usually 1 mole to 3 moles with respect to 1 mole of the compound represented by Formula (25).

The reaction temperature of the reaction is usually −60° C. to 180° C., and preferably −10° C. to 100° C. The reaction time of the reaction is usually 10 minutes to 30 hours.

The completion of the reaction may be confirmed by analyzing a portion of the reaction mixture by thin-layer chromatography or high-performance liquid chromatography. After the reaction is completed, for example, operations in which after acid is added to the reaction mixture, the resultant product is mixed with water and extracted with an organic solvent, and the obtained organic layer is dried and concentrated are performed, whereby the compound represented by Formula (24) can be obtained.

Step 5

The compound represented by Formula (23) can be produced by a reaction of the compound represented by Formula (24) with the compound represented by $G^3$-$X^1$ in the presence of a base. The reaction is usually performed in a solvent. Examples of the solvent include, for example, aromatic hydrocarbons such as benzene and toluene; ethers such as diethylether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethyl sulfoxide; sulfones such as sulfolane; and mixtures of these.

Examples of the compound represented by Formula $G^3$-$X^1$ used in the reaction include, for example, halides of carboxylic acid such as acetyl chloride, propionyl chloride, isobutyryl chloride, pivaloyl chloride, benzoyl chloride, and cyclohexanecarboxylic acid chloride; anhydrides of carboxylic acid such as acetic anhydride and trifluoroacetic anhydride; halides of carbonic acid ester such as methyl chloroformate, ethyl chloroformate, and phenyl chloroformate; halides of carbamic acid such as dimethylcarbamoyl chloride; halides of sulfonic acid such as methanesulfonyl chloride and p-toluenesulfonyl chloride; anhydrides of sulfonic acid such as methanesulfonic anhydride and trifluoromethanesulfonic anhydride; and alkyl halogenoalkyl ether such as chloromethyl methyl ether and ethyl chloromethyl ether.

The amount of the compound represented by Formula $G^3$-$X^1$ used in the reaction is usually equal to or greater than 1 mole, and preferably 1 mole to 3 moles with respect to 1 mole of the compound represented by Formula (24).

Examples of the base used in the reaction include, for example, organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, and sodium hydride.

The amount of the base is usually 0.5 moles to 10 moles, and preferably 1 mole to 5 moles with respect to 1 mole of the compound represented by Formula (24).

The reaction temperature of the reaction is usually −30° C. to 180° C., and preferably −10° C. to 50° C. The reaction time of the reaction is usually 10 minutes to 30 hours.

The completion of the reaction may be confirmed by analyzing a portion of the reaction mixture by thin-layer chromatography or high-performance liquid chromatography. After the reaction is completed, for example, operations in which the reaction mixture is mixed with water, and extracted with an organic solvent, and the obtained organic layer is dried and concentrated are performed, whereby the compound represented by Formula (23) can be obtained.

The compound represented by Formula $G^3$-$X^1$ may be a known compound, or can be produced from a known compound.

Step 6

The compound represented by Formula (22) can be produced by a reaction of the compound represented by Formula (23) with a metal.

The reaction is usually performed in a solvent. Examples of the solvent include, for example, aromatic hydrocarbons such as benzene and toluene; ethers such as diethylether, diisopropylether, dioxane, tetrahydrofuran, and dimethoxyethane; alcohols such as methanol and ethanol; esters such as ethyl acetate; and mixtures of these.

Examples of the metal used in the reaction include, for example, palladium and platinum. The amount of the metal used in the reaction is usually equal to or greater than 0.01 moles, and preferably 0.01 moles to 0.5 moles with respect to 1 mole of the compound represented by Formula (23).

The reaction temperature of the reaction is usually −30° C. to 180° C., and preferably −10° C. to 50° C. The reaction time of the reaction is usually 10 minutes to 30 hours.

The completion of the reaction may be confirmed by analyzing a portion of the reaction mixture by thin-layer chromatography or high-performance liquid chromatography. After the reaction is completed, for example, operations in which the reaction mixture is filtered using Celite (registered trademark), and the obtained liquid is concentrated under reduced pressure are performed, whereby the compound represented by Formula (22) can be obtained.

Reference Production Example 5

The compound represented by Formula (34) can be produced by a reaction of the compound represented by Formula (22) with the compound represented by Formula (35).

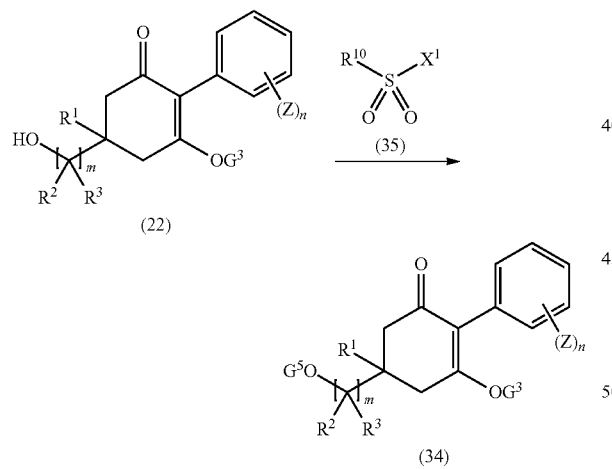

[In the formula, $R^{10}$, $X^1$, $R^1$, $R^2$, $R^3$, n, m, $G^3$, and Z each have the same definition as described above.]

The reaction is usually performed in a solvent. Examples of the solvent include, for example, aromatic hydrocarbons such as benzene and toluene; ethers such as diethylether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethyl sulfoxide; sulfones such as sulfolane; and mixtures of these.

Examples of the compound represented by Formula (35) used in the reaction include, for example, halides of sulfonic acid such as methanesulfonyl chloride and p-toluenesulfonyl chloride; and anhydrides of sulfonic acid such as methanesulfonic anhydride and trifluoromethanesulfonic anhydride. The amount of the compound represented by Formula (35) used in the reaction is usually equal to or greater than 1 mole, and preferably 1 mole to 3 moles with respect to 1 mole of the compound represented by Formula (22).

The reaction is usually performed in the presence of a base. Examples of the base used in the reaction include, for example, organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, and sodium hydride. The amount of the base is usually 0.5 moles to 10 moles, and preferably 1 mole to 5 moles with respect to 1 mole of the compound represented by Formula (22).

The reaction temperature of the reaction is usually −30° C. to 180° C., and preferably −10° C. to 50° C. The reaction time of the reaction is usually 10 minutes to 30 hours.

The completion of the reaction may be confirmed by analyzing a portion of the reaction mixture by thin-layer chromatography or high-performance liquid chromatography.

After the reaction is completed, for example, operations in which the reaction mixture is mixed with water, and extracted with an organic solvent, and the obtained organic layer is dried and concentrated are performed, whereby the compound represented by Formula (34) can be obtained.

The compound represented by Formula (35) may be a known compound, or can be produced from a known compound.

Reference Production Example 6

The compound represented by Formula (35) can be produced by a reaction of the compound represented by Formula (34-a) with sodium azide in the presence of 15-crown 5-ether.

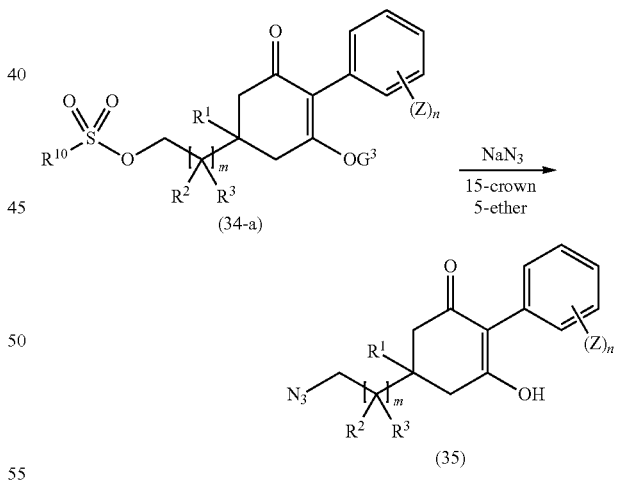

In the formula, $R^{10}$, $R^1$, $R^2$, $R^3$, $G^3$, n, m, and Z each have the same definition as described above.

The reaction is usually performed in a solvent. Examples of the solvent include, for example, amides such as dimethylformamide and dimethylacetamide; sulfoxides such as dimethyl sulfoxide; and mixtures of these. The amount of the sodium azide used in this reaction is usually 1 molar equivalent to 20 molar equivalents, and preferably 2 molar equivalents to 10 molar equivalents with respect to 1 mole of the compound represented by Formula (34-a). The amount of the 15-crown 5-ether used in this reaction is usually 0.02 molar equivalents to 0.2 molar equivalents with respect to 1 mole of the compound represented by Formula (34-a).

The reaction temperature of the reaction is preferably −10° C. to 120° C. The reaction time of the reaction is usually 10 minutes to 30 hours.

The completion of the reaction may be confirmed by analyzing a portion of the reaction mixture by thin-layer chromatography or high-performance liquid chromatography.

After this reaction is completed, the compound represented by Formula (35) can be obtained by, for example, concentrating the reaction mixture.

The compound represented by Formula (34-a) can be produced according to, for example, the method described in Reference Production Example 5.

Some of the compounds which can be produced by the above production methods are shown below.

(1-1)

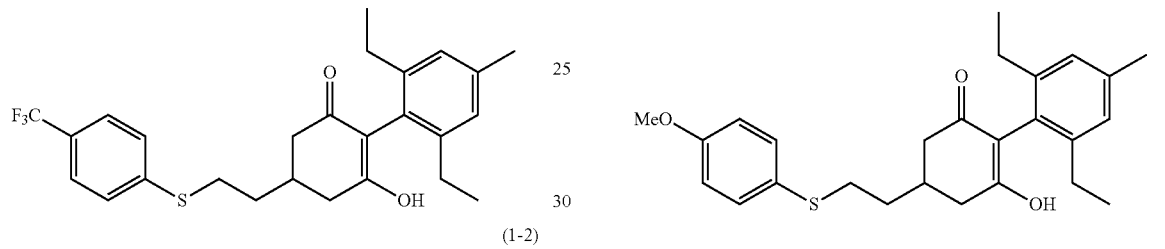

(1-2)

(1-3)

(1-4)

(1-5)

-continued (1-6)

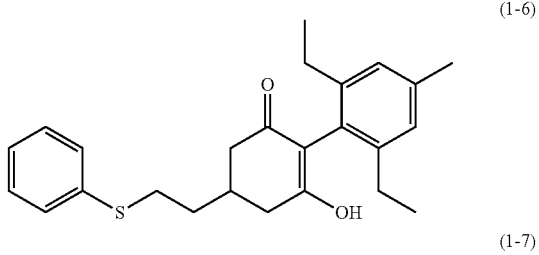

(1-7)

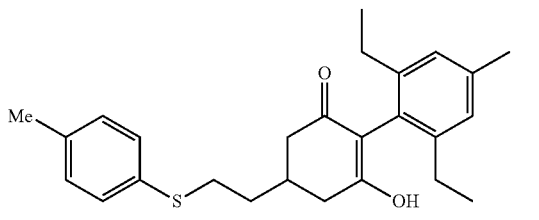

(1-8)

(1-9)

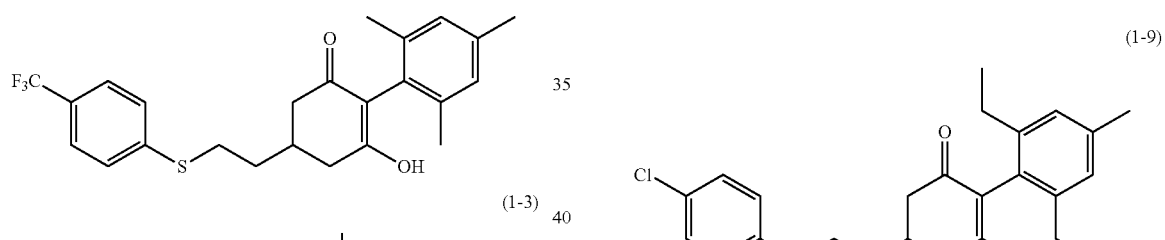

(1-10)

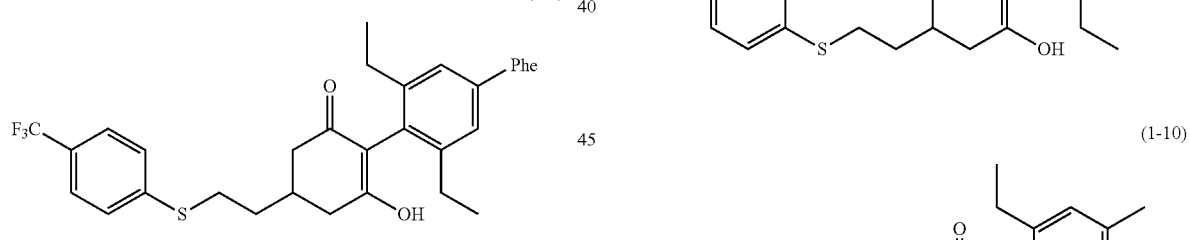

(1-11)

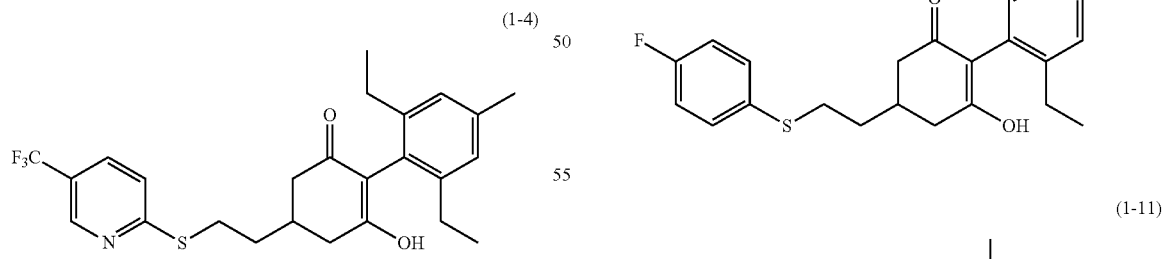

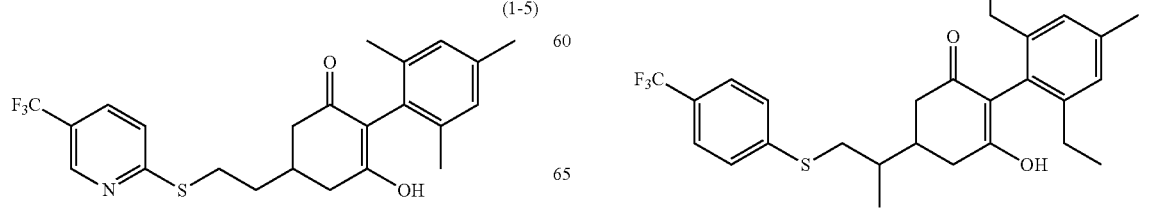

(1-12)
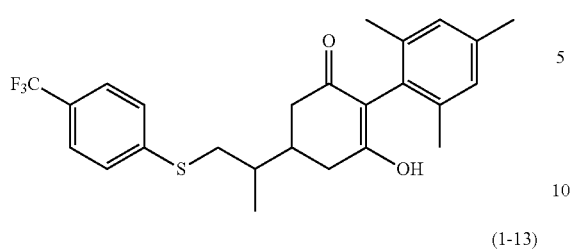
(1-13)
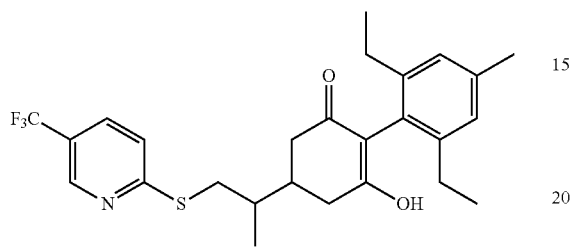
(1-14)
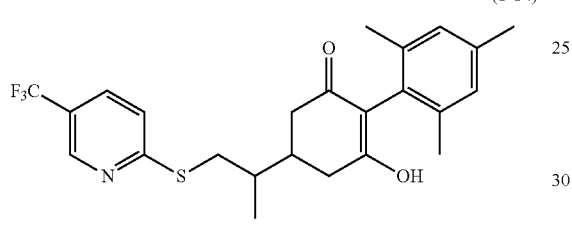
(1-15)
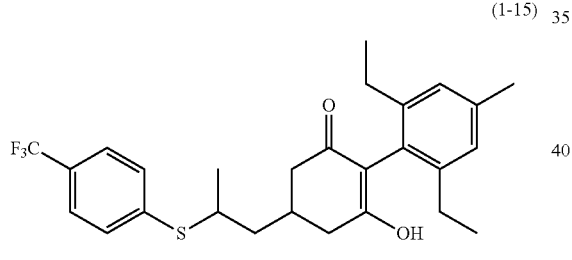
(1-16)
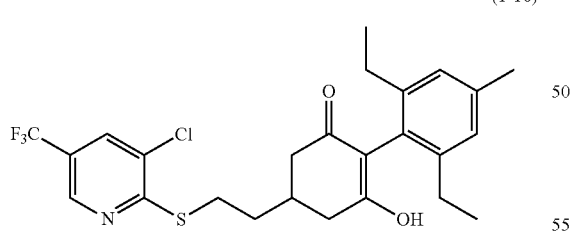
(1-17)
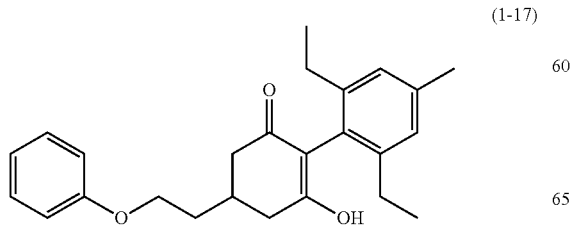
(1-18)
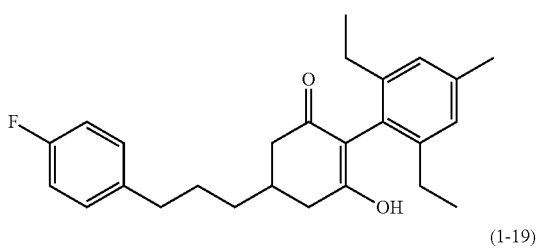
(1-19)
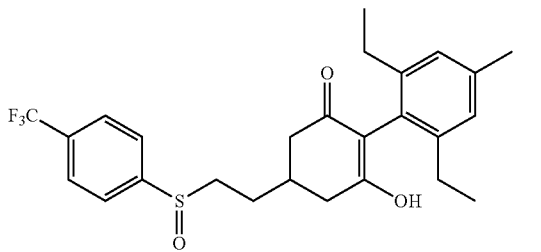
(1-20)
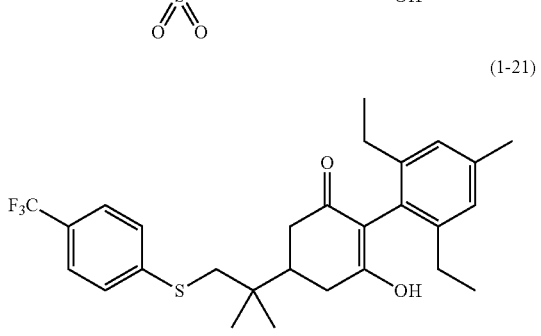
(1-21)
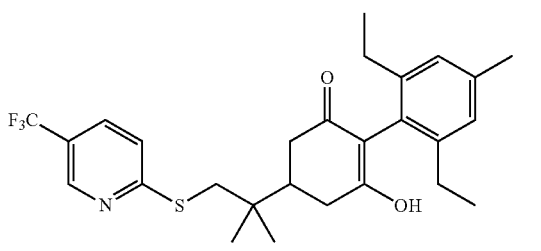
(1-22)
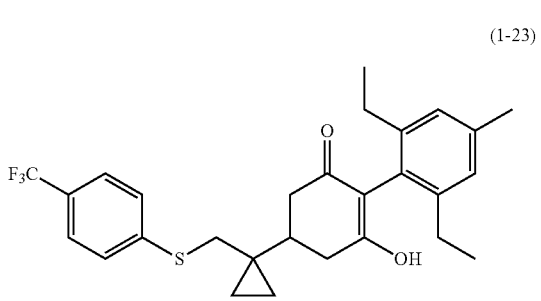
(1-23)

-continued
(1-24)
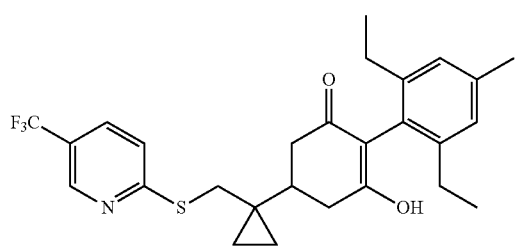
(1-25)
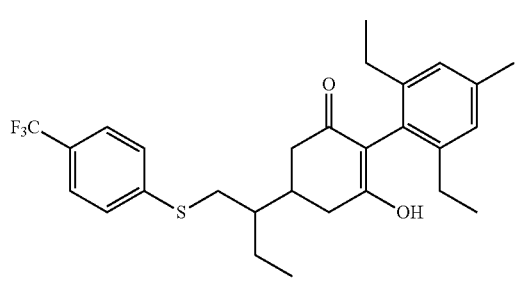
(1-26)
(1-27)
(1-28)
(1-29)
-continued
(1-30)
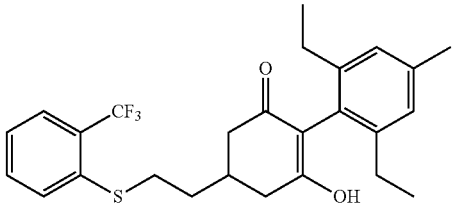
(1-31)
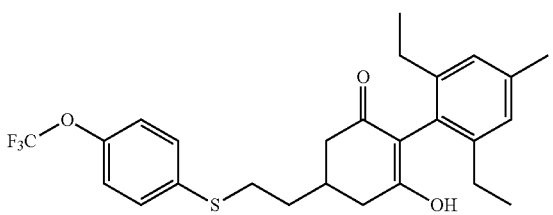
(1-32)
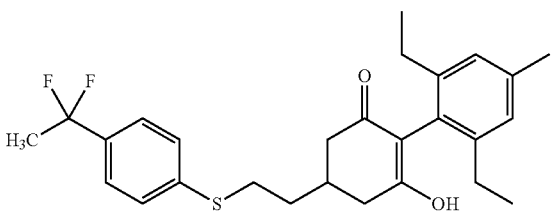
(1-33)
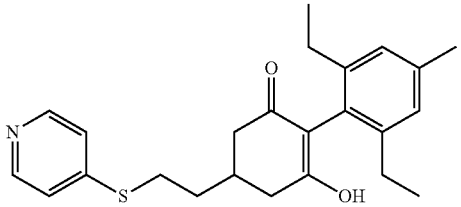
(1-34)
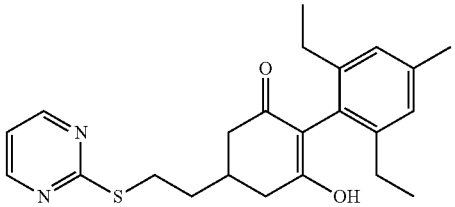
(1-35)
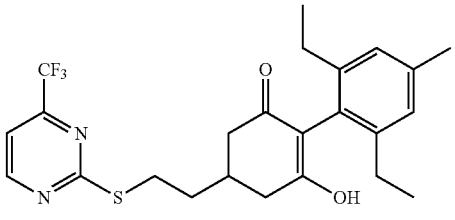
(1-36)
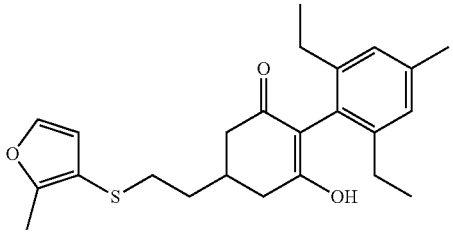

(1-37)
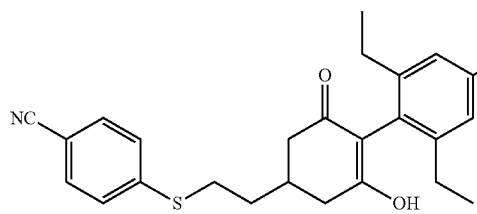
(1-38)
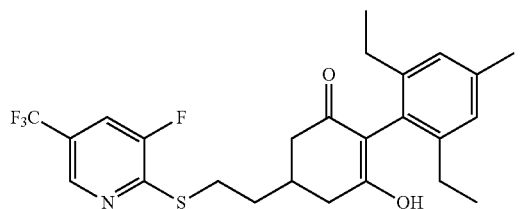
(1-39)
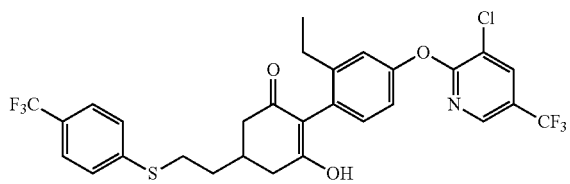
(1-40)
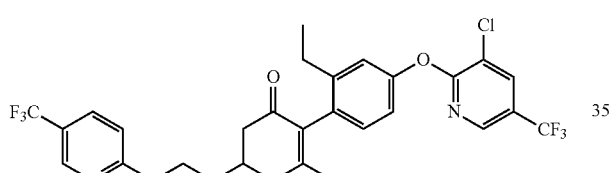
(1-41)
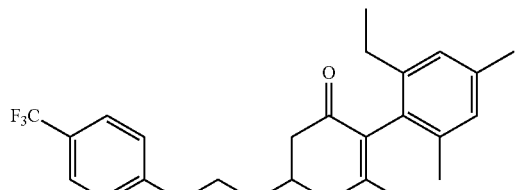
(1-42)
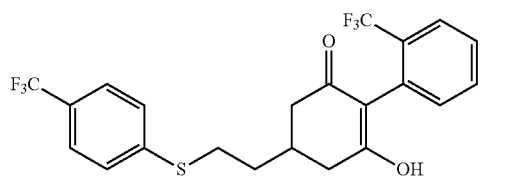
(1-43)
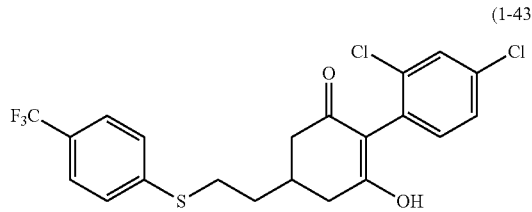
(1-44)
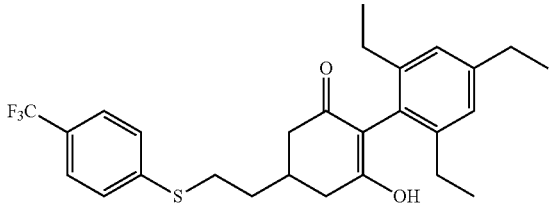
(1-45)
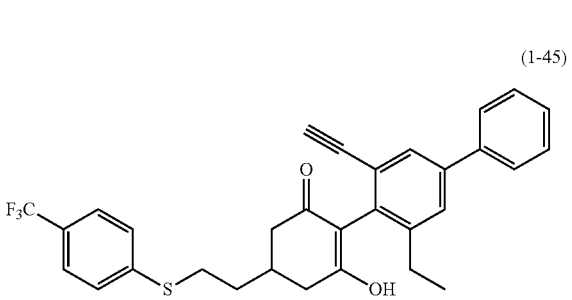
(1-46)
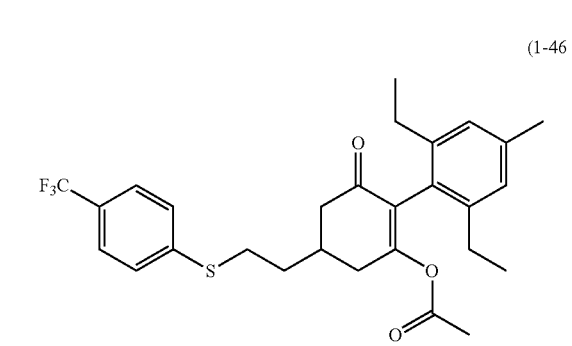
(1-47)
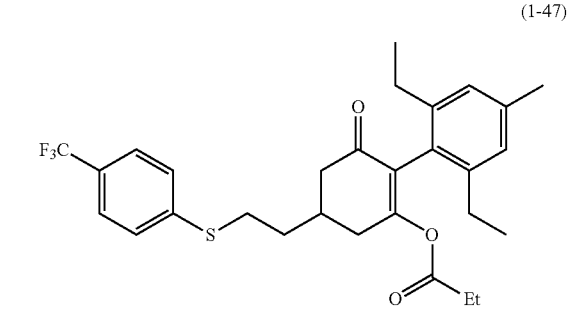
(1-48)
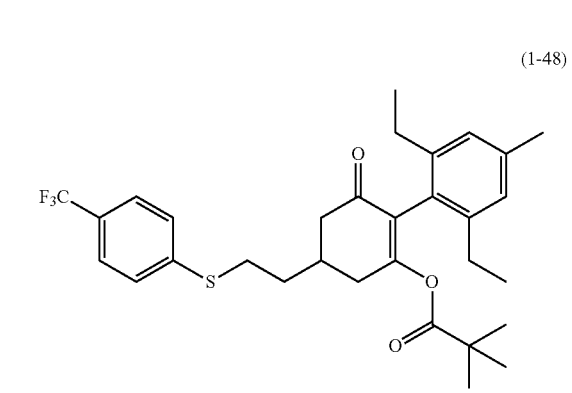

(1-49)
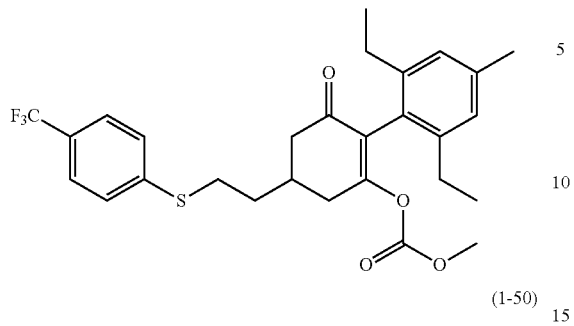
(1-50)
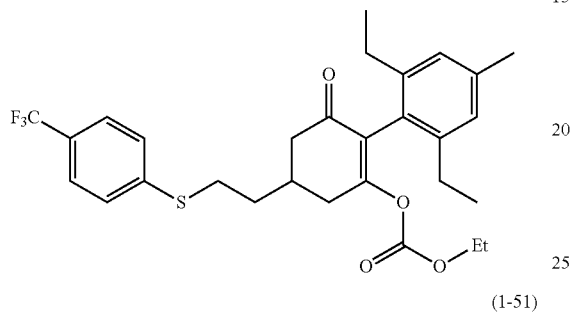
(1-51)
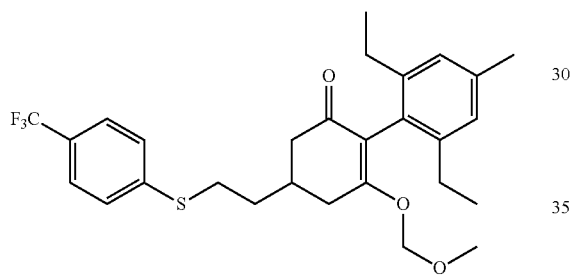
(1-52)
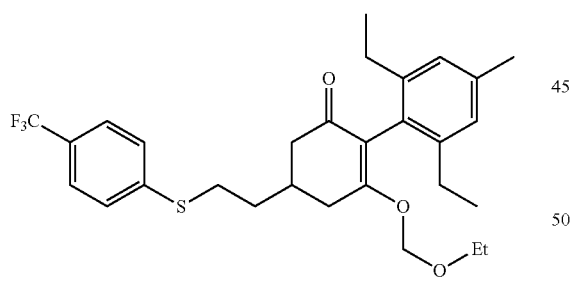
(1-53)
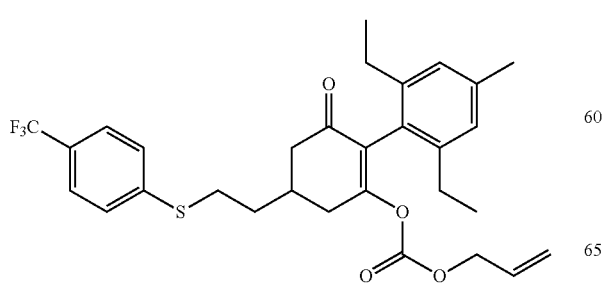
(1-54)
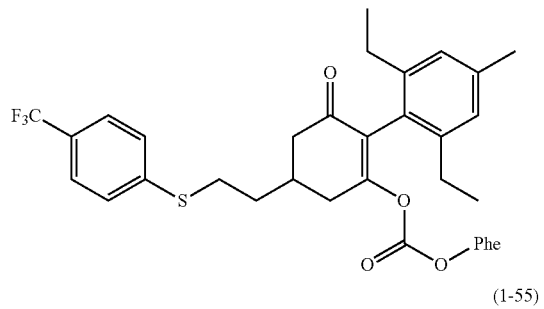
(1-55)
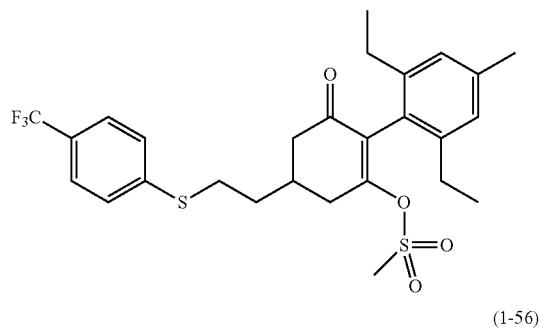
(1-56)
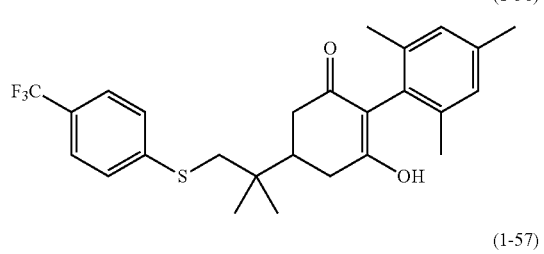
(1-57)
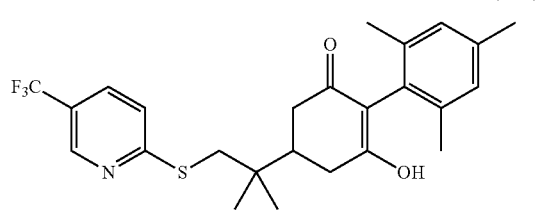
(1-58)
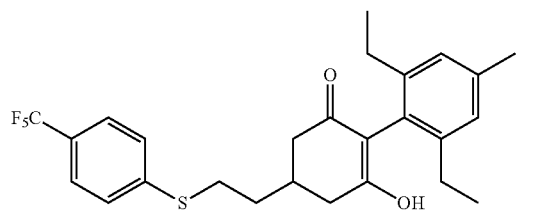
(1-59)

(1-60)
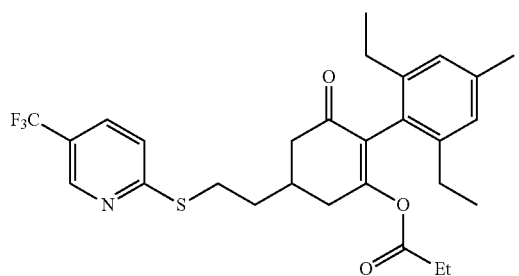
(1-61)
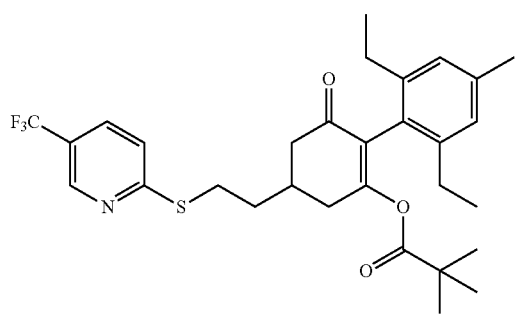
(1-62)
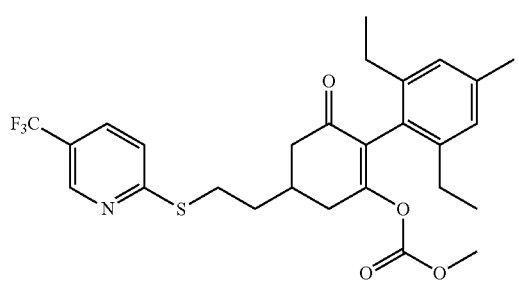
(1-63)
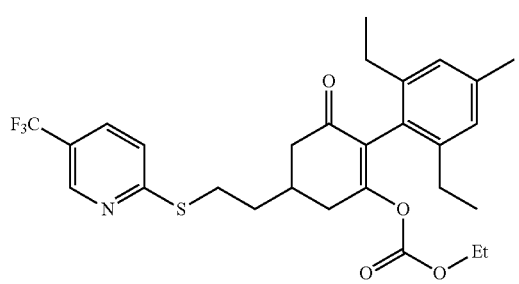
(1-64)
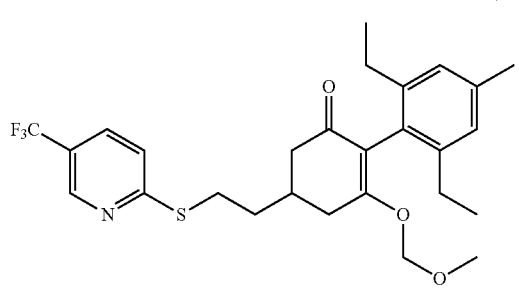
(1-65)
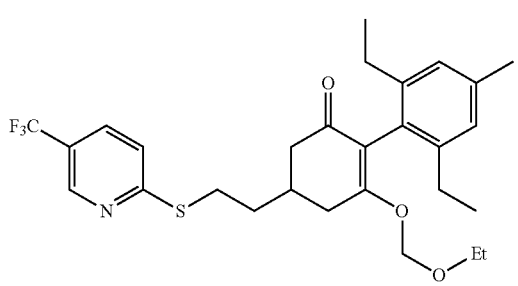
(1-66)
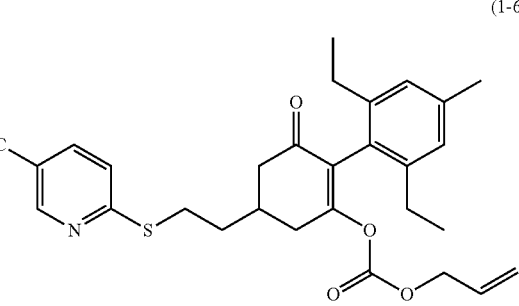
(1-67)
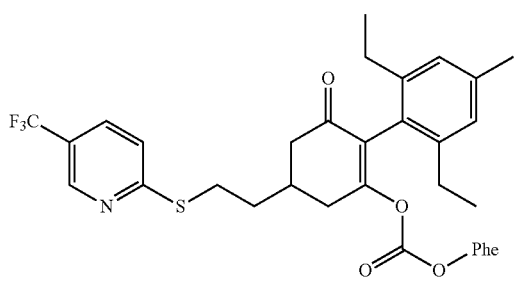
(1-68)
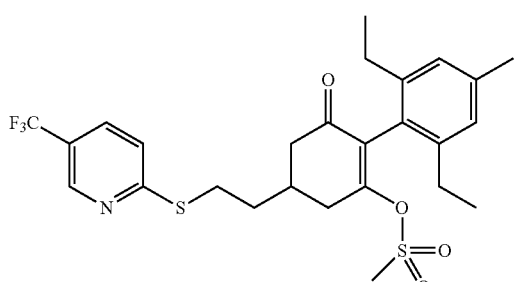

(1-70)
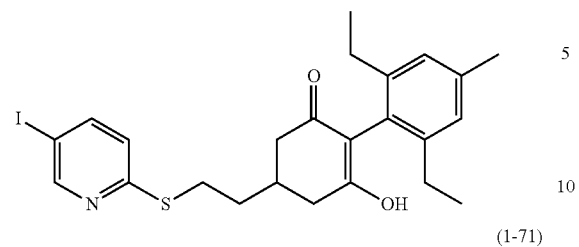
(1-71)
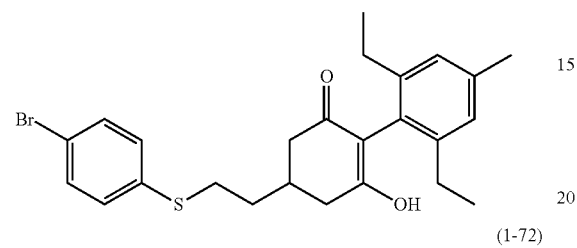
(1-72)
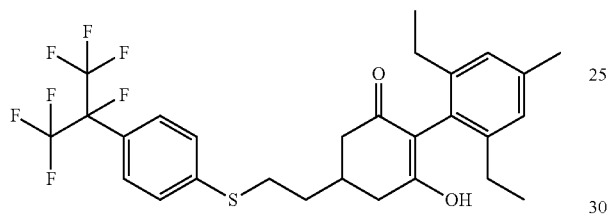
(1-73)
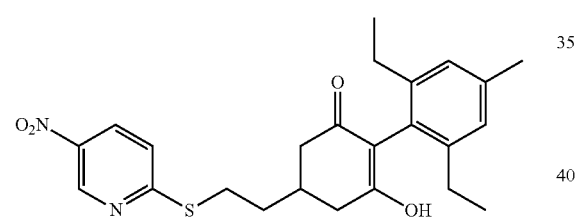
(1-74)
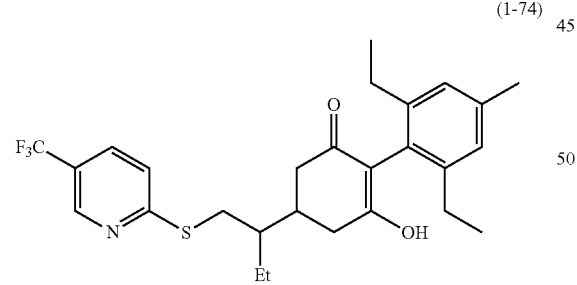
(1-75)
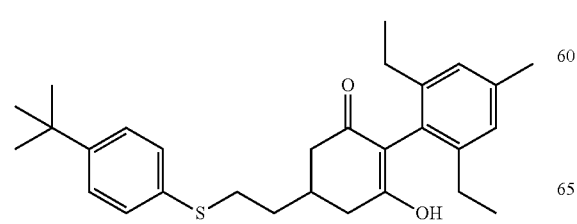
(1-76)
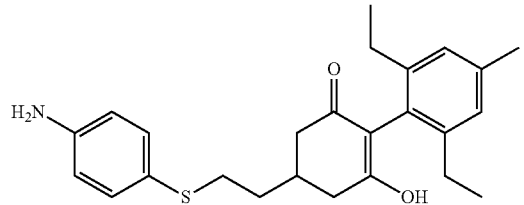
(1-77)
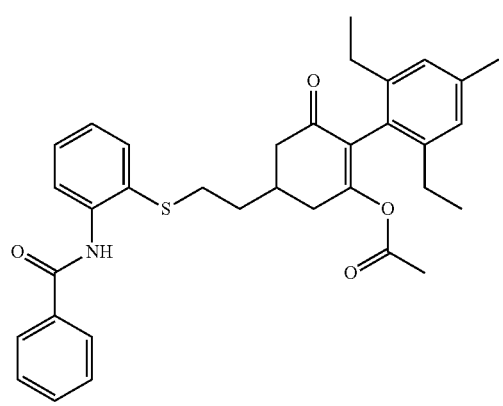
(1-78)
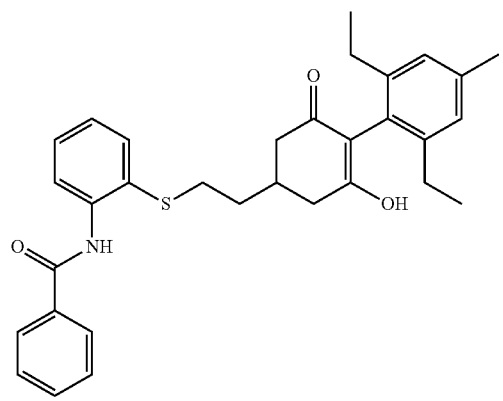
(1-79)

(1-80)
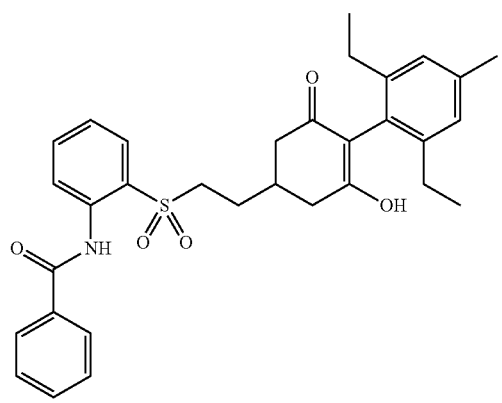
(1-85)
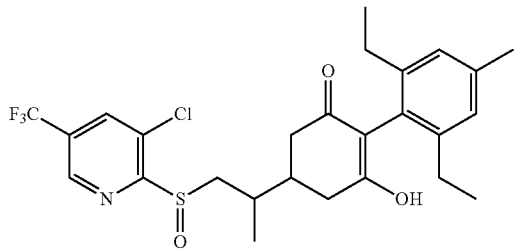
(1-81)
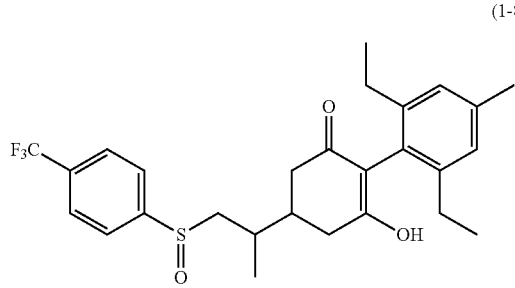
(1-86)
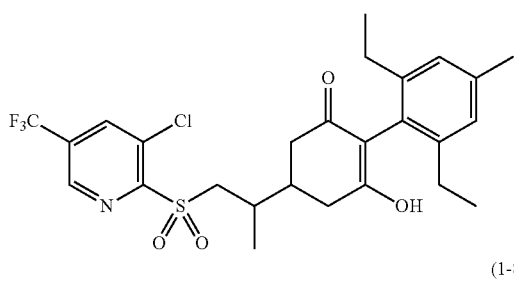
(1-82)
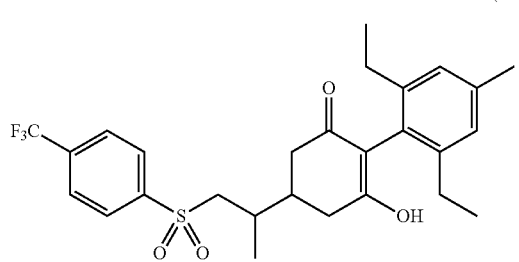
(1-87)
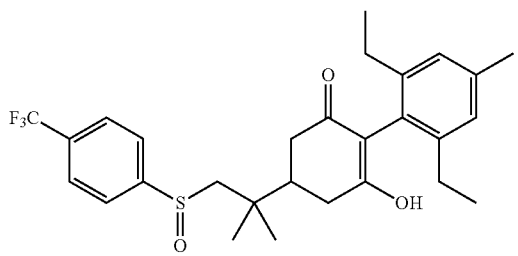
(1-88)
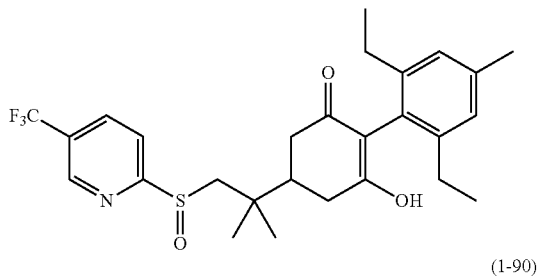
(1-83)
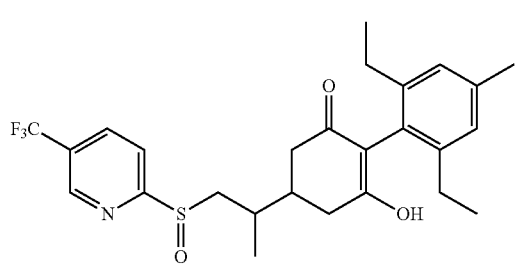
(1-89)
(1-84)
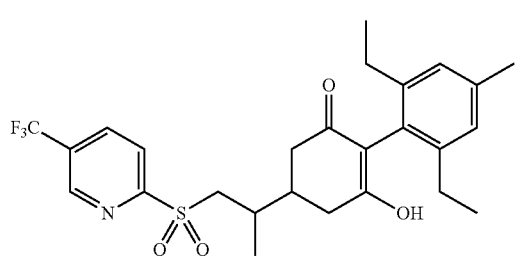
(1-90)

(1-91)
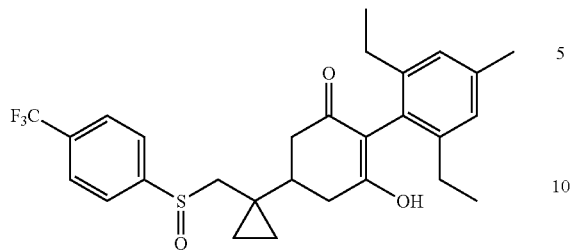
(1-92)
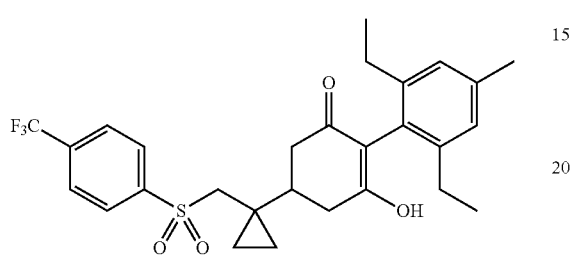
(1-93)
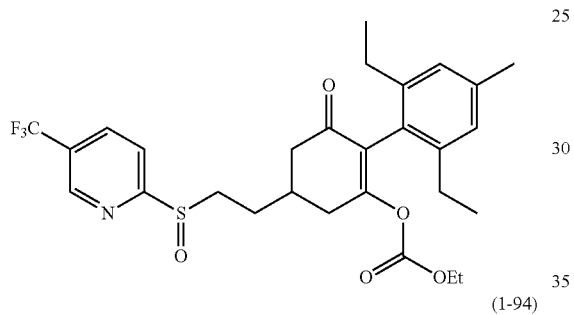
(1-94)
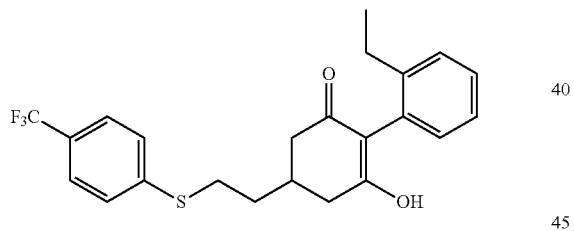
(1-95)
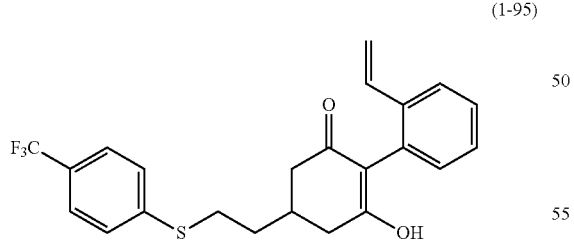
(1-96)
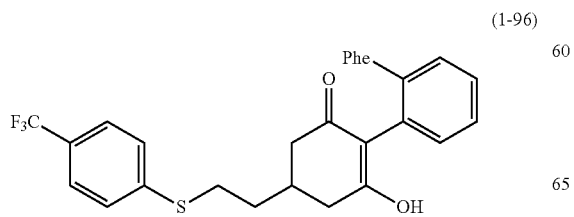
(1-97)
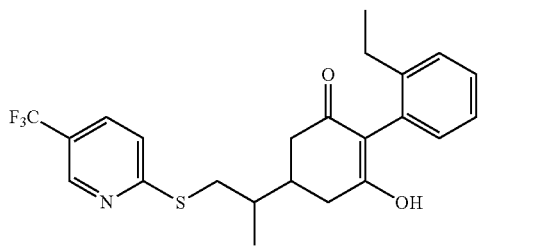
(1-98)
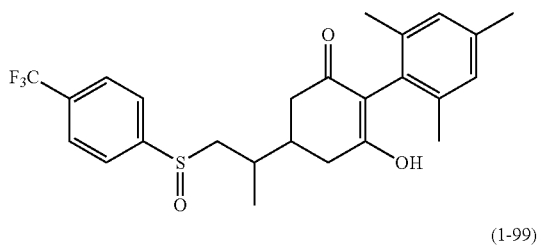
(1-99)
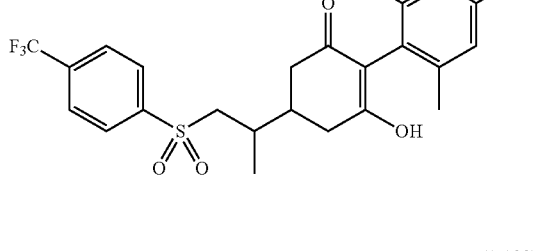
(1-100)
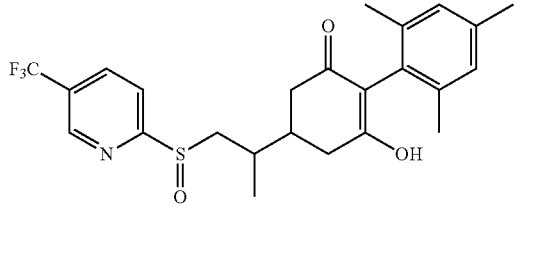
(1-101)
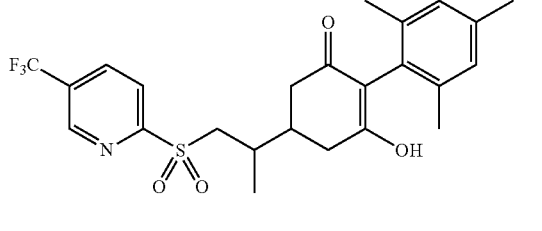
(1-102)
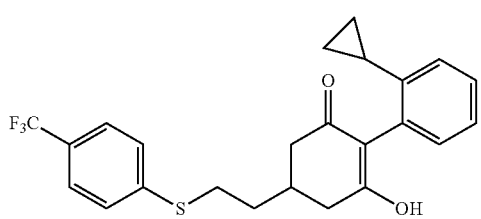

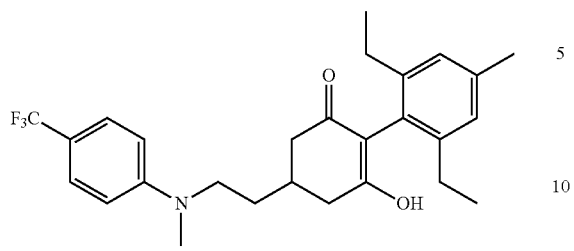
(1-103)
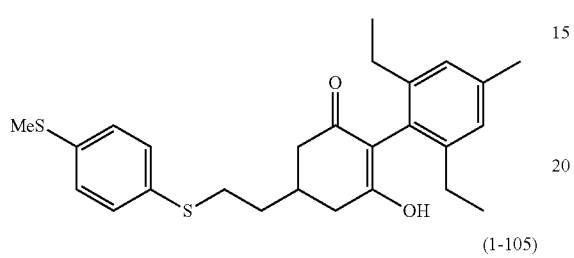
(1-104)
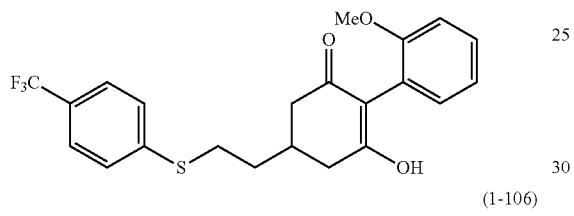
(1-105)
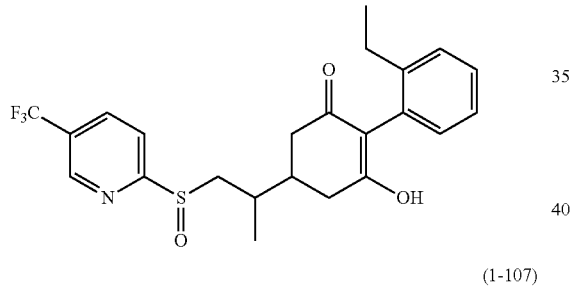
(1-106)
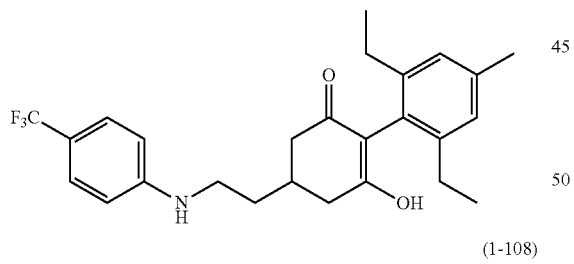
(1-107)
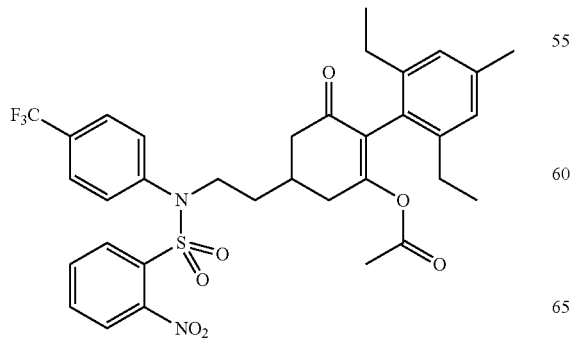
(1-108)
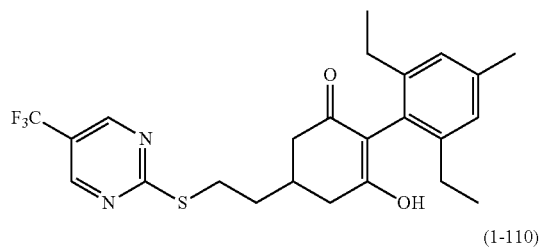
(1-109)
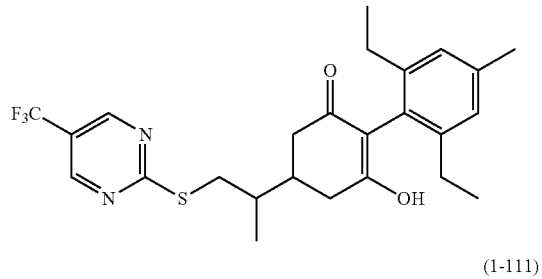
(1-110)
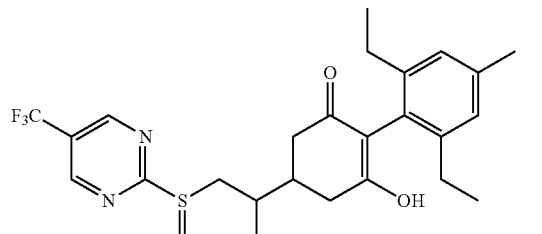
(1-111)
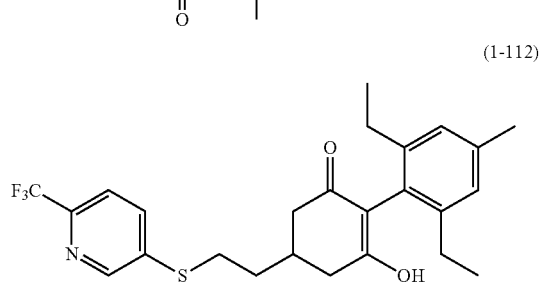
(1-112)
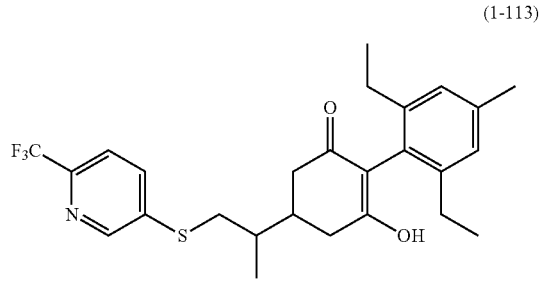
(1-113)
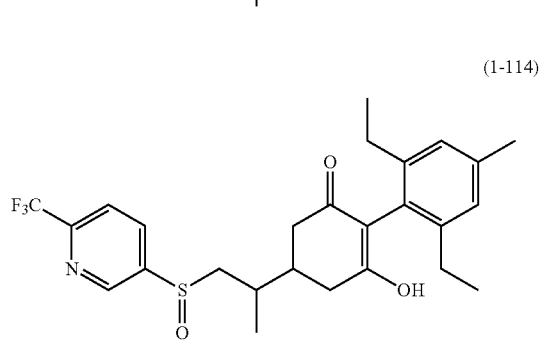
(1-114)

(1-115)
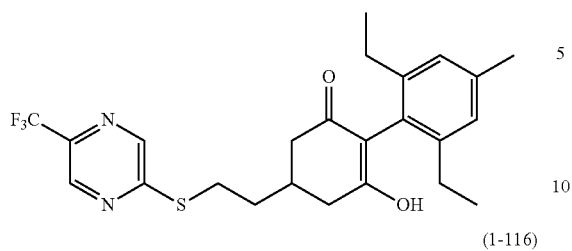
(1-116)
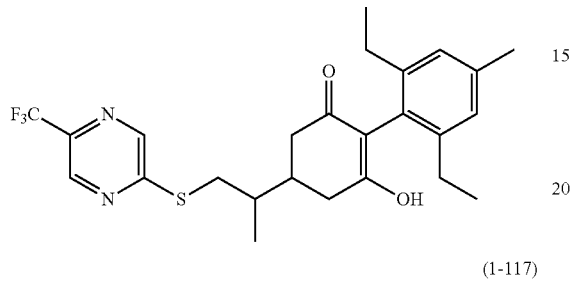
(1-117)
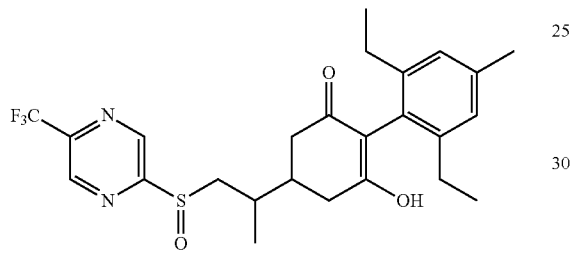
(1-118)
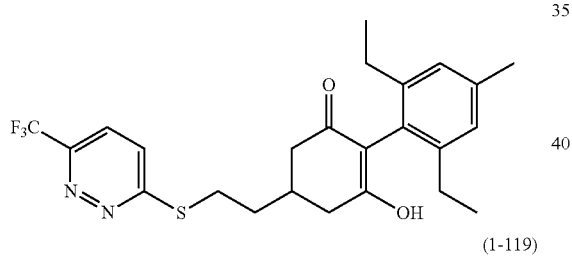
(1-119)
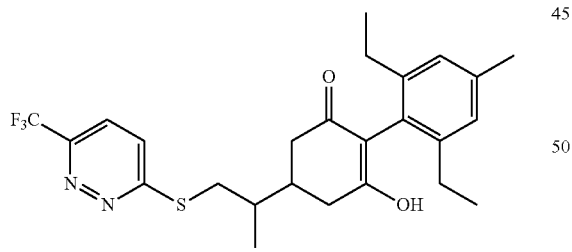
(1-120)
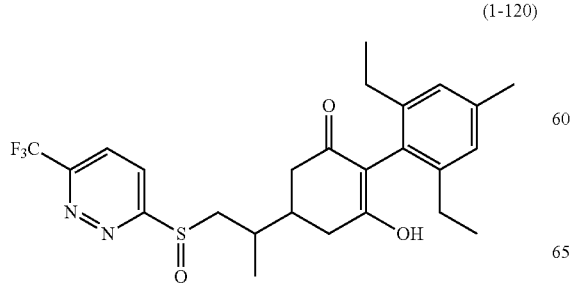
(1-121)
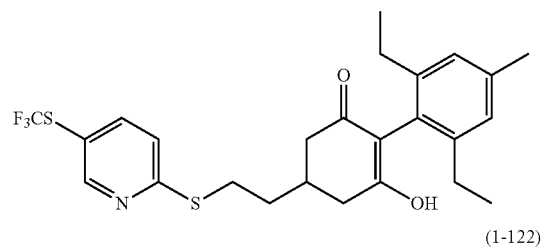
(1-122)
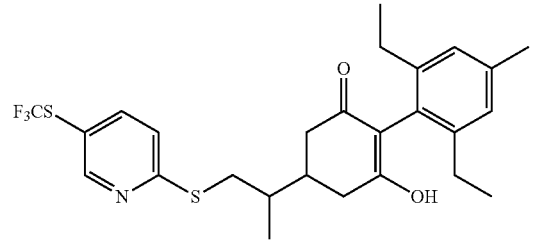
(1-123)
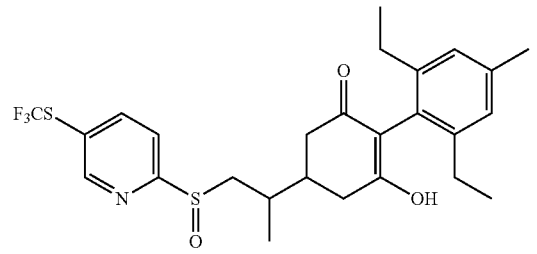
(1-124)
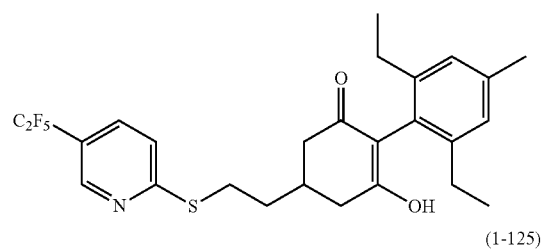
(1-125)
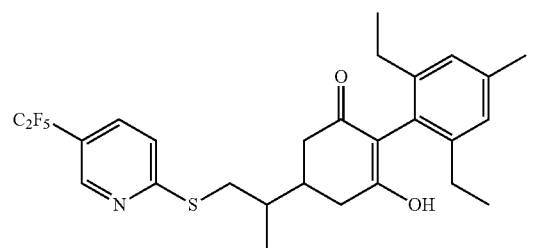
(1-126)
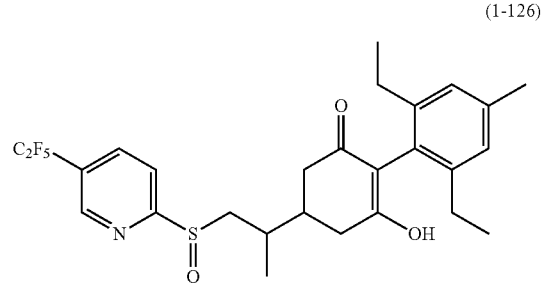

(1-127)
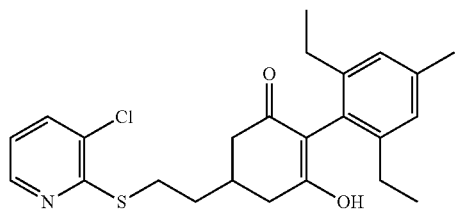
(1-128)
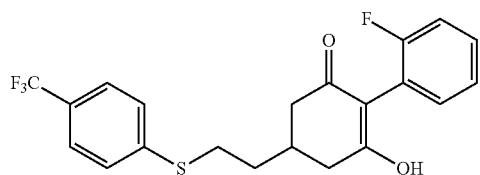
(1-129)
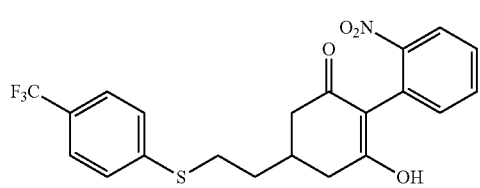
(1-130)
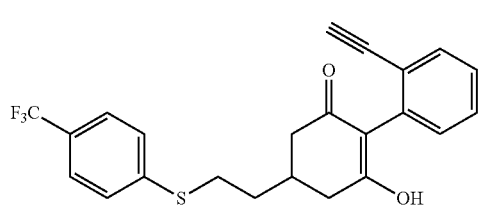
(1-131)
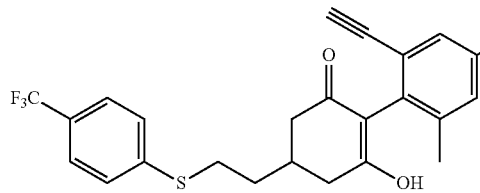
(1-132)
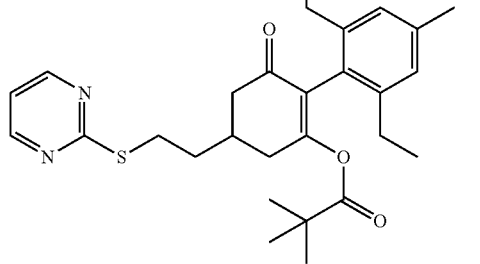
(1-133)
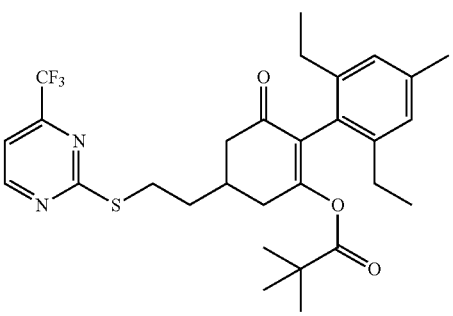
(1-134)
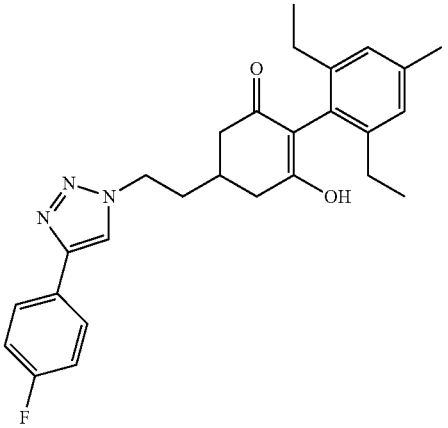
(1-135)
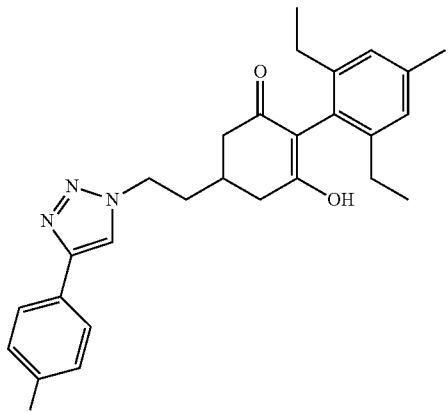
(1-136)
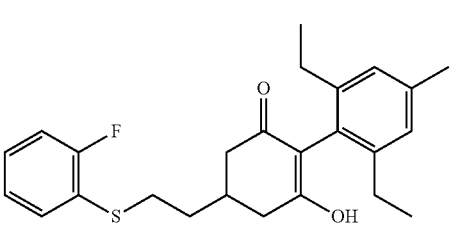
(1-137)
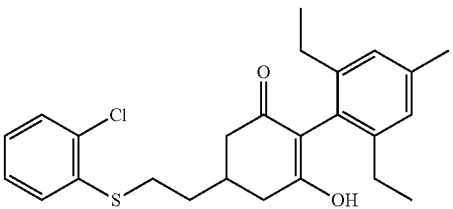

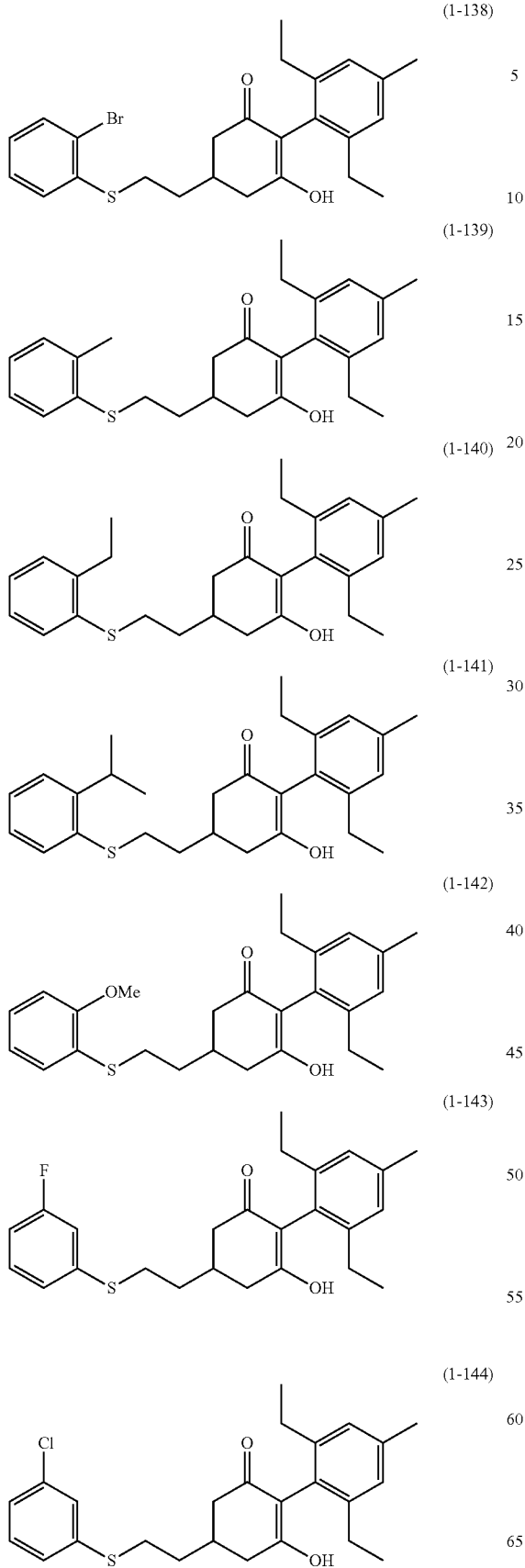
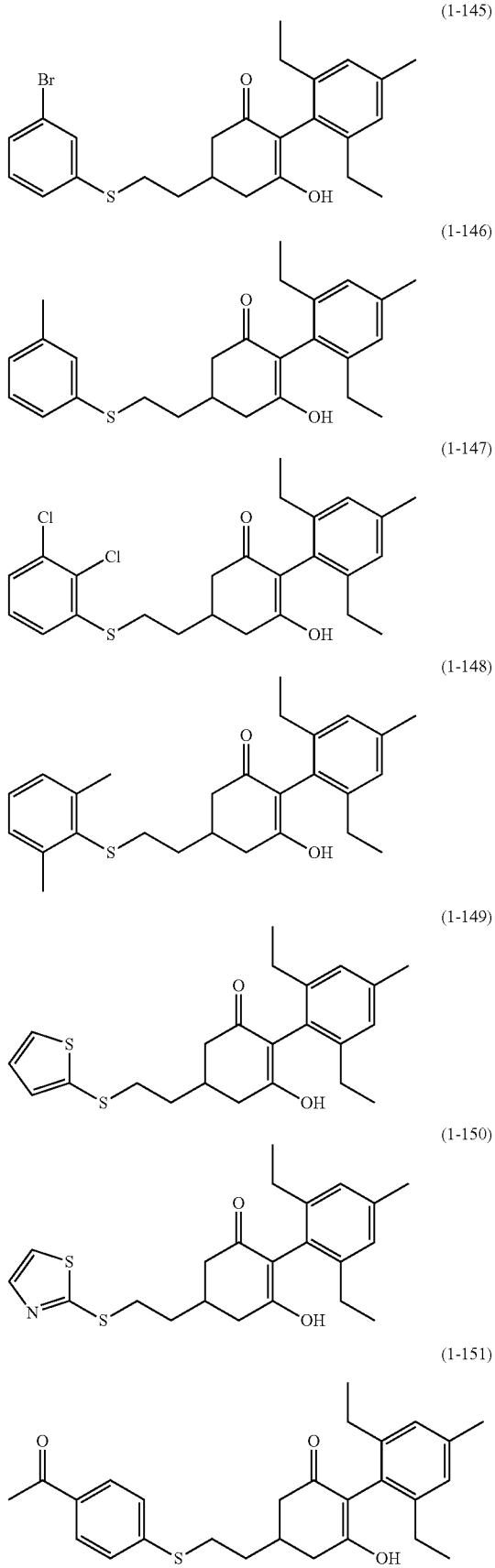

-continued
(1-152)
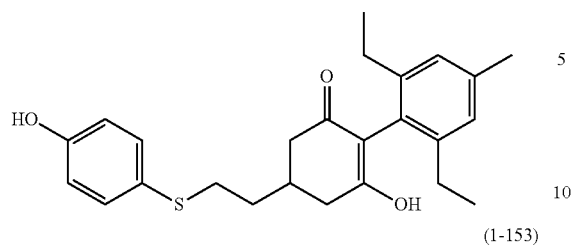
(1-153)
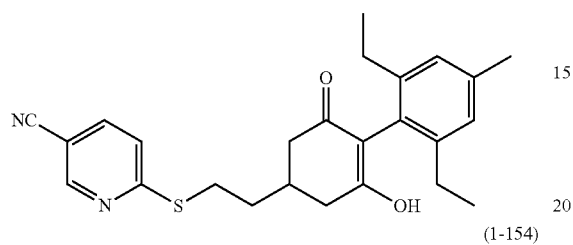
(1-154)
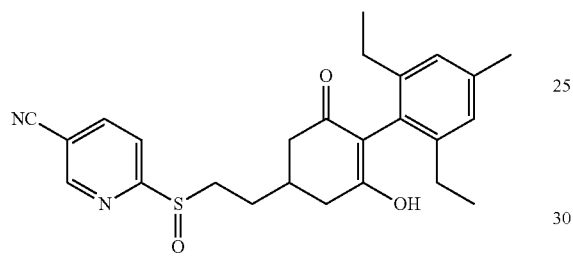
(1-155)
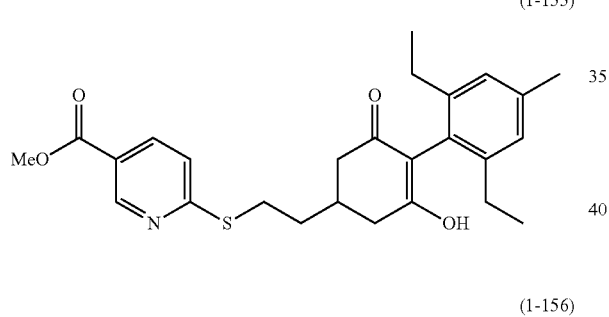
(1-156)
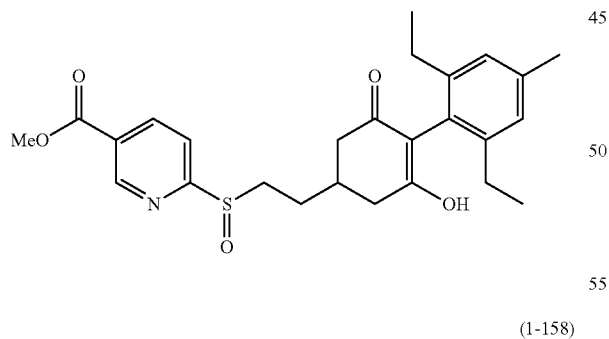
(1-158)
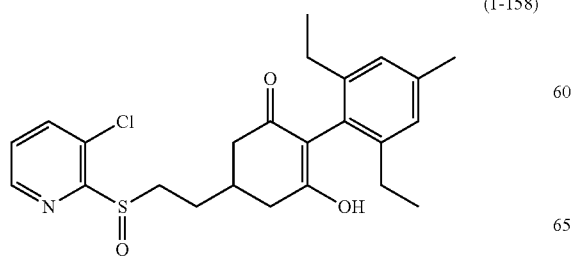
-continued
(1-159)
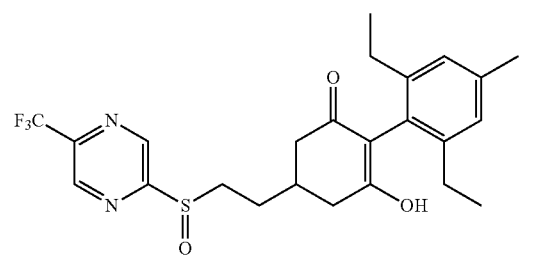
(1-160)
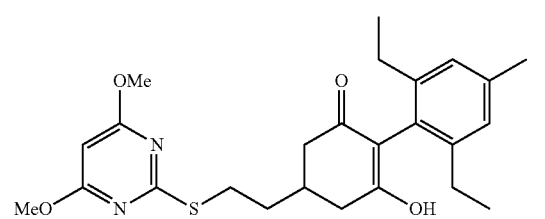
(1-161)
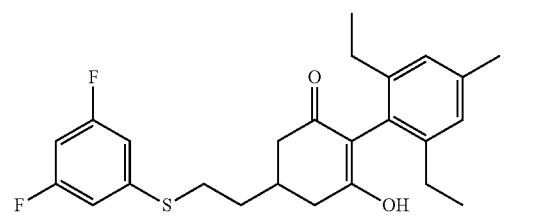
(1-162)
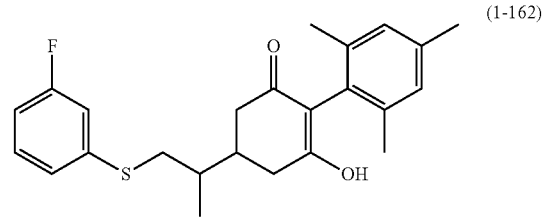
(1-163)
(1-164)
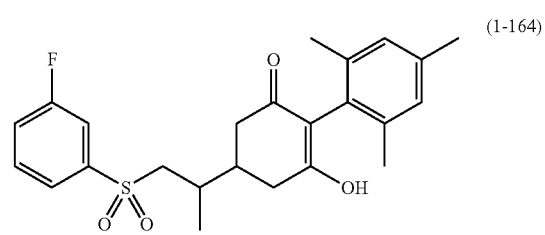

(1-165)
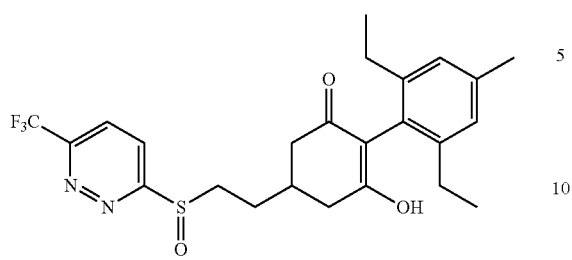
(1-166)
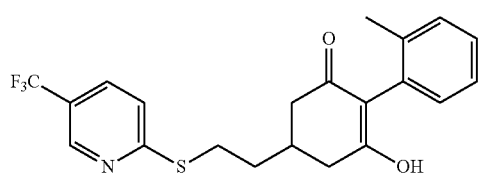
(1-167)
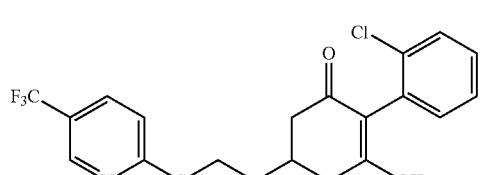
(1-168)
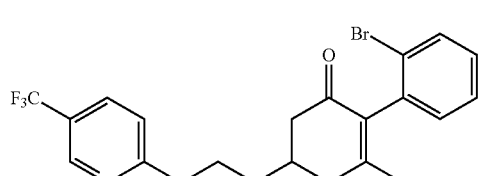
(1-169)
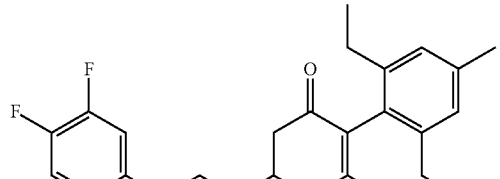
(1-170)
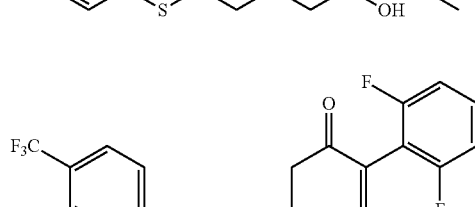
(1-171)
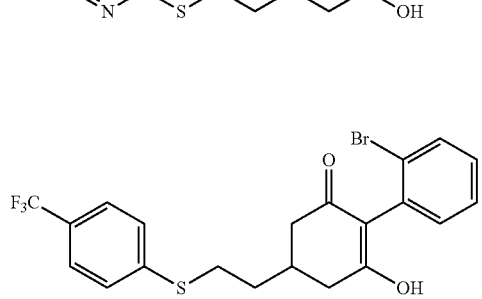
(1-172)
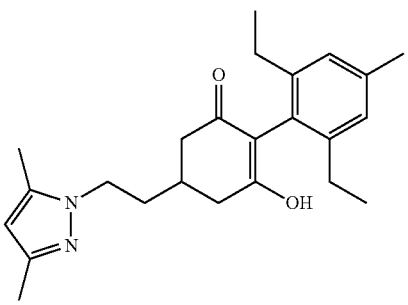
(1-173)
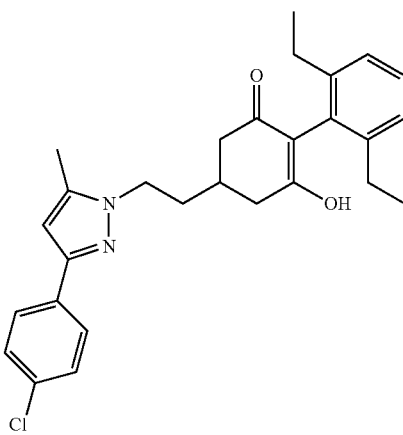
(1-174)
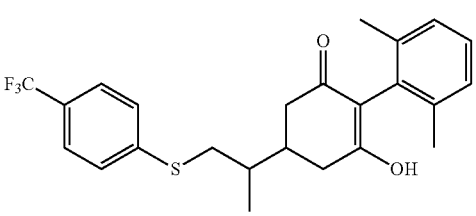
(1-175)
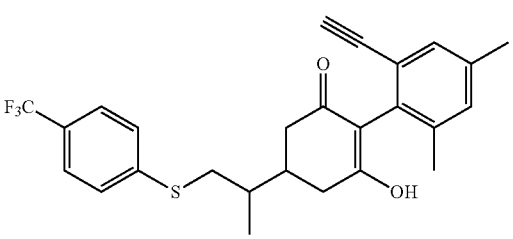
(1-176)
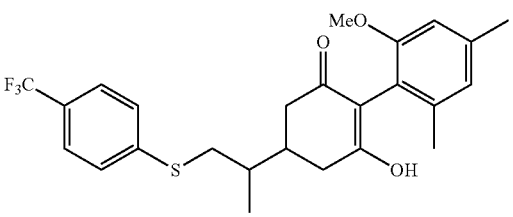

(1-177)
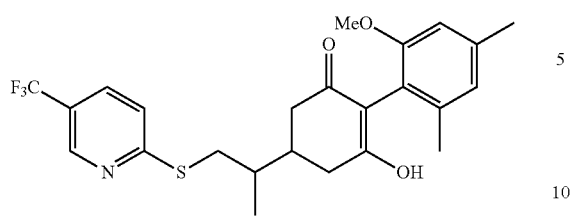
(1-178)
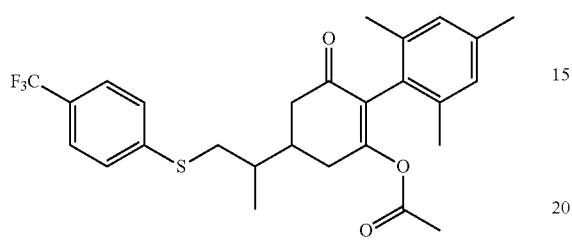
(1-179)
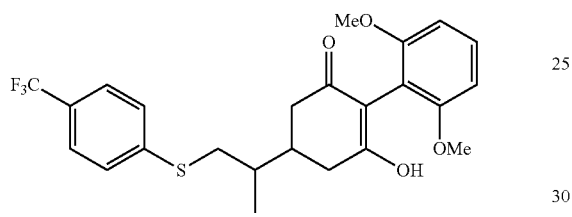
(1-180)
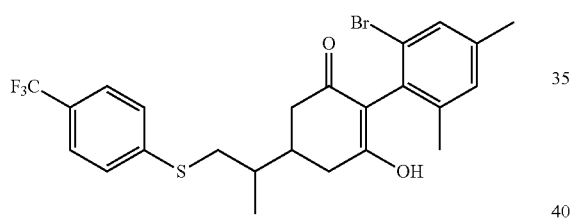
(1-181)
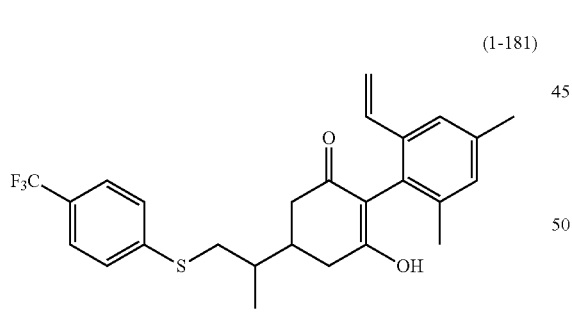
(1-182)
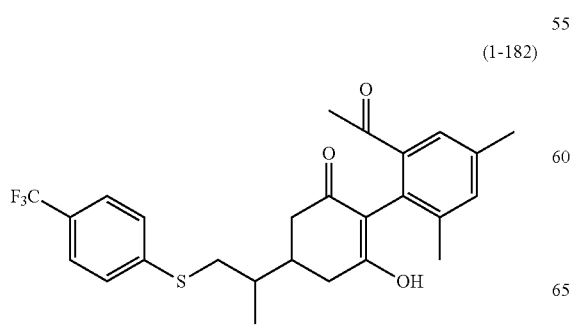
(1-183)
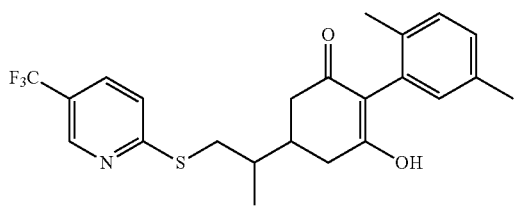
(1-184)
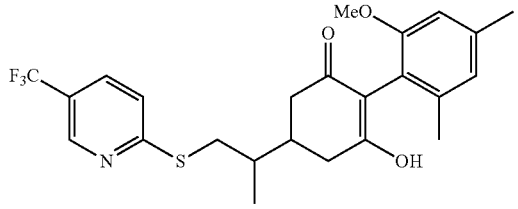
(1-185)
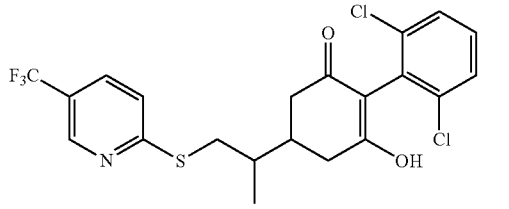
(1-186)
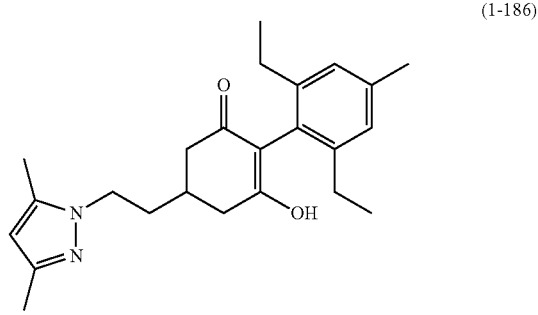
(1-187)
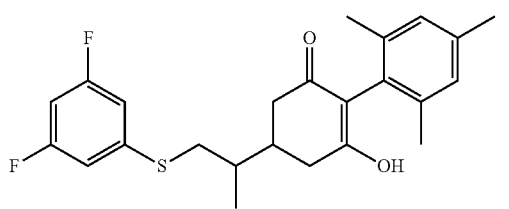
(1-188)
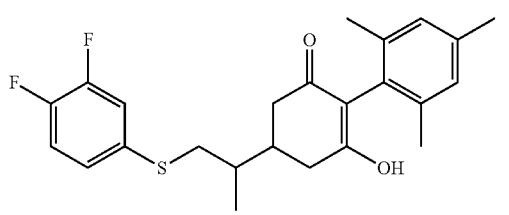

-continued (1-189)
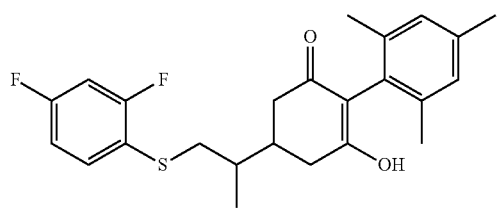

(1-190)
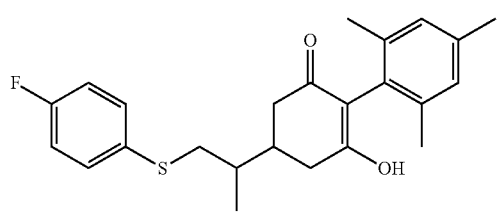

(1-191)
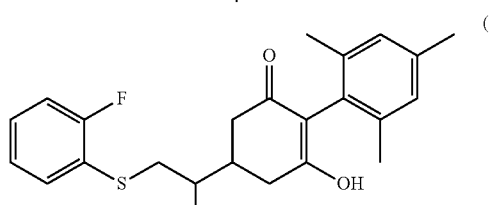

(1-192)
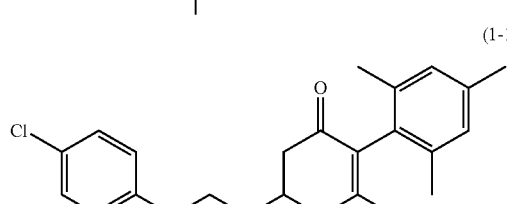

(1-193)
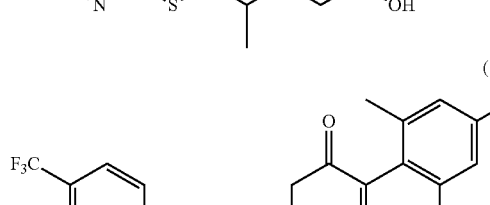

(1-194)
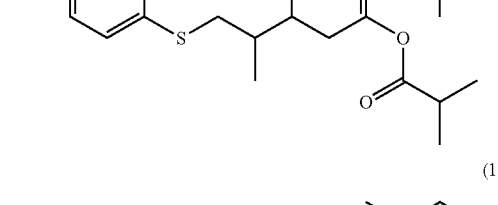

(1-195)
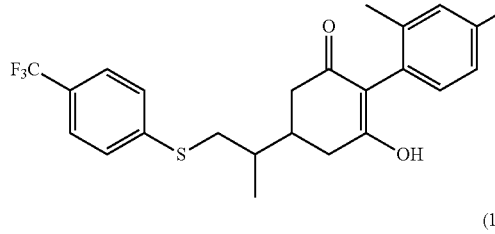

-continued (1-196)
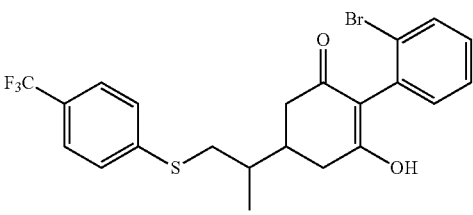

(1-197)
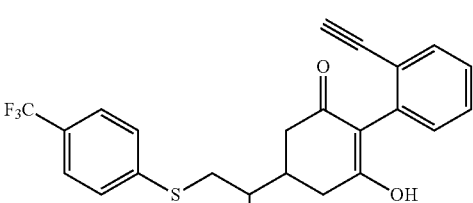

(1-198)
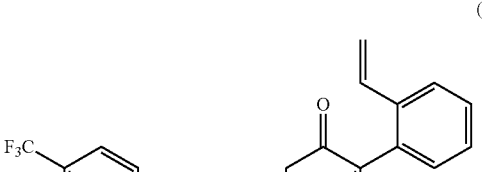

(1-199)
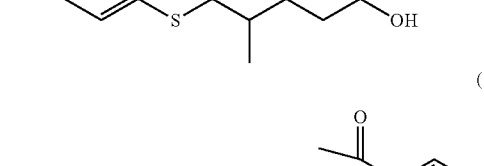

(1-200)

EXAMPLES

Hereinafter, Production Examples, Reference Production Examples, Formulation Examples, and Test Examples will be described, and the invention will be described more specifically, but the invention is not limited to these Examples.

In Production Examples and Reference Production Examples, room temperature means usually 10° C. to 30° C. $^1$H NMR means a proton nuclear magnetic resonance spectrum, tetramethylsilane was used as an internal standard, and a chemical shift (δ) is shown in ppm.

Symbols used in Production Examples and Reference Production Examples have the following meanings.

CDCl$_3$: deuterated chloroform, s: singlet, d: doublet, t: triplet, q: quartet, brs: broad singlet, m: multiplet, J: coupling constant, Me: methyl group, Et: ethyl group, Phe: phenyl based, OMe: methoxy group, OAc: acetoxy group, Pyr: pyridyl group, Bn: benzyl group, Ts: p-toluenesulfonyl group.

Production Example 1-1

Production of Compound Represented by Formula (1-1)

Production of Compound Represented by Formula 9-1

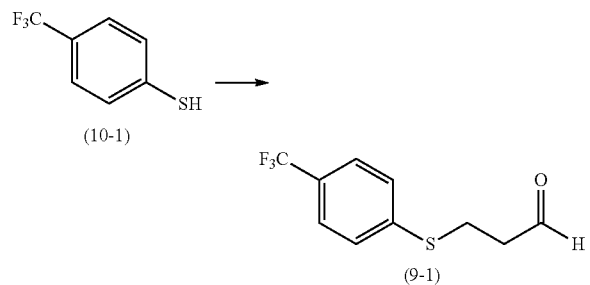

10 g of the compound represented by Formula (10-1) and 15 ml of tetrahydrofuran were mixed at room temperature, followed by stirring, then, the obtained mixture was cooled to 0° C., and 4.0 g of 95% acrolein and 0.1 g of triethylamine were added dropwise thereto. The obtained mixture was stirred for 1.5 hours under ice-cooling. Next, the obtained mixture was added to water. The obtained mixture was extracted with tert-butyl methyl ether. The organic layer was washed with water, dried over anhydrous sodium sulfate, and concentrated under reduced pressure, whereby 18.1 g of the compound represented by Formula (9-1) was obtained.

1H NMR (CDCl$_3$)

δ ppm: 9.77 (1H, s), 7.51 (2H, d), 7.36 (2H, d), 3.28-3.20 (2H, m), 2.87-2.80 (2H, m)

Production of Compound Represented by Formula 7-1

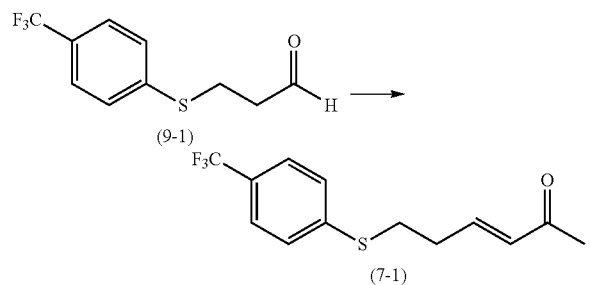

65.7 g of the compound represented by Formula (9-1) and 100 g of triphenylphosphineacetylmethylene were dissolved in 330 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 28.6 g of the compound represented by Formula (7-1) was obtained.

1H NMR (CDCl$_3$)

δ ppm: 7.52 (2H, d), 7.39 (2H, d), 6.82-6.74 (1H, m), 6.13 (1H, dd), 3.11 (2H, m), 2.63-2.56 (2H, m), 2.23 (3H, s)

Production of Compound Represented by Formula 6-1

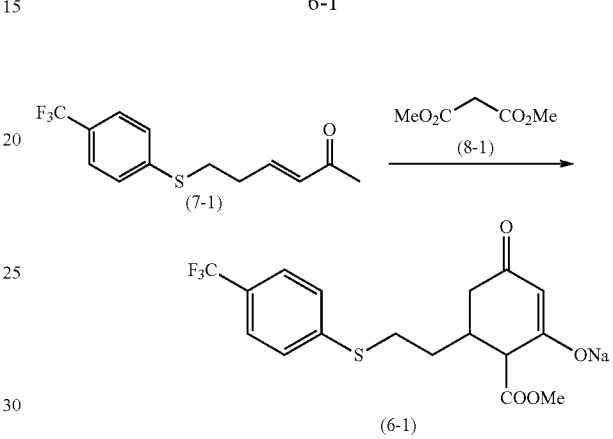

22 g of a 28% sodium methoxide methanol solution and 7.6 g of the compound represented by Formula (8-1) were dissolved in 250 ml of tetrahydrofuran at room temperature. The obtained solution was heated under reflux for 15 minutes. Next, the heating was stopped, and 28.6 g of the compound represented by Formula (7-1) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 24.5 g of the compound represented by Formula (6-1) was obtained.

1H NMR (d-DMSO)

δ ppm: 7.63 (2H, d), 7.45 (2H, d), 4.39 (1H, s), 3.46 (3H, s), 3.11 (1H, m), 2.95 (1H, m), 2.83 (1H, d), 2.34-2.26 (1H, m), 2.12 (1H, dd), 1.78 (1H, dd), 1.53-1.47 (2H, m)

Production of Compound Represented by Formula 2-1

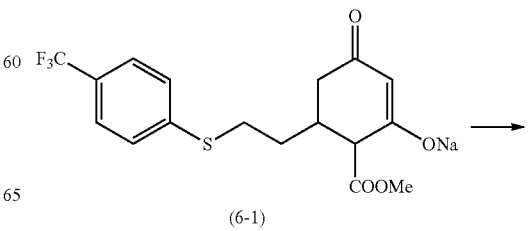

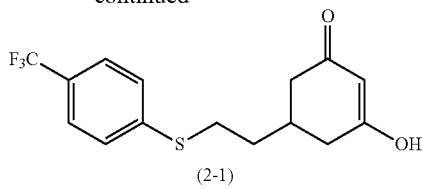

(2-1)

12 g of the compound represented by Formula (6-1) was dissolved in 180 ml of water at room temperature. 10 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 18 g of the compound represented by Formula (2-1) was obtained.

1H NMR (d-DMSO)
δ
ppm: 11.07 (1H, s), 7.63 (2H, d), 7.48 (2H, d), 5.22 (1H, s),3.16-3.05 (2H, m), 2.33-1.69 (7H, m)

Production of Compound Represented by Formula 3-1

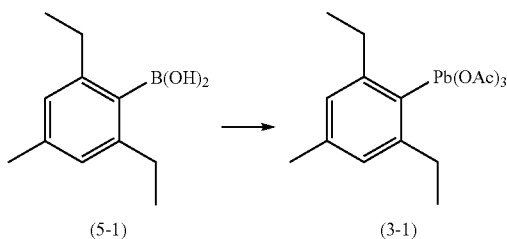

26.5 g of lead tetraacetate, 0.83 g of mercury acetate, and 10 g of the compound represented by Formula (5-1) were dissolved in 110 ml of chloroform at room temperature in a nitrogen atmosphere. The obtained solution was stirred at room temperature for 15 minutes in a nitrogen atmosphere. Next, the reaction liquid was stirred at 40° C. for 4 hours in a nitrogen atmosphere. The reaction liquid was cooled to room temperature, and filtered using Celite (registered trademark). The obtained filtrate was concentrated under reduced pressure, whereby a yellow oily matter was obtained. Hexane was added to the obtained oily matter, and the resultant product was concentrated under reduced pressure, whereby a yellow solid was obtained. The obtained solid was dissolved in 260 ml of chloroform at room temperature in a nitrogen atmosphere. 86.2 g of potassium carbonate was added to the obtained solution, and the resultant product was quickly stirred for 10 minutes. Next, the reaction liquid was filtered using Celite (registered trademark). The obtained filtrate was concentrated under reduced pressure, whereby 21 g of the compound represented by Formula (3-1) was obtained.

1H NMR (CDCl$_3$)
δ
ppm: 7.05 (2H, s), 2.90 (4H, m), 2.35 (3H, s), 2.06 (9H, s), 1.33-1.27 (6H, m)

Production of Compound Represented by Formula 1-1

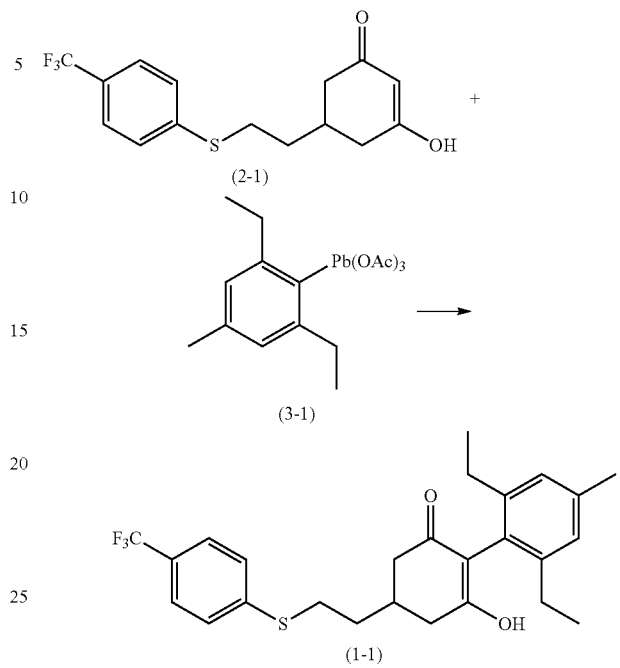

240 mg of the compound represented by Formula (2-1) and 460 mg of dimethylaminopyridine were dissolved in a mixture of 2.5 ml of chloroform and 0.5 ml of toluene at room temperature in a nitrogen atmosphere. The obtained solution was stirred at room temperature for 15 minutes in a nitrogen atmosphere. Next, 440 mg of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 120 mg of the compound represented by Formula (1-1) was obtained.

1H NMR (CDCl$_3$)
δ
ppm: 7.54 (2H, d), 7.38 (2H, d), 6.98 (2H, s), 5.50 (1H, s), 3.07 (2H, ddd), 2.71 (2H, td), 2.47-2.24 (10H, m), 1.88 (2H, q), 1.10-1.03 (6H, m)

Production Example 1-2

Production of Compound Represented by Formula (1-2)

Production of Compound Represented by Formula 3-2

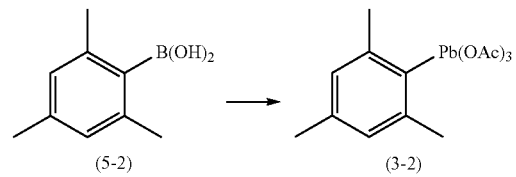

6.2 g of lead tetraacetate, 194 mg of mercury acetate, and 2 g of the compound represented by Formula (5-2) were dissolved in 25 ml of chloroform at room temperature in a nitrogen atmosphere. The obtained solution was stirred at room temperature for 15 minutes in a nitrogen atmosphere. Next, the reaction liquid was stirred at 40° C. for 4 hours in a nitrogen atmosphere. The reaction liquid was cooled to room temperature, and filtered using Celite (registered trademark). The obtained filtrate was concentrated under reduced pressure, whereby a yellow oily matter was obtained. Hexane was added to the obtained oily matter, and the resultant product was concentrated under reduced pressure, whereby a yellow solid was obtained. The obtained solid was dissolved in 50 ml of chloroform at room temperature in a nitrogen atmosphere. 20 g of potassium carbonate was added to the obtained solution, and the resultant product was quickly stirred for 10 minutes. Next, the reaction liquid was filtered using Celite (registered trademark). The obtained filtrate was concentrated under reduced pressure, whereby 4 g of the compound represented by Formula (3-2) was obtained.

1H NMR (CDCl$_3$)

δ ppm: 6.99 (2H, s), 2.57 (6H, s), 2.30 (3H, s), 2.06 (9H, s)

Production of Compound Represented by Formula 1-2

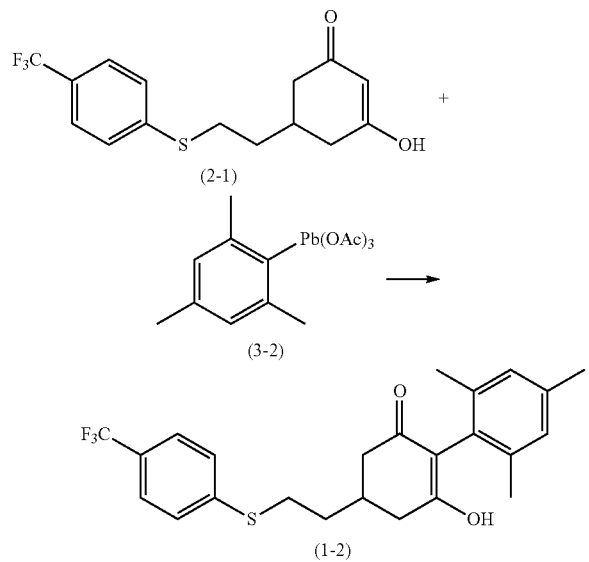

240 mg of the compound represented by Formula (2-1) and 460 mg of dimethylaminopyridine were dissolved in a mixture of 2.5 ml of chloroform and 0.5 ml of toluene at room temperature in a nitrogen atmosphere. The obtained solution was stirred at room temperature for 15 minutes in a nitrogen atmosphere.

Next, 420 mg of the compound represented by Formula (3-2) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 125 mg of the compound represented by Formula (1-2) was obtained.

1H NMR (CDCl$_3$)

δ ppm: 7.54 (2H, d), 7.37 (2H, d), 6.94 (2H, s), 5.72 (1H, s), 3.11-3.01 (2H, m), 2.70 (2H, td), 2.44-2.01 (12H, m), 1.87 (2H, q)

Production Example 1-3

Production of Compound Represented by Formula (1-3)

Production of Compound Represented by Formula 3-3

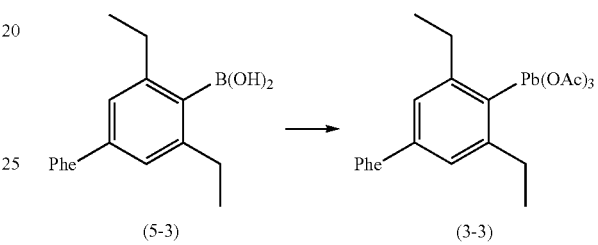

8.4 g of lead tetraacetate, 263 mg of mercury acetate, and 4.2 g of the compound represented by Formula (5-3) were dissolved in 35 ml of chloroform at room temperature in a nitrogen atmosphere. The obtained solution was stirred at room temperature for 15 minutes in a nitrogen atmosphere. Next, the reaction liquid was stirred at 40° C. for 4 hours in a nitrogen atmosphere. The reaction liquid was cooled to room temperature, and filtered using Celite (registered trademark). The obtained filtrate was concentrated under reduced pressure, whereby a yellow oily matter was obtained. Hexane was added to the obtained oily matter, and the resultant product was concentrated under reduced pressure, whereby a yellow solid was obtained. The obtained solid was dissolved in 80 ml of chloroform at room temperature in a nitrogen atmosphere. 27.4 g of potassium carbonate was added to the obtained solution, and the resultant product was quickly stirred for 10 minutes. Next, the reaction liquid was filtered using Celite (registered trademark). The obtained filtrate was concentrated under reduced pressure, whereby 6.4 g of the compound represented by Formula (3-3) was obtained.

1H NMR (CDCl$_3$)

δ ppm: 7.60-7.31 (7H, m), 3.06-2.93 (4H, m), 2.07 (9H, s), 1.39-1.32 (6H, m)

Production of Compound Represented by Formula 1-3

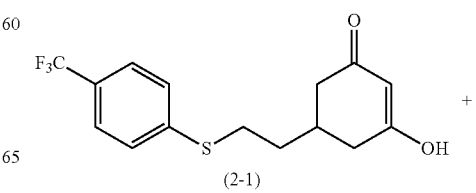

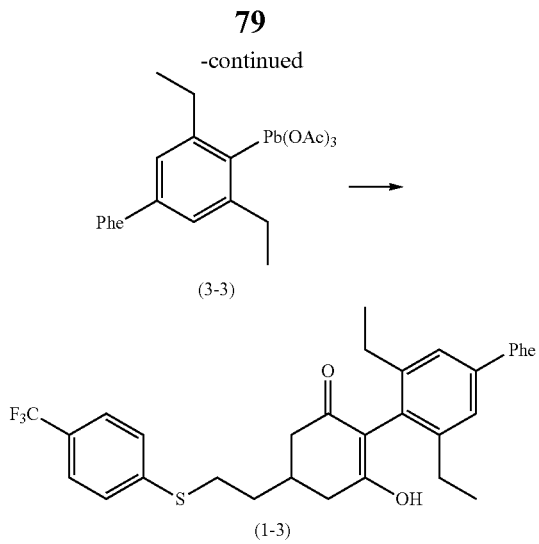

240 mg of the compound represented by Formula (2-1) and 460 mg of dimethylaminopyridine were dissolved in a mixture of 2.5 ml of chloroform and 0.5 ml of toluene at room temperature in a nitrogen atmosphere. The obtained solution was stirred at room temperature for 15 minutes in a nitrogen atmosphere. Next, 500 mg of the compound represented by Formula (3-3) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 190 mg of the compound represented by Formula (1-3) was obtained.

1H NMR (CDCl$_3$)

δ ppm: 7.57 (4H, td), 7.45 (2H, dd), 7.40-7.34 (5H, m), 5.56 (1H, s), 3.10 (2H, dt), 2.78-2.71 (2H, m), 2.53-2.30 (7H, m), 1.90 (2H, q), 1.17-1.09 (6H, m)

Production Example 1-4

Production of Compound Represented by Formula (1-4)

Production of Compound Represented by Formula 9-2

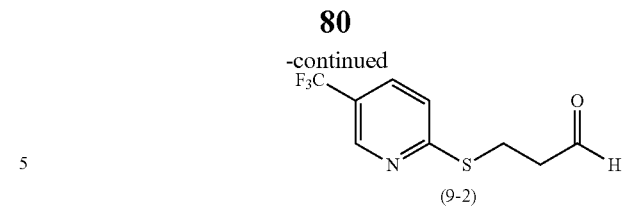

10 g of the compound represented by Formula (10-2) and 30 ml of tetrahydrofuran were mixed at room temperature, followed by stirring, then, the obtained mixture was cooled to 0° C., and 4.0 g of 95% acrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 13 g of the compound represented by Formula (9-2) was obtained.

1H NMR (CDCl$_3$)

δ ppm: 9.80 (1H, s), 8.67-8.66 (1H, m), 7.67 (1H, dd), 7.26 (1H, dd), 3.48 (2H, ddd), 2.98-2.95 (2H, m)

Production of Compound Represented by Formula 7-2

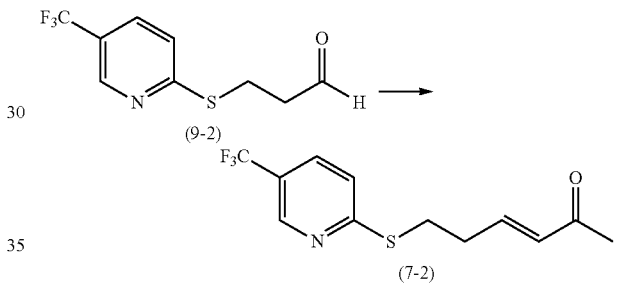

13 g of the compound represented by Formula (9-2) and 20 g of triphenylphosphineacetylmethylene were dissolved in 65 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 13 g of the compound represented by Formula (7-2) was obtained.

1H NMR (CDCl$_3$)

δ ppm: 8.67 (1H, dd), 7.69-7.66 (1H, m), 7.29 (1H, d), 6.88-6.80 (1H, m), 6.16 (1H, dt), 3.36 (2H, t), 2.67 (2H, tt), 2.24 (3H, s)

Production of Compound Represented by Formula 6-2

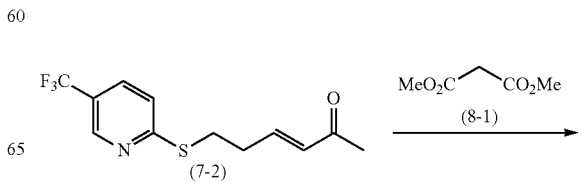

-continued

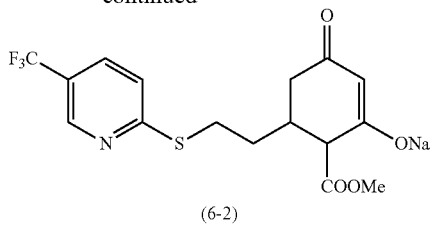

(6-2)

10 g of a 28% sodium methoxide methanol solution and 6.7 g of the compound represented by Formula (8-1) were dissolved in 130 ml of tetrahydrofuran at room temperature. The obtained solution was heated under reflux for 15 minutes. Next, the heating was stopped, and 13 g of the compound represented by Formula (7-2) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 15.4 g of the compound represented by Formula (6-2) was obtained.

1H NMR (d-DMSO)

δ ppm: 8.78 (1H, d), 7.98 (1H, dd), 7.50 (1H, d), 4.40 (1H, s), 3.49 (3H, s), 3.26 (1H, dq), 3.06 (1H, dt), 2.83 (1H, d), 2.34-2.24 (1H, m), 2.13 (1H, dd), 1.79 (1H, dt), 1.63-1.49 (2H, m)

Production of Compound Represented by Formula 2-2

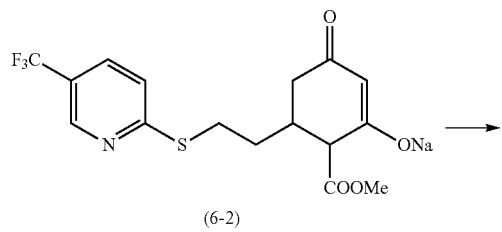

5 g of the compound represented by Formula (6-2) was dissolved in 70 ml of water at room temperature. 4 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 3.1 g of the compound represented by Formula (2-2) was obtained.

1H NMR (d-DMSO)

δ ppm: 11.07 (1H, s), 8.80 (1H, d), 7.98 (1H, dd), 7.52 (1H, d), 5.21 (1H, s), 3.23 (2H, t), 2.34 (2H, d), 2.13 (3H, m), 1.73 (2H, m)

Production of Compound Represented by Formula 1-4

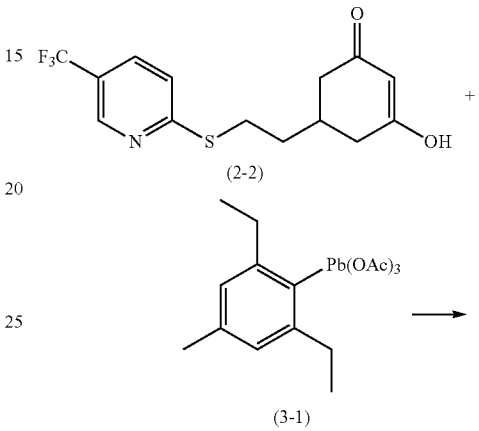

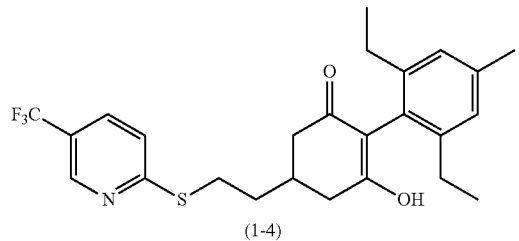

540 mg of the compound represented by Formula (2-2) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 320 mg of the compound represented by Formula (1-4) was obtained.

1H NMR (CDCl₃)

δ ppm: 8.68-8.67 (1H, m), 7.67 (1H, dd), 7.27 (1H, d), 6.98 (2H, s), 5.52 (1H, s), 3.31 (2H, tt), 2.75 (2H, ddd), 2.51-2.23 (10H, m), 1.92 (2H, ddd), 1.5 (6H, dt)

Production Example 1-5

Production of Compound Represented by Formula (1-5)

Production of Compound Represented by Formula 1-5

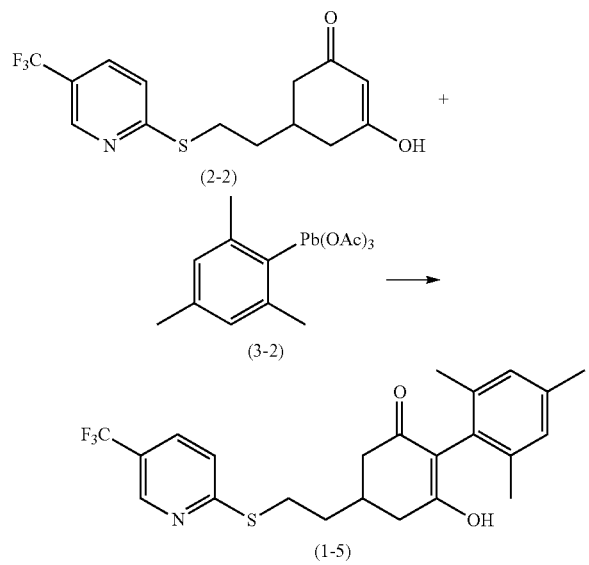

570 mg of the compound represented by Formula (2-2) and 1.1 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-2) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 410 mg of the compound represented by Formula (1-5) was obtained.

1H NMR (CDCl$_3$)

δ ppm: 8.66 (1H, s), 7.66 (1H, dd), 7.26 (1H, d), 6.93 (2H, s), 5.66 (1H, s), 3.32-3.28 (2H, m), 2.74 (2H, t), 2.46-2.04 (12H, m), 1.91 (2H, m)

Production Example 1-6

Production of Compound Represented by Formula (1-6)

Production of Compound Represented by Formula 9-3

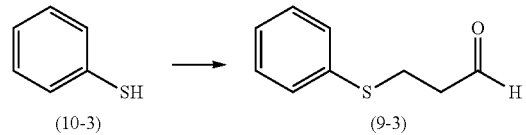 [SMILES: Sc1ccccc1 ; O=CCCSc1ccccc1]

10 g of the compound represented by Formula (10-3) and 30 ml of tetrahydrofuran were mixed at room temperature, followed by stirring, then, the obtained mixture was cooled to 0° C., and 6.6 g of 95% acrolein and 0.2 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 15 g of the compound represented by Formula (9-3) was obtained.

1H NMR (CDCl$_3$)

δ ppm: 9.74 (1H, s), 7.36-7.17 (5H, m), 3.17 (2H, t), 2.75 (2H, t)

Production of Compound Represented by Formula 7-3

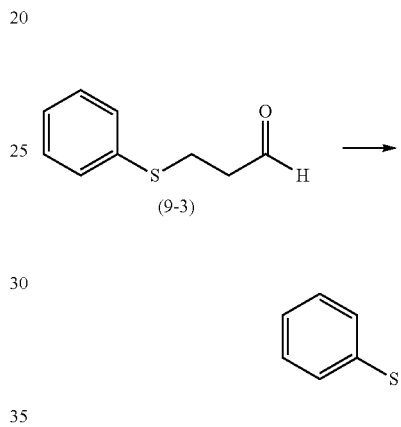

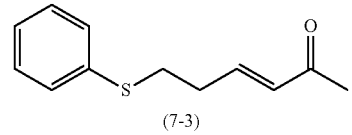

10 g of the compound represented by Formula (9-3) and 21 g of triphenylphosphineacetylmethylene were dissolved in 70 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 7.2 g of the compound represented by Formula (7-3) was obtained.

1H NMR (CDCl$_3$)

δ ppm: 7.35-7.25 (4H, m), 7.18 (1H, m), 6.80-6.71 (1H, m), 6.07 (1H, dt), 3.01 (2H, tt), 2.51 (2H, ddd), 2.23 (3H, s)

Production of Compound Represented by Formula 6-3

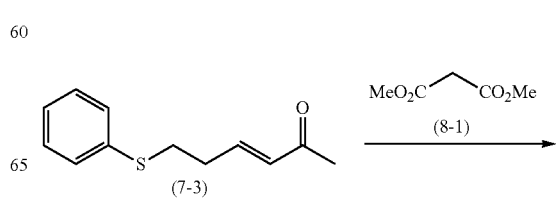

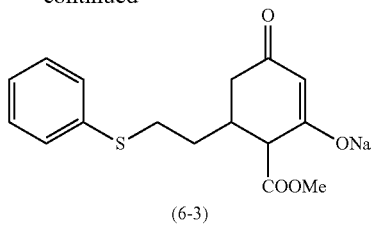
(6-3)

7.5 g of a 28% sodium methoxide methanol solution and 5 g of the compound represented by Formula (8-1) were dissolved in 100 ml of tetrahydrofuran at room temperature. The obtained solution was heated under reflux for 15 minutes. Next, the heating was stopped, and 7.2 g of the compound represented by Formula (7-3) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 10 g of the compound represented by Formula (6-3) was obtained.

1H NMR (d-DMSO)

δ ppm: 7.33-7.27 (4H, m), 7.17 (1H, dq), 4.37 (1H, s), 3.48 (3H, s), 3.02-2.96 (1H, m), 2.87-2.78 (2H, m), 2.33-2.23 (1H, m), 2.08 (1H, dd), 1.74 (1H, dd), 1.44 (2H, m)

Production of Compound Represented by Formula 2-3

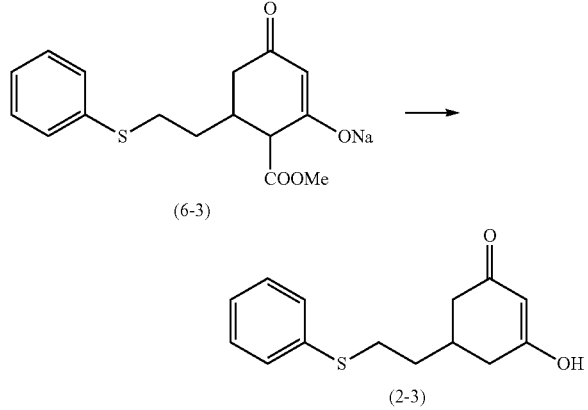

5 g of the compound represented by Formula (6-3) was dissolved in 80 ml of water at room temperature. 4.8 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 3.4 g of the compound represented by Formula (2-3) was obtained.

1H NMR (d-DMSO)

δ ppm: 11.05 (1H, s), 7.31 (4H, m), 7.18 (1H, m), 5.19 (1H, s), 3.00 (2H, t), 2.33-1.99 (5H, m), 1.63 (2H, m)

Production of Compound Represented by Formula 1-6

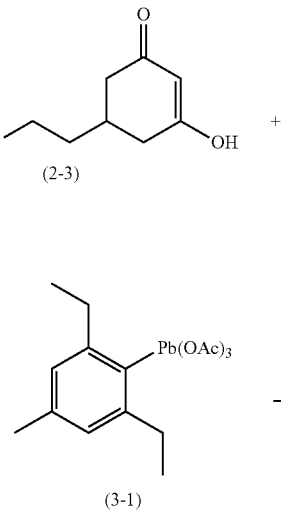

430 mg of the compound represented by Formula (2-3) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 310 mg of the compound represented by Formula (1-6) was obtained.

1H NMR (CDCl$_3$)

δ ppm: 7.36-7.20 (5H, m), 6.97 (2H, s), 5.59 (1H, s), 3.00 (2H, ddd), 2.67 (2H, ddt), 2.47-2.20 (10H, m), 1.82 (2H, q), 1.10-1.02 (6H, m)

Production Example 1-7

Production of Compound Represented by Formula (1-7)

Production of Compound Represented by Formula 9-4

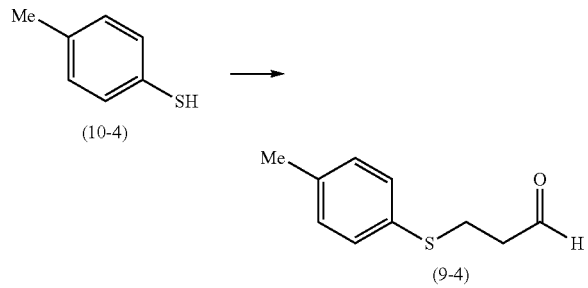

5 g of the compound represented by Formula (10-4) and 15 ml of tetrahydrofuran were mixed at room temperature, followed by stirring, then, the obtained mixture was cooled to 0° C., and 3.0 g of 95% acrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 7.4 g of the compound represented by Formula (9-4) was obtained.

1H NMR (CDCl$_3$)
δ
ppm: 9.72 (1H, s), 7.24 (2H, d), 7.18 (2H, d), 3.12 (2H, t), 2.71 (2H, t), 2.31 (3H, s)

Production of Compound Represented by Formula 6-4

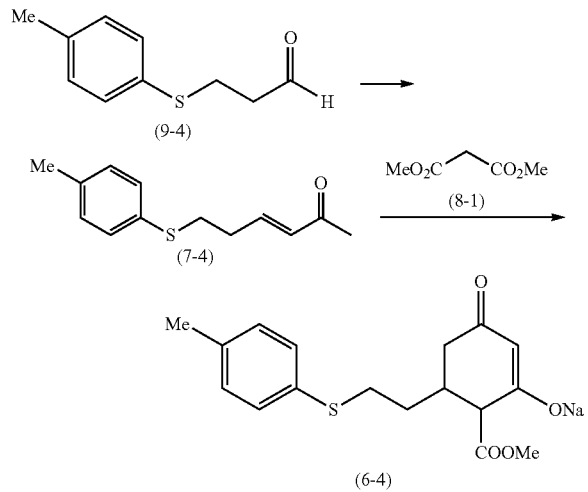

7.4 g of the compound represented by Formula (9-4) and 14.4 g of triphenylphosphineacetylmethylene were dissolved in 50 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 6.0 g of the compound represented by Formula (7-4) was obtained.

Then, 5.8 g of a 28% sodium methoxide methanol solution and 4.0 g of the compound represented by Formula (8-1) were dissolved in 80 ml of tetrahydrofuran at room temperature. The obtained solution was heated under reflux for 15 minutes. Next, the heating was stopped, and 6.0 g of the compound represented by Formula (7-4) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 6.7 g of the compound represented by Formula (6-4) was obtained.

1H NMR (d-DMSO)
δ
ppm: 7.19 (2H, d), 7.12 (2H, d), 4.39 (1H, s), 3.48 (3H, s), 2.97-2.90 (1H, m), 2.82-2.75 (2H, m), 2.24 (3H, s), 2.10-2.04 (1H, m), 1.72 (1H, dd), 1.49-1.35 (2H, m)

Production of Compound Represented by Formula 2-4

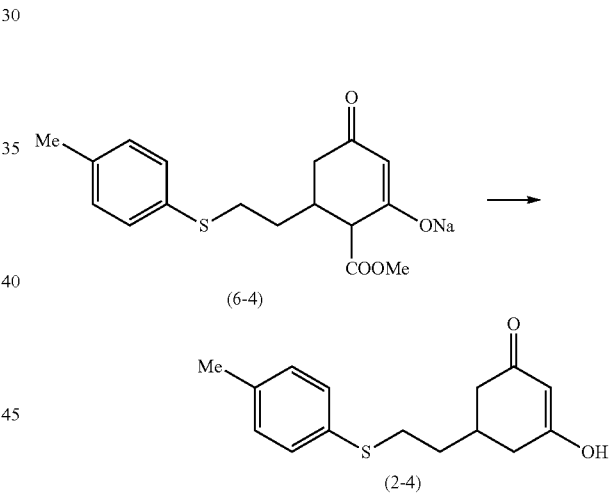

5 g of the compound represented by Formula (6-4) was dissolved in 80 ml of water at room temperature. 4.6 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 2.9 g of the compound represented by Formula (2-4) was obtained.

1H NMR (d-DMSO)
δ
ppm: 11.04 (1H, s), 7.23 (2H, d), 7.13 (2H, d), 5.19 (1H, s), 2.95 (2H, t), 2.42-1.99 (8H, m), 1.60-1.58 (2H, m)

Production of Compound Represented by Formula 1-7

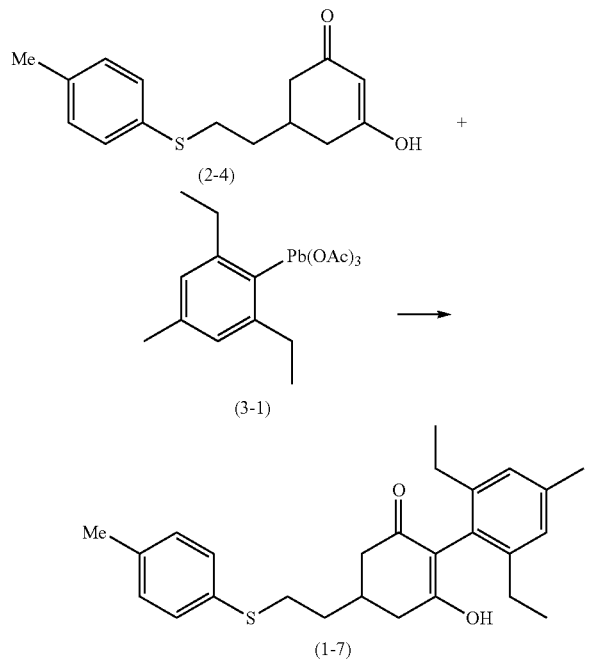

450 mg of the compound represented by Formula (2-4) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 340 mg of the compound represented by Formula (1-7) was obtained.

1H NMR (CDCl$_3$)
δ
ppm: 7.27 (2H, d), 7.12 (2H, d), 6.98 (2H, s), 5.47 (1H, s), 2.96 (2H, dt), 2.67 (2H, ddd), 2.45-2.21 (13H, m), 1.80 (2H, q), 1.06 (6H, dt)

Production Example 1-8

Production of Compound Represented by Formula (1-8)

Production of Compound Represented by Formula 9-5

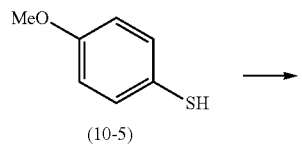

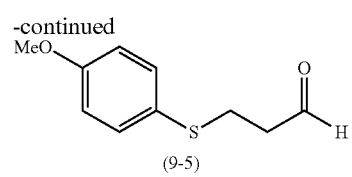

4 g of the compound represented by Formula (10-5) and 15 ml of tetrahydrofuran were mixed at room temperature, followed by stirring, then, the obtained mixture was cooled to 0° C., and 2.5 g of 95% acrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 5.5 g of the compound represented by Formula (9-5) was obtained.

1H NMR (CDCl$_3$)
δ
ppm: 9.73 (1H, s), 7.36 (2H, d), 6.85 (2H, d), 3.80 (3H, s), 3.06 (2H, t), 2.68 (2H, t)

Production of Compound Represented by Formula 6-5

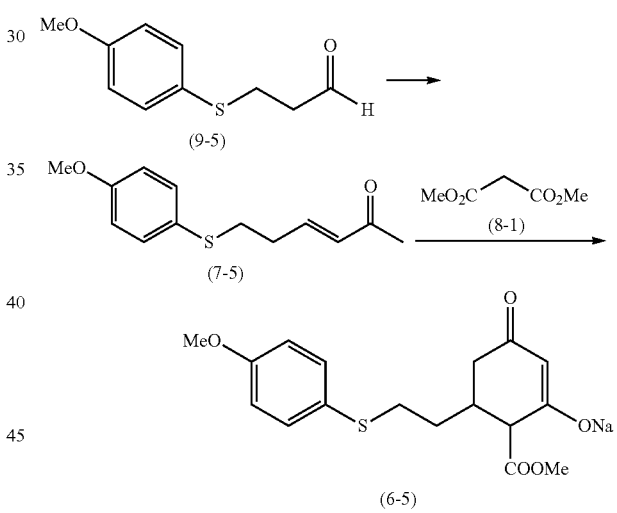

5.5 g of the compound represented by Formula (9-5) and 10 g of triphenylphosphineacetylmethylene were dissolved in 40 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 5.4 g of the compound represented by Formula (7-5) was obtained.

Then, 4.8 g of a 28% sodium methoxide methanol solution and 3.3 g of the compound represented by Formula (8-1) were dissolved in 70 ml of tetrahydrofuran at room temperature. The obtained solution was heated under reflux for 15 minutes. Next, the heating was stopped, and 5.4 g of the compound represented by Formula (7-5) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 5.7 g of the compound represented by Formula (6-5) was obtained.

1H NMR (d-DMSO)
δ
ppm: 7.28 (2H, d), 6.90 (2H, d), 4.38 (1H, s), 3.75 (3H, s), 3.47 (3H, s), 2.90-2.69 (3H, m), 2.30-2.22 (1H, m), 2.04 (1H, dd), 1.74-1.66 (1H, m), 1.45-1.33 (2H, m)

Production of Compound Represented by Formula 1-8

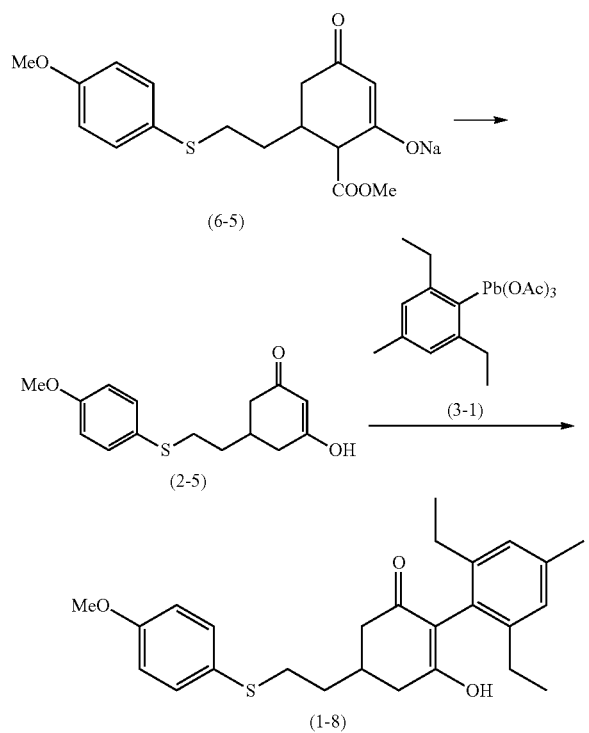

5 g of the compound represented by Formula (6-5) was dissolved in 80 ml of water at room temperature. 4.4 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 3.8 g of the compound represented by Formula (2-5) was obtained.

Then, 480 mg of the compound represented by Formula (2-5) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 174 mg of the compound represented by Formula (1-8) was obtained.

1H NMR (CDCl₃)
δ
ppm: 7.36 (2H, dd), 6.97 (2H, d), 6.86 (2H, dd), 5.57 (1H, s), 3.80 (3H, 3H), 2.92-2.88 (2H, m), 2.69-2.60 (2H, m), 2.44-2.19 (10H, m), 1.75 (2H, dd), 1.06 (6H, dt)

Production Example 1-9

Production of Compound Represented by Formula (1-9)

Production of Compound Represented by Formula 9-6

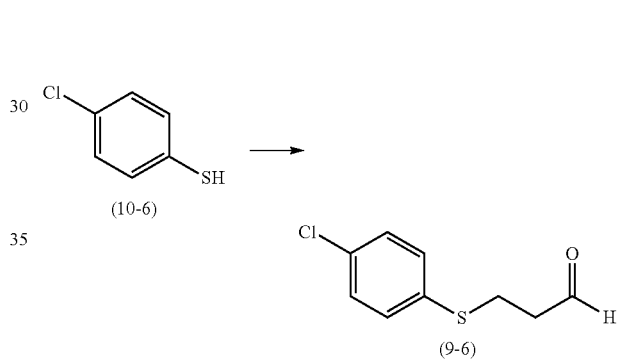

10 g of the compound represented by Formula (10-6) and 20 ml of tetrahydrofuran were mixed at room temperature, followed by stirring, then, the obtained mixture was cooled to 0° C., and 5.6 g of 95% acrolein and 0.2 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 13 g of the compound represented by Formula (9-6) was obtained.

1H NMR (CDCl₃)
δ ppm: 9.73 (1H, s), 7.29-7.20 (4H, m), 3.14 (2H, t), 2.75 (2H, t)

Production of Compound Represented by Formula 7-6

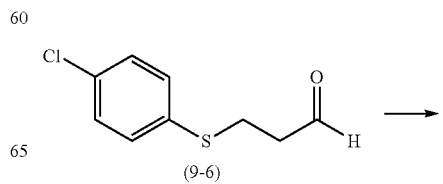

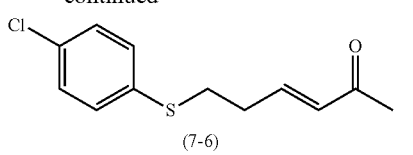

(7-6)

10 g of the compound represented by Formula (9-6) and 17.4 g of triphenylphosphineacetylmethylene were dissolved in 60 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 9.4 g of the compound represented by Formula (7-6) was obtained.

1H NMR (CDCl$_3$)

δ ppm: 7.31-7.22 (4H, m), 6.80-6.70 (1H, m), 6.08 (1H, d), 3.00 (2H, m), 2.52 (2H, m), 2.23 (3H, s)

Production of Compound Represented by Formula 6-6

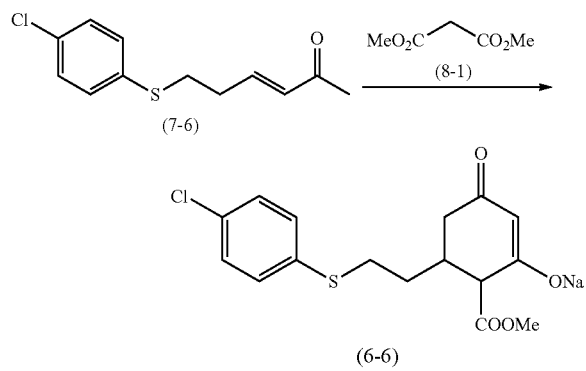

8.3 g of a 28% sodium methoxide methanol solution and 5.7 g of the compound represented by Formula (8-1) were dissolved in 100 ml of tetrahydrofuran at room temperature. The obtained solution was heated under reflux for 15 minutes. Next, the heating was stopped, and 9.4 g of the compound represented by Formula (7-6) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 10 g of the compound represented by Formula (6-6) was obtained.

1H NMR (d-DMSO)

δ ppm: 7.36 (2H, d), 7.30 (2H, d), 4.38 (1H, s), 3.48 (3H, s), 3.00 (1H, m), 2.84 (2H, m), 2.32-2.22 (1H, m), 2.09 (1H, m), 1.78-1.71 (1H, m), 1.44 (2H, m)

Production of Compound Represented by Formula 2-6

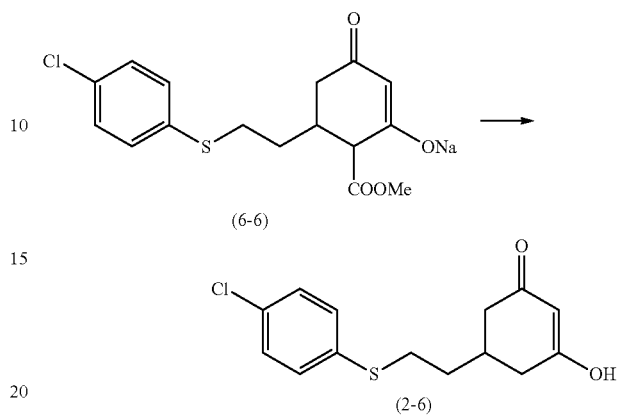

5 g of the compound represented by Formula (6-6) was dissolved in 80 ml of water at room temperature. 4.4 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 2.9 g of the compound represented by Formula (2-6) was obtained.

1H NMR (d-DMSO)

δ ppm: 11.06 (1H, s), 7.36 (4H, m), 5.19 (1H, s), 3.01 (2H, t), 2.32-1.99 (5H, m), 1.62 (2H, m)

Production of Compound Represented by Formula 1-9

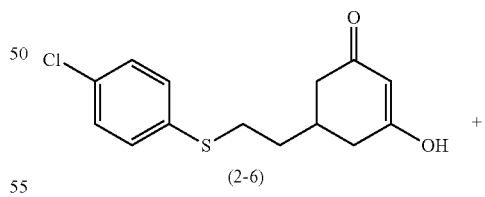

+

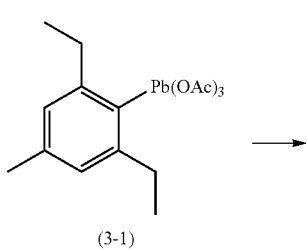

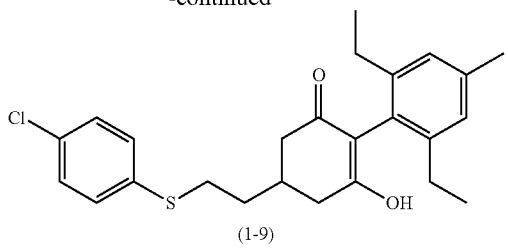

(1-9)

490 mg of the compound represented by Formula (2-6) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 350 mg of the compound represented by Formula (1-9) was obtained.

1H NMR (CDCl$_3$)

δ ppm: 7.29-7.24 (4H, m), 6.97 (2H, s), 5.66 (1H, s), 3.02-2.93 (2H, m), 2.66 (2H, tt), 2.45-2.21 (10H, m), 1.80 (2H, q), 1.10-1.01 (6H, m)

Production Example 1-10

Production of Compound Represented by Formula (1-10)

Production of Compound Represented by Formula 6-7

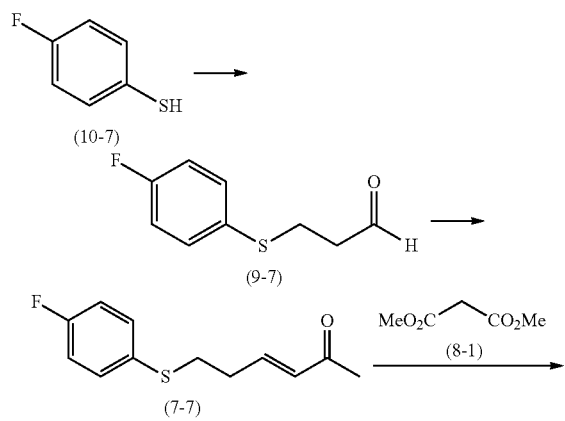

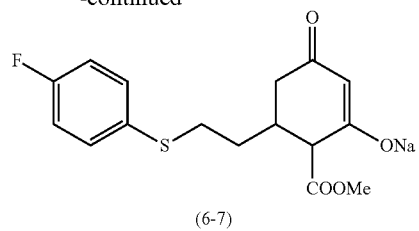

(6-7)

10 g of the compound represented by Formula (10-7) and 25 ml of tetrahydrofuran were mixed at room temperature, followed by stirring, then, the obtained mixture was cooled to 0° C., and 6.7 g of 95% acrolein and 0.2 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 14 g of the compound represented by Formula (9-7) was obtained.

Then, 14 g of the compound represented by Formula (9-7) and 30 g of triphenylphosphineacetylmethylene were dissolved in 100 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 13 g of the compound represented by Formula (7-7) was obtained.

Then, 12 g of a 28% sodium methoxide methanol solution and 8.4 g of the compound represented by Formula (8-1) were dissolved in 150 ml of tetrahydrofuran at room temperature. The obtained solution was heated under reflux for 15 minutes. Next, the heating was stopped, and 13 g of the compound represented by Formula (7-7) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 14.2 g of the compound represented by Formula (6-7) was obtained.

1H NMR (d-DMSO)

δ ppm: 7.36 (2H, ddd), 7.17 (2H, tt), 4.37 (1H, s), 3.49 (3H, s), 3.00-2.93 (1H, m), 2.85-2.77 (2H, m), 2.27 (1H, tdd), 2.06 (1H, dd), 1.73 (1H, dt), 1.42 (2H, tt)

Production of Compound Represented by Formula 2-7

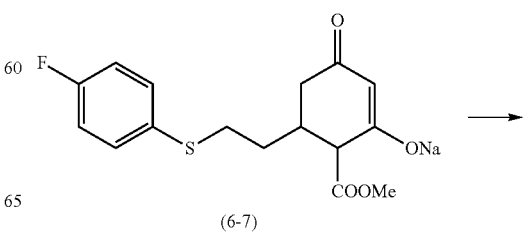

(6-7)

-continued

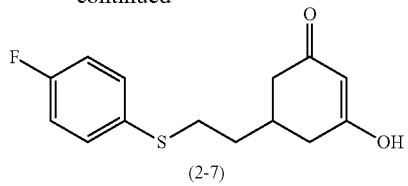

5 g of the compound represented by Formula (6-7) was dissolved in 80 ml of water at room temperature. 4.6 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 2.4 g of the compound represented by Formula (2-7) was obtained.

1H NMR (d-DMSO)

δ ppm: 11.04 (1H, s), 7.40 (2H, ddd), 7.17 (2H, tt), 5.19 (1H, s), 2.98 (2H, t), 2.28-1.91 (5H, m), 1.60 (2H, dd)

Production of Compound Represented by Formula 1-10

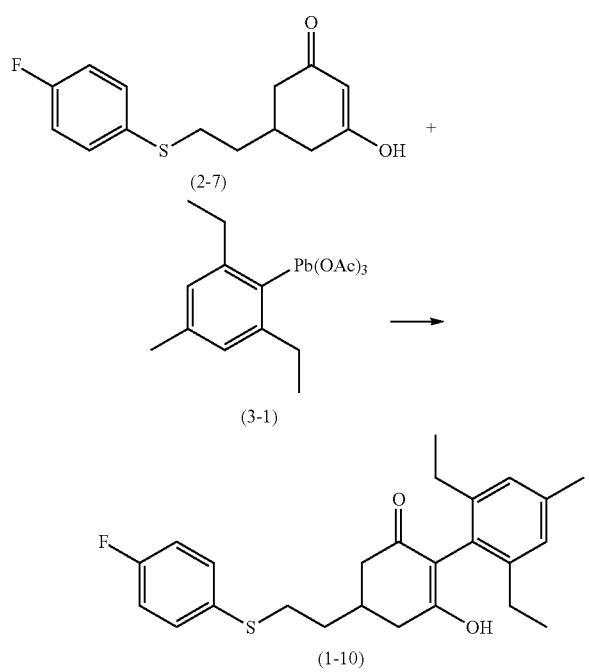

460 mg of the compound represented by Formula (2-7) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 330 mg of the compound represented by Formula (1-10) was obtained.

1H NMR (CDCl₃)

δ ppm: 7.39-7.33 (2H, m), 7.04-6.98 (2H, m), 6.97 (2H, s), 5.62 (1H, s), 2.95 (2H, ddd), 2.65 (2H, dd), 2.45-2.21 (10H, m), 1.78 (2H, q), 1.06 (6H, ddd)

Production Example 1-11

Production of Compound Represented by Formula (1-11)

Production of Compound Represented by Formula 9-8

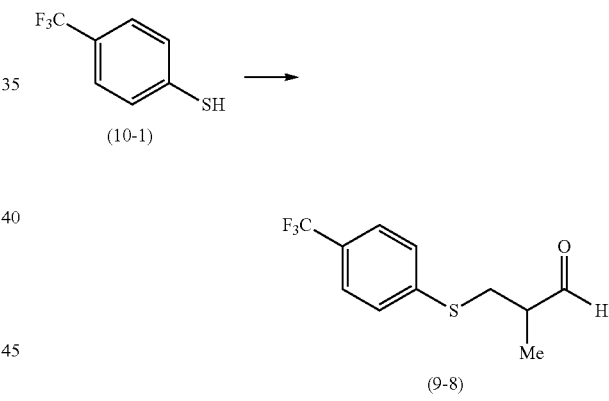

5 g of the compound represented by Formula (10-1) and 15 ml of tetrahydrofuran were mixed at room temperature, followed by stirring, then, the obtained mixture was cooled to 0° C., and 2.6 g of methacrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 6.9 g of the compound represented by Formula (9-8) was obtained.

1H NMR (CDCl₃)

δ ppm: 9.69 (1H, s), 7.53 (2H, d), 7.40 (2H, d), 3.42-3.35 (1H, m), 3.00-2.95 (1H, m), 2.67 (1H, dd), 1.28 (3H, dd)

Production of Compound Represented by Formula 7-8

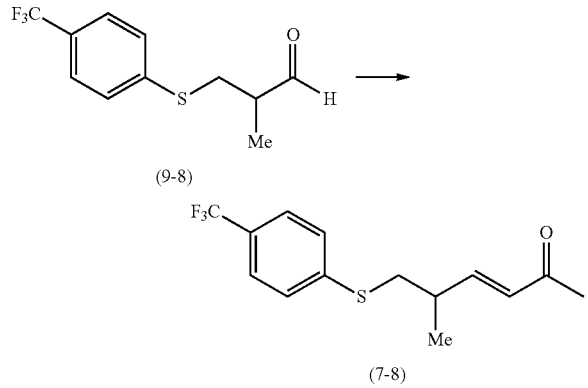

6.9 g of the compound represented by Formula (9-8) and 10 g of triphenylphosphineacetylmethylene were dissolved in 50 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 5.3 g of the compound represented by Formula (7-8) was obtained.

1H NMR (CDCl$_3$)

δ ppm: 7.52 (2H, d), 7.36 (2H, d), 6.72 (1H, dd), 6.09 (1H, dd), 3.03 (2H, d dd), 2.67 (1H, dt), 2.24 (3H, s), 1.25 (3H, d)

Production of Compound Represented by Formula 2-8

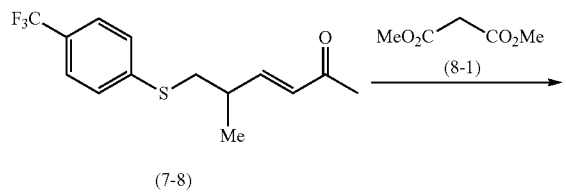

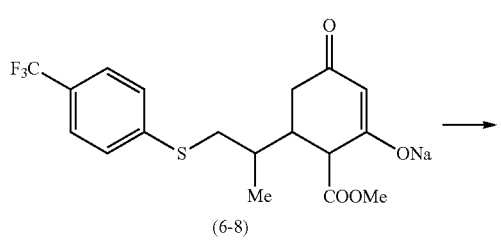

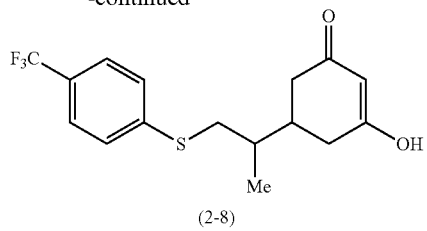

3.9 g of a 28% sodium methoxide methanol solution and 2.7 g of the compound represented by Formula (8-1) were dissolved in 60 ml of tetrahydrofuran at room temperature. The obtained solution was heated under reflux for 15 minutes. Next, the heating was stopped, and 5.3 g of the compound represented by Formula (7-8) was added to the obtained reaction mixture. Next, the obtained mixed liquid was heated under reflux for 30 minutes. The obtained reaction liquid was cooled to room temperature, and hexane was added thereto. Next, the reaction liquid was cooled by ice, and the precipitated crystals were collected by filtration, and thoroughly washed with hexane, whereby 4.4 g of the compound represented by Formula (6-8) was obtained.

Then, 1.6 g of the compound represented by Formula (6-8) was dissolved in 30 ml of water at room temperature. 1.3 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, whereby 1.3 g of the compound represented by Formula (2-8) was obtained.

1H NMR (d-DMSO)

δ ppm: 7.52 (2H, t), 7.35 (2H, d), 5.51 (1H, s), 3.42 (1H, s), 3.09-2.82 (2H, m), 2.67 (1H, d), 2.46 (2H, dt), 2.25 (2H, ddd), 1.90-1.84 (1H, m), 1.09 (3H, dd)

Production of Compound Represented by Formula 1-11

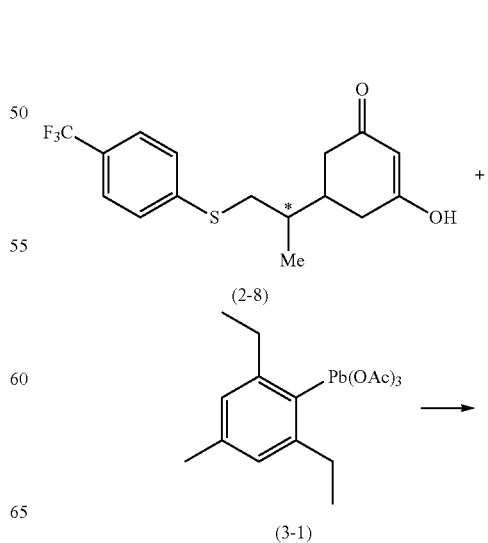

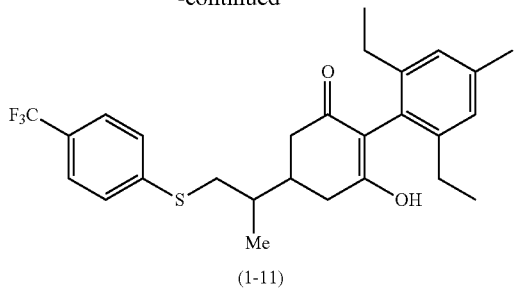

(1-11)

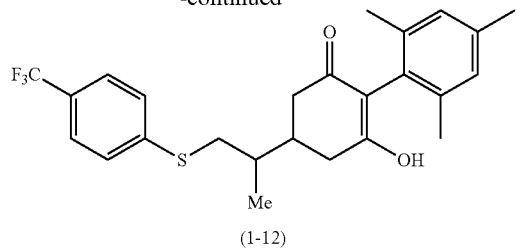

(1-12)

570 mg of the compound represented by Formula (2-8) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 480 mg of the compound represented by Formula (1-11) was obtained.

1H NMR (CDCl$_3$)

δ ppm: 7.53 (2H, d), 7.38 (2H, d), 6.98 (2H, s), 5.54 (1H, s), 3.22-3.14 (1H, m), 2.87 (1H, ddd), 2.67-2.23 (12H, m), 1.95-1.88 (1H, m), 1.16 (3H, dd), 1.11-1.04 (6H, m)

Production Example 1-12

Production of Compound Represented by Formula (1-12)

Production of Compound Represented by Formula 1-12

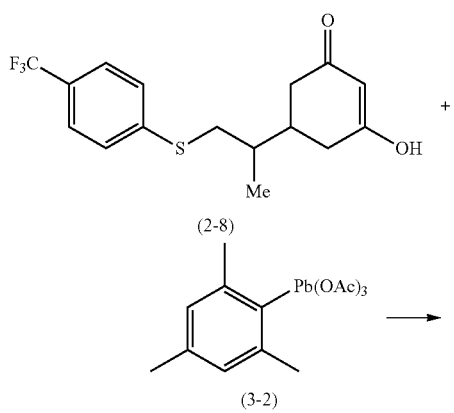

600 mg of the compound represented by Formula (2-8) and 1.1 g of dimethylaminopyridine were dissolved in a mixture of 4.8 ml of chloroform and 1.2 ml of toluene at room temperature in a nitrogen atmosphere in a flask. The obtained solution was stirred at room temperature for 15 minutes in a nitrogen atmosphere. Next, 1.0 g of the compound represented by Formula (3-2) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 540 mg of the compound represented by Formula (1-12) was obtained.

1H NMR (CDCl$_3$)

δ ppm: 7.53 (2H, d), 7.38 (2H, d), 6.94 (2H, s), 5.56 (1H, s), 3.16 (1H, ddd), 2.87 (1H, ddd), 2.65-2.25 (8H, m), 2.08 (3H, d), 2.01 (3H, s), 1.90 (1H, td), 1.15 (3H, dd)

The compound produced according to Production Example 1-12 is shown below.

Compound Represented by Formula 1-162

1H NMR (CDCl$_3$)

δ ppm: 7.28-7.22 (1H, m), 7.09 (1H, d), 7.03 (1H, dt), 6.93 (2H, s), 6.90-6.85 (1H, m), 5.73 (1H, s), 3.10 (1H, s), 2.83 (1H, dt), 2.60-2.22 (8H, m), 2.06-1.97 (6H, m), 1.86 (1H, s), 1.13 (3H, d)

Production Example 1-13

Production of Compound Represented by Formula (1-13)

Production of Compound Represented by Formula 9-9

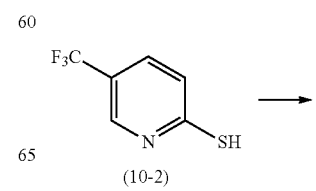

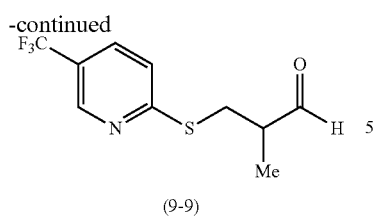

(9-9)

5 g of the compound represented by Formula (10-2) and 15 ml of tetrahydrofuran were mixed at room temperature, followed by stirring, then, the obtained mixture was cooled to 0° C., and 2.6 g of methacrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 6.3 g of the compound represented by Formula (9-9) was obtained.

1H NMR (CDCl$_3$)

δ ppm: 9.72 (1H, s), 8.66 (1H, s), 7.66 (1H, d), 7.27 (1H, d), 3.56 (1H, ddd), 3.38-3.31 (1H, m), 2.84 (1H, dd), 1.27-1.25 (3H, m)

Production of Compound Represented by Formula 7-9

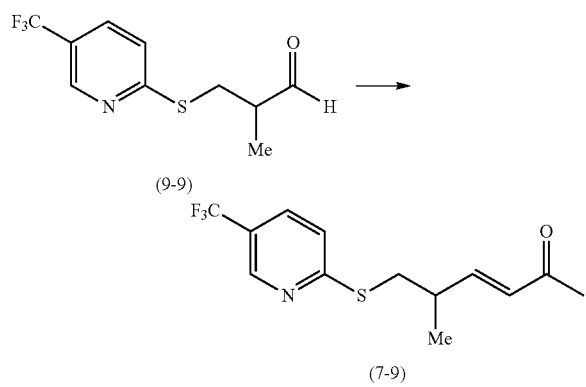

6.6 g of the compound represented by Formula (9-9) and 9 g of triphenylphosphineacetylmethylene were dissolved in 40 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 2.8 g of the compound represented by Formula (7-9) was obtained.

1H NMR (CDCl$_3$)

δ ppm: 8.66 (1H, s), 7.67-7.65 (1H, m), 7.28 (1H, d), 6.77 (1H, dd), 6.10 (1H, dd), 3.32 (2H, ddd), 2.79-2.72 (1H, m), 2.22 (3H, s), 1.25 (3H, d)

Production of Compound Represented by Formula 2-9

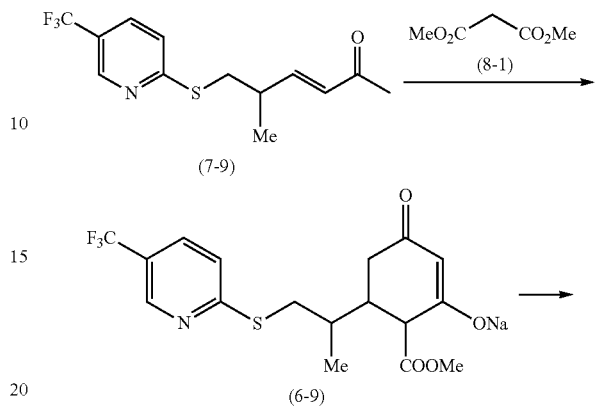

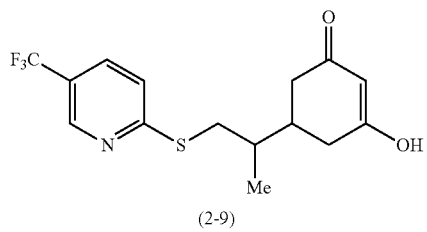

(2-9)

2.1 g of a 28% sodium methoxide methanol solution and 1.4 g of the compound represented by Formula (8-1) were dissolved in 40 ml of tetrahydrofuran at room temperature. The obtained solution was heated under reflux for 15 minutes. Next, the heating was stopped, and 2.8 g of the compound represented by Formula (7-9) was added to the obtained reaction mixture. Next, the obtained mixed liquid was heated under reflux for 30 minutes.

The obtained reaction liquid was cooled to room temperature, and hexane was added thereto. Next, the reaction liquid was cooled by ice, and the precipitated crystals were collected by filtration, and thoroughly washed with hexane, whereby 2.0 g of the compound represented by Formula (6-9) was obtained.

Then, 1.8 g of the compound represented by Formula (6-9) was dissolved in 25 ml of water at room temperature in a flask. 1.5 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, whereby 1.3 g of the compound represented by Formula (2-9) was obtained.

1H NMR (CDCl$_3$)

δ ppm: 8.66 (1H, s), 7.67-7.64 (1H, m), 7.25-7.19 (1H, m), 5.52 (1H, s), 3.49-3.41 (1H, m), 3.05-2.96 (1H, m), 2.75 (1H, dd), 2.58-2.45 (2H, m), 2.37-2.18 (2H, m), 1.98-1.88 (1H, m), 1.06 (3H, dd)

Production of Compound Represented by Formula 1-13

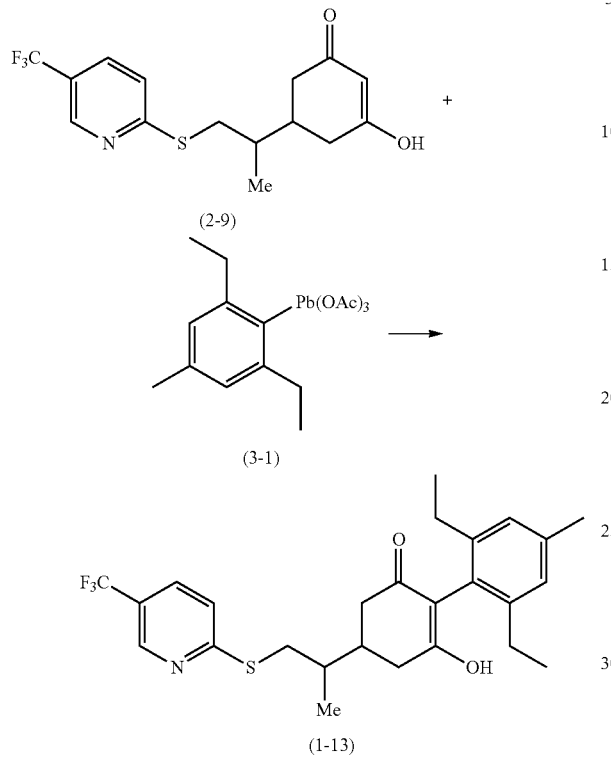

570 mg of the compound represented by Formula (2-9) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 570 mg of the compound represented by Formula (1-13) was obtained. The obtained compound represented by Formula (1-13) was separated into a peak at a retention time of 13 minutes (hereinafter, referred to as 1-13-A) and a peak at a retention time of 16 minutes (hereinafter, referred to as 1-13-B) using a chiral column (CHIRALPAK (registered trademark) IC-3 (manufactured by Daicel Corporation, 4.6 mm×250 mm, 3 μm, detector: 254 nm) under the conditions of a column temperature of 40° C., a mobile phase flow rate of 2.0 mL/min of $CO_2$ and 0.15 ml/min of MeOH, and a back pressure of 15 MPa.

1H NMR ($CDCl_3$)

δ ppm: 8.67 (1H, s), 7.66 (1H, dd), 7.28 (1H, d), 6.98 (2H, s), 5.54 (1H, s), 3.59 (1H, ddd), 3.02 (1H, dddd), 2.76-2.26 (12H, m), 1.95 (1H, t), 1.15 (3H, dt), 1.09-1.02 (6H, m)

Production Example 1-14

Production of Compound Represented by Formula (1-14)

Production of Compound Represented by Formula 1-14

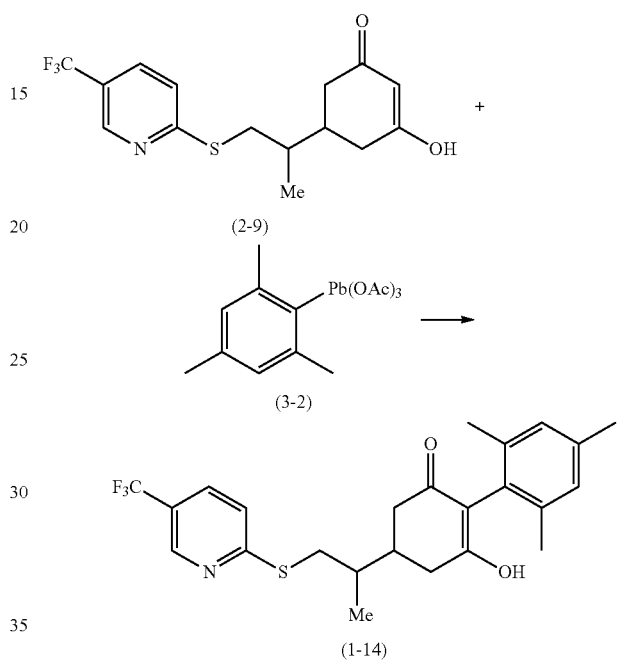

450 mg of the compound represented by Formula (2-9) and 600 mg of dimethylaminopyridine were dissolved in a mixture of 2.5 ml of chloroform and 0.5 ml of toluene at room temperature in a nitrogen atmosphere. The obtained solution was stirred at room temperature for 15 minutes in a nitrogen atmosphere. Next, 500 mg of the compound represented by Formula (3-2) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 320 mg of the compound represented by Formula (1-14) was obtained.

1H NMR ($CDCl_3$)

δ ppm: 8.66 (1H, s), 7.66 (1H, dd), 7.27 (1H, d), 6.93 (2H, s), 5.65 (1H, s), 3.57 (1H, ddd), 3.07-2.96 (1H, m), 2.74-2.27 (6H, m), 2.07-1.94 (9H, m), 1.17-1.10 (3H, m)

Production Example 1-15

Production of Compound Represented by Formula (1-15)

Production of Compound Represented by Formula 7-10

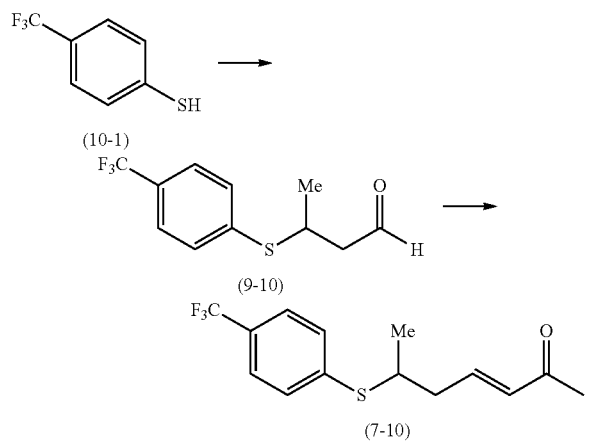

3 g of the compound represented by Formula (10-1) and 10 ml of tetrahydrofuran were mixed at room temperature, followed by stirring, then, the obtained mixture was cooled to 0° C., and 1.5 g of crotonic aldehyde and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 4.4 g of the compound represented by Formula (9-10) was obtained.

Then, 4.4 g of the compound represented by Formula (9-10) and 6.2 g of triphenylphosphineacetylmethylene were dissolved in 25 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 3.7 g of the compound represented by Formula (7-10) was obtained.

1H NMR (CDCl$_3$)

δ ppm: 7.54 (2H, d), 7.45 (2H, d), 6.79 (1H, dt), 6.14-6.10 (1H, m), 3.51 (1H, q), 2.60-2.45 (2H, m), 2.24 (3H, s), 1.36 (3H, d)

Production of Compound Represented by Formula 2-10

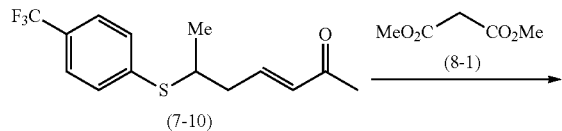

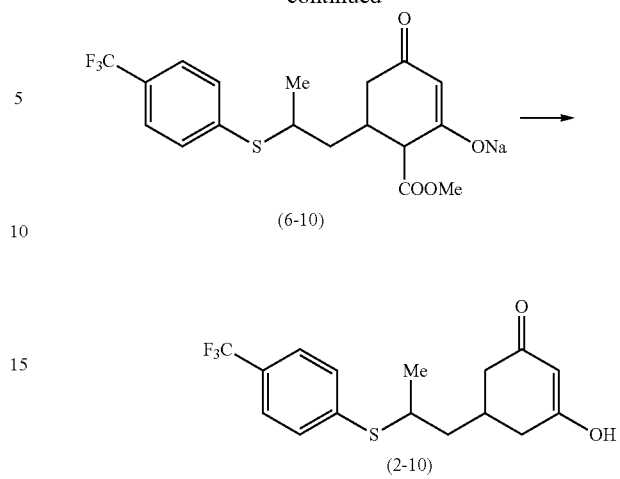

2.7 g of a 28% sodium methoxide methanol solution and 1.8 g of the compound represented by Formula (8-1) were dissolved in 40 ml of tetrahydrofuran at room temperature. The obtained solution was heated under reflux for 15 minutes. Next, the heating was stopped, and 3.7 g of the compound represented by Formula (7-10) was added to the obtained reaction mixture. Next, the obtained mixed liquid was heated under reflux for 30 minutes. The obtained reaction liquid was cooled to room temperature, and hexane was added thereto. Next, the reaction liquid was cooled by ice, and the precipitated crystals were collected by filtration, and thoroughly washed with hexane, whereby 2.9 g of the compound represented by Formula (6-10) was obtained.

Then, 2.9 g of the compound represented by Formula (6-10) was dissolved in 40 ml of water at room temperature. 2.3 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, whereby 2.1 g of the compound represented by Formula (2-10) was obtained.

1H NMR (CDCl$_3$)

δ ppm: 7.54 (2H, t), 7.42 (2H, dd), 5.48 (1H, s), 3.36 (2H, tt), 2.78 (2H, d), 2.53-2.34 (2H, m), 2.13 (1H, dd), 1.75-1.53 (2H, m), 1.34-1.29 (3H, m)

Production of Compound Represented by Formula 1-15

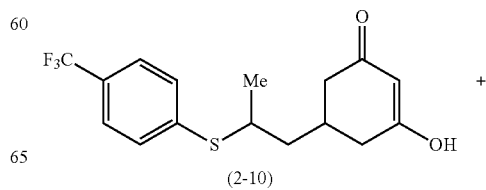

-continued

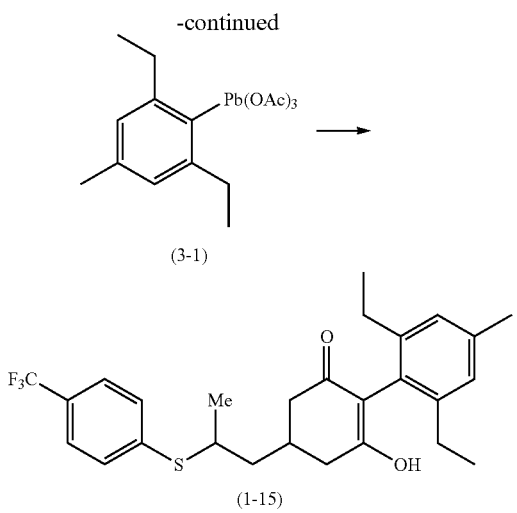

570 mg of the compound represented by Formula (2-10) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 360 mg of the compound represented by Formula (1-15) was obtained.

1H NMR (CDCl$_3$)

δ ppm: 7.56-7.52 (2H, m), 7.46-7.41 (2H, m), 6.98 (2H, s), 5.53 (1H, s), 3.49-3.42 (1H, m), 2.76-2.23 (12H, m), 1.83-1.71 (2H, m), 1.38 (3H, dd), 1.06 (6H, tt)

Production Example 1-16

Production of Compound Represented by Formula (1-16)

Production of Compound Represented by Formula 9-11

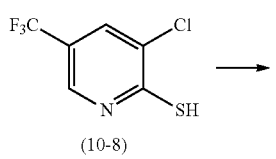

-continued

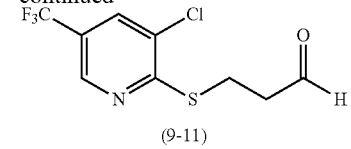

2 g of the compound represented by Formula (10-8) and 10 ml of tetrahydrofuran were mixed at room temperature, followed by stirring, then, the obtained mixture was cooled to 0° C., and 0.8 g of 95% acrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 2.5 g of the compound represented by Formula (9-11) was obtained.

1H NMR (CDCl$_3$)

δ ppm: 9.84 (1H, s), 8.59 (1H, s), 7.76 (1H, s), 3.49 (2H, t), 2.96 (2H, t)

Production of Compound Represented by Formula 7-11

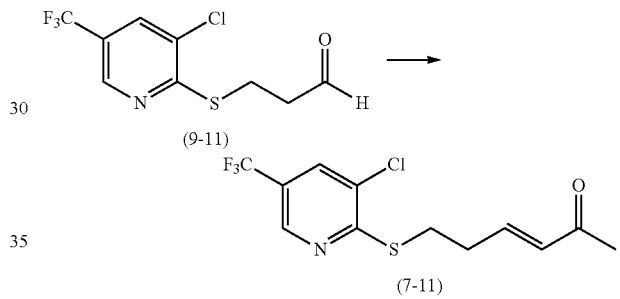

2.5 g of the compound represented by Formula (9-11) and 3.4 g of triphenylphosphineacetylmethylene were dissolved in 15 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 1.2 g of the compound represented by Formula (7-11) was obtained.

1H NMR (CDCl$_3$)

δ ppm: 8.60 (1H, s), 7.76 (1H, s), 6.84 (1H, dt), 6.16 (1H, dt), 3.36 (2H, t), 2.68 (2H, ddd), 2.26 (3H, s)

Production of Compound Represented by Formula 6-11

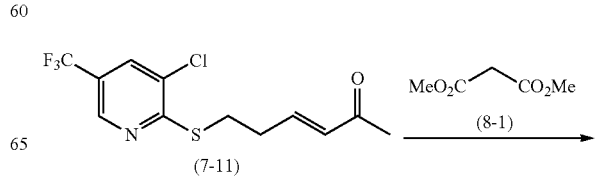

-continued

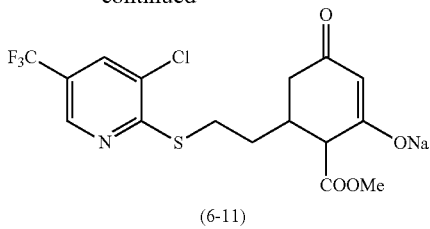

(6-11)

0.8 g of a 28% sodium methoxide methanol solution and 0.56 g of the compound represented by Formula (8-1) were dissolved in 15 ml of tetrahydrofuran at room temperature. The obtained solution was heated under reflux for 15 minutes. Next, the heating was stopped, and 1.2 g of the compound represented by Formula (7-11) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 0.8 g of the compound represented by Formula (6-11) was obtained.

1H NMR (d-DMSO)

δ ppm: 8.81 (1H, s), 8.34 (1H, s), 4.38 (1H, s), 3.50 (3H, s), 3.42-3.25 (1H, m), 3.15-3.07 (1H, m), 2.82 (1H, d), 2.33-2.23 (1H, m), 2.12 (1H, dd), 1.79 (1H, dt), 1.63-1.50 (2H, m)

Production of Compound Represented by Formula 2-11

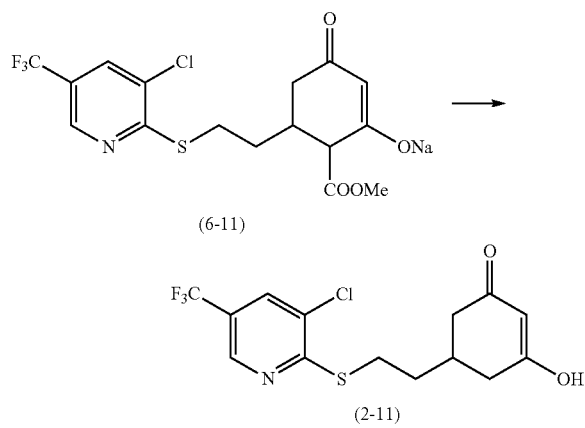

0.8 g of the compound represented by Formula (6-11) was dissolved in 10 ml of water at room temperature in a flask. 0.6 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 0.6 g of the compound represented by Formula (2-11) was obtained.

1H NMR (d-DMSO)

δ ppm: 11.06 (1H, s), 8.81 (1H, d), 8.35 (1H, d), 5.20 (1H, s), 3.27 (2H, t), 2.51-1.91 (5H, m), 1.74 (2H, d)

Production of Compound Represented by Formula 1-16

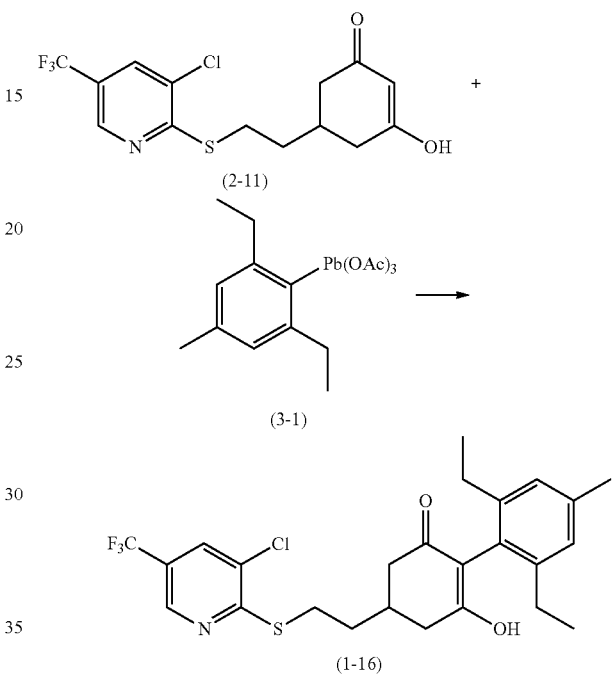

600 mg of the compound represented by Formula (2-11) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 360 mg of the compound represented by Formula (1-16) was obtained.

1H NMR (CDCl$_3$)

δ ppm: 8.60 (1H, s), 7.75 (1H, d), 6.97 (2H, s), 5.71 (1H, s), 3.31 (2H, ddd), 2.75 (2H, t), 2.51-2.23 (10H, m), 1.94-1.88 (2H, m), 1.09-1.00 (6H, m)

Production Example 1-17

Production of Compound Represented by Formula (1-17)

Production of Compound Represented by Formula 7-12

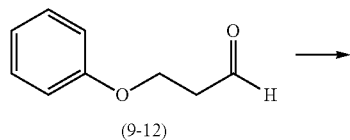

(9-12)

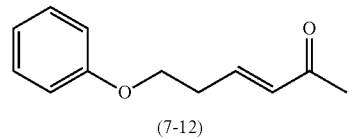

(7-12)

9.3 g of the compound represented by Formula (9-12) and 22 g of triphenylphosphineacetylmethylene were dissolved in 90 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 2.1 g of the compound represented by Formula (7-12) was obtained.

1H NMR (CDCl$_3$)

δ ppm: 7.31-7.23 (2H, m), 6.95 (1H, tt), 6.92-6.82 (3H, m), 6.21-6.14 (1H, m), 4.09 (2H, t), 2.69 (2H, q), 2.24 (3H, s)

Production of Compound Represented by Formula 6-12

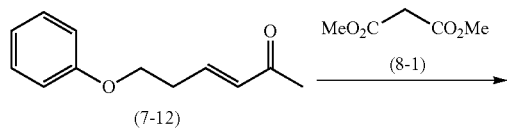

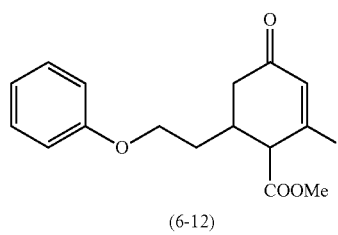

(6-12)

2.3 g of a 28% sodium methoxide methanol solution and 1.6 g of the compound represented by Formula (8-1) were dissolved in 40 ml of tetrahydrofuran at room temperature. The obtained solution was heated under reflux for 15 minutes. Next, the heating was stopped, and 2.1 g of the compound represented by Formula (7-12) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 2.6 g of the compound represented by Formula (6-12) was obtained.

1H NMR (d-DMSO)

δ ppm: 7.27 (2H, t), 6.92-6.89 (3H, m), 4.40 (1H, s), 4.38-3.89 (2H, m), 3.54 (3H, s), 2.87 (1H, d), 2.40-2.30 (1H, m), 2.08 (1H, dd), 1.81 (1H, dd), 1.72-1.64 (1H, m), 1.60-1.51 (1H, m)

Production of Compound Represented by Formula 2-12

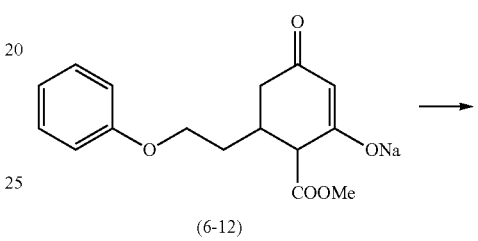

(6-12)

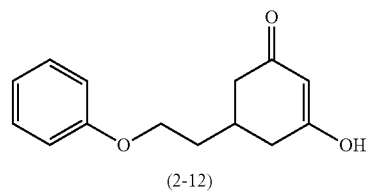

(2-12)

2.0 g of the compound represented by Formula (6-12) was dissolved in 40 ml of water at room temperature. 2.0 g of anhydrous sodium carbonate was added to the obtained solution. The obtained solution was heated under reflux for 5 hours. The reaction liquid was cooled to room temperature, then, impurities were washed with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 1.2 g of the compound represented by Formula (2-12) was obtained.

1H NMR (d-DMSO)

δ ppm: 11.06 (1H, s), 7.28 (2H, t), 6.92 (2H, dd), 5.20 (1H, s), 4.02 (2H, t), 2.50-1.99 (5H, m), 1.79 (2H, d)

Production of Compound Represented by Formula 1-17

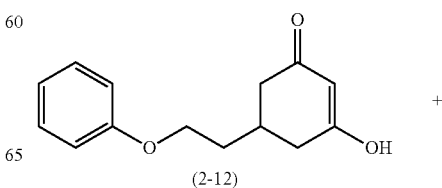

(2-12)

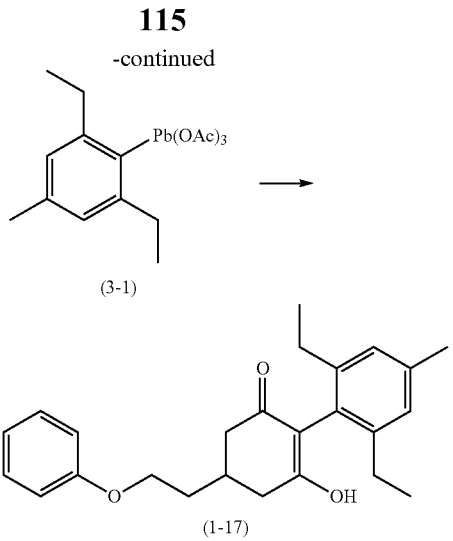

400 mg of the compound represented by Formula (2-12) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 380 mg of the compound represented by Formula (1-17) was obtained.

1H NMR (CDCl$_3$)

δ ppm: 7.32-7.27 (2H, m), 6.97-6.89 (5H, m), 5.68 (1H, s), 4.11-4.06 (2H, m), 2.78-2.69 (2H, m), 2.60-2.25 (10H, m), 1.97 (2H, ddd), 1.11-1.05 (6H, m)

Production Example 1-18

Production of Compound Represented by Formula (1-18)

Production of Compound Represented by Formula 7-13

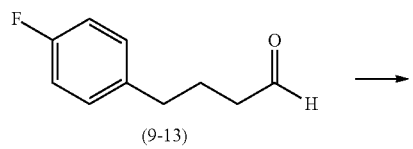

3.5 g of the compound represented by Formula (9-13) and 7.5 g of triphenylphosphineacetylmethylene were dissolved in 30 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 1.1 g of the compound represented by Formula (7-13) was obtained.

1H NMR (CDCl$_3$)

δ ppm: 7.14-7.09 (2H, m), 6.99-6.93 (2H, m), 6.79 (1H, dt), 6.08 (1H, dt), 2.62 (2H, t), 2.27-2.20 (5H, m), 1.82-1.74 (2H, m)

Production of Compound Represented by Formula 2-13

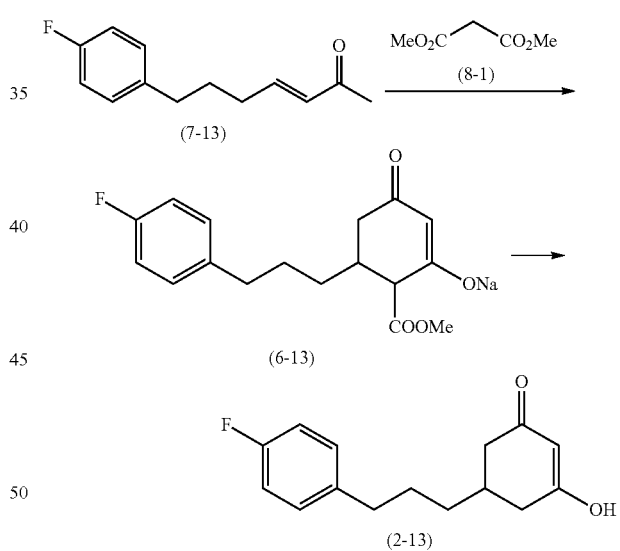

1.1 g of a 28% sodium methoxide methanol solution and 0.8 g of the compound represented by Formula (8-1) were dissolved in 20 ml of tetrahydrofuran at room temperature. The obtained solution was heated under reflux for 15 minutes. Next, the heating was stopped, and 1.1 g of the compound represented by Formula (7-13) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 1.0 g of the compound represented by Formula (6-13) was obtained.

Then, 1.0 g of the compound represented by Formula (6-13) was dissolved in 20 ml of water at room temperature. 1.0 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 650 mg of the compound represented by Formula (2-13) was obtained.
1H NMR (d-DMSO)
δ
ppm: 10.99 (1H, s), 7.25-7.21 (2H, m), 7.11-7.05 (2H, m), 5.18 (1H, s), 2.55 (2H, t), 2.43-1.91 (5H, m), 1.61-1.53 (2H, m), 1.35-1.32 (2H, m)

Production of Compound Represented by Formula 1-18

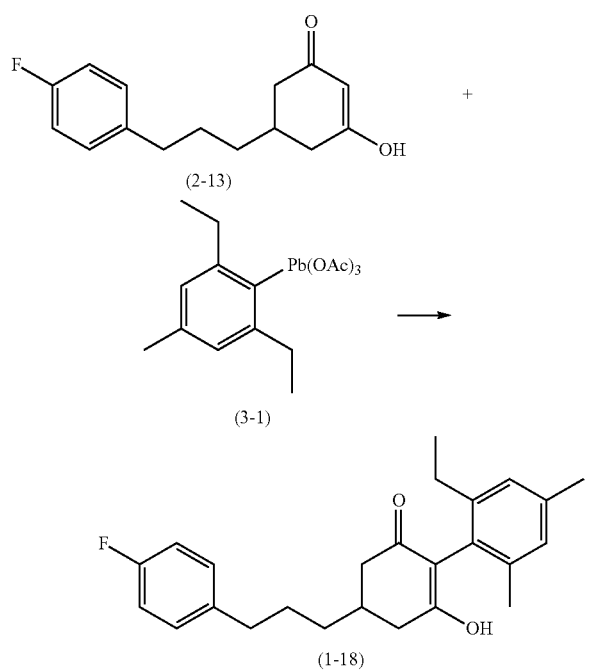

430 mg of the compound represented by Formula (2-13) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 440 mg of the compound represented by Formula (1-18) was obtained.
1H NMR (CDCl$_3$)
δ
ppm: 7.15-7.11 (2H, m), 6.99-6.93 (4H, m), 5.60 (1H, s), 2.67-2.61 (4H, m), 2.40-2.19 (10H, m), 1.74-1.66 (2H, m), 1.52-1.46 (2H, m), 1.08-1.00 (6H, m)

Production Example 1-19

Production of Compound Represented by Formula (1-69)

Production of Compound Represented by Formula 7-14

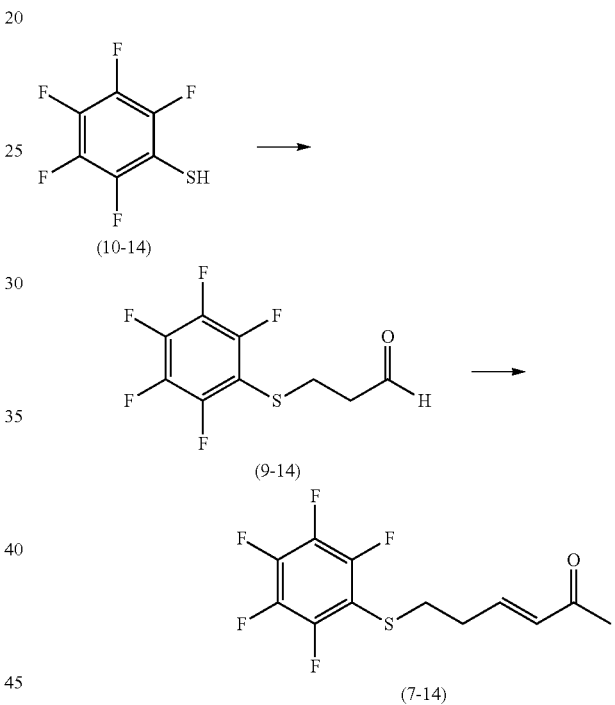

9.0 g of the compound represented by Formula (10-14) and 30 ml of tetrahydrofuran were mixed at room temperature, followed by stirring, then, the obtained mixture was cooled to 0° C., and 3.6 g of 95% acrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 11 g of the compound represented by Formula (9-14) was obtained.
Then, 11 g of the compound represented by Formula (9-14) and 15.8 g of triphenylphosphineacetylmethylene were dissolved in 50 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:5), whereby 2.65 g of the compound represented by Formula (7-14) was obtained.

1H NMR (CDCl$_3$)

δ ppm: 6.79-6.71 (1H, m), 6.11 (1H, dt), 3.02 (2H, td), 2.51 (2H, dt), 2.25 (3H, dd)

Production of Compound Represented by Formula 6-14

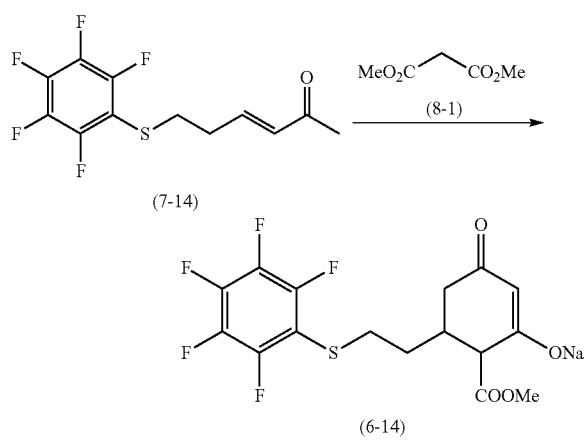

1.9 g of a 28% sodium methoxide methanol solution and 1.3 g of the compound represented by Formula (8-1) were dissolved in 35 ml of tetrahydrofuran at room temperature. The obtained solution was heated under reflux for 15 minutes. Next, the heating was stopped, and 2.65 g of the compound represented by Formula (7-14) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 1.1 g of the compound represented by Formula (6-14) was obtained.

1H NMR (d-DMSO)

δ ppm: 4.39 (1H, s), 3.49 (3H, s), 2.99-2.92 (1H, m), 2.86-2.76 (2H, m), 2.28-2.19 (1H, m), 2.05-1.99 (1H, m), 1.76-1.65 (1H, m), 1.44-1.33 (2H, m)

Production of Compound Represented by Formula 1-69

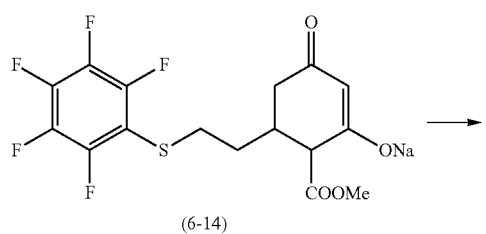

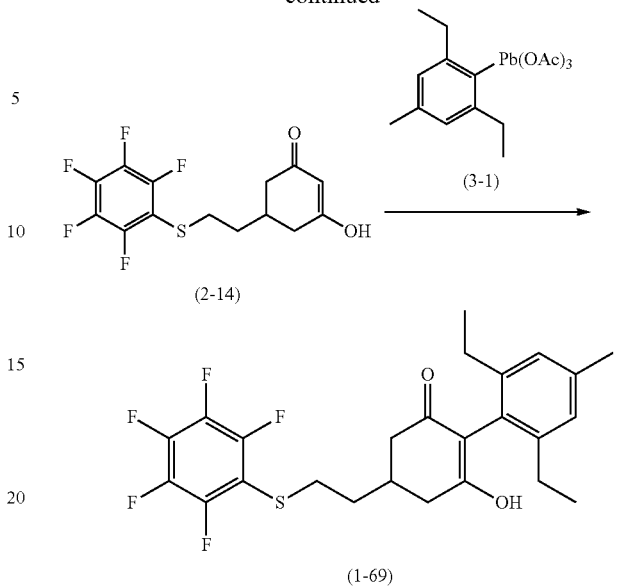

1.1 g of the compound represented by Formula (6-14) was dissolved in 20 ml of water at room temperature. 840 mg of anhydrous sodium carbonate was added to the obtained solution. The obtained solution was heated under reflux for 5 hours. After the reaction liquid was cooled to room temperature, impurities were removed by washing with tert-butyl methyl ether, and the reaction liquid was acidified by adding 2 N hydrochloric acid, followed by extracting with ethyl acetate. The ethyl acetate layer was concentrated under reduced pressure, and the obtained crystals were washed sequentially with tert-butyl methyl ether and hexane, whereby 800 mg of the compound represented by Formula (2-14) was obtained.

Then, 580 mg of the compound represented by Formula (2-14) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 150 mg of the compound represented by Formula (1-69) was obtained.

1H NMR (CDCl$_3$)

δ ppm: 6.99 (2H, s), 5.56 (1H, s), 3.00-2.95 (2H, m), 2.71-2.62 (2H, m), 2.47-2.22 (10H, m), 1.75 (2H, dd), 1.10-1.04 (6H, m)

Production Example 1-20

Production of Compound Represented by Formula (1-31)

Production of Compound Represented by Formula 9-15

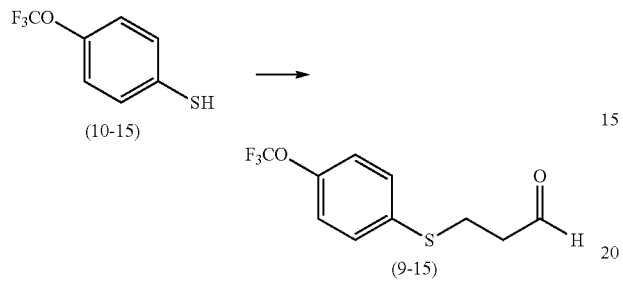

3.3 g of the compound represented by Formula (10-15) and 15 ml of tetrahydrofuran were mixed at room temperature, followed by stirring, then, the obtained mixture was cooled to 0° C., and 1.4 g of 95% acrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 4.2 g of the compound represented by Formula (9-15) was obtained.

1H NMR (CDCl$_3$)
δ
ppm: 9.76 (1H, s), 7.52 (2H, d), 7.37 (2H, d), 3.21-3.16 (2H, m), 2.80-2.76 (2H, m)

Production of Compound Represented by Formula 7-15

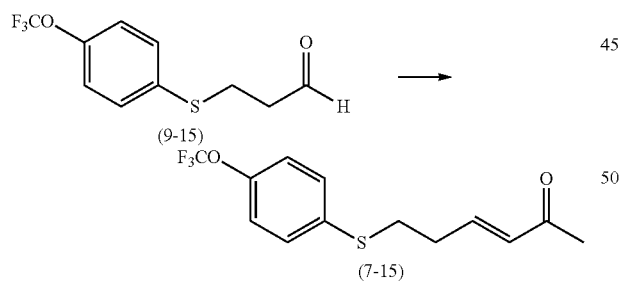

4.2 g of the compound represented by Formula (9-15) and 6.0 g of triphenylphosphineacetylmethylene were dissolved in 20 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 2.7 g of the compound represented by Formula (7-15) was obtained.

1H NMR (CDCl$_3$)
δ
ppm: 7.37 (2H, d), 7.16 (2H, d), 6.77 (1H, dt), 6.09 (1H, d), 3.04 (2H, t), 2.58-2.52 (2H, m), 2.23 (3H, s)

Production of Compound Represented by Formula 6-15

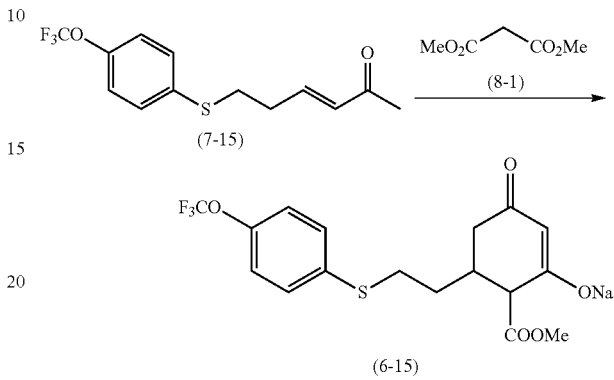

2 g of a 28% sodium methoxide methanol solution and 1.4 a of the compound represented by Formula (8-1) were dissolved in 40 ml of tetrahydrofuran at room temperature. The obtained solution was heated under reflux for 15 minutes. Next, the heating was stopped, and 2.7 g of the compound represented by Formula (7-15) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 1.8 g of the compound represented by Formula (6-15) was obtained.

1H NMR (d-DMSO)
δ
ppm: 7.39 (2H, d), 7.31 (2H, d), 4.40 (1H, s), 3.47 (3H, s), 3.07-3.01 (1H, m), 2.92-2.80 (2H, m), 2.34-2.24 (1H, m), 2.09 (1H, dd), 1.75 (1H, dd), 1.51-1.40 (2H, m)

Production of Compound Represented by Formula 1-31

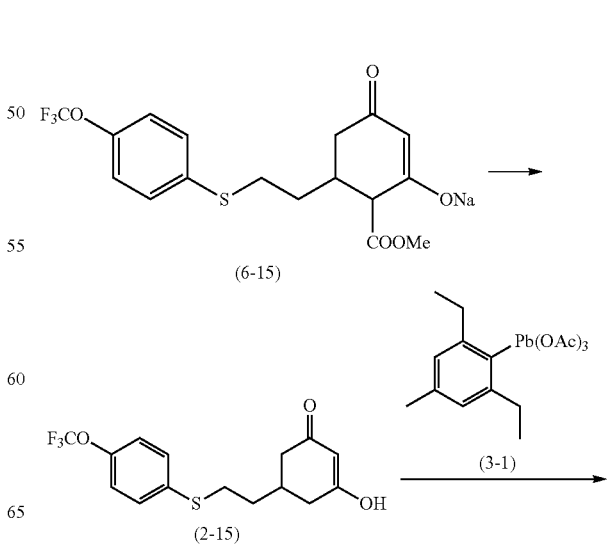

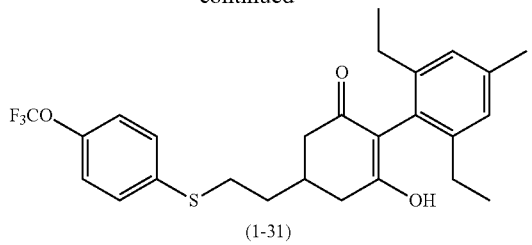

(1-31)

1.8 g of the compound represented by Formula (6-15) was dissolved in 35 ml of water at room temperature. 1.4 g of anhydrous sodium carbonate was added to the obtained solution. The obtained solution was heated under reflux for 5 hours. After the reaction liquid was cooled to room temperature, impurities were removed by washing with tert-butyl methyl ether, and the reaction liquid was acidified by adding 2 N hydrochloric acid, followed by extracting with ethyl acetate. The ethyl acetate layer was concentrated under reduced pressure, and the obtained crystals were washed sequentially with tert-butyl methyl ether and hexane, whereby 1.6 g of the compound represented by Formula (2-15) was obtained.

Then, 570 mg of the compound represented by Formula (2-15) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=1:4), whereby 290 mg of the compound represented by Formula (1-31) was obtained.

1H NMR (CDCl$_3$)
δ
ppm: 7.36 (2H, d), 7.15 (2H, d), 6.98 (2H, s), 5.59 (1H, s), 3.00 (2H, ddd), 2.71-2.65 (2H, m), 2.48-2.22 (10H, m), 1.83 (2H, q), 1.10-1.03 (6H, m)

Production Example 1-21

Production of Compound Represented by Formula (1-73)

Production of Compound Represented by Formula 7-16

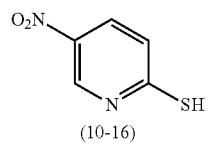

(10-16)

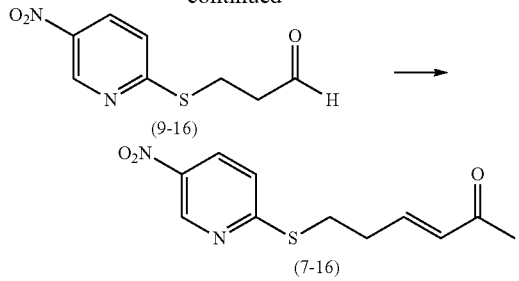

5.0 g of the compound represented by Formula (10-16) and 30 ml of tetrahydrofuran were mixed at room temperature, followed by stirring, then, the obtained mixture was cooled to 0° C., and 2.8 g of 95% acrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 6.7 g of the compound represented by Formula (9-16) was obtained.

Then, 6.7 g of the compound represented by Formula (9-16) and 11.2 g of triphenylphosphineacetylmethylene were dissolved in 40 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:3), whereby 5.0 g of the compound represented by Formula (7-16) was obtained.

1H NMR (CDCl$_3$)
δ
ppm: 9.23 (1H, d), 8.25-8.21 (1H, m), 7.32-7.28 (1H, m), 6.83 (1H, dt), 6.16 (1H, d), 3.41 (2H, t), 2.72-2.67 (2H, m), 2.24 (3H, s)

Production of Compound Represented by Formula 6-14

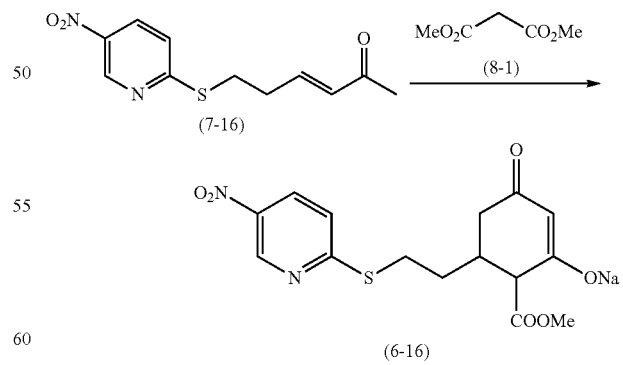

4.2 g of a 28% sodium methoxide methanol solution and 2.9 g of the compound represented by Formula (8-1) were dissolved in 80 ml of tetrahydrofuran at room temperature. The obtained solution was heated under reflux for 15 minutes. Next, the heating was stopped, and 5.0 g of the compound represented by Formula (7-16) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 4.9 g of the compound represented by Formula (6-16) was obtained.

1H NMR (d-DMSO)
δ
ppm: 9.21 (1H, d), 8.36 (1H, dd), 7.54 (1H, dd), 4.38 (1H, s), 3.52 (3H, s), 3.34-2.82 (3H, m), 2.33-2.24 (1H, m), 2.16-2.11 (1H, m), 1.83-1.74 (1H, m), 1.61-1.53 (2H, m)

Production of Compound Represented by Formula 1-73

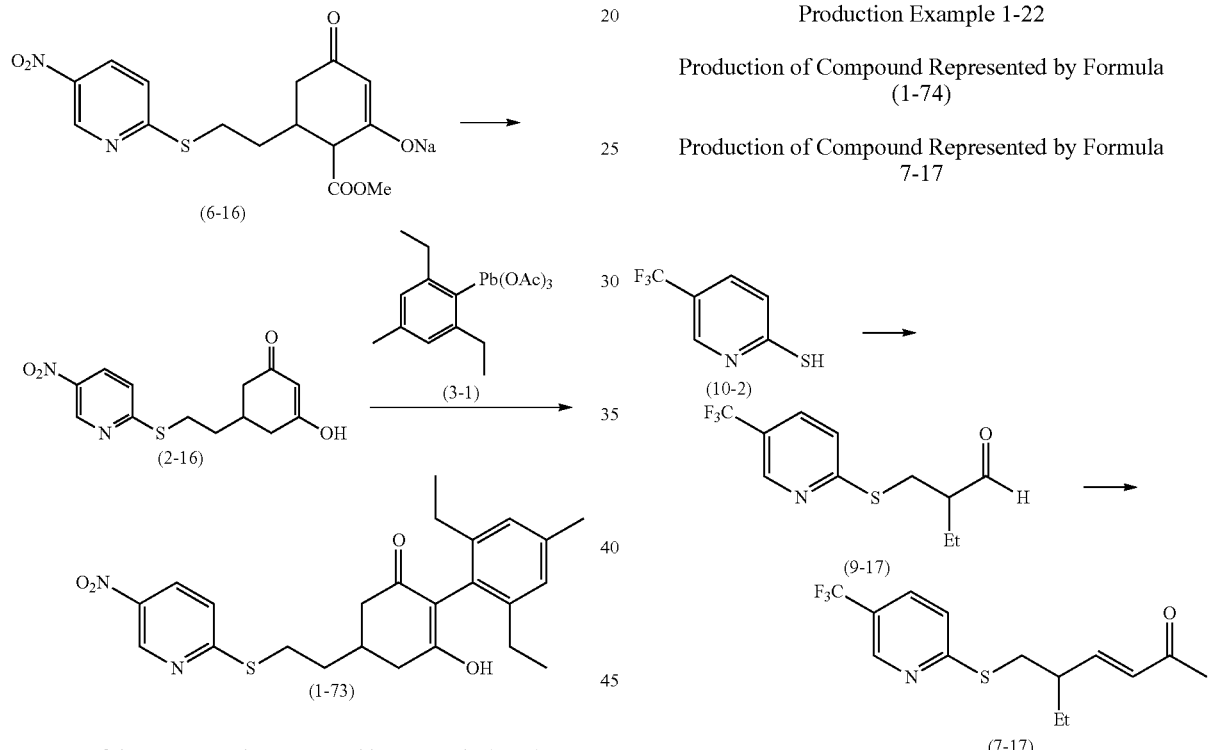

3.0 g of the compound represented by Formula (6-16) was dissolved in 65 ml of water at room temperature. 2.7 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 1.1 g of the compound represented by Formula (2-16) was obtained.

Then, 500 mg of the compound represented by Formula (2-16) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=2:3), whereby 50 mg of the compound represented by Formula (1-73) was obtained.

1H NMR (CDCl$_3$)
δ
ppm: 9.25 (1H, d), 8.23 (1H, dt), 7.30 (1H, d), 6.98 (2H, s), 5.58 (1H, s), 3.36 (2H, t), 2.80-2.71 (2H, m), 2.52-2.25 (10H, m), 1.96-1.90 (2H, m), 1.09-1.03 (6H, m)

Production Example 1-22

Production of Compound Represented by Formula (1-74)

Production of Compound Represented by Formula 7-17

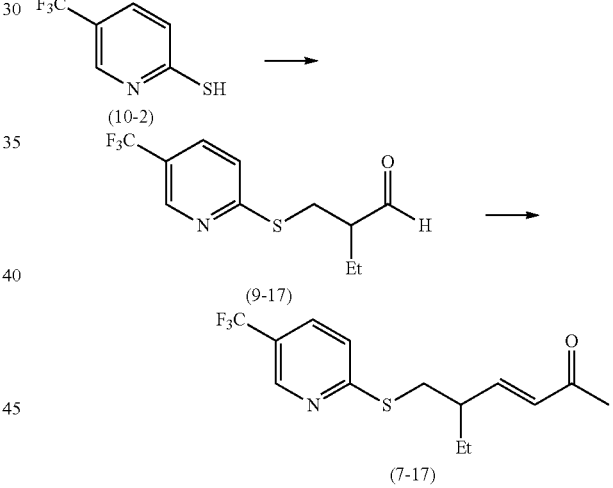

3.0 g of the compound represented by Formula (10-2) and 15 ml of tetrahydrofuran were mixed at room temperature, followed by stirring, then, the obtained mixture was cooled to 0° C., and 1.85 g of 2-ethylacrolein and 0.1 g of triethylamine were added dropwise thereto. The obtained mixture was stirred for 1.5 hours under ice-cooling. Next, water was added to the obtained mixture. The obtained mixture was extracted with tert-butyl methyl ether. The organic layer was washed with water, dried over anhydrous sodium sulfate, and concentrated under reduced pressure, whereby 4.3 g of the compound represented by Formula (9-17) was obtained.

Then, 4.3 g of the compound represented by Formula (9-17) and 5.8 g of triphenylphosphineacetylmethylene were dissolved in 20 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 1.1 g of the compound represented by Formula (7-17) was obtained.

1H NMR (CDCl₃)

δ ppm: 8.66 (1H, s), 7.67-7.64 (1H, m), 7.28-7.24 (1H, m), 6.66-6.59 (1H, m), 6.10 (1H, dd), 3.45-3.24 (2H, m), 2.53-2.47 (1H, m), 2.20 (3H, s), 1.79-1.46 (2H, m), 0.96-0.92 (3H, m)

Production of Compound Represented by Formula 1-74

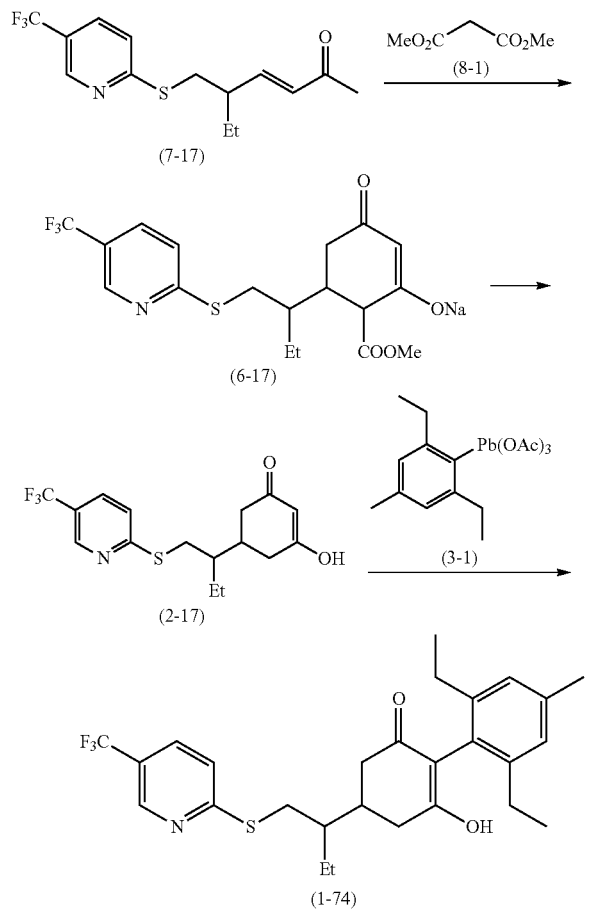

810 mg of a 28% sodium methoxide methanol solution and 560 mg of the compound represented by Formula (8-1) were dissolved in 15 ml of tetrahydrofuran at room temperature. The obtained solution was heated under reflux for 15 minutes. Next, the heating was stopped, and 1.1 g of the compound represented by Formula (7-17) was added to the obtained reaction mixture. Next, the obtained mixed liquid was heated under reflux for 30 minutes. The obtained reaction liquid was cooled to room temperature, and the precipitated crystals were collected by filtration, and thoroughly washed sequentially with tert-butyl methyl ether and hexane, whereby 1.6 g of the compound represented by Formula (6-17) was obtained.

Then, 1.6 g of the compound represented by Formula (6-17) was dissolved in 30 ml of water at room temperature.

1.2 g of anhydrous sodium carbonate was added to the obtained solution. The obtained solution was heated under reflux for 5 hours. After the reaction liquid was cooled to room temperature, impurities were removed by washing with tert-butyl methyl ether, and the reaction liquid was acidified by adding 2 N hydrochloric acid, followed by extracting with ethyl acetate. The ethyl acetate layer was concentrated under reduced pressure, and the obtained crystals were washed sequentially with tert-butyl methyl ether and hexane, whereby 1.2 g of the compound represented by Formula (2-17) was obtained.

Then, 600 mg of the compound represented by Formula (2-17) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=1:5), whereby 200 mg of the compound represented by Formula (1-74) was obtained.

1H NMR (CDCl₃)

δ ppm: 8.67 (1H, s), 7.66 (1H, dd), 7.27 (1H, d), 6.98 (2H, s), 5.52 (1H, s), 3.57-3.46 (1H, m), 3.31-3.17 (1H, m), 2.71-2.58 (3H, m), 2.44-2.25 (10H, m), 1.75-1.62 (2H, m), 1.08-1.00 (9H, m)

Production Example 1-23

Production of Compound Represented by Formula (1-21)

Production of Compound Represented by Formula 12-1

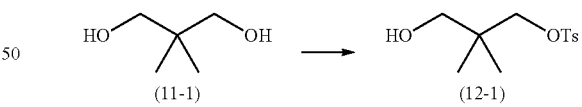

31 g of the compound represented by Formula (11-1), 17 ml of pyridine, and 100 ml of methylene chloride were mixed at room temperature, followed by stirring, then, the obtained mixture was cooled to 0° C., and added dropwise to a mixed liquid obtained by dissolving 11.4 g of paratoluenesulfonyl chloride in 60 ml of methylene chloride. The obtained mixed liquid was stirred at 0° C. for 3 hours under ice-cooling. The obtained reaction mixed liquid was diluted with ethyl acetate, and the resultant product was washed with an aqueous saturated sodium hydrogen carbonate solution. The obtained ethyl acetate layer was washed with a saturated saline solution, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=3:2), whereby 16 g (colorless oily matter) of the compound represented by Formula (12-1) was obtained.

1H NMR (CDCl₃)

δ ppm: 7.80-7.78 (2H, m), 7.34-7.30 (2H, m), 3.82 (2H, s), 3.37 (2H, s), 2.45 (3H, s), 0.88 (6H, s)

Production of Compound Represented by Formula 13-1

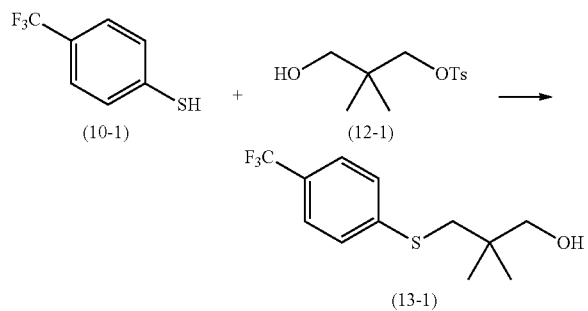

30 ml of anhydrous N,N-dimethylformamide was added to 1.55 g of a 60% sodium hydride in a nitrogen atmosphere. 7.2 g of the compound represented by Formula (10-1) was added dropwise to the obtained mixture under ice-cooling. After the obtained mixture was stirred for 25 minutes under ice-cooling, a solution of 8 g of the compound represented by Formula (12-1) in 15 ml of anhydrous DMF was added dropwise thereto, and after the obtained mixture was stirred at room temperature for 1 hour, the reaction temperature was raised to 90° C., and the mixture was stirred for 8 hours. The obtained reaction mixed liquid was extracted with t-butyl methyl ether. The organic layers were combined, washed with water, dried over anhydrous sodium sulfate, and concentrated under reduced pressure, whereby a crude product was obtained. The crude product was subjected to silica gel column chromatography (eluent, ethyl acetate:hexane=1:4→2:3), whereby 7.6 g of the compound represented by Formula (13-1) was obtained (oily matter).

1H NMR (CDCl₃)

δ ppm: 7.48 (2H, d), 7.39 (2H, d), 3.45 (2H, s), 3.02 (2H, s), 2.03 (1H, s), 1.01 (6H, s)

Production of Compound Represented by Formula 9-18

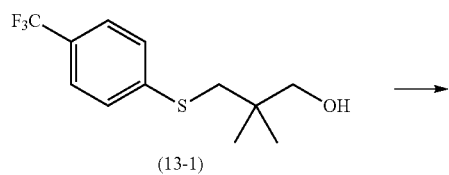

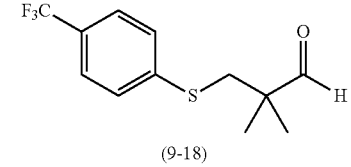

In a nitrogen atmosphere, a mixed liquid of 3.4 ml of oxalyl chloride and 120 ml of methylene chloride was cooled to −78° C., and 5.7 ml of dimethyl sulfoxide was slowly added dropwise thereto, followed by stirring for 10 minutes. Next, a solution of 7.6 g of the compound represented by Formula (13-1) in 50 ml of methylene chloride was added dropwise to the obtained mixed liquid, followed by stirring for 30 minutes. Next, 11.6 g of triethylamine was added to the obtained mixed liquid, and the resultant product was stirred at −78° C. for 1 hour, and further stirred at 0° C. for 6 hours under ice-cooling. The obtained reaction liquid was diluted with chloroform, and the resultant product was washed with a 1 N aqueous sodium hydroxide solution. The obtained chloroform layer was washed with a saturated saline solution, dried over anhydrous sodium sulfate, and filtered. The obtained filtrate was concentrated under reduced pressure, whereby 6.7 g (oily matter) of the compound represented by Formula (9-18) was obtained.

1H NMR (CDCl₃)

δ ppm: 9.50 (1H, s), 7.51 (2H, d), 7.40 (2H, d), 3.16 (2H, s), 1.24 (6H, s)

Production of Compound Represented by Formula 7-18

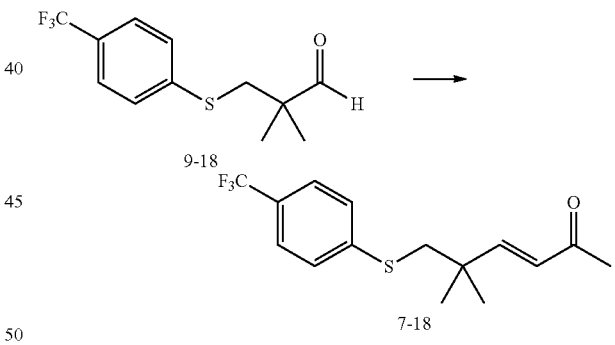

4.2 g of the compound represented by Formula (9-18) and 5.6 g of triphenylphosphineacetylmethylene were dissolved in 20 ml of xylene at room temperature. The obtained solution was heated under reflux for 8 hours. Next, xylene was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 4.1 g of the compound represented by Formula (7-18) was obtained.

1H NMR (CDCl₃)

δ ppm: 7.50 (2H, d), 7.38 (2H, d), 6.73 (1H, dd), 6.05 (1H, dd), 3.06 (2H, s), 2.17 (3H, s), 1.23 (6H, s)

Production of Compound Represented by Formula 1-21

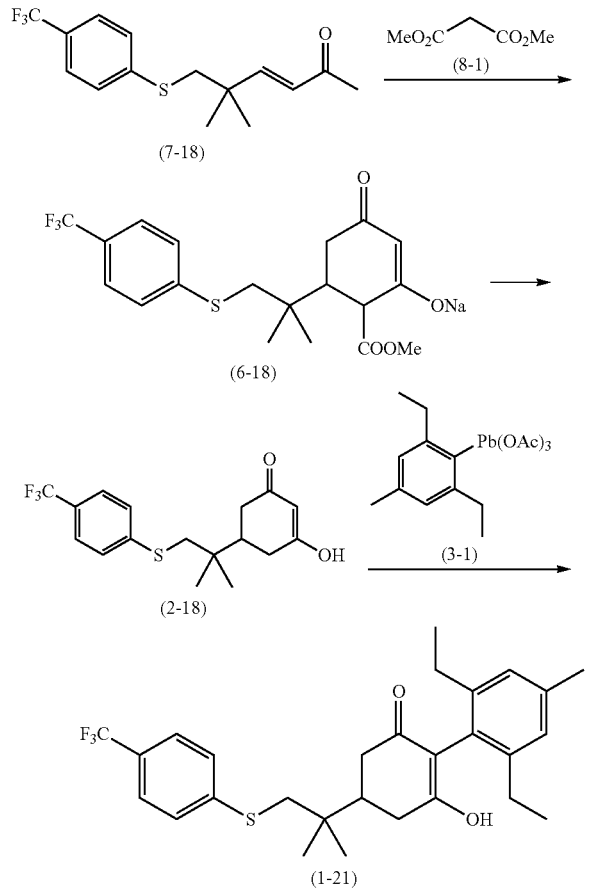

2.9 g of a 28% sodium methoxide methanol solution and 2.0 g of the compound represented by Formula (8-1) were dissolved in 35 ml of 1,4-dioxane at room temperature. The obtained solution was heated under reflux for 15 minutes. Next, the heating was stopped, and 4.1 g of the compound represented by Formula (7-18) was added to the obtained reaction mixture. Next, the obtained mixed liquid was heated under reflux for 1 hour. The obtained reaction liquid was cooled to room temperature, and concentrated under reduced pressure, and the precipitated crude crystals were thoroughly washed sequentially with tert-butyl methyl ether and hexane, whereby 5.7 g of the compound represented by Formula (6-18) was obtained.

Then, 5.7 g of the compound represented by Formula (6-18) was dissolved in 25 ml of water at room temperature. 1.05 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 970 mg of the compound represented by Formula (2-18) was obtained.

Then, 970 mg of the compound represented by Formula (2-18) and 1.7 g of dimethylaminopyridine were dissolved in a mixture of 7.5 ml of chloroform and 2 ml of toluene at room temperature in a nitrogen atmosphere. The obtained solution was stirred at room temperature for 15 minutes in a nitrogen atmosphere. Next, 1.5 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=1:4), whereby 300 mg (white solid) of the compound represented by Formula (1-21) was obtained.

1H NMR (CDCl$_3$)
δ
ppm: 7.52 (2H, d), 7.41 (2H, d), 6.99 (2H, s), 5.54 (1H, s), 3.04 (2H, dd), 2.67-2.24 (12H, m), 1.13-1.06 (12H, m)

Production Example 1-24

Production of Compound Represented by Formula (1-22)

Production of Compound Represented by Formula 13-2

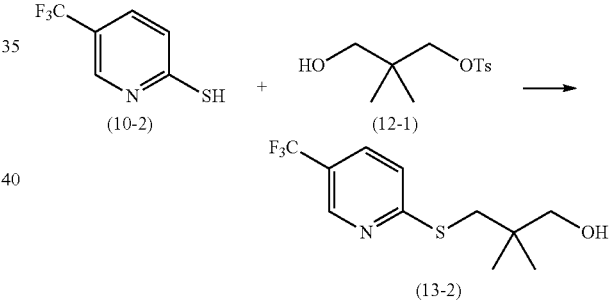

30 ml of anhydrous N,N-dimethylformamide was added to 1.55 g of a 60% sodium hydride in a nitrogen atmosphere. 7.2 g of the compound represented by Formula (10-2) was added dropwise to the obtained mixture under ice-cooling. After the obtained mixture was stirred for 25 minutes under ice-cooling, a solution of 8 g of the compound represented by Formula (12-1) in 15 ml of anhydrous N,N-dimethylformamide was added dropwise thereto, and after the obtained mixture was stirred at room temperature for 1 hour, the reaction temperature was raised to 90° C., and the mixture was stirred for 8 hours. The obtained reaction mixed liquid was extracted with tert-butyl methyl ether. The organic layers were combined, washed with water, dried over anhydrous sodium sulfate, and concentrated under reduced pressure, whereby a crude product was obtained. The crude product was subjected to silica gel column chromatography (eluent, ethyl acetate:hexane=1:3), whereby 6.7 g of the compound represented by Formula (13-2) was obtained.

1H NMR (CDCl$_3$)
δ
ppm: 8.61 (1H, s), 7.70-7.67 (1H, m), 7.36-7.32 (2H, m), 3.30 (2H, d), 3.23 (2H, d), 1.04 (6H, s)

Production of Compound Represented by Formula 9-19

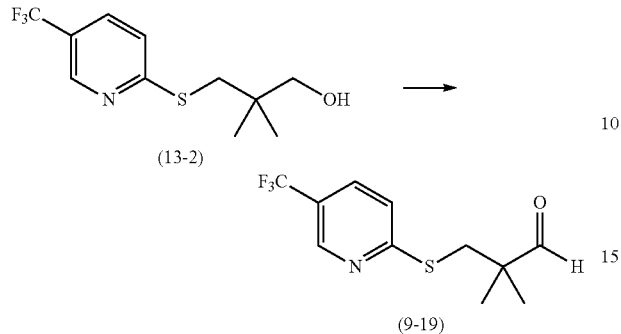

In a nitrogen atmosphere, a mixed liquid of 3.1 ml of oxalyl chloride and 120 ml of methylene chloride was cooled to −78° C., and 5.0 ml of dimethyl sulfoxide was slowly added dropwise thereto, followed by stirring for 10 minutes. Next, a solution of 6.7 g of the compound represented by Formula (13-2) in 50 ml of methylene chloride was added dropwise to the obtained mixed liquid, followed by stirring for 30 minutes. Next, 10.3 g of triethylamine was added to the obtained mixed liquid, and the resultant product was stirred at −78° C. for 1 hour, and stirred at 0° C. for 6 hours under ice-cooling. The obtained reaction liquid was diluted with chloroform, and the resultant product was washed with a 1 N aqueous sodium hydroxide solution.

The obtained chloroform layer was washed with a saturated saline solution, dried over anhydrous sodium sulfate, and filtered. The obtained filtrate was concentrated under reduced pressure, whereby 6.2 g of the compound represented by Formula (9-19) was obtained.

1H NMR (CDCl$_3$)
δ
ppm: 9.51 (1H, s), 8.64 (1H, s), 7.65 (1H, d), 7.27 (1H, d), 3.52 (2H, s), 1.24 (6H, s)

Production of Compound Represented by Formula 7-19

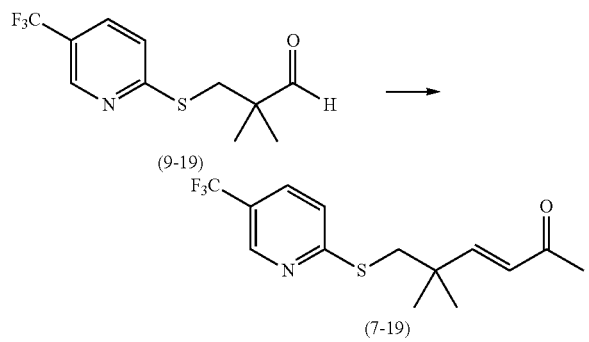

4.6 g of the compound represented by Formula (9-19) and 6.2 g of triphenylphosphineacetylmethylene were dissolved in 25 ml of xylene at room temperature. The obtained solution was heated under reflux for 8 hours. Next, xylene was removed from the obtained reaction liquid under reduced pressure. tert-Butyl methyl ether and hexane were added to the obtained residue. Then, the obtained mixture was filtered, and the obtained filtrate was concentrated under reduced pressure. The obtained oily matter was subjected to silica gel column chromatography (eluent, ethyl acetate:hexane=1:4), whereby 3.8 g of the compound represented by Formula (7-19) was obtained.

1H NMR (CDCl$_3$)
δ
ppm: 8.64 (1H, s), 7.64 (1H, dd), 7.27 (1H, d), 6.04 (1H, d), 6.04 (1H, d), 3.43 (2H, s), 2.17 (3H, s), 1.22 (6H, s)

Production of Compound Represented by Formula 1-22

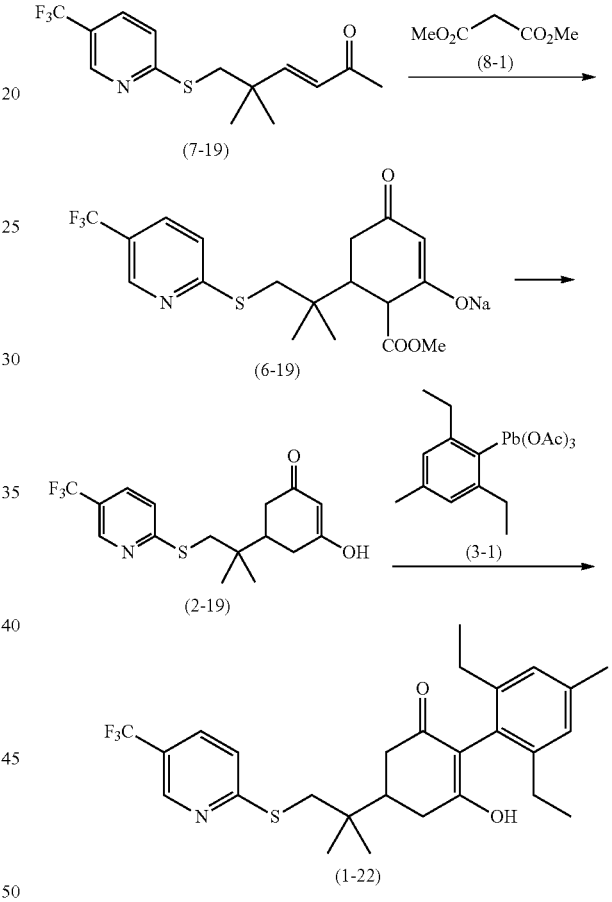

2.7 g of a 28% sodium methoxide methanol solution and 1.8 g of the compound represented by Formula (8-1) were dissolved in 35 ml of 1,4-dioxane at room temperature. The obtained solution was heated under reflux for 15 minutes. Next, the heating was stopped, and 3.8 g of the compound represented by Formula (7-19) was added to the obtained reaction mixture. Next, the obtained mixed liquid was heated under reflux for 1 hour. The obtained reaction liquid was cooled to room temperature, and concentrated under reduced pressure, and the precipitated crude crystals were thoroughly washed sequentially with tert-butyl methyl ether and hexane, whereby 5.3 g of the compound represented by Formula (6-19) was obtained.

Then, 5.3 g of the compound represented by Formula (6-19) was dissolved in 95 ml of water at room temperature. 4.0 g of anhydrous sodium carbonate was added to the obtained solution. The obtained solution was heated under reflux for 5 hours. The reaction liquid was cooled to room temperature, then, impurities were removed by washing with tert-butyl methyl ether, and the aqueous layer which had been acidified by adding 2 N hydrochloric acid was extracted with ethyl acetate. The ethyl acetate layer was concentrated under reduced pressure, and the obtained crystals were washed sequentially with tert-butyl methyl ether and hexane, whereby 2.8 g of the compound represented by Formula (2-19) was obtained.

Then, 600 mg of the compound represented by Formula (2-19) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.0 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=1:5), whereby 290 mg (white solid) of the compound represented by Formula (1-22) was obtained.

1H NMR (CDCl$_3$)

δ ppm: 8.65 (1H, s), 7.65 (1H, dd), 7.30 (1H, d), 6.98 (2H, s), 5.54 (1H, s), 3.41 (2H, dd), 2.78-2.51 (3H, m), 2.48-2.26 (9H, m), 1.18-1.00 (12H, m)

Production Example 1-25

Production of Compound Represented by Formula (1-40)

Production of Compound Represented by Formula 3-3

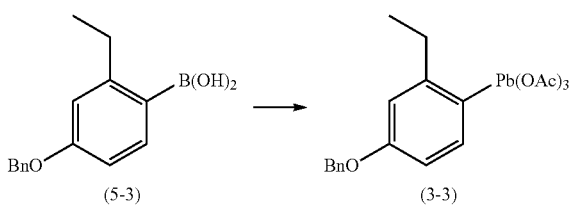

10 g of lead tetraacetate, 310 mg of mercury acetate, and 5 g of the compound represented by Formula (5-3) were dissolved in 40 ml of chloroform at room temperature in a nitrogen atmosphere. The obtained solution was stirred at room temperature for 15 minutes in a nitrogen atmosphere. Next, the reaction liquid was stirred at 40° C. for 4 hours in a nitrogen atmosphere. The reaction liquid was cooled to room temperature, and filtered using Celite (registered trademark). The obtained filtrate was concentrated under reduced pressure, whereby a red oily matter was obtained. Hexane was added to the obtained oily matter, and the resultant product was concentrated under reduced pressure, whereby 10.2 g (red solid) of the compound represented by Formula (3-3) was obtained.

1H NMR (CDCl$_3$)

δ ppm: 7.61-7.59 (1H, m), 7.41-7.34 (5H, m), 7.00-6.97 (2H, m), 5.08 (2H, s), 2.83 (2H, q), 2.09 (9H, s), 1.29 (3H, t)

Production of Compound Represented by Formula 34-1

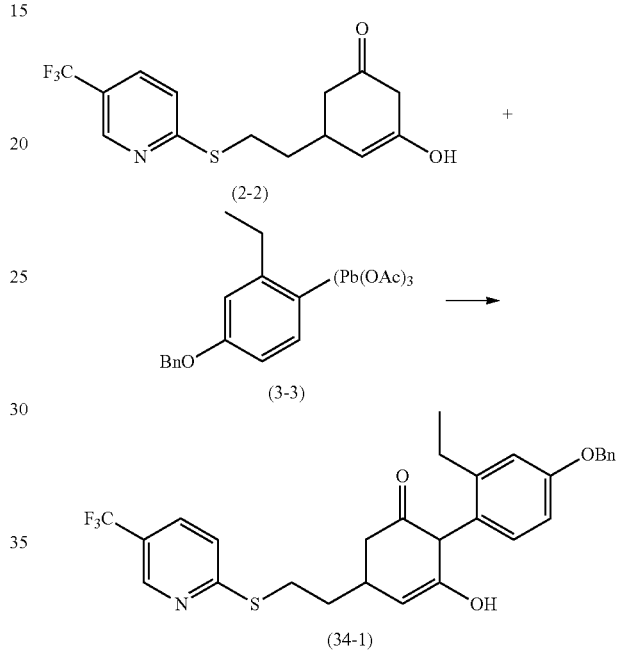

540 mg of the compound represented by Formula (2-2) and 1.05 g of dimethylaminopyridine were dissolved in a mixture of 4.8 ml of chloroform and 1.2 ml of toluene at room temperature in a nitrogen atmosphere. The obtained solution was stirred at room temperature for 15 minutes in a nitrogen atmosphere. Next, 1.1 g of the compound represented by Formula (3-3) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=1:2), whereby 386 mg of the compound represented by Formula (34-1) was obtained.

1H NMR (CDCl$_3$)

δ ppm: 8.67 (1H, s), 7.67 (1H, dd), 7.46-7.26 (6H, m), 6.98-6.92 (2H, m), 6.86 (1H, dt), 5.74 (1H, s), 5.08 (2H, s), 3.30 (2H, t), 2.79-2.67 (2H, m), 2.50-2.24 (5H, m), 1.93-1.87 (2H, m), 1.08 (3H, dt)

Production of Compound Represented by Formula 1-40

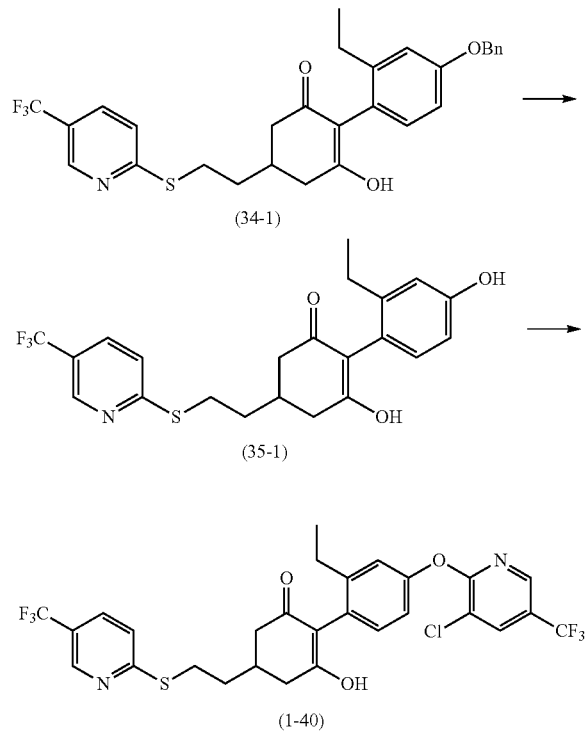

At room temperature, 300 mg of the compound represented by Formula (34-1) was dissolved in 2.2 ml of acetic acid, and 0.7 ml of 47% hydrobromic acid was added dropwise to the obtained mixed liquid. The obtained reaction liquid was heated to 100° C., followed by stirring for 30 minutes. 10 ml of ice water was added to the reaction liquid, and the resultant product was extracted by ethyl acetate. The obtained ethyl acetate layer was washed with water, dried over anhydrous sodium sulfate, and filtered. The obtained filtrate was concentrated under reduced pressure, whereby 240 mg of the compound represented by Formula (35-1) was obtained.

Then, 240 mg of the compound represented by Formula (35-1), 200 mg of cesium carbonate, and 118 mg of 2,3-dichloro-5-trifluoromethylpyridine were dissolved in 2 ml of N,N-dimethylformamide at room temperature. The obtained reaction liquid was heated to 70° C., followed by stirring for 2 hours. The obtained reaction liquid was extracted with ethyl acetate, and the obtained ethyl acetate layer was washed with a saturated saline solution, dried over anhydrous sodium sulfate, and filtered. The obtained filtrate was concentrated under reduced pressure, and the resultant product was subjected to silica gel column chromatography (eluent, ethyl acetate:hexane=1:2), whereby 80 mg of the compound represented by Formula (1-40) was obtained.

1H NMR (CDCl$_3$)

δ ppm: 8.68 (1H, s), 8.24 (1H, dd), 8.00 (1H, d), 7.67 (1H, dd), 7.28-7.26 (1H, m), 7.14-7.03 (3H, m), 6.33 (1H, s), 3.31 (2H, t), 2.79-2.68 (2H, m), 2.52-2.26 (5H, m), 1.94-1.89 (2H, m), 1.10 (3H, dt)

Production Example 1-26

Production of Compound Represented by Formula (1-75)

Production of Compound Represented by Formula 7-20

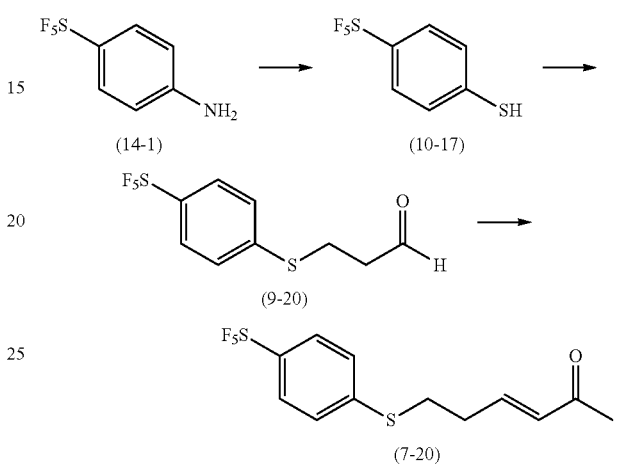

10 g of the compound represented by Formula (7-20) was dissolved in 33 ml of acetic acid at room temperature. 100 ml of 35% sulfuric acid was added to the obtained mixed liquid. Next, the obtained reaction mixed liquid was cooled to 0° C., and a mixture of 3.3 g of sodium nitrite and 25 ml of water was added dropwise thereto, followed by stirring at 0° C. for 10 minutes.

Next, the obtained reaction liquid was added dropwise to a mixture obtained by dissolving 15 g of sodium sulfide, 2 g of sulfur, and 3.3 g of sodium hydroxide in 100 ml of water at 60° C., followed by stirring for 30 minutes. The reaction liquid was cooled to room temperature, extracted with tert-butyl methyl ether, washed with 10% hydrochloric acid water, dried over anhydrous sodium sulfate, and filtered. The obtained filtrate was dried under reduced pressure, and dissolved in 300 ml of diethyl ether, and 1.8 g of lithium aluminum hydride was added thereto at 0° C. in a nitrogen atmosphere, followed by stirring at room temperature for 1 hour. 500 ml of 10% hydrochloric acid water was added to the obtained reaction mixed liquid, and the resultant product was extracted with diethyl ether. The obtained organic layer was washed with a saturated saline solution, dried over anhydrous sodium sulfate, and filtered. The obtained filtrate was concentrated under reduced pressure, whereby a crude product of the compound represented by Formula (10-17) was obtained. The obtained crude product was subjected to silica gel column chromatography (eluent, ethyl acetate:hexane=1:4), whereby 3.1 g of the compound represented by Formula (10-17) was obtained.

Next, 3.0 g of the compound represented by Formula (10-17) and 10 ml of tetrahydrofuran were mixed at room temperature, followed by stirring, then, the obtained mixture was cooled to 0° C., and 1.05 g of acrolein and 0.1 g of triethylamine were added dropwise thereto. The obtained mixture was stirred for 2 hours under ice-cooling. Next, water was added to the obtained mixture, and the resultant product was extracted with tert-butyl methyl ether. The organic layer was washed with water, dried over anhydrous sodium sulfate, and concentrated under reduced pressure, whereby 1.2 g of the compound represented by Formula (9-20) was obtained.

Then, 1.2 g of the compound represented by Formula (9-20) and 1.4 g of triphenylphosphineacetylmethylene were dissolved in 5 ml of chloroform at room temperature. The obtained solution was stirred at 0° C. for 8 hours. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 340 mg of the compound represented by Formula (7-20) was obtained.

1H NMR (CDCl$_3$)

δ ppm: 7.66 (2H, d), 7.32 (2H, d), 6.78 (1H, dt), 6.14 (1H, d), 3.12 (2H, t), 2.61 (2H, q), 2.25 (3H, s)

Production of Compound Represented by Formula 6-20

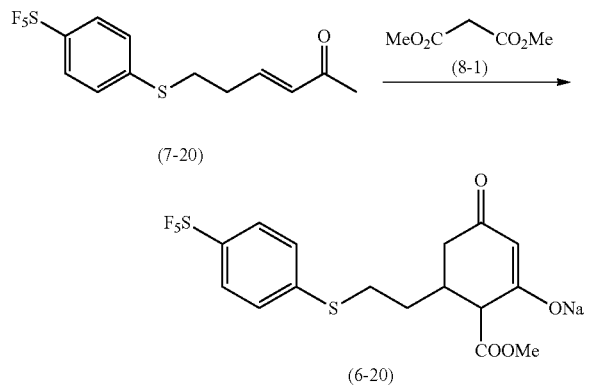

(7-20)

(6-20)

220 g of a 28% sodium methoxide methanol solution and 150 mg of the compound represented by Formula (8-1) were dissolved in 4 ml of tetrahydrofuran at room temperature. The obtained solution was heated under reflux for 15 minutes. Next, the heating was stopped, and 340 mg of the compound represented by Formula (7-20) was added to the obtained reaction mixture. Next, the obtained mixed liquid was heated under reflux for 30 minutes. After the obtained reaction liquid was cooled to 0° C., hexane was added thereto, and the precipitated crystals were collected by filtration, and washed sequentially with tert-butyl methyl ether and hexane, whereby 460 mg of the compound represented by Formula (6-20) was obtained.

1H NMR (d-DMSO)

δ ppm: 7.80 (2H, d), 7.44 (2H, d), 4.39 (1H, s), 3.65-3.48 (4H, m), 3.17-3.10 (1H, m), 2.99-2.91 (1H, m), 2.83 (1H, d), 2.32-2.25 (1H, m), 2.15-2.03 (1H, m), 1.85-1.74 (1H, m), 1.53-1.47 (1H, m)

Production of Compound Represented by Formula 1-75

(6-20)

(2-20)

(1-75)

460 mg of the compound represented by Formula (6-20) was dissolved in 10 ml of water at room temperature. 323 mg of anhydrous sodium carbonate was added to the obtained solution. The obtained solution was heated under reflux for 5 hours. The reaction liquid was cooled to room temperature, and washed with tert-butyl methyl ether, and after 2 N hydrochloric acid was added to the aqueous layer, the resultant product was extracted with ethyl acetate. The ethyl acetate layer was concentrated under reduced pressure, and the obtained crystals were washed sequentially with tert-butyl methyl ether and hexane, whereby 400 mg of the compound represented by Formula (2-20) was obtained.

Then, 400 mg of the compound represented by Formula (2-20) and 620 mg of dimethylaminopyridine were dissolved in a mixture of 3 ml of chloroform and 1 ml of toluene at room temperature in a nitrogen atmosphere. The obtained solution was stirred at room temperature for 15 minutes in a nitrogen atmosphere. Next, 600 mg of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:3), whereby 150 mg of the compound represented by Formula (1-75) was obtained.

1H NMR (CDCl$_3$)

δ ppm: 7.66 (2H, d), 7.32 (2H, d), 6.98 (2H, s), 5.57 (1H, s), 3.13-3.01 (2H, m), 2.77-2.68 (2H, m), 2.49-2.22 (10H, m), 1.88 (2H, q), 1.06 (6H, ddd)

Production Example 1-27

Production of Compound Represented by Formula (1-23)

Production of Compound Represented by Formula 21-1

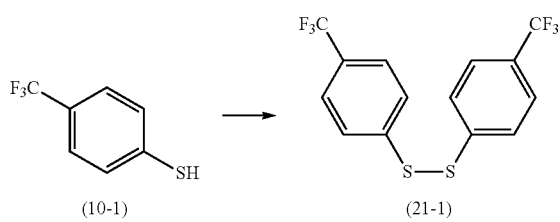 [SMILES: FC(F)(F)c1ccc(S)cc1 ; FC(F)(F)c1ccc(SSc2ccc(C(F)(F)F)cc2)cc1]

10 g of the compound represented by Formula (10-1) was dissolved in 50 ml of dimethylformamide at room temperature. 5.7 g of triethylamine was added to the obtained mixed liquid at room temperature, and the resultant product was stirred for 6 hours while applying ultrasonic waves. The obtained reaction mixed liquid was extracted with tert-methyl ethyl ether, and the obtained organic layer was washed with water, dried over anhydrous sodium sulfate, and filtered. The obtained filtrate was concentrated under reduced pressure, whereby 9.3 g of the compound represented by Formula (21-1) was obtained. (colorless solid).

1H NMR (CDCl$_3$)

δ ppm: 7.60-7.53 (8H, m)

Production of Compound Represented by Formula 13-3

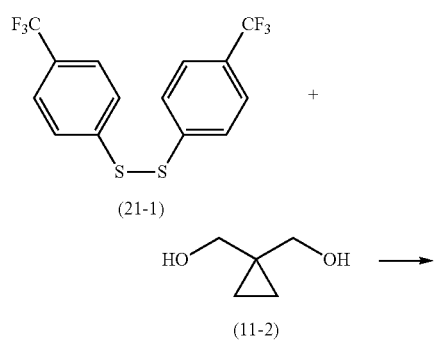

5 g of the compound represented by Formula (11-2) and 9.3 g of the compound represented by Formula (21-1) were dissolved in 250 ml of tetrahydrofuran. 5.8 g of tributylphosphine was added dropwise to the obtained mixed liquid at room temperature in a nitrogen atmosphere, followed by stirring for 2 hours. The obtained reaction mixed liquid was concentrated under reduced pressure, and the obtained crude product was subjected to silica gel column chromatography (eluent, ethyl acetate:hexane=1:4), whereby 4.5 g of the compound represented by Formula (13-3) was obtained. (colorless solid).

1H NMR (CDCl$_3$)

δ ppm: 7.50 (2H, d), 7.41 (2H, d), 3.58 (2H, s), 3.17 (2H, s), 0.58 (4H, s)

Production of Compound Represented by Formula 7-21

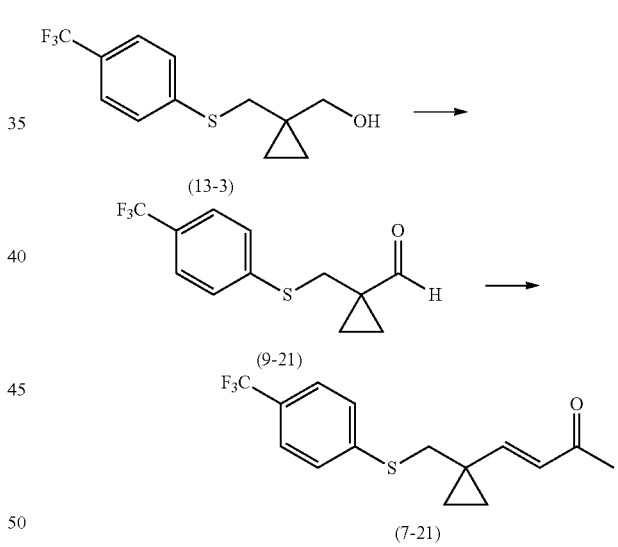

In a nitrogen atmosphere, a mixed liquid of 2.5 g of oxalyl chloride and 45 ml of methylene chloride was cooled to −78° C., and a solution of 2.7 g of dimethyl sulfoxide in 20 ml of methylene chloride was added dropwise thereto, followed by stirring for 10 minutes. Next, a solution of 4.5 g of the compound represented by Formula (13-3) in 5 ml of methylene chloride was added dropwise to the obtained mixed liquid, followed by stirring for 30 minutes. Next, 8.8 g of triethylamine was added to the obtained mixed liquid, and the temperature was raised to room temperature, followed by stirring for 3 hours. The obtained reaction liquid was poured into 60 ml of 1 N hydrochloric acid water, and the resultant product was extracted with chloroform. The obtained organic layer was dried over anhydrous sodium sulfate, and filtered. The obtained filtrate was concentrated under reduced pressure, whereby 4.5 g of a crude product of the compound represented by Formula (9-21) was obtained.

Then, 4.5 g of the crude product of the compound represented by Formula (9-21) and 6.1 g of triphenylphosphineacetylmethylene were dissolved in 45 ml of xylene at room temperature. The obtained reaction mixed solution was heated under reflux for 8 hours. Next, xylene was removed from the obtained reaction liquid under reduced pressure. tert-Butyl methyl ether and hexane were added to the obtained residue. Then, the obtained mixture was filtered, and the obtained filtrate was concentrated under reduced pressure. The obtained oily matter was subjected to silica gel column chromatography (eluent, ethyl acetate:hexane=1:4), whereby 3.8 g of the compound represented by Formula (7-21) was obtained.

1H NMR (CDCl$_3$)

δ ppm: 7.52 (2H, d), 7.35 (2H, d), 6.49 (1H, d), 6.17 (1H, d), 3.19 (2H, s), 2.22 (3H, s), 1.10-1.00 (4H, m)

Production of Compound Represented by Formula 6-21

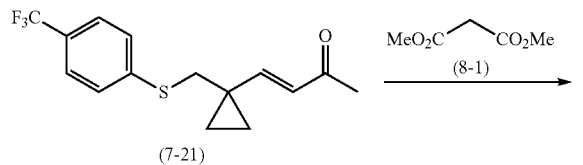

2.7 g of a 28% sodiummethoxide methanol solution and 1.8 g of the compound represented by Formula (8-1) were dissolved in 30 ml of 1,4-dioxane at room temperature. The obtained solution was heated under reflux for 15 minutes. Next, the heating was stopped, and 3.8 g of the compound represented by Formula (7-21) was added to the obtained reaction mixture. Next, the obtained mixed liquid was heated under reflux for 1 hour. After the obtained reaction liquid was cooled to 0° C., hexane was added thereto, and the precipitated crystals were filtered, and washed sequentially with tert-butyl methyl ether and hexane, whereby 4.5 g of the compound represented by Formula (6-21) was obtained.

1H NMR (CDCl$_3$)

δ ppm: 7.62 (2H, d), 7.45 (2H, d), 4.42 (1H, s), 3.57 (3H, s), 3.39-3.35 (1H, m), 3.23 (1H, d), 3.07 (1H, d), 2.32 (1H, t), 1.93 (1H, dd), 1.76 (1H, td), 0.46-0.34 (4H, m)

Production of Compound Represented by Formula 1-23

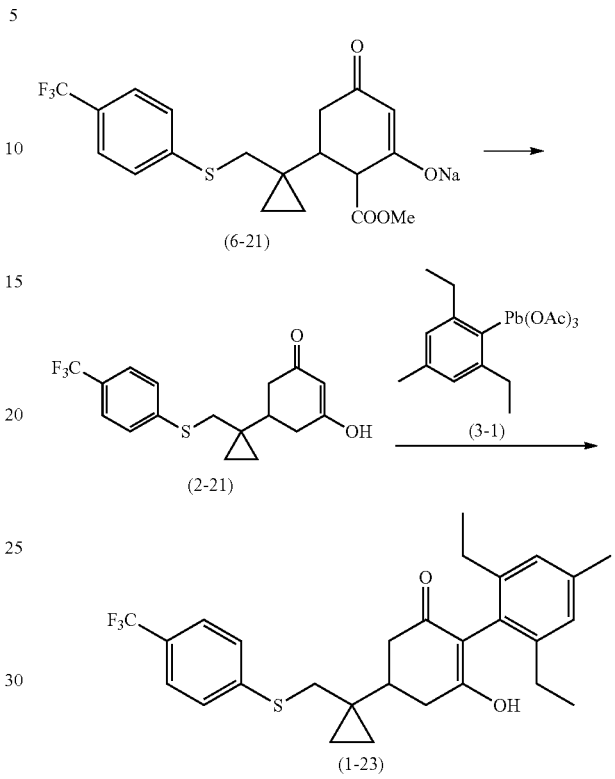

4.5 g of the compound represented by Formula (6-21) was dissolved in 100 ml of water at room temperature. 3.37 g of anhydrous sodium carbonate was added to the obtained solution. The obtained solution was heated under reflux for 5 hours. The reaction liquid was cooled to room temperature, and washed with tert-butyl methyl ether, and after 2 N hydrochloric acid was added to the aqueous layer, the resultant product was extracted with ethyl acetate. The ethyl acetate layer was dried over anhydrous sodium sulfate, filtered, and concentrated under reduced pressure, whereby 3.4 g of a crude product of the compound represented by Formula (2-21) was obtained.

Then, 1.75 g of the crude product of the compound represented by Formula (2-21) and 3.13 g of dimethylaminopyridine were dissolved in a mixture of 14 ml of chloroform and 4 ml of toluene at room temperature in a nitrogen atmosphere. The obtained solution was stirred at room temperature for 15 minutes in a nitrogen atmosphere. Next, 3 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 1.9 g of the compound represented by Formula (1-23) was obtained.

1H NMR (CDCl$_3$)

δ ppm: 7.52 (2H, d), 7.35 (2H, d), 6.97 (2H, s), 5.99 (1H, s), 3.12 (2H, dd), 2.65-2.58 (3H, m), 2.46-2.13 (9H, m), 1.07 (6H, t), 0.64 (4H, s)

Production Example 1-28

Production of Compound Represented by Formula (1-36)

Production of Compound Represented by Formula 27-1

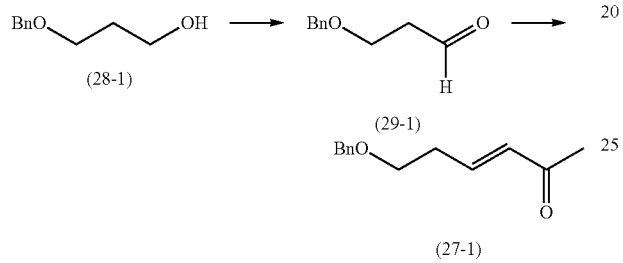

In a nitrogen atmosphere, a mixed liquid of 8.6 g of oxalyl chloride and 150 ml of methylene chloride was cooled to −78° C., and a solution of 9.4 g of dimethyl sulfoxide in 60 ml of methylene chloride was added dropwise to the obtained mixed liquid, followed by stirring for 10 minutes. Next, a solution of 10 g of the compound represented by Formula (28-1) in 20 ml of methylene chloride was added dropwise to the obtained mixed liquid, followed by stirring for 30 minutes. Next, 30.4 g of triethylamine was added to the obtained mixed liquid, and the temperature was raised to room temperature, followed by stirring for 1 hour. The obtained reaction liquid was poured into 200 ml of 1 N hydrochloric acid water, and the resultant product was extracted with chloroform. The obtained organic layer was dried over anhydrous sodium sulfate, and filtered.

The obtained filtrate was concentrated under reduced pressure, whereby 9.8 g of a crude product of the compound represented by Formula (29-1) was obtained.

Then, 9.8 g of the crude product of the compound represented by Formula (29-1) and 22.6 g of 1-triphenylphosphoranylidene-2-propanone were dissolved in 80 ml of chloroform at room temperature. The obtained reaction mixed solution was heated under reflux for 8 hours. Next, chloroform was removed from the obtained reaction liquid under reduced pressure. tert-Butyl methyl ether and hexane were added to the obtained residue. Then, the obtained mixture was filtered, and the obtained filtrate was concentrated under reduced pressure. The obtained oily matter was subjected to silica gel column chromatography (eluent, ethyl acetate:hexane=1:4), whereby 7.4 g of the compound represented by Formula (27-1) was obtained (colorless oily matter).

1H NMR (CDCl$_3$)

δ ppm: 7.38-7.26 (5H, m), 6.82 (1H, dt), 6.13 (1H, dt), 4.51 (2H, s), 3.63-3.57 (2H, m), 2.53 (2H, ddd), 2.24 (3H, s)

Production of Compound Represented by Formula 25-1

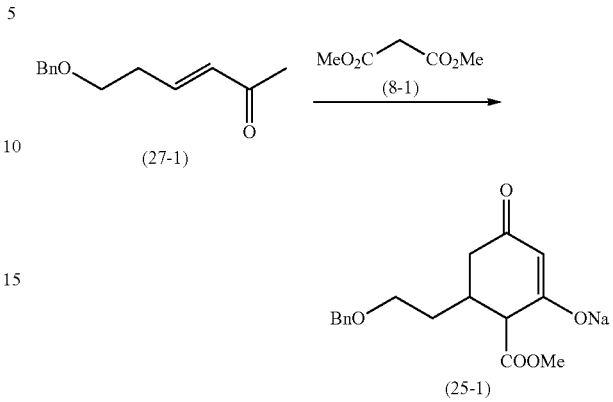

7.7 g of a 28% sodium methoxide methanol solution and 5.3 g of the compound represented by Formula (8-1) were dissolved in 100 ml of tetrahydrofuran at room temperature. The obtained solution was heated under reflux for 15 minutes. Next, the heating was stopped, and 7.4 g of the compound represented by Formula (27-1) was added to the obtained reaction mixture. Next, the obtained mixed liquid was heated under reflux for 1 hour. After the obtained reaction liquid was cooled to 0° C., hexane was added thereto, and the precipitated crystals were filtered, and washed sequentially with tert-butyl methyl ether and hexane, whereby 7.2 g of the compound represented by Formula (25-1) was obtained.

1H NMR (CDCl$_3$)

δ ppm: 7.37-7.26 (5H, m), 4.50-4.38 (3H, m), 3.59 (3H, s), 3.43-3.40 (3H, m), 2.84 (1H, d), 2.32-2.24 (1H, m), 2.08 (1H, dd), 1.76 (1H, dd), 1.57-1.36 (2H, m)

Production of Compound Represented by Formula 24-1

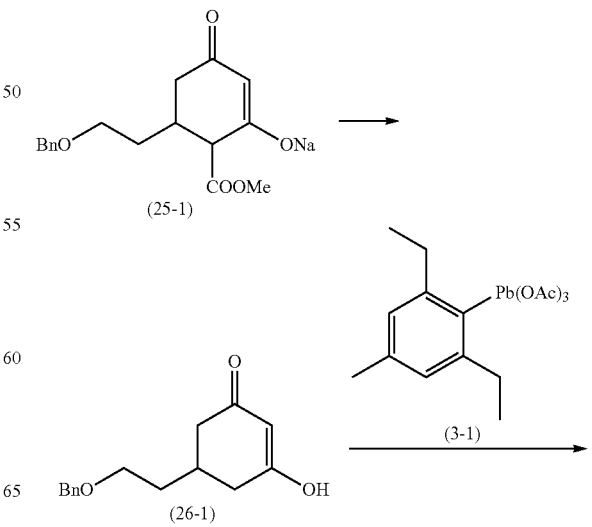

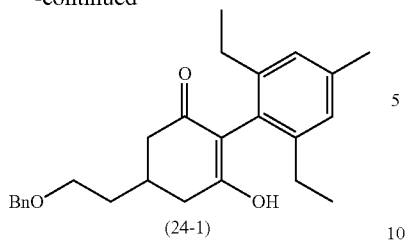
(24-1)

3 g of the compound represented by Formula (25-1) was dissolved in 90 ml of water at room temperature. 2.9 g of anhydrous sodium carbonate was added to the obtained solution. The obtained solution was heated under reflux for 5 hours. The reaction liquid was cooled to room temperature, and washed with tert-butyl methyl ether, and after 2 N hydrochloric acid was added to the aqueous layer, the resultant product was extracted with ethyl acetate. The ethyl acetate layer was dried over anhydrous sodium sulfate, filtered, and concentrated under reduced pressure, whereby 2 g of a crude product of the compound represented by Formula (26-1) was obtained (yellow solid).

Then, 730 mg of the crude product of the compound represented by Formula (26-1) and 1.8 g of dimethylaminopyridine were dissolved in a mixture of 8 ml of chloroform and 2 ml of toluene at room temperature in a nitrogen atmosphere. The obtained solution was stirred at room temperature for 15 minutes in a nitrogen atmosphere. Next, 1.7 g of the compound represented by Formula (3-1) was added to the obtained solution in a nitrogen atmosphere. The obtained mixture was stirred at 75° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=1:2), whereby 890 mg of the compound represented by Formula (24-1) was obtained.

1H NMR (CDCl$_3$)

δ ppm: 7.39-7.27 (5H, m), 6.97 (2H, s), 5.70 (1H, s), 4.53 (2H, s), 3.62-3.53 (2H, m), 2.69-2.62 (2H, m), 2.52-2.22 (10H, m), 1.83-1.74 (2H, m), 1.08 (6H, ddd)

Production of Compound Represented by Formula 23-1

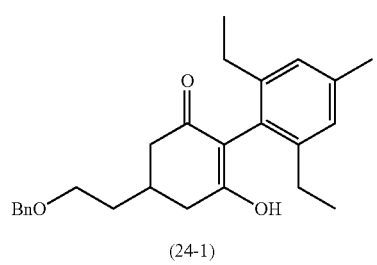
(24-1)

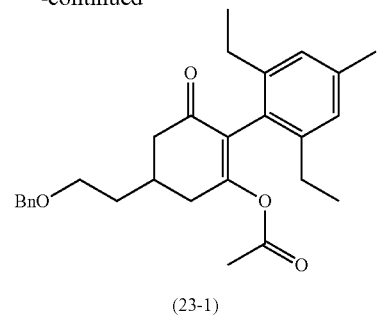
(23-1)

A solution of 1.8 g of triethylamine in 30 ml of anhydrous tetrahydrofuran was added to 4.5 g of the compound represented by Formula (24-1). A solution of 1.8 g of acetyl chloride in 10 ml of anhydrous tetrahydrofuran was added to the obtained mixture under ice-cooling. The obtained mixture was stirred for 12 hours at room temperature. Water was added to the reaction mixture, and the resultant product was extracted with chloroform. The extracted chloroform layer was dried over anhydrous sodium sulfate, and concentrated under reduced pressure, and the resultant product was subjected to silica gel column chromatography (eluent, ethyl acetate:hexane=1:4), whereby 3.7 g of the compound represented by Formula (23-1) was obtained (colorless oily matter).

1H NMR (CDCl$_3$)

δ ppm: 7.35-7.24 (5H, m), 6.88 (2H, s), 4.50 (2H, dd), 3.56 (2H, t), 2.72-2.28 (12H, m), 1.86-1.73 (5H, m), 1.12-1.03 (6H, m)

Production of Compound Represented by Formula 23-1

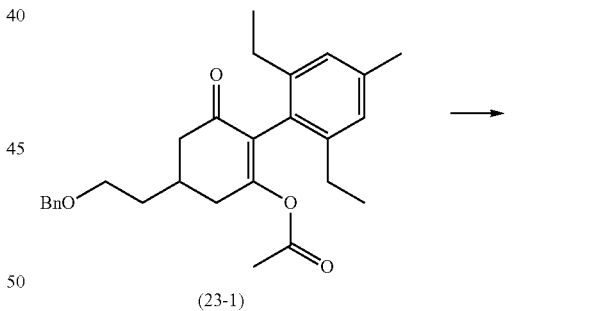
(23-1)

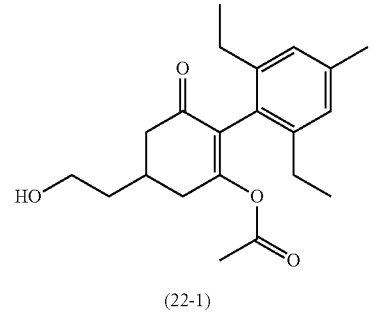
(22-1)

3.7 g of the compound represented by Formula (23-1) was dissolved in 150 ml of ethyl acetate. 1.5 g of 10% palladium-carbon was added to the obtained mixed liquid, followed by

149 stirring at 35° C. for 4 hours in a hydrogen atmosphere. The obtained reaction mixed liquid was filtered using Celite (registered trademark), and the obtained filtrate was concentrated under reduced pressure, whereby 2.4 g of the compound represented by Formula (22-1) was obtained (colorless solid).

1H NMR (CDCl₃)

δ ppm: 6.89 (2H, s), 3.79 (2H, d), 2.79-2.69 (3H, m), 2.60-2.53 (1H, m), 2.42-2.25 (7H, m), 1.88 (3H, s), 1.82-1.73 (2H, m), 1.63-1.61 (2H, m), 1.07 (6H, q)

Production of Compound Represented by Formula 1-36

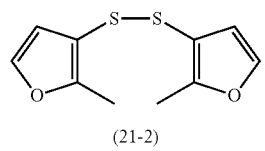

(21-2)

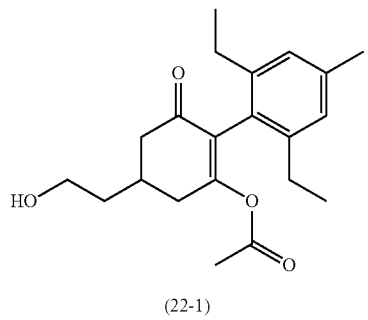

(22-1)

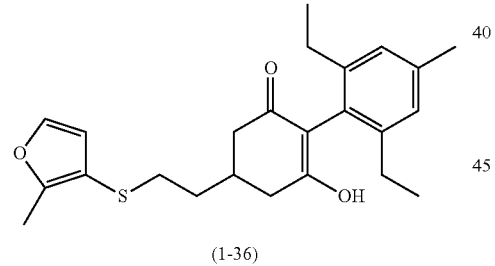

(1-36)

344 mg of the compound represented by Formula (22-1) and 227 mg of the compound represented by Formula (21-2) were dissolved in 5 ml of tetrahydrofuran. 223 mg of tributylphosphine was added dropwise to the obtained mixed liquid at room temperature in a nitrogen atmosphere, followed by stirring for 2 hours. The obtained reaction mixed liquid was concentrated under reduced pressure, and the obtained crude product was subjected to silica gel column chromatography (eluent, ethyl acetate:hexane=1:4), whereby 400 mg of the compound represented by Formula (1-36) was obtained. (colorless oily matter).

1H NMR (CDCl₃)

δ ppm: 7.29 (1H, d), 6.96 (2H, s), 6.34 (1H, d), 5.88 (1H, s), 2.71-2.60 (4H, m), 2.44-2.16 (13H, m), 1.70 (2H, dd), 1.10-1.01 (6H, m)

150

Production Example 1-29

Production of Compound Represented by Formula (1-33)

Production of Compound Represented by Formula 1-33

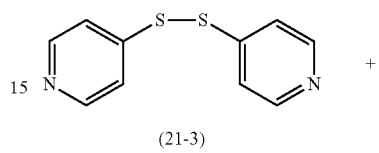

(21-3)

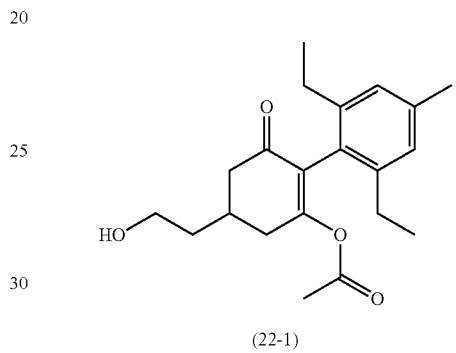

(22-1)

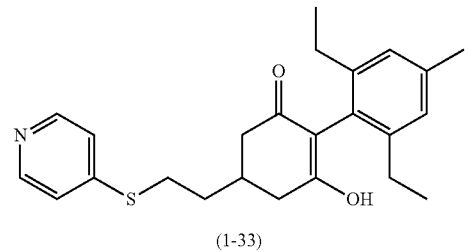

(1-33)

344 mg of the compound represented by Formula (22-1) and 121 mg of the compound represented by Formula (21-3) were dissolved in 5 ml of tetrahydrofuran. 121 mg of tributylphosphine was added dropwise to the obtained mixed liquid at room temperature in a nitrogen atmosphere, followed by stirring for 2 hours. The obtained reaction mixed liquid was concentrated under reduced pressure, and the obtained crude product was subjected to silica gel column chromatography (eluent, ethyl acetate:hexane=1:2), whereby 80 mg of the compound represented by Formula (1-33) was obtained.

1H NMR (CDCl₃)

δ ppm: 8.41 (2H, dd), 7.13 (2H, dd), 6.90 (1H, s), 3.08 (2H, t), 2.82-2.67 (3H, m), 2.58-2.24 (9H, m), 1.95-1.84 (3H, m), 1.13-1.03 (6H, m)

Production Example 1-30
Production of Compound Represented by Formula (1-76)
Production of Compound Represented by Formula 1-76

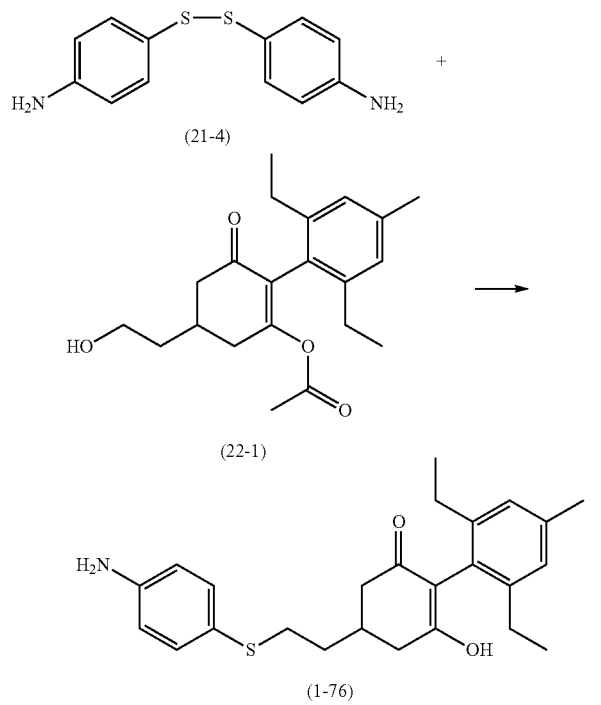

172 mg of the compound represented by Formula (22-1) and 124 mg of the compound represented by Formula (21-4) were dissolved in 2.5 ml of tetrahydrofuran. 0.14 ml of tributylphosphine was added dropwise to the obtained mixed liquid at room temperature in a nitrogen atmosphere, followed by stirring for 2 hours. The obtained reaction mixed liquid was concentrated under reduced pressure, and the obtained crude product was subjected to silica gel column chromatography (eluent, ethyl acetate:hexane=1:3→1:2→1:1), whereby 160 mg of the compound represented by Formula (1-76) was obtained.

1H NMR (CDCl$_3$)
δ
ppm: 7.26-7.22 (2H, m), 6.97 (2H, s), 6.61 (2H, dt), 2.86-2.82 (2H, m), 2.67-2.59 (2H, m), 2.44-2.18 (10H, m), 1.73 (2H, dd), 1.11-1.02 (6H, m)

Production Example 1-31
Production of Compound Represented by Formula (1-77)
Production of Compound Represented by Formula 1-77

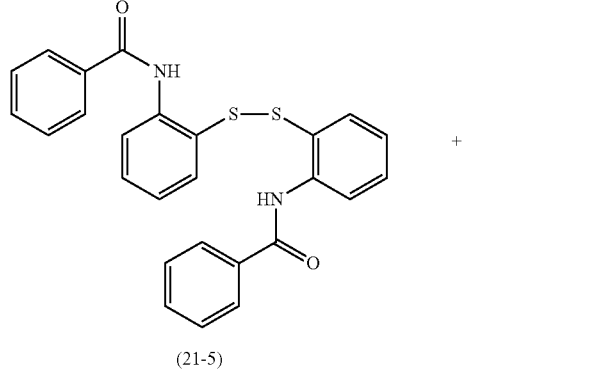

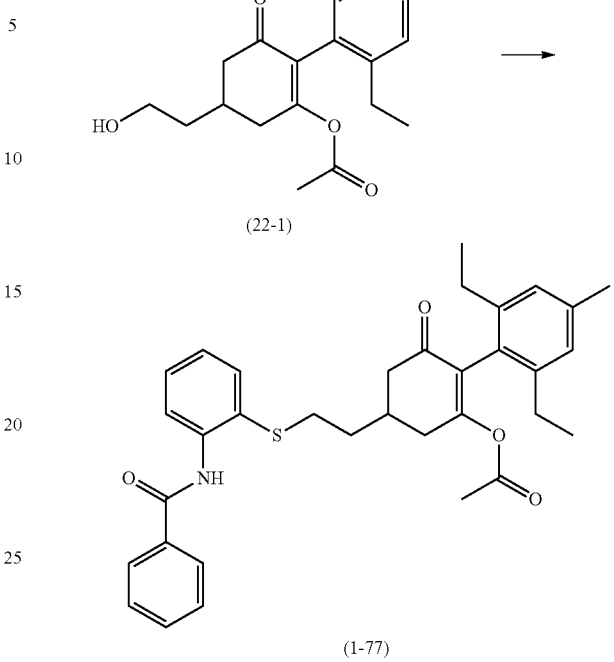

344 mg of the compound represented by Formula (22-1) and 456 mg of the compound represented by Formula (21-5) were dissolved in 5 ml of tetrahydrofuran. 111 mg of tributylphosphine was added dropwise to the obtained mixed liquid at room temperature in a nitrogen atmosphere, followed by stirring for 2 hours. The obtained reaction mixed liquid was concentrated under reduced pressure, and the obtained crude product was subjected to silica gel column chromatography (eluent, ethyl acetate:hexane=1:4→1:2), whereby 210 mg of the compound represented by Formula (1-77) was obtained.

1H NMR (CDCl$_3$)
δ
ppm: 9.40 (1H, s), 8.61 (1H, dd), 7.98-7.95 (2H, m), 7.61-7.51 (4H, m), 7.42 (1H, td), 7.11 (1H, td), 6.87 (2H, s), 2.87-2.83 (2H, m), 2.68-2.54 (3H, m), 2.46-2.22 (9H, m), 1.85 (3H, s), 1.79-1.73 (2H, m), 1.04 (6H, dt)

Production Example 1-32
Production of Compound Represented by Formula (1-78)
Production of Compound Represented by Formula 1-78

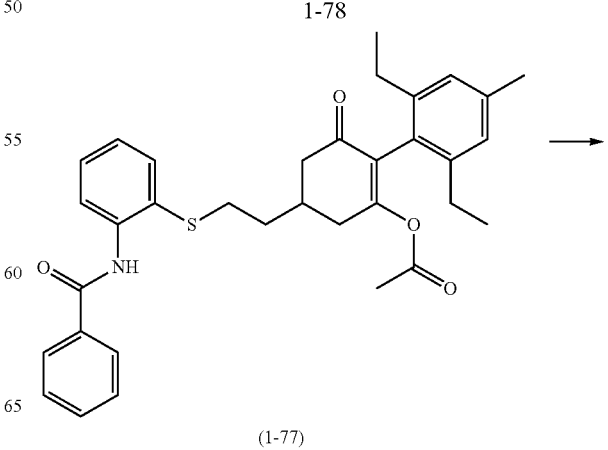

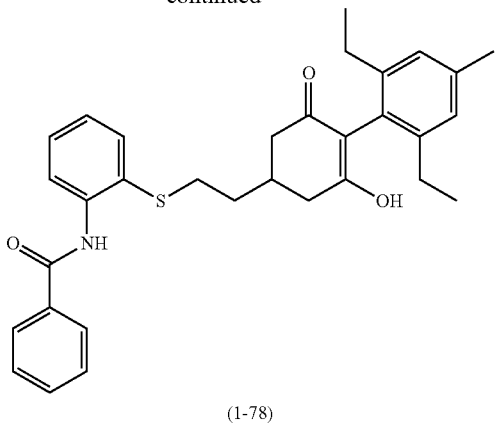

(1-78)

At room temperature, 150 mg of the compound represented by Formula (1-77) was dissolved in 20 ml of methanol, and 100 mg of potassium carbonate was added thereto, followed by stirring for 1 hour. The obtained reaction liquid was concentrated under reduced pressure, whereby a crude product of the compound represented by Formula (1-78) was obtained. Next, the obtained crude product was subjected to silica gel column chromatography (eluent, ethyl acetate:hexane=1:4), whereby 160 mg of the compound represented by Formula (1-78) was obtained.

1H NMR (CDCl$_3$)
δ
ppm: 9.39 (1H, s), 8.59 (1H, dd, 7.95 (2H, m), 7.60-7.51 (4H, m), 7.44-7.39 (1H, m), 7.11 (1H, td), 6.94 (2H, s), 5.91 (1H, s), 2.88-2.83 (2H, m), 2.60-2.57 (2H, m), 2.32-2.15 (9H, m), 1.76-1.71 (2H, m), 1.06-0.97 (6H, dt)

Production Example 1-33

Production of Compound Represented by Formula (1-97)

Production of Compound Represented by Formula 31-1

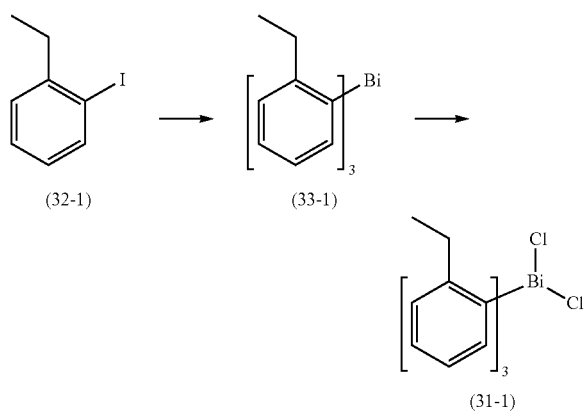

16 ml of n-butyllithium (1.6M hexane solution) was added to 3.2 ml of tetramethylenediamine at 0° C. in a nitrogen atmosphere, followed by stirring for 10 minutes. Next, 5 g of the compound represented by Formula (32-1) was added thereto at 0° C. under ice-cooling. Next, the obtained solution was cooled to −78° C., a suspension of 2.3 g of trichlorobismuth in 15 ml of tetrahydrofuran was added thereto, followed by stirring for 1 hour while heating to room temperature. Next, 20 ml of water was added to the obtained reaction liquid, and the aqueous layer was extracted with chloroform. The obtained chloroform layer was washed with a saturated saline solution, dried over anhydrous sodium sulfate, and filtered, and the obtained filtrate was concentrated under reduced pressure, whereby 2.6 g of a crude product of the compound represented by Formula (33-1) was obtained.

Then, 2.6 g of the obtained crude product of the compound represented by Formula (33-1) was dissolved in 25 ml of dehydrated chloroform at room temperature, then, the resultant product was cooled to 0° C., and 0.4 ml of sulfuryl chloride was added thereto. Then, the temperature was raised to room temperature, followed by stirring for 1 hour. The obtained reaction liquid was concentrated under reduced pressure, then, crystals were precipitated by adding hexane to the obtained oily matter, and the crystals were filtered, whereby 1.3 g of the compound represented by Formula (31-1) was obtained.

1H NMR (CDCl$_3$)
δ
ppm: 8.00 (1H, dd), 7.66 (1H, dd), 7.54-7.46 (2H, m), 3.03 (2H, q), 1.38 (3H, t)

Production of Compound Represented by Formula 1-97

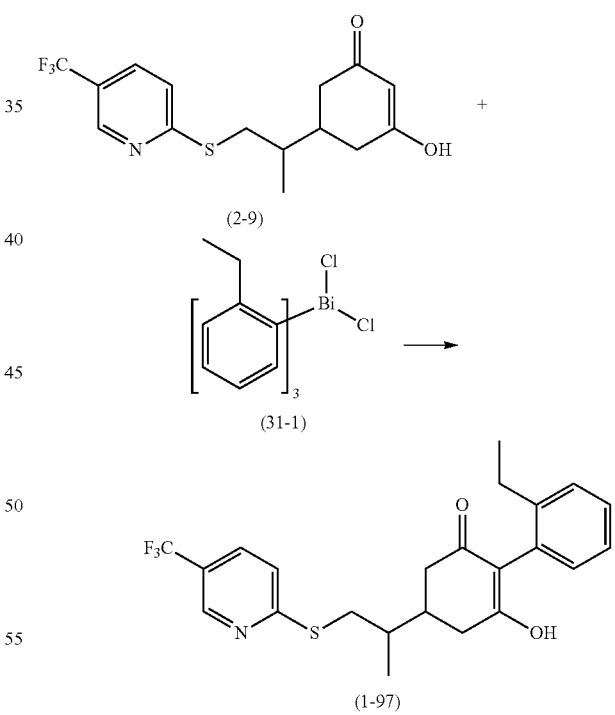

550 mg of the compound represented by Formula (31-1) and 290 mg of the compound represented by Formula (2-9) were dissolved in a mixture of 1 ml of chloroform and 4 ml of toluene at room temperature in a nitrogen atmosphere. The obtained solution was stirred at room temperature for 15 minutes in a nitrogen atmosphere. Next, 0.17 ml of diazabicycloundecene was added to the obtained solution in a nitrogen atmosphere. The obtained mixture was stirred at room temperature for 12 hours in a nitrogen atmosphere. The obtained reaction liquid was extracted with chloroform. The obtained diluted liquid was washed with hydrochloric acid water which had been controlled to have a pH of 1 to 2, and washed with a saturated saline solution. Next, the obtained organic layer was dried over anhydrous sodium sulfate, and filtered, and the obtained filtrate was concentrated under reduced pressure, whereby an oily matter was obtained. The obtained oily matter was subjected to silica gel column chromatography (eluent, ethyl acetate:hexane=1:3), whereby 240 mg of the compound represented by Formula (1-97) was obtained.

1H NMR (CDCl$_3$)
δ
ppm: 8.67 (1H, s), 7.66 (1H, dd), 7.36-7.23 (4H, m), 7.04-7.01 (1H, m), 5.91-5.87 (1H, m), 3.61-3.51 (1H, m), 3.08-2.98 (1H, m), 2.74-2.28 (7H, m), 2.04-1.95 (1H, m), 1.17-1.03 (6H, m)

Production Example 1-34

Production of Compound Represented by Formula (1-19)

Production of Compound Represented by Formula 1-19

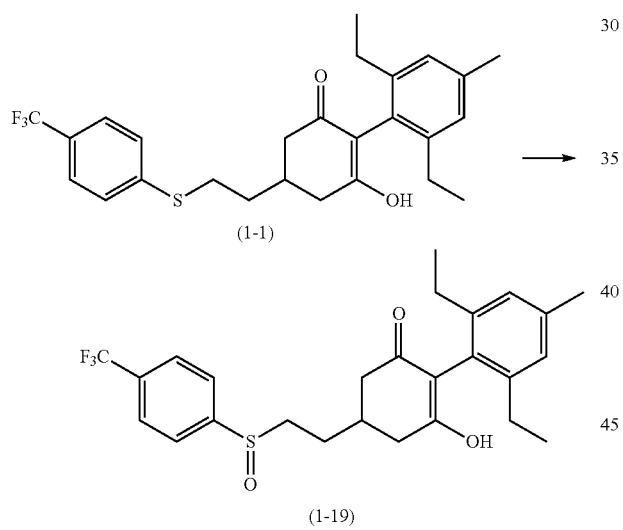

3 ml of chloroform was added to 250 mg of the compound represented by Formula (1-1) at room temperature. The obtained mixture was cooled to 0° C. with stirring, and a mixed liquid obtained by dissolving 120 mg of metachloroperbenzoic acid in 2 ml of chloroform was added dropwise thereto. The obtained mixture was stirred for 1 hour. Next, the obtained mixture was heated to room temperature, followed by stirring at room temperature overnight. The reaction liquid was diluted with chloroform, and the resultant product was washed with a 10% aqueous sodium sulfite solution. The obtained chloroform layer was washed with a saturated saline solution, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=9:1), whereby 154 mg of the compound represented by Formula (1-19) was obtained.

1H NMR (CDCl$_3$)
δ ppm: 7.83-7.75 (4H, m), 6.97 (2H, s), 5.53 (1H, s), 3.03-2.94 (1H, m), 2.89-2.62 (3H, m), 2.46-2.19 (10H, m), 2.13-1.78 (2H, m), 1.08-1.00 (6H, m)

The compound produced according to Production Example 1-34 is shown below.

Compound Represented by Formula 1-79

1H NMR (CDCl$_3$)
δ
ppm: 11.51 (1H, s), 8.72 (1H, d), 8.05 (2H, d), 7.60-7.50 (4H, m), 7.31 (1H, d), 7.19 (1H, t), 6.94 (2H, s), 5.82 (1H, s), 3.34-3.24 (1H, m), 3.09-3.01 (1H, m), 2.62-2.55 (2H, m), 2.36-2.14 (10H, m), 1.96-1.80 (2H, m), 1.05-1.01 (6H, m)

Compound Represented by Formula 1-81

1H NMR (CDCl$_3$)
δ
ppm: 7.83-7.77 (4H, m), 6.90-6.88 (2H, m), 2.99-2.19 (15H, m), 1.35-1.02 (9H, m)

Compound Represented by Formula 1-83

1H NMR (CDCl$_3$)
δ
ppm: 8.89 (1H, s), 8.23-8.16 (2H, m), 6.96 (2H, d), 3.36-3.28 (1H, m), 3.01-2.84 (1H, m), 2.70-2.21 (13H, m), 1.37-1.17 (3H, m), 1.11-1.03 (6H, m)

Compound Represented by Formula 1-85

1H NMR (CDCl$_3$)
δ
ppm: 8.99 (1H, s), 8.04 (1H, s), 6.97 (2H, s), 5.78 (1H, s), 3.21-3.13 (2H, m), 2.76-2.65 (2H, m), 2.48-1.82 (12H, m), 1.06-1.02 (6H, m)

Compound Represented by Formula 1-87

1H NMR (CDCl$_3$)
δ
ppm: 7.80 (4H, dd), 6.98 (2H, s), 3.00-2.92 (1H, m), 2.76-2.22 (13H, m), 1.36-1.33 (6H, m), 1.11-1.05 (6H, m)

Compound Represented by Formula 1-89

1H NMR (CDCl$_3$)
δ
ppm: 8.90 (1H, s), 8.24-8.18 (2H, m), 6.98 (2H, s), 3.24 (1H, dd), 2.89 (1H, dd), 2.76-2.67 (2H, m), 2.57-2.23 (10H, m), 1.40-1.35 (6H, m), 1.11-1.05 (6H, m)

Compound Represented by Formula 1-91

1H NMR (CDCl$_3$)
δ
ppm: 7.84-7.76 (4H, m), 6.98 (1H, s), 5.86 (1H, s), 2.95-2.25 (14H, m), 1.11-1.06 (6H, m), 1.00-0.94 (1H, m), 0.86-0.74 (2H, s), 0.64-0.59 (1H, s)

Compound Represented by Formula 1-98

1H NMR (CDCl$_3$)
δ
ppm: 7.96-7.93 (4H, m), 6.92 (1H, d), 3.01-2.84 (2H, m), 2.66-2.26 (10H, m), 2.09-1.97 (6H, m), 1.40-1.15 (3H, m)

Compound Represented by Formula 1-154

1H NMR (CDCl$_3$)
δ
ppm: 8.90 (1H, s), 8.24 (1H, dt), 8.18 (1H, dd), 6.98 (2H, s), 5.50 (1H, d), 3.35-3.19 (1H, m), 3.11-2.99 (1H, m), 2.73-2.64 (2H, m), 2.44-2.23 (12H, m), 1.08-1.03 (6H, m)

Compound Represented by Formula 1-156

1H NMR (CDCl$_3$)
δ
ppm: 9.21 (1H, s), 8.55 (1H, d), 8.12 (1H, dd), 6.97 (2H, s), 5.48 (1H, d), 4.00 (3H, s), 3.34-3.24 (1H, m), 3.11-3.00 (1H, m), 2.68-2.63 (2H, m), 2.38-2.06 (12H, m), 1.08-1.01 (6H, m)

Compound Represented by Formula 1-158

1H NMR (CDCl$_3$)
δ
ppm: 8.76 (1H, d), 7.79 (1H, d), 7.45 (1H, dd), 6.97 (2H, s), 5.50 (1H, d), 3.18-3.14 (2H, m), 2.72-2.65 (2H, m), 2.47-2.24 (11H, m), 2.05-2.01 (1H, m), 1.09-1.02 (6H, m)

Compound Represented by Formula 1-159

1H NMR (CDCl$_3$)
δ
ppm: 9.33 (1H, d), 8.98 (1H, s), 6.98 (2H, s), 5.53 (1H, d), 3.36-3.28 (1H, m), 3.20-3.11 (1H, m), 2.75-2.66 (2H, m), 2.49-2.20 (11H, m), 1.84-1.63 (1H, m), 1.08-1.01 (6H, m)

Compound Represented by Formula 1-165

1H NMR (CDCl$_3$)
δ
ppm: 8.39 (1H, dd), 8.12 (1H, dd), 6.97 (2H, s), 5.52 (1H, d), 3.49-3.42 (1H, m), 3.27-3.20 (1H, m), 2.74-2.64 (2H, m), 2.46-2.14 (11H, m), 1.76-1.66 (1H, m), 1.08-1.02 (6H, m)

Production Example 1-35

Production of Compound Represented by Formula (1-20)

Production of Compound Represented by Formula 1-20

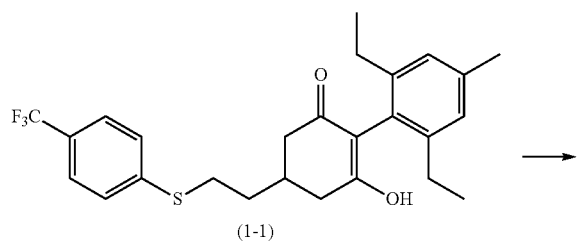

(1-1)

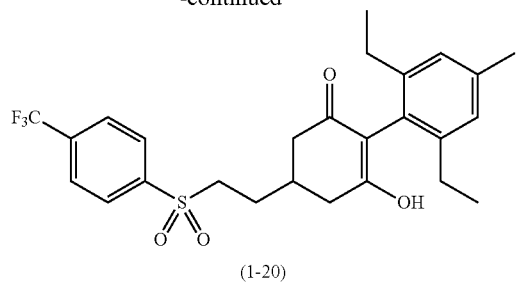

(1-20)

3 ml of chloroform was added to 250 mg of the compound represented by Formula (1-1) at room temperature. The obtained mixture was cooled to 0° C. with stirring, and a mixed liquid obtained by dissolving 440 mg of metachloroperbenzoic acid in 2 ml of chloroform was added dropwise thereto. The obtained mixture was stirred for 1 hour. Next, the obtained mixture was heated to room temperature, followed by stirring at room temperature overnight. The reaction liquid was diluted with chloroform, and the obtained diluted liquid was washed with a 10% aqueous sodium sulfite solution. The obtained chloroform layer was washed with a saturated saline solution, dried over anhydrous sodium sulfate, and filtered. The obtained filtrate was concentrated under reduced pressure, whereby an oily matter was obtained. The obtained oily matter was subjected to silica gel column chromatography (eluent, ethyl acetate:hexane=1:2), whereby 154 mg of the compound represented by Formula (1-20) was obtained.

1H NMR (CDCl$_3$)
δ
ppm: 8.08 (2H, d), 7.88 (2H, d), 6.97 (2H, s), 5.52 (1H, s), 3.27-3.15 (2H, m), 2.73-2.60 (2H, m), 2.45-2.21 (10H, m), 2.02-1.90 (2H, m), 1.08-1.00 (6H, m)

The compound produced according to Production Example 1-35 is shown below.

Compound Represented by Formula 1-80

1H NMR (CDCl$_3$)
δ
ppm: 10.46 (1H, s), 8.69 (1H, d), 8.05-7.91 (2H, m), 7.73 (1H, td), 7.64-7.52 (4H, m), 7.34 (1H, td), 6.95 (2H, s), 3.26-3.16 (2H, m), 2.61-2.52 (2H, m), 2.35-2.11 (10H, m), 1.93-1.87 (2H, m), 1.03 (6H, dd)

Compound Represented by Formula 1-82

1H NMR (CDCl$_3$)
δ
ppm: 8.09 (2H, d), 7.88 (2H, d), 6.98 (2H, s), 3.28-2.99 (2H, m), 2.61-2.21 (13H, m), 1.28-1.22 (3H, m), 1.08-1.04 (6H, m)

Compound Represented by Formula 1-84

1H NMR (CDCl$_3$)
δ
ppm: 9.02 (1H, s), 8.27 (2H, s), 6.98 (2H, s), 5.67 (1H, s), 3.69 (1H, dt), 3.32 (1H, ddd), 2.66-2.21 (13H, m), 1.28-1.24 (3H, m), 1.10-1.02 (6H, m)

Compound Represented by Formula 1-86

1H NMR (CDCl$_3$)
δ
ppm: 8.79 (1H, s), 8.18 (1H, s), 6.99 (2H, s), 3.86-3.66 (2H, m), 2.86-2.72 (2H, m), 2.54-2.09 (12H, m), 1.10-1.01 (6H, m)

Compound Represented by Formula 1-88

1H NMR (CDCl$_3$)
δ
ppm: 8.09 (2H, d), 7.86 (2H, d), 6.99 (2H, d), 3.11 (2H, dd), 2.68-2.24 (12H, m), 1.35 (6H, d), 1.08 (6H, dt)

Compound Represented by Formula 1-90

1H NMR (CDCl$_3$)
δ
ppm: 9.01 (1H, s), 8.27-8.22 (2H, m), 6.98 (2H, s), 3.59-3.49 (2H, m), 2.59-2.48 (2H, m), 2.59-2.48 (2H, m), 2.42-2.27 (8H, m), 1.33-1.27 (6H, m), 1.08 (6H, td)

Compound Represented by Formula 1-92

1H NMR (CDCl$_3$)
δ
ppm: 8.08 (2H, d), 7.86 (2H, d), 6.98 (2H, d), 5.86 (1H, s), 3.26-3.08 (2H, m), 2.88-2.73 (1H, m), 2.68-2.52 (2H, m), 2.47-2.17 (9H, m), 1.12-1.05 (6H, m), 0.83-0.53 (4H, m)

Compound Represented by Formula 1-99

1H NMR (CDCl$_3$)
δ
ppm: 8.09 (2H, d), 7.88 (2H, d), 6.93 (2H, s), 5.59 (1H, s), 3.23 (1H, td), 3.05-2.98 (1H, m), 2.59-2.23 (9H, m), 2.06-1.97 (6H, m), 1.21 (3H, dt)

Production Example 1-36

Production of Compound Represented by Formula (1-59)

Production of Compound Represented by Formula 1-59

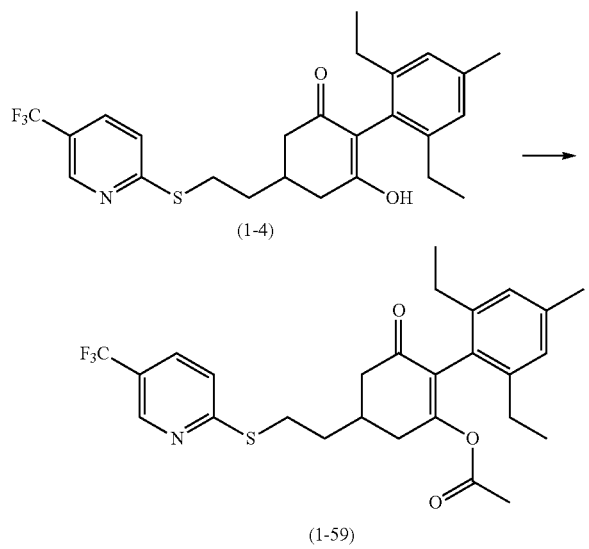

A solution of 175 mg of triethylamine in 3 ml of anhydrous tetrahydrofuran was added to 500 mg of the compound represented by Formula (1-4). A solution of 170 mg of acetyl chloride in 1 ml of anhydrous tetrahydrofuran was added to the obtained mixture under ice-cooling. The obtained mixture was stirred for 12 hours at room temperature. 5 ml of water was added to the reaction mixture, and the resultant product was extracted with chloroform. The obtained chloroform layer was dried over anhydrous sodium sulfate, and concentrated under reduced pressure, and the resultant product was subjected to silica gel column chromatography (eluent, ethyl acetate:hexane=1:6), whereby 530 mg of the compound represented by Formula (1-59) was obtained (colorless oily matter).

1H NMR (CDCl$_3$)
δ
ppm: 8.67 (1H, m), 7.67 (1H, dd), 7.27 (1H, d), 6.89 (2H, s), 3.30 (2H, t), 2.84-2.25 (12H, m), 1.98-1.89 (5H, m), 1.09-1.02 (6H, m)

The compound produced according to Production Example 1-36 is shown below.

Compound Represented by Formula 1-60

1H NMR (CDCl$_3$)
δ
ppm: 8.67 (1H, m), 7.67 (1H, dd), 7.27 (1H, d), 6.88 (2H, s), 3.31 (2H, t), 2.77-2.23 (12H, m), 2.17-2.11 (2H, m), 1.98-1.88 (2H, m), 1.05 (6H, d dd), 0.84 (3H, t)

Compound Represented by Formula 1-61

1H NMR (CDCl$_3$)
δ
ppm: 8.67 (1H, m), 7.67 (1H, dd), 7.27 (1H, d), 6.87 (2H, s), 3.31 (2H, td), 2.84-2.25 (12H, m), 1.94 (2H, dt), 1.05 (6H, dt), 0.88 (9H, s)

Compound Represented by Formula 1-62

1H NMR (CDCl$_3$)
δ
ppm: 8.67 (1H, dd), 7.67 (1H, dd), 7.27 (1H, d), 6.90 (2H, s), 3.70 (3H, s), 3.31 (2H, t), 2.92-2.26 (12H, m), 1.99-1.89 (2H, m), 1.09-1.02 (6H, m)

Compound Represented by Formula 1-63

1H NMR (CDCl$_3$)
δ
ppm: 8.67 (1H, dd), 7.67 (1H, dd), 7.27 (1H, d), 6.90 (2H, s), 4.12-4.07 (2H, m), 3.34-3.27 (2H, m), 2.91-2.27 (12H, m), 1.99-1.88 (2H, m), 1.18 (3H, t), 1.09-1.00 (6H, m)

Compound Represented by Formula 1-66

1H NMR (CDCl$_3$)
δ
ppm: 8.67 (1H, dd), 7.66 (1H, dd), 7.26 (1H, d), 6.90 (2H, s), 5.80-5.71 (1H, m), 5.21-5.15 (2H, m), 4.52-4.50 (2H, m), 3.30 (2H, t), 2.82-2.26 (12H, m), 1.97-1.88 (2H, m), 1.09-1.00 (6H, m)

Compound Represented by Formula 1-67

1H NMR (CDCl$_3$)
δ
ppm: 8.67 (1H, t), 7.66 (1H, dd), 7.35-7.18 (4H, m), 6.95 (2H, s), 6.87-6.83 (2H, m), 3.31 (2H, t), 2.99-2.29 (12H, m), 2.00-1.90 (2H, m), 1.08-1.03 (6H, m)

Compound Represented by Formula 1-68

1H NMR (CDCl$_3$)
δ
ppm: 8.69 (1H, t), 7.67 (1H, dd), 7.27 (1H, d), 6.93 (2H, s), 3.66-3.27 (2H, m), 3.06 (1H, dd), 2.84-2.76 (2H, m), 2.56-2.26 (12H, m), 1.99-1.88 (2H, m), 1.14-1.04 (6H, m)

Compound Represented by Formula 1-93

1H NMR (CDCl$_3$)
δ
ppm: 8.91 (1H, s), 8.24-8.18 (2H, m), 6.90 (2H, d), 4.13-4.05 (2H, m), 3.33 (1H, ddd), 3.07-2.24 (14H, m), 1.39-1.02 (12H, m)

Production Example 1-37

Production of Compound Represented by Formula (1-64)

Production of Compound Represented by Formula 1-64

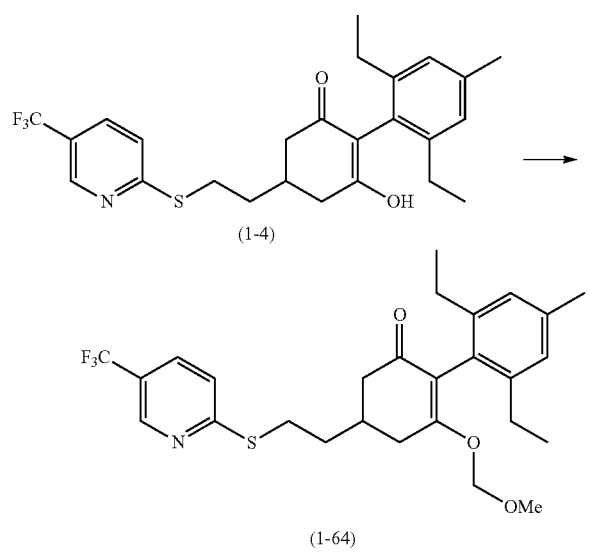

1 ml of anhydrous N,N-dimethylformamide was added to 110 mg of a 60% sodium hydride. A solution of 500 mg of the compound represented by Formula (1-4) in 3 ml of N,N-dimethylformamide was added dropwise to the obtained mixture under ice-cooling. After the obtained mixture was stirred for 10 minutes under ice-cooling, a solution of 200 mg of chloromethyl methyl ether in 1 ml of anhydrous N,N-dimethylformamide was added dropwise thereto, and the obtained mixture was stirred at room temperature for 2 hours. 5 ml of water was added to the reaction mixture, and the resultant product was extracted by ethyl acetate. The obtained ethyl acetate layer was washed with water, dried over anhydrous sodium sulfate, and concentrated under reduced pressure, and the resultant product was subjected to silica gel column chromatography (eluent, ethyl acetate:hexane=1:4), whereby 208 mg of the compound represented by Formula (1-64) was obtained (yellow oily matter).

1H NMR (CDCl$_3$)
δ
ppm: 8.67 (1H, m), 7.67 (1H, dd), 7.27 (1H, d), 6.90 (2H, s), 4.98 (2H, s), 3.39-3.22 (5H, m), 3.03-2.25 (12H, m), 1.99-1.89 (2H, m), 1.08-1.02 (6H, m)

The compound produced according to Production Example 1-37 is shown below.

Compound Represented by Formula 1-65

1H NMR (CDCl$_3$)
δ
ppm: 8.67 (1H, m), 7.67 (1H, dd), 7.27 (1H, d), 6.91 (2H, s), 5.05-4.99 (2H, m), 3.56-3.51 (2H, m), 3.37-3.28 (2H, m), 3.04-2.23 (12H, m), 1.97-1.90 (2H, m), 1.17-0.99 (9H, m)

Production Example 1-38

Production of Compound Represented by Formula (1-30)

Production of Compound Represented by Formula 9-30

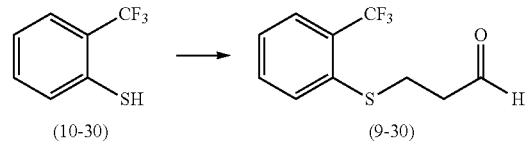 [SMILES: FC(F)(F)c1ccccc1S ; O=CCCSc1ccccc1C(F)(F)F]

7.10 g of the compound represented by Formula (10-30) and 60 ml of tetrahydrofuran were mixed at room temperature, followed by stirring, and 3.64 g of 95% acrolein and 1.21 g of triethylamine were added dropwise to the obtained mixture. The obtained mixture was stirred for 5.5 hours at room temperature. Next, the obtained reaction liquid was concentrated under reduced pressure, whereby 9.32 g of the compound represented by Formula (9-30) was obtained.

1H NMR (CDCl$_3$)
δ
ppm: 9.78 (1H, s), 7.67 (1H, d), 7.54-7.46 (2H, m), 7.35-7.31 (1H, m), 3.24 (2H, t), 2.80 (2H, dt)

Production of Compound Represented by Formula 7-30

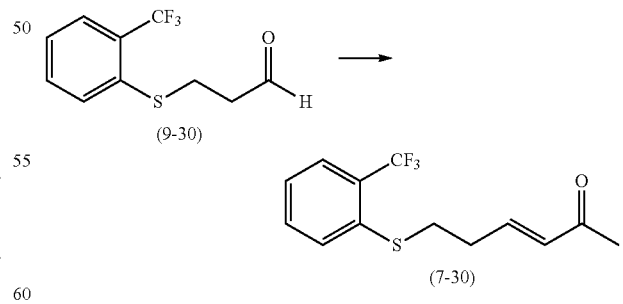

9.32 g of the compound represented by Formula (9-30) was dissolved in 40 ml of chloroform at room temperature. 16.5 g of triphenylphosphineacetylmethylene was added to the obtained solution under ice-cooling. The obtained solution was stirred for 17 hours at room temperature. Next, chloroform was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 9.76 g of the compound represented by Formula (7-30) was obtained.

1H NMR (CDCl$_3$)

δ ppm: 7.67 (1H, d), 7.52-7.43 (2H, m), 7.34-7.30 (1H, m) 6.79 (1H, dt), 6.11 (1H, dt), 3.10 (2H, t), 2.57 (2H, qd), 2.24 (3H, s)

Production of Compound Represented by Formula 6-30

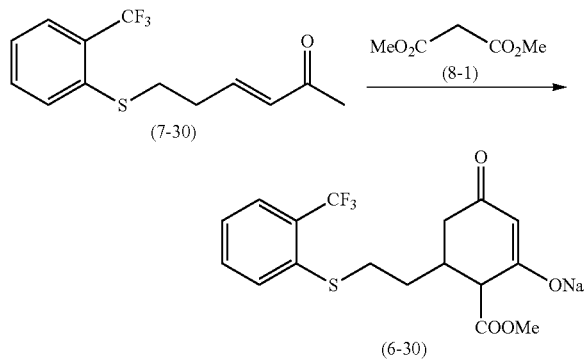

7.55 g of a 28% sodium methoxide methanol solution and 5.17 g of the compound represented by Formula (8-1) were dissolved in 70 ml of tetrahydrofuran at room temperature. The obtained solution was heated under reflux for 10 minutes. Next, the heating was stopped, and 9.76 g of the compound represented by Formula (7-30) was added to the obtained reaction mixture. Next, the obtained mixed liquid was heated under reflux for 2 hours. The obtained reaction liquid was cooled to room temperature, and the precipitated crystals were collected by filtration, and washed sequentially with tert-butyl methyl ether and hexane, whereby 6.80 g of the compound represented by Formula (6-30) was obtained.

1H NMR (d-DMSO)

δ ppm: 7.70 (1H, d), 7.61 (2H, dd), 7.36 (1H, q), 4.39 (1H, s), 3.47 (3H, s), 3.15-3.08 (1H, m), 3.00-2.93 (1H, m), 2.83 (1H, d), 2.33-2.23 (1H, m), 2.11 (1H, dd), 1.77 (1H, dd), 1.53-1.44 (2H, m)

Production of Compound Represented by Formula 1-30

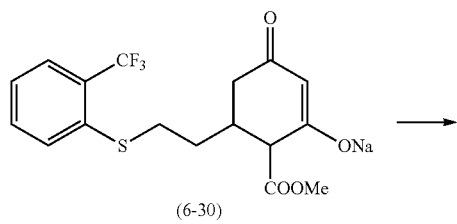

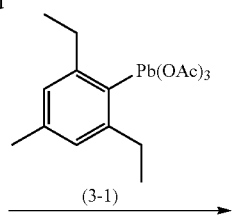

6.80 g of the compound represented by Formula (6-30) was dissolved in 90 ml of water at room temperature. 5.78 g of anhydrous sodium carbonate was added to the obtained solution. The obtained solution was heated under reflux for 5 hours. The reaction liquid was cooled to room temperature, and acidified by adding 2 N hydrochloric acid. The obtained reaction liquid was extracted with ethyl acetate, whereby 6.01 g of the compound represented by Formula (2-30) was obtained.

541 mg of the compound represented by Formula (2-30) and 1.04 g of dimethylaminopyridine were dissolved in a mixture of 5.0 ml of chloroform and 2.0 ml of toluene at room temperature in a nitrogen atmosphere. The obtained solution was stirred at room temperature for 15 minutes in a nitrogen atmosphere. Next, 1.00 g of the compound represented by Formula (3-1) was added to the obtained solution in a nitrogen atmosphere. The obtained mixture was stirred at 75° C. for 1.5 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous sodium sulfate, and filtered. The obtained filtrate was concentrated under reduced pressure, whereby a yellow oily matter was obtained. The obtained oily matter was subjected to silica gel column chromatography (eluent, ethyl acetate:hexane=1:4), whereby 387 mg of the compound represented by Formula (1-30) was obtained.

1H NMR (CDCl$_3$)

δ ppm: 7.67 (1H, d), 7.49 (2H, t), 7.32-7.28 (1H, m), 6.98 (2H, s), 5.54 (1H, s), 3.07 (2H, ddd), 2.69 (2H, td), 2.48-2.24 (10H, m), 1.85 (2H, q), 1.08 (3H, t), 1.05 (3H, t)

Production Example 1-39

Production of Compound Represented by Formula (1-29)

Production of Compound Represented by Formula 7-29

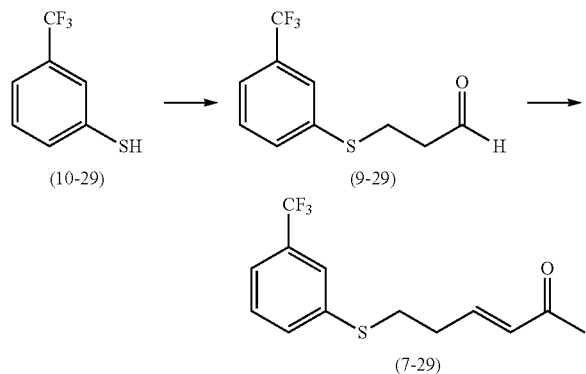

5.0 g of the compound represented by Formula (10-29) and 56 ml of tetrahydrofuran were mixed at room temperature, followed by stirring, and 2.56 g of 95% acrolein and 852 mg of triethylamine were added dropwise to the obtained mixture. The obtained mixture was stirred for 2 hours at room temperature. Next, the obtained reaction liquid was concentrated under reduced pressure, whereby 6.61 g of the compound represented by Formula (9-29) was obtained.

6.61 g of the compound represented by Formula (9-29) and 11.6 g of triphenylphosphineacetylmethylene were dissolved in 28 ml of tetrahydrofuran at room temperature. The obtained solution was stirred for 5 hours at room temperature. Next, tetrahydrofuran was removed from the obtained reaction liquid under reduced pressure. tert-Butyl methyl ether and hexane were added to the obtained residue. The obtained mixture was filtered, and the obtained filtrate was concentrated under reduced pressure. The obtained oily matter was subjected to silica gel column chromatography (eluent, ethyl acetate:hexane=1:4), whereby 1.01 g of the compound represented by Formula (7-29) was obtained.

1H NMR (CDCl$_3$)

δ ppm: 7.56 (1H, s), 7.51-7.40 (3H, m), 6.78 (1H, dt), 6.13 (1H, dt), 3.10 (2H, t), 2.59 (2H, qd), 2.25 (3H, s)

Production of Compound Represented by Formula 6-29

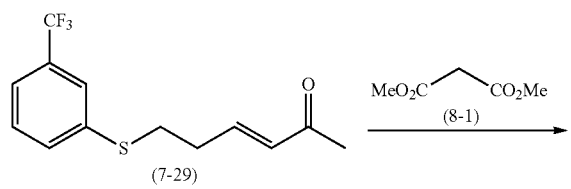

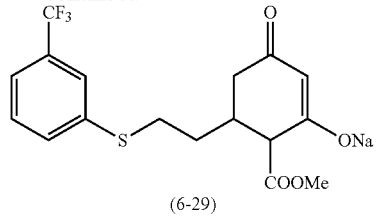

781 mg of a 28% sodium methoxide methanol solution and 464 mg of the compound represented by Formula (8-1) were dissolved in 7 ml of tetrahydrofuran at room temperature. The obtained solution was heated under reflux for 10 minutes. Next, the heating was stopped, and 1.01 g of the compound represented by Formula (7-29) was added to the obtained reaction mixture. Next, the obtained mixed liquid was heated under reflux for 1 hour. The obtained reaction liquid was cooled to room temperature, and the precipitated crystals were collected by filtration, and washed sequentially with tert-butyl methyl ether and hexane, whereby 873 mg of the compound represented by Formula (6-29) was obtained.

1H NMR (CDCl$_3$)

δ ppm: 7.57-7.51 (4H, m), 4.38 (1H, s), 3.45 (3H, s), 3.10 (1H, m), 2.96 (1H, m), 2.81 (1H, d), 2.28 (1H, m), 2.11 (1H, d), 1.75 (1H, t), 1.47 (2H, m)

Production of Compound Represented by Formula 1-29

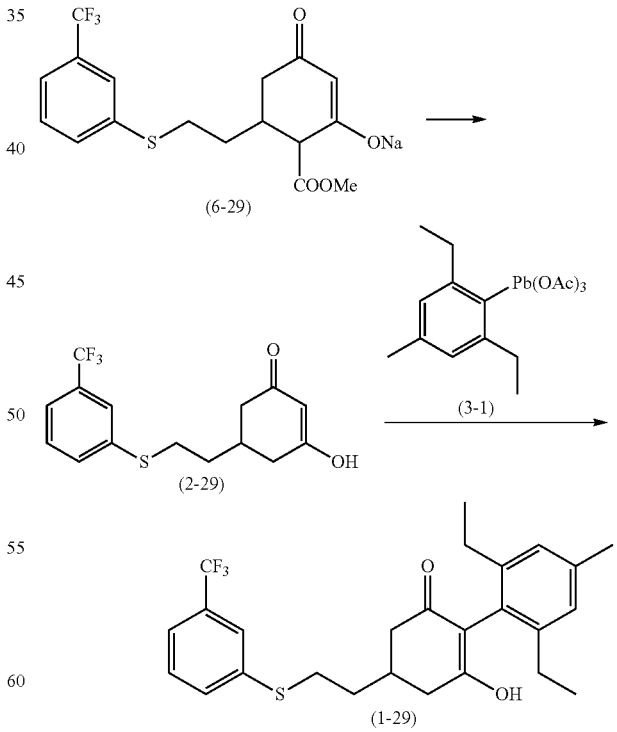

873 mg of the compound represented by Formula (6-29) was dissolved in 12 ml of water at room temperature. 741 mg of anhydrous sodium carbonate was added to the obtained solution. The obtained solution was heated under reflux for 6.5 hours. The reaction liquid was cooled to room temperature, and acidified by adding 2 N hydrochloric acid. The obtained reaction liquid was extracted with ethyl acetate. The ethyl acetate layer was concentrated under reduced pressure, and the obtained crystals were washed sequentially with tert-butyl methyl ether and hexane, whereby 434 mg of the compound represented by Formula (2-29) was obtained.

430 mg of the compound represented by Formula (2-29) and 831 mg of dimethylaminopyridine were dissolved in a mixture of 4 ml of chloroform and 1 ml of toluene at room temperature in a nitrogen atmosphere. The obtained solution was stirred at room temperature for 15 minutes in a nitrogen atmosphere. Next, 795 mg of the compound represented by Formula (3-1) was added to the obtained solution in a nitrogen atmosphere. The obtained mixture was stirred at 80° C. for 1 hour in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous magnesium sulfate, and filtered. The obtained filtrate was concentrated under reduced pressure, whereby a yellow oily matter was obtained. The obtained oily matter was subjected to silica gel column chromatography (eluent, ethyl acetate:hexane=15:85), whereby 144 mg of the compound represented by Formula (1-29) was obtained.

1H NMR (CDCl$_3$)
δ
ppm: 7.56 (1H, s), 7.50-7.40 (3H, m), 6.98 (2H, s), 5.54 (1H, s), 3.10-3.01 (2H, m), 2.70 (2H, t), 2.47-2.24 (10H, m), 1.86 (2H, q), 1.10-1.03 (6H, m)

Production Example 1-40

Production of Compound Represented by Formula (1-41)

Production of Compound Represented by Formula 3-1

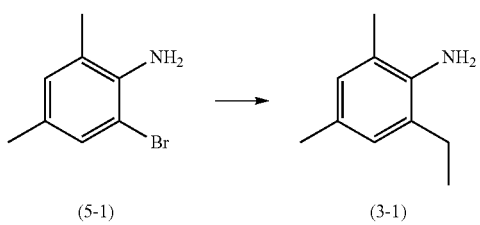

2.04 g of 1,1'-bis(diphenylphosphino) ferrocene-palladium(II) dichloride-dichloromethane complex, 48.8 g of cesium carbonate, and 10 g of the compound represented by Formula (5-1) were dissolved in 125 ml of N,N-dimethylformamide at room temperature in a nitrogen atmosphere. 32.5 ml (1.0 M hexane solution) of triethylborane was added dropwise to the obtained solution, followed by stirring at room temperature for 16 hours in a nitrogen atmosphere. After the reaction liquid was filtered using Celite (registered trademark), water was added to the filtrate, the resultant product was extracted with tert-butyl methyl ether, and the organic layer was washed with a saturated saline solution, and dried over anhydrous magnesium sulfate. The obtained organic layer was concentrated under reduced pressure, and the resultant product was subjected to silica gel column chromatography (eluent, ethyl acetate:hexane=1:19→1:9), whereby 3.18 g of the compound represented by Formula (3-1) was obtained.

1H NMR (CDCl$_3$)
δ
ppm: 6.78 (2H, s), 3.49 (2H, s), 2.51 (2H, q), 2.23 (3H, s), 2.16 (3H, s), 1.24 (3H, t)

Production of Compound Represented by Formula 11-4

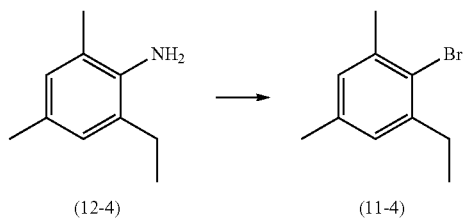

3.18 g of the compound represented by Formula (12-4) was dissolved in 25 ml of water at room temperature. 26.6 ml of 48% hydrobromic acid was added to the obtained solution, followed by stirring at 40° C. for 15 minutes. 10 ml of a 2.34 M aqueous sodium nitrite solution was added dropwise to the obtained reaction liquid at 0° C., followed by stirring for 20 minutes under ice-cooling. The obtained mixture was added dropwise to a mixture obtained by adding 26.6 ml of 48% hydrobromic acid to 3.19 g of copper(II) sulfate pentahydrate and 1.27 g of copper (powder) at 0° C. and cooling. The obtained solution was stirred for 3.5 hours at room temperature. The obtained reaction liquid was filtered using Celite (registered trademark), and the obtained filtrate was extracted with ethyl acetate. The organic layer was washed with a saturated saline solution, and dried over anhydrous magnesium sulfate. The obtained organic layer was concentrated under reduced pressure, and the resultant product was subjected to silica gel column chromatography (eluent, hexane), whereby 1.91 g of the compound represented by Formula (11-4) was obtained.

1H NMR (CDCl$_3$)
δ
ppm: 6.90 (1H, s), 6.88 (1H, s), 2.74 (2H, q), 2.38 (3H, s), 2.25 (3H, s), 1.21 (3H, t)

Production of Compound Represented by Formula 3-4

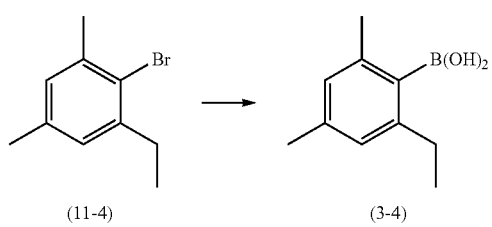

1.91 g of the compound represented by Formula (11-4) was dissolved in 23 ml of tetrahydrofuran at room temperature in a nitrogen atmosphere. The obtained solution was cooled to −78° C., and n-butyllithium (1.63 M hexane solution) was added dropwise thereto in a nitrogen atmosphere. Next, the reaction liquid was stirred at 40° C. for 4 hours in a nitrogen atmosphere. The obtained solution was cooled to −78° C., and 1.12 g of trimethoxyborane was added dropwise thereto in a nitrogen atmosphere, followed by stirring at room temperature for 23 hours. The obtained solution was cooled to 0° C., and acidified by adding 1N hydrochloric acid. The obtained reaction liquid was extracted with chloroform, and the organic layer was washed with a saturated saline solution, and dried over anhydrous magnesium sulfate. The organic layer was concentrated under reduced pressure, and filtered, and the residue was washed with hexane, whereby 654 mg of the compound represented by Formula (3-4) was obtained.

1H NMR (CDCl$_3$)

δ ppm: 6.86 (1H, s), 6.85 (1H, s), 4.58 (2H, d), 2.63 (2H, q), 2.35 (3H, s), 2.29 (3H, s), 1.23 (3H, t)

Production of Compound Represented by Formula 1-41

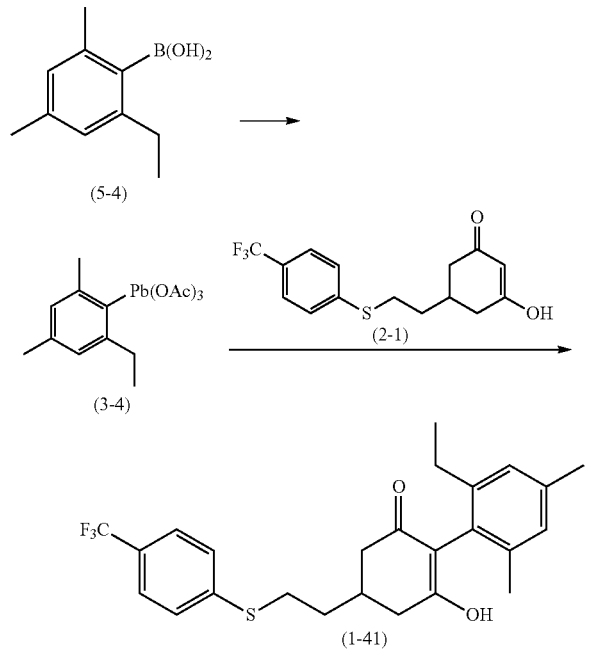

1.87 g of lead tetraacetate, 58.5 mg of mercury acetate, and 654 mg of the compound represented by Formula (5-4) were dissolved in 7 ml of chloroform at room temperature in a nitrogen atmosphere. The obtained solution was stirred at room temperature for 15 minutes in a nitrogen atmosphere. Next, the reaction liquid was stirred at 45° C. for 4 hours in a nitrogen atmosphere. The reaction liquid was cooled to room temperature, and filtered using Celite (registered trademark). The obtained filtrate was concentrated under reduced pressure, whereby a yellow oily matter was obtained. Hexane was added to the obtained oily matter, and the obtained mixture was concentrated under reduced pressure, whereby a yellow solid was obtained. The obtained solid was dissolved in 16 ml of chloroform at room temperature in a nitrogen atmosphere. 6.09 g of potassium carbonate was added to the obtained solution, followed by stirring for 15 minutes.

Next, the reaction liquid was filtered using Celite (registered trademark). The obtained filtrate was concentrated under reduced pressure, whereby 21 g of the compound represented by Formula (3-4) was obtained. 332 mg of the compound represented by Formula (2-1) and 644 mg of dimethylaminopyridine were dissolved in a mixture of 3 ml of chloroform and 1 ml of toluene at room temperature in a nitrogen atmosphere.

The obtained solution was stirred at room temperature for 15 minutes in a nitrogen atmosphere. Next, 600 mg of the compound represented by Formula (3-4) was added to the obtained solution in a nitrogen atmosphere. The obtained mixture was heated under reflux for 2 hours in a nitrogen atmosphere. The obtained reaction liquid was cooled to room temperature, controlled to have a pH of 1 with 2 N hydrochloric acid, and filtered using Celite (registered trademark). The obtained filtrate was extracted with chloroform. The obtained chloroform layer was washed with water, dried over anhydrous magnesium sulfate, and filtered. The obtained filtrate was concentrated under reduced pressure, whereby a yellow oily matter was obtained.

The obtained oily matter was subjected to silica gel column chromatography (eluent, ethyl acetate:hexane=1:9→3:17), whereby 361 mg of the compound represented by Formula (1-41) was obtained.

1H NMR (CDCl$_3$)

δ ppm: 7.54 (2H, d), 7.37 (2H, d), 6.96 (2H, s), 5.50 (1H, s), 3.13-3.03 (2H, m), 2.71 (2H, t), 2.47-2.25 (8H, m), 2.06-2.00 (3H, m), 1.90-1.85 (2H, m), 1.10-1.02 (3H, m)

The compound produced according to Production Example 1-40 is shown below.

Production of Compound Represented by Formula 1-128

1H NMR (CDCl$_3$)

δ ppm: 7.53 (2H, d), 7.37 (3H, d), 7.23-7.12 (3H, m), 3.05 (2H, td), 2.69 (2H, d), 2.47-2.30 (3H, m), 1.87-1.81 (2H, m)

Production of Compound Represented by Formula 1-167

1H NMR (CDCl$_3$)

δ ppm: 7.55-7.49 (3H, m), 7.38-7.26 (3H, m), 7.19-7.14 (1H, m), 5.62 (1H, s), 3.07-3.06 (2H, m), 2.72-2.63 (2H, m), 2.48-2.21 (3H, m), 1.87 (2H, dt)

Production of Compound Represented by Formula 1-168

1H NMR (CDCl$_3$)

δ ppm: 8.67 (1H, s), 7.70-7.65 (2H, m), 7.38 (1H, tt), 7.29-7.23 (2H, m), 7.16 (1H, ddd), 5.58 (1H, d), 3.31 (2H, t), 2.81-2.67 (2H, m), 2.55-2.24 (3H, m), 1.97-1.88 (2H, m)

Production of Compound Represented by Formula 1-170

1H NMR (CDCl$_3$)

δ ppm: 8.63 (1H, s), 7.66 (1H, dd), 7.25 (1H, d), 6.61 (2H, s), 3.25-3.21 (2H, m), 2.69 (2H, d), 2.37-2.31 (3H, m), 1.86-1.83 (2H, m)

Production of Compound Represented by Formula 1-171

1H NMR (CDCl$_3$)

δ ppm: 7.69 (1H, ddd), 7.54 (2H, d), 7.38 (3H, d), 7.28-7.13 (2H, m), 5.58 (1H, s), 3.07 (2H, q), 2.77-2.25 (5H, m), 1.91-1.85 (2H, m)

Production of Compound Represented by Formula 1-175

δ
ppm: 7.53 (2H, d), 7.39 (2H, d), 7.29 (1H, s), 7.11 (1H, s), 5.57 (1H, s), 3.21-3.12 (1H, m), 2.92-2.82 (1H, m), 2.66-1.91 (13H, m), 1.19-1.14 (3H, m)

Production of Compound Represented by Formula 1-176

δ
ppm: 7.52 (2H, d), 7.36 (2H, d), 6.71 (1H, d), 6.59 (1H, s), 6.13 (1H, s), 3.70-3.63 (3H, m), 3.15 (1H, dd), 2.84 (1H, td), 2.59-1.88 (12H, m), 1.13 (3H, d)

Production of Compound Represented by Formula 1-179

δ
ppm: 7.58-7.35 (5H, m), 6.67 (2H, dd), 6.00 (1H, s), 3.81 (3H, s), 3.79 (3H, s), 3.24 (1H, d), 2.88 (1H, t), 2.64-1.95 (6H, m), 1.19 (3H, d)

Production of Compound Represented by Formula 1-180

δ
ppm: 7.53-7.04 (6H, m), 5.87 (1H, s), 3.78-1.93 (14H, m), 1.14 (3H, ddd)

Production of Compound Represented by Formula 1-181

δ
ppm: 7.53 (2H, d), 7.38 (2H, d), 7.30 (1H, d), 7.04 (1H, d), 6.49 (1H, ddd), 5.71-5.62 (2H, m), 5.22-5.16 (1H, m), 3.21-3.12 (1H, m), 2.87 (1H, m), 2.63-1.90 (12H, m), 1.19-1.14 (3H, m)

Production of Compound Represented by Formula 1-182

1H NMR (CDCl$_3$)
δ
ppm: 7.55 (2H, d), 7.40 (2H, d), 7.31-7.26 (2H, m), 3.18-2.08 (17H, m), 1.15 (3H, s)

Production Example 1-41

Production of Compound Represented by Formula (1-105)

Production of Compound Represented by Formula 31-2

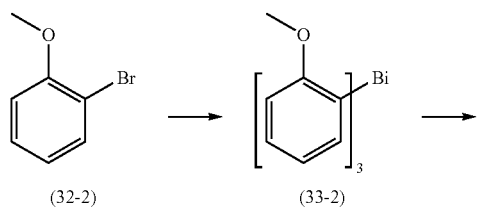

(32-2)    (33-2)

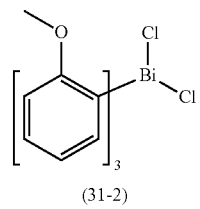

(31-2)

2.52 g of the compound represented by Formula (32-2) was dissolved in 15 ml of tetrahydrofuran at room temperature in a nitrogen atmosphere. The obtained solution was cooled to −78° C., and 10 ml of n-butyllithium (1.6 M hexane solution) was added thereto, followed by stirring for 1 hour. Next, a suspension of 1.44 g of trichlorobismuth in 10 ml of tetrahydrofuran was added thereto, followed by stirring for 1 hour while heating to room temperature. 20 ml of water was added to the obtained reaction liquid, and the resultant product was filtered using Celite (registered trademark). The filtrate was extracted with chloroform. The obtained chloroform layer was washed with a saturated saline solution, dried over anhydrous magnesium sulfate, and filtered, and the obtained filtrate was concentrated under reduced pressure, whereby 2.18 g of a crude product of the compound represented by Formula (33-2) was obtained.

Then, 2.18 g of the obtained crude product of the compound represented by Formula (33-2) was dissolved in 5 ml of dehydrated chloroform at room temperature, then, the resultant product was cooled to 0° C., and 0.55 ml of sulfuryl chloride was added thereto. Then, the temperature was raised to room temperature, followed by stirring for 30 minutes. Crystals were precipitated by adding tert-butyl methyl ether to the obtained reaction liquid, and the crystals were concentrated under reduced pressure, and filtered, whereby 1.86 g of the compound represented by Formula (31-2) was obtained.

1H NMR (d-DMSO)
δ
ppm: 8.03 (3H, dd), 7.62 (3H, t), 7.51 (3H, d), 7.34 (3H, t), 3.82 (9H, s)

Production of Compound Represented by Formula 1-105

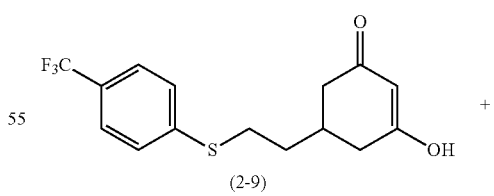

(2-9)

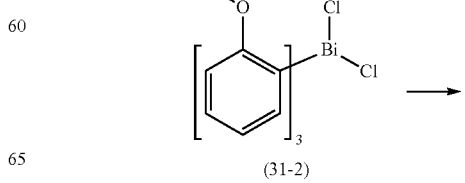

(31-2)

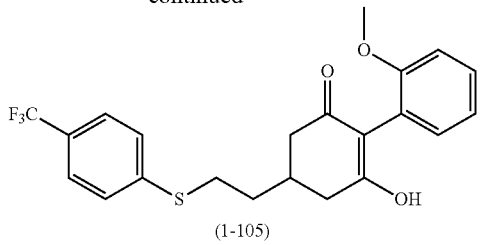

(1-105)

475 mg of the compound represented by Formula (2-9), 274 mg of 1,8-diazabicyclo[5.4.0]undeca-7-ene, and 1.08 g of the compound represented by Formula (31-2) were dissolved in a mixture of 1 ml of chloroform and 5 ml of toluene at room temperature in a nitrogen atmosphere, followed by stirring at room temperature for 24 hours in a nitrogen atmosphere. The obtained reaction liquid was diluted with chloroform, washed with hydrochloric acid water which had been controlled to have a pH of 1 to 2, and washed with a saturated saline solution. Next, the obtained organic layer was dried over anhydrous magnesium sulfate, and filtered, and the obtained filtrate was concentrated under reduced pressure, whereby an oily matter was obtained. The obtained oily matter was subjected to silica gel column chromatography (eluent, ethyl acetate:hexane=1:9→3:7), whereby 72.4 mg of the compound represented by Formula (1-105) was obtained.

1H NMR (CDCl$_3$)

δ ppm: 7.53 (2H, d), 7.38-7.34 (3H, m), 7.14-6.98 (3H, m), 6.30 (1H, s), 3.80 (3H, s), 3.10-3.02 (2H, m), 2.73-2.65 (2H, m), 2.47-2.39 (2H, m), 2.31-2.24 (1H, m), 1.88-1.82 (2H, m)

Production Example 1-42

Production of Compound Represented by Formula (1-96)

Production of Compound Represented by Formula 31-3

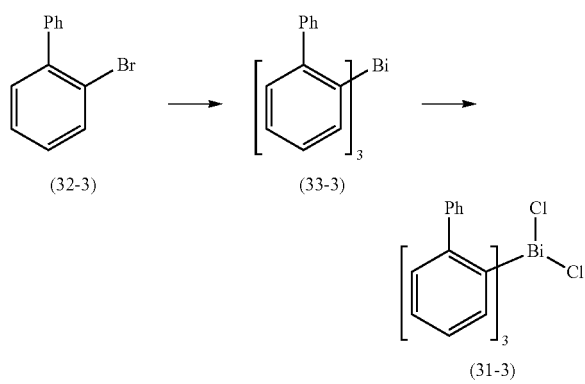

3.20 g of the compound represented by Formula (32-3) was dissolved in 15 ml of tetrahydrofuran at room temperature in a nitrogen atmosphere. The obtained solution was cooled to −78° C., and 10 ml of n-butyllithium (1.6 M hexane solution) was added thereto, followed by stirring for 1 hour. Next, a solution of 1.44 g of trichlorobismuth suspended in 10 ml of tetrahydrofuran was added thereto, followed by stirring for 1 hour while heating to room temperature. 20 ml of water was added to the obtained reaction liquid, and the aqueous layer was extracted with chloroform. The obtained chloroform layer was washed with a saturated saline solution, dried over anhydrous magnesium sulfate, and filtered, and the obtained filtrate was concentrated under reduced pressure, whereby 3.07 g of a crude product of the compound represented by Formula (33-3) was obtained.

Then, 3.07 g of the obtained crude product of the compound represented by Formula (33-3) was dissolved in 5 ml of dehydrated chloroform at room temperature, then, the resultant product was cooled to 0° C., and 0.55 ml of sulfuryl chloride was added thereto. Then, the temperature was raised to room temperature, followed by stirring for 30 minutes. The obtained reaction liquid was concentrated under reduced pressure, and crystals were precipitated by adding hexane to the obtained oily matter. The obtained crystals were filtered, whereby 1.25 g of the compound represented by Formula (31-3) was obtained.

1H NMR (CDCl$_3$)

δ ppm: 8.11 (3H, d), 7.51-7.45 (9H, m), 7.30 (6H, d), 7.19-7.15 (3H, m), 7.05 (6H, t)

Production of Compound Represented by Formula 1-96

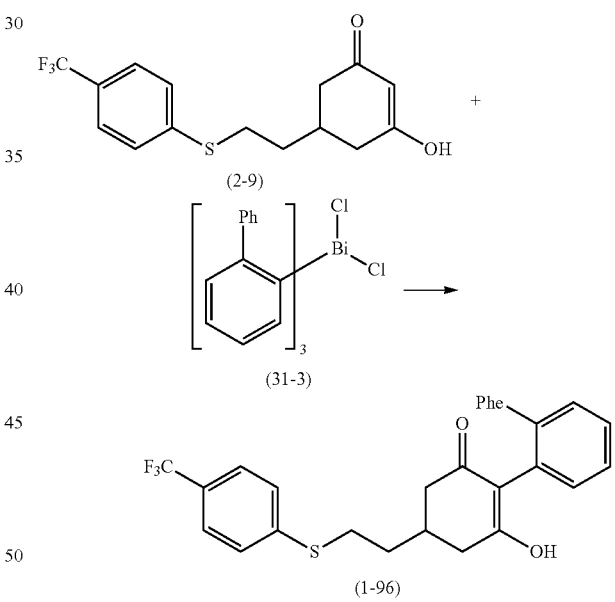

3.16 mg of the compound represented by Formula (2-9), 183 mg of 1,8-diazabicyclo[5.4.0]undeca-7-ene, and 887 mg of the compound represented by Formula (31-3) were dissolved in a mixture of 1 ml of chloroform and 4 ml of toluene at room temperature in a nitrogen atmosphere, followed by stirring at room temperature for 24 hours in a nitrogen atmosphere. The obtained reaction liquid was diluted with chloroform, and the obtained diluted liquid was washed with hydrochloric acid water which had been controlled to have a pH of 1 to 2, and washed with a saturated saline solution. Next, the obtained organic layer was dried over anhydrous magnesium sulfate, and filtered, and the obtained filtrate was concentrated under reduced pressure, whereby an oily matter was obtained. The obtained oily matter was subjected to silica gel column chromatography (eluent, ethyl acetate:hexane=3:7), whereby 99 mg of the compound represented by Formula (1-96) was obtained.

1H NMR (CDCl$_3$)

δ ppm: 7.54-7.17 (13H, m), 5.66 (1H, s), 3.02 (2H, m), 2.73 (2H, m), 2.59-2.17 (3H, m), 1.82-1.77 (2H, m)

The compound produced according to Production Example 1-42 is shown below.

Production of Compound Represented by Formula 1-42

1H NMR (CDCl$_3$)

δ ppm: 7.79 (1H, d), 7.63-7.53 (4H, m), 7.38 (2H, d), 7.20 (1H, dd), 5.40 (1H, s), 3.06 (2H, t), 2.75-2.25 (5H, m), 1.86 (2H, dt)

Production of Compound Represented by Formula 1-166

1H NMR (CDCl$_3$)

δ ppm: 7.54 (2H, d), 7.38 (2H, d), 7.31-7.06 (2H, m), 7.04 (1H, m), 5.65 (1H, d), 3.11-3.03 (2H, m), 2.75-2.65 (2H, m), 2.49-2.39 (2H, m), 2.32-2.23 (1H, m), 2.11 (3H, d), 1.87 (2H, q)

Production Example 1-43

Production of Compound Represented by Formula (1-102)

Production of Compound Represented by Formula 32-4

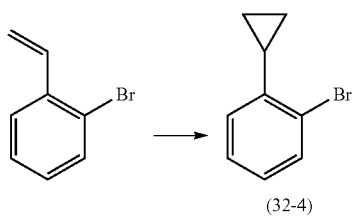

(32-4)

20 ml of diethyl zinc (1.0M hexane solution) was dissolved in 20 ml of dichloromethane under ice-cooling in a nitrogen atmosphere, and a solution of 2.28 g of trifluoroacetic acid in 20 ml of dichloromethane was added thereto. The obtained mixed liquid was stirred for 20 minutes under ice-cooling, and a solution of 5.36 g of diiodomethane in 20 ml of dichloromethane was added thereto, followed by stirring for 20 minutes. A solution of 1.83 g of 2-bromostyrene in 10 ml of dichloromethane was added to the obtained solution under ice-cooling, followed by stirring at room temperature for 6 hours. The obtained reaction liquid was controlled to have a pH of 1 to 2 by adding 2 N hydrochloric acid water, and the resultant product was extracted with hexane. The organic layer was washed with a saturated saline solution, dried over anhydrous magnesium sulfate, and filtered, and the obtained filtrate was concentrated under reduced pressure, whereby 1.76 g of a crude product of the compound represented by Formula (32-4) was obtained.

1H NMR (CDCl$_3$)

δ ppm: 7.54 (1H, dd), 7.20 (1H, td), 7.02 (1H, td), 6.93 (1H, dd), 2.16 (1H, tt), 1.01 (2H, ddd), 0.68 (2H, dt)

Production of Compound Represented by Formula 31-4

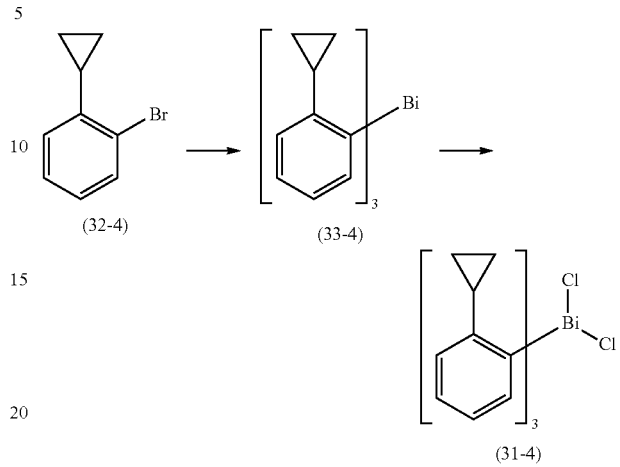

1.76 g of the compound represented by Formula (32-4) was dissolved in 9 ml of tetrahydrofuran at room temperature in a nitrogen atmosphere. The obtained solution was cooled to −78° C., and 6.6 ml of n-butyllithium (1.6 M hexane solution) was added thereto, followed by stirring for 30 minutes. Next, a suspension of 939 mg of trichlorobismuth in 5 ml of tetrahydrofuran was added to the obtained mixture, followed by stirring for 1 hour while heating to room temperature. 20 ml of water was added to the obtained reaction liquid, and the resultant product was extracted with chloroform.

The obtained chloroform layer was washed with a saturated saline solution, dried over anhydrous magnesium sulfate, and filtered, and the obtained filtrate was concentrated under reduced pressure, whereby 2.27 g of a crude product of the compound represented by Formula (33-4) was obtained.

Then, 2.27 g of the obtained crude product of the compound represented by Formula (33-4) was dissolved in 5 ml of dehydrated chloroform at room temperature, then, the resultant product was cooled to 0° C., and 0.36 ml of sulfuryl chloride was added thereto. Then, the temperature was raised to room temperature, followed by stirring for 1 hour. Crystals were precipitated by adding tert-butyl methyl ether to the obtained reaction liquid, and the crystals were concentrated under reduced pressure. The obtained crystals were filtered, whereby 1.05 g of the compound represented by Formula (31-4) was obtained.

1H NMR (d-DMSO)

δ ppm: 7.92 (3H, t), 7.58-7.52 (6H, m), 7.26 (3H, t), 2.36-2.28 (3H, m), 1.03-0.94 (12H, m)

Production of Compound Represented by Formula 1-102

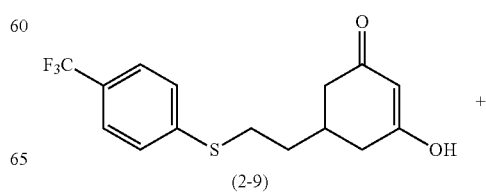

(2-9)

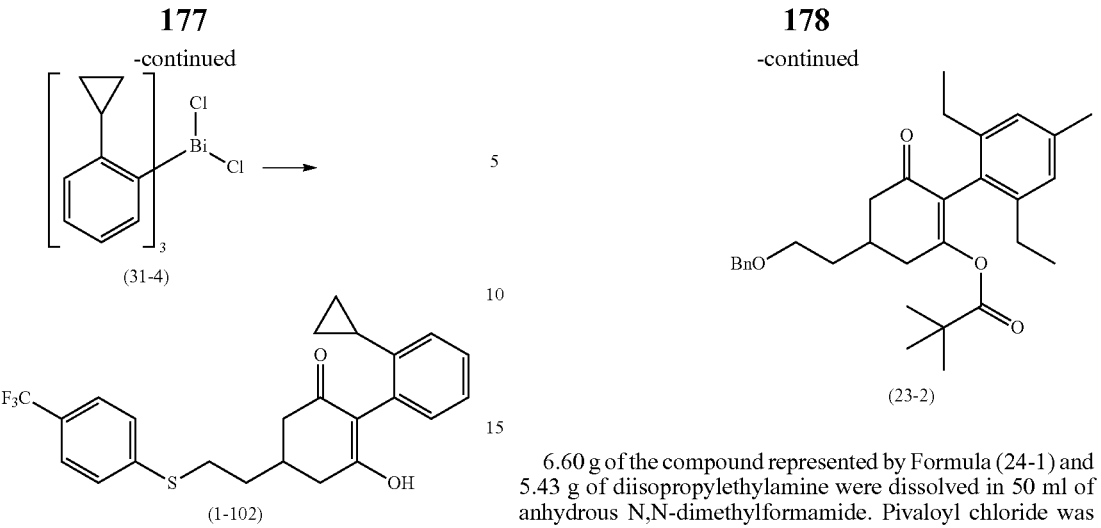

3.16 mg of the compound represented by Formula (2-9), 183 mg of 1,8-diazabicyclo[5.4.0]undeca-7-ene, and 887 mg of the compound represented by Formula (31-4) were dissolved in a mixture of 1 ml of chloroform and 4 ml of toluene at room temperature in a nitrogen atmosphere. The obtained mixture was stirred at room temperature for about 24 hours in a nitrogen atmosphere. The obtained reaction liquid was diluted with chloroform, washed with hydrochloric acid water which had been controlled to have a pH of 1 to 2, and washed with a saturated saline solution. Next, the obtained organic layer was dried over anhydrous magnesium sulfate, and filtered, and the obtained filtrate was concentrated under reduced pressure, whereby an oily matter was obtained. The obtained oily matter was subjected to silica gel column chromatography (eluent, ethyl acetate:hexane=3:7), whereby 56 mg of the compound represented by Formula (1-102) was obtained.

1H NMR (CDCl$_3$)

δ ppm: 7.54 (2H, d), 7.38-7.22 (4H, m), 7.06-7.00 (2H, m), 5.76 (1H, d), 3.08-3.02 (2H, m), 2.75-2.68 (2H, m), 2.55-2.10 (4H, m), 1.90-1.86 (2H, m), 0.87-0.65 (3H, m), 0.57-0.47 (1H, m)

Production Example 1-44

Production of Compound Represented by Formula (1-71)

Production of Compound Represented by Formula 23-2

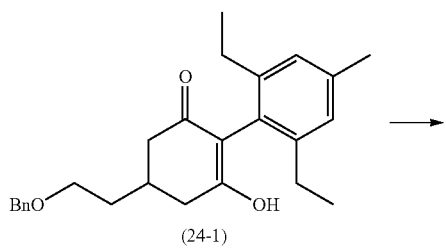

6.60 g of the compound represented by Formula (24-1) and 5.43 g of diisopropylethylamine were dissolved in 50 ml of anhydrous N,N-dimethylformamide. Pivaloyl chloride was added dropwise to the obtained mixture under ice-cooling, followed by stirring at room temperature for 30 minutes. Water was added to the obtained mixture, and the resultant product was extracted with tert-butyl methyl ether. The organic layer was dried over anhydrous magnesium sulfate, and concentrated under reduced pressure, whereby a crude product was obtained. The crude product was subjected to silica gel column chromatography (eluent, ethyl acetate:hexane=3:17), whereby 7.14 g of the compound represented by Formula (23-2) was obtained.

1H NMR (CDCl$_3$)

δ ppm: 7.38-7.26 (5H, m), 6.87 (2H, s), 4.53 (2H, dd), 3.63-3.54 (2H, m), 2.75-2.22 (12H, m), 1.86-1.76 (2H, m), 1.10-1.03 (6H, m), 0.87 (9H, s)

Production of Compound Represented by Formula 22-2

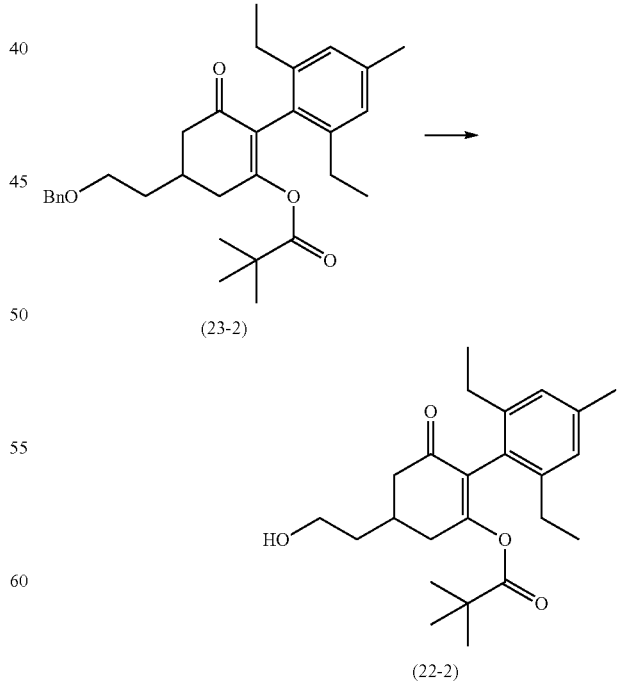

7.14 g of the compound represented by Formula (23-2) was dissolved in 45 ml of ethyl acetate. 3.57 g of 10% palladium-carbon was added to the obtained mixed liquid, followed by stirring at 35° C. for 18 hours in a hydrogen atmosphere. The reaction mixed liquid was filtered using Celite (registered trademark), and the obtained filtrate was concentrated under reduced pressure, whereby 5.10 g of the compound represented by Formula (22-2) was obtained.

1H NMR (CDCl$_3$)

δ ppm: 6.87 (2H, s), 3.81 (2H, d), 2.78-2.24 (12H, m), 1.83-1.73 (2H, m), 1.39-1.36 (1H, m), 1.10-1.04 (6H, m), 0.87 (9H, s)

Production of Compound Represented by Formula 21-1

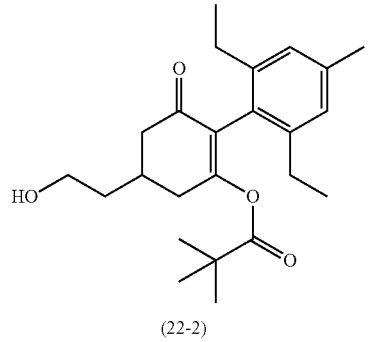

(22-2)

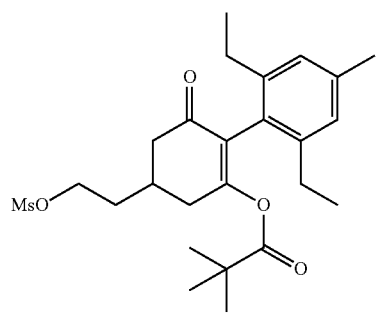

(21-1)

193 mg of the compound represented by Formula (21-2) and 162 mg of diisopropylethylamine were dissolved in a solution of 5 ml of N,N-dimethylformamide. 68.7 mg of methanesulfonyl chloride was added dropwise to the obtained mixture under ice-cooling, followed by stirring at room temperature for 1 hour. Water was added to the reaction mixture, and the resultant product was extracted with tert-butyl methyl ether. The organic layer was dried over anhydrous magnesium sulfate, and concentrated under reduced pressure. Hexane was added to the residue, and the resultant product was filtered, whereby 208 mg of the compound represented by Formula (21-1) was obtained.

1H NMR (CDCl$_3$)

δ ppm: 6.87 (2H, s), 4.37 (2H, dd), 3.05 (3H, s), 2.74-2.25 (12H, m), 2.00-1.97 (2H, m), 1.10-1.04 (6H, m), 0.88 (9H, s)

Production of Compound Represented by Formula 1-71

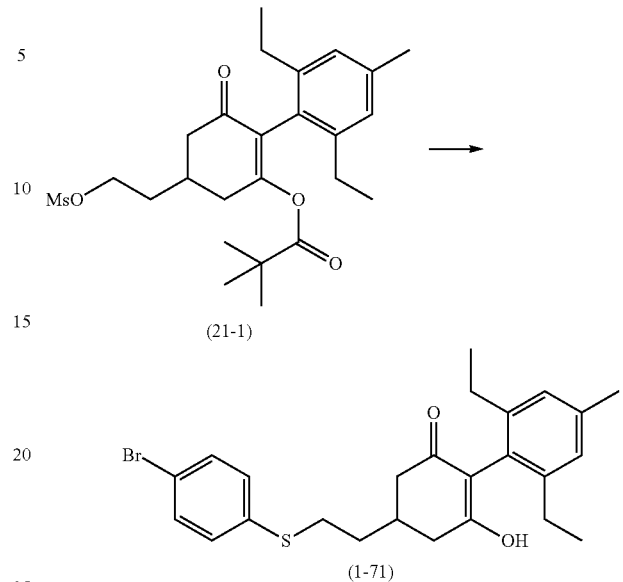

200 mg of the compound represented by Formula (21-1) and 167 mg of diisopropylethylamine were dissolved in 5 ml of N,N-dimethylformamide. 195 mg of parabromothiophenol was added to the obtained mixed liquid, followed by stirring at room temperature for 16 hours. The obtained mixture was heated to 80° C., and stirred for 2 hours. Water was added thereto, and the resultant product was extracted with tert-butyl methyl ether. The obtained organic layer was washed with water, dried over anhydrous magnesium sulfate, and filtered. The obtained filtrate was concentrated under reduced pressure, and the resultant product was subjected to silica gel column chromatography (eluent, ethyl acetate:hexane=0:100→1:4), whereby 193 mg of the compound represented by Formula (1-71) was obtained.

1H NMR (CDCl$_3$)

δ ppm: 7.42 (2H, dt), 7.21 (2H, dt), 6.98 (2H, s), 5.61 (1H, s), 3.05-2.93 (2H, m), 2.73-2.64 (2H, m), 2.48-2.21 (10H, m), 1.81 (2H, q), 1.10-1.03 (6H, m)

Production Example 1-45

Production of Compound Represented by Formula (1-132)

Production of Compound Represented by Formula 1-132

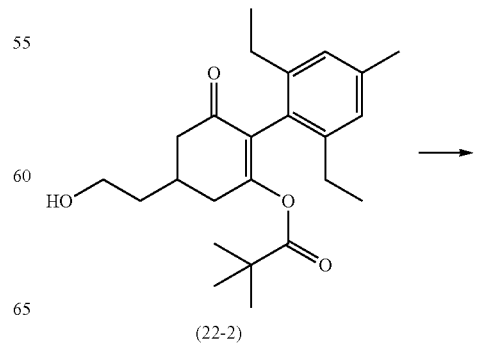

(22-2)

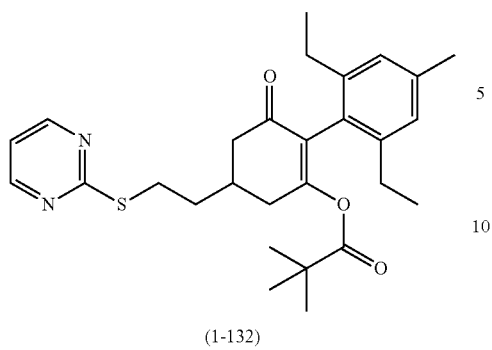

(1-132)

193 mg of the compound represented by Formula (22-2) and 258 mg of diisopropylethylamine were dissolved in a solution of 5 ml of N,N-dimethylformamide. 68.7 mg of methanesulfonyl chloride was added dropwise to the obtained mixture under ice-cooling, followed by stirring at room temperature for 30 minutes. 123 mg of 2-mercaptopyrimidine was added to the obtained mixed liquid, followed by stirring at 80° C. for 9 hours. The obtained reaction liquid was controlled to have a pH of 1 by adding 2 N hydrochloric acid, and the resultant product was extracted with tert-butyl methyl ether. The obtained organic layer was washed with water, dried over anhydrous magnesium sulfate, and filtered. The obtained filtrate was concentrated under reduced pressure, and the resultant product was subjected to silica gel column chromatography (eluent, ethyl acetate:hexane=7:13), whereby 171 mg of the compound represented by Formula (1-132) was obtained.

1H NMR (CDCl$_3$)

δ ppm: 8.52 (2H, dd), 6.98 (1H, dt), 6.87 (2H, d), 3.30-3.18 (2H, m), 2.85-2.67 (2H, m), 2.57-2.23 (10H, m), 1.96 (2H, q), 1.09-1.02 (6H, m), 0.87 (9H, s)

Production Example 1-46

Production of Compound Represented by Formula (1-34)

Production of Compound Represented by Formula 1-34

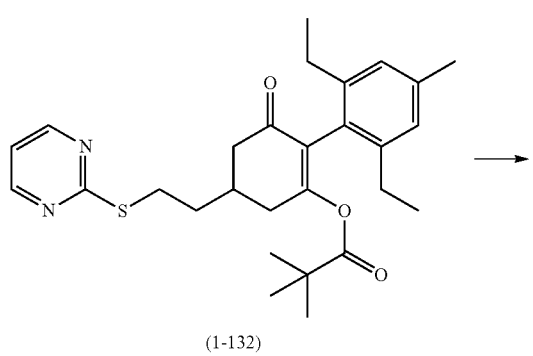

(1-132)

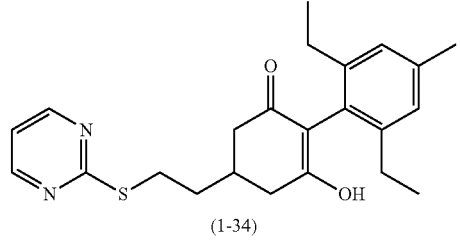

(1-34)

170 mg of the compound represented by Formula (1-132) was dissolved in a mixed solution of 10 ml of tetrahydrofuran, 10 ml of methanol, and 10 ml of water. 44.5 mg of lithium hydroxide monohydrate was added to the obtained solution, followed by stirring for 10 minutes at room temperature. The reaction liquid was concentrated under reduced pressure, and controlled to have a pH of 1 by adding 2 N hydrochloric acid, and the resultant product was extracted with tert-butyl methyl ether. The obtained organic layer was washed with water, dried over anhydrous magnesium sulfate, and filtered. The obtained filtrate was concentrated under reduced pressure, and the resultant product was subjected to silica gel column chromatography (eluent, ethyl acetate:hexane=2:3), whereby 126 mg of the compound represented by Formula (1-34) was obtained.

1H NMR (CDCl$_3$)

δ ppm: 8.53 (2H, d), 7.00-6.96 (3H, m), 5.57 (1H, s), 3.29-3.21 (2H, m), 2.81-2.73 (2H, m), 2.51-2.43 (2H, m), 2.41-2.25 (8H, m), 1.95 (2H, s), 1.09-1.03 (6H, m)

Production Example 1-47

Production of Compound Represented by Formula (1-104)

Production of Compound Represented by Formula 1-104

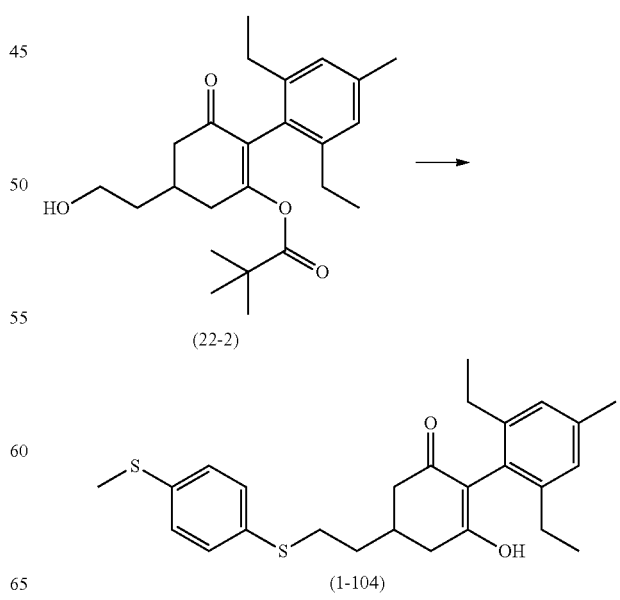

178 mg of the compound represented by Formula (22-2) and 238 mg of diisopropylethylamine were dissolved in a solution of 5 ml of N,N-dimethylformamide. 63.3 mg of methanesulfonyl chloride was added dropwise to the obtained mixture under ice-cooling, followed by stirring at room temperature for 30 minutes. 158 mg of para(methylthio)thiophenol was added to the obtained solution, followed by stirring at room temperature for 1.5 hours. The obtained reaction liquid was controlled to have a pH of 1 by adding 2 N hydrochloric acid, and the resultant product was extracted with tert-butyl methyl ether. The obtained organic layer was washed with water, dried over anhydrous magnesium sulfate, and filtered. The filtrate was concentrated under reduced pressure, and the resultant product was subjected to silica gel column chromatography (eluent, ethyl acetate:hexane=1:9→7:13), whereby 100 mg of the compound represented by Formula (1-104) was obtained.

1H NMR (CDCl$_3$)
δ
ppm: 7.30 (2H, dt), 7.20 (2H, dt), 6.98 (2H, s), 5.58 (1H, s), 2.97 (2H, td), 2.70-2.64 (2H, m), 2.47 (3H, s), 2.45-2.22 (10H, m), 1.80 (2H, q), 1.10-1.03 (6H, m)

Production Example 1-48

Production of Compound Represented by Formula (1-133)

Production of Compound Represented by Formula 1-133

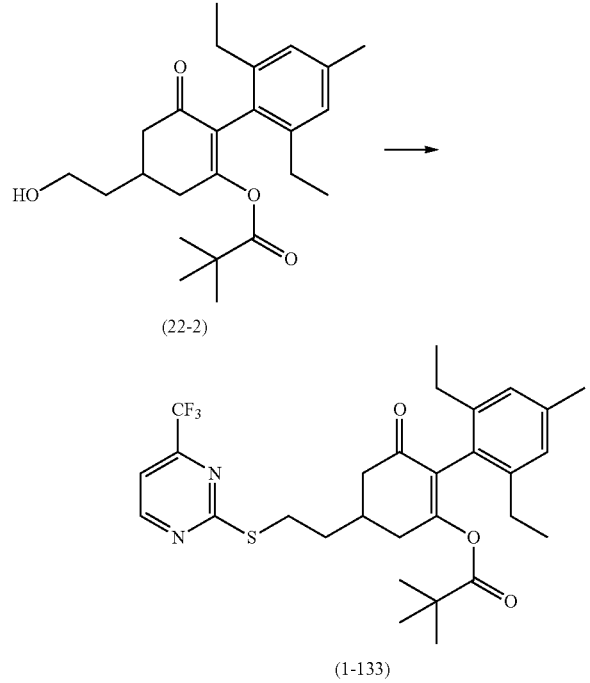

387 mg of the compound represented by Formula (22-2) and 516 mg of diisopropylethylamine were dissolved in a solution of 10 ml of N,N-dimethylformamide. 137 mg of methanesulfonyl chloride was added dropwise to the obtained mixture under ice-cooling, followed by stirring at room temperature for 1 hour. 396 mg of 4-trifluoromethyl-2-pyrimidinethiol was added to the obtained mixed liquid, followed by stirring at 80° C. for 30 minutes. The reaction liquid was controlled to have a pH of 1 by adding 2 N hydrochloric acid, and the resultant product was extracted with tert-butyl methyl ether. The obtained organic layer was washed with water, dried over anhydrous magnesium sulfate, and filtered. The obtained filtrate was concentrated under reduced pressure, and the resultant product was subjected to silica gel column chromatography (eluent, ethyl acetate:hexane=1:3), whereby 546 mg of the compound represented by Formula (1-133) was obtained.

1H NMR (CDCl$_3$)
δ
ppm: 8.76 (1H, d), 7.29 (1H, d), 6.87 (2H, d), 3.33-3.23 (2H, m), 2.82-2.68 (3H, m), 2.59-2.24 (9H, m), 1.97 (2H, q), 1.10-1.03 (6H, m), 0.88 (9H, s)

Production Example 1-49

Production of Compound Represented by Formula (1-35)

Production of Compound Represented by Formula 1-35

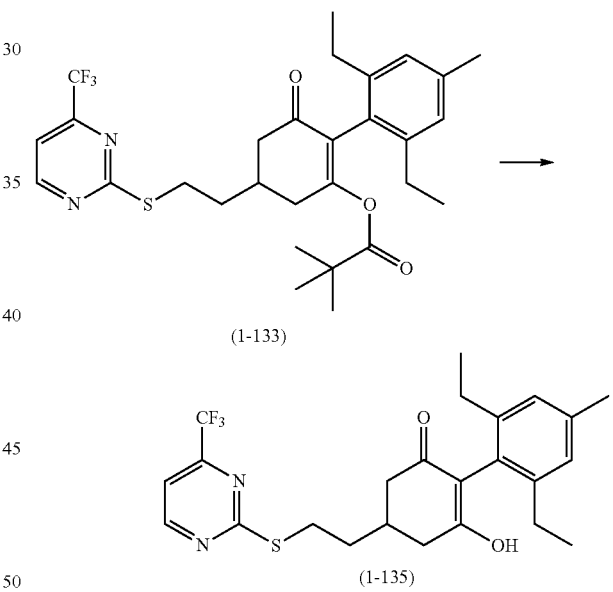

546 mg of the compound represented by Formula (1-133) was dissolved in a mixed solution of 10 ml of tetrahydrofuran, 10 ml of methanol, and 10 ml of water. 126 mg of lithium hydroxide monohydrate was added to the obtained solution, followed by stirring for 20 minutes at room temperature. The reaction liquid was concentrated under reduced pressure, and controlled to have a pH of 1 by adding 2 N hydrochloric acid, and the resultant product was extracted with tert-butyl methyl ether. The obtained organic layer was washed with water, dried over anhydrous magnesium sulfate, and filtered. The obtained filtrate was concentrated under reduced pressure, and the resultant product was subjected to silica gel column chromatography (eluent, ethyl acetate:hexane=1:3), whereby 435 mg of the compound represented by Formula (1-35) was obtained.

1H NMR (CDCl₃)

δ ppm: 8.76 (1H, d), 7.29 (1H, d), 6.99 (2H, d), 5.62 (1H, s), 3.27 (2H, td), 2.78-2.71 (2H, m), 2.51-1.93 (12H, m), 1.07 (6H, m)

The compound produced according to Production Example 1-49 is shown below.

Production of Compound Represented by Formula 1-136

1H NMR (CDCl₃)

δ ppm: 7.38 (1H, t), 7.26 (1H, m), 7.10 (2H, m), 6.98 (2H, s), 5.51 (1H, s), 3.00 (2H, t), 2.77 (2H, t), 2.50-2.20 (10H, m), 1.79 (2H, q), 1.06 (6H, q)

Production of Compound Represented by Formula 1-137

1H NMR (CDCl₃)

δ ppm: 7.37 (1H, d), 7.30-7.20 (2H, m), 7.15-7.06 (1H, m), 6.98 (2H, s), 5.51 (1H, s), 3.02 (2H, q), 2.71 (2H, t), 2.51-2.22 (10H, m), 1.87 (2H, q), 1.06 (6H, q)

Production of Compound Represented by Formula 1-138

1H NMR (CDCl₃)

δ ppm: 7.57 (1H, d), 7.55-7.25 (2H, m), 7.07-7.04 (1H, m), 6.98 (2H, s), 5.51 (1H, s), 3.04-3.00 (2H, m), 2.71 (2H, t), 2.50-2.28 (10H, m), 1.89 (2H, q), 1.06 (6H, q)

Production of Compound Represented by Formula 1-139

1H NMR (CDCl₃)

δ ppm: 7.28-7.26 (1H, d), 7.19-7.05 (3H, m), 6.97 (2H, s), 5.51 (1H, s), 2.98 (2H, t), 2.70 (2H, t), 2.50-2.20 (13H, m), 1.85 (2H, q), 1.06 (6H, q)

Production of Compound Represented by Formula 1-140

1H NMR (CDCl₃)

δ ppm: 7.30-7.18 (4H, m), 6.97 (2H, s), 5.46 (1H, s), 3.00 (2H, t), 2.78 (2H, q), 2.65 (2H, t), 2.50-2.21 (10H, m), 1.84 (2H, q), 1.23 (3H, t), 1.06 (6H, q)

Production of Compound Represented by Formula 1-141

1H NMR (CDCl₃)

δ ppm: 7.34-7.10 (4H, m), 6.97 (2H, s), 5.53 (1H, s), 3.55-3.45 (1H, m), 2.98 (2H, t), 2.70 (2H, t), 2.50-2.22 (10H, m), 1.85 (2H, q), 1.24 (6H, d), 1.06 (6H, q)

Production of Compound Represented by Formula 1-142

1H NMR (CDCl₃)

δ ppm: 7.32-7.19 (2H, m), 6.98-6.84 (4H, m), 5.53 (1H, s), 3.91 (3H, s), 3.08-2.94 (2H, m), 2.69 (2H, t), 2.48-2.20 (10H, m), 1.80 (2H, q), 1.06 (6H, q)

Production of Compound Represented by Formula 1-143

1H NMR (CDCl₃)

δ ppm: 7.30-7.20 (1H, m), 7.10-6.98 (4H, m), 6.90-6.80 (1H, t), 5.52 (1H, s), 3.05-3.00 (2H, m), 2.70 (2H, t), 2.49-2.23 (10H, m), 1.83 (2H, q), 1.06 (6H, q)

Production of Compound Represented by Formula 1-144

1H NMR (CDCl₃)

δ ppm: 7.30-7.15 (4H, m), 6.97 (2H, s), 5.54 (1H, s), 3.05-3.00 (2H, m), 2.70 (2H, t), 2.48-2.22 (10H, m), 1.85 (2H, q), 1.06 (6H, q)

Production of Compound Represented by Formula 1-145

1H NMR (CDCl₃)

δ ppm: 7.48 (1H, s), 7.31-7.11 (3H, m), 6.95 (2H, s), 5.53 (1H, s), 3.09-3.00 (2H, m), 2.70 (2H, t), 2.47-2.25 (10H, m), 1.85 (2H, q), 1.06 (6H, q)

Production of Compound Represented by Formula 1-146

1H NMR (CDCl₃)

δ ppm: 7.20-7.10 (3H, m), 7.12-6.98 (3H, m), 5.51 (1H, s), 3.01-2.95 (2H, m), 2.65 (2H, t), 2.45-2.20 (13H, m), 1.82 (2H, q), 1.06 (6H, q)

Production of Compound Represented by Formula 1-147

1H NMR (CDCl₃)

δ ppm: 7.30-7.12 (3H, m), 6.98 (2H, s), 5.48 (1H, s), 3.10-3.00 (2H, m), 2.72 (2H, t), 2.52-2.22 (10H, m), 1.89 (2H, q), 1.06 (6H, q)

Production of Compound Represented by Formula 1-148

1H NMR (CDCl₃)

δ ppm: 7.12-7.05 (3H, m), 6.92 (2H, s), 5.50 (1H, s), 2.71 (2H, t), 2.55 (6H, s), 2.61 (2H, t), 2.42-2.17 (10H, m), 1.80 (2H, q), 1.06 (6H, q)

Production of Compound Represented by Formula 1-149

1H NMR (CDCl₃)

δ ppm: 7.36 (1H, dd), 7.14 (1H, dd), 6.99 (1H, dd), 6.96 (2H, s), 5.80 (1H, s), 2.86 (2H, t), 2.67-2.59 (2H, m), 2.47-2.18 (10H, m), 1.78 (2H, q), 1.07 (3H, t), 1.05 (3H, t)

Production of Compound Represented by Formula
1-150

1H NMR (CDCl$_3$)
δ
ppm: 7.68 (1H, d), 7.24 (1H, d), 6.99 (2H, s), 5.49 (1H, s), 3.32 (2H, t), 2.76-2.68 (2H, m), 2.46-2.25 (10H, m), 1.97 (2H, q), 1.08 (3H, t), 1.05 (3H, t)

Production of Compound Represented by Formula
1-151

1H NMR (CDCl$_3$)
δ
ppm: 7.88 (2H, d), 7.33 (2H, d), 6.99 (2H, s), 5.52 (1H, s), 3.10 (2H, dt), 2.75-2.69 (2H, m), 2.58 (3H, s), 2.47-2.24 (10H, m), 1.90 (2H, q), 1.09 (3H, t), 1.05 (3H, t)

Production of Compound Represented by Formula
1-152

1H NMR (CDCl$_3$)
δ
ppm: 7.31 (2H, d), 6.97 (2H, s), 6.78 (2H, d), 5.57 (1H, s), 5.18 (1H, s), 2.89 (2H, t), 2.68-2.61 (2H, m), 2.43-2.18 (10H, m), 1.76 (2H, q), 1.08 (3H, t), 1.04 (3H, t)

Production of Compound Represented by Formula
1-153

1H NMR (CDCl$_3$)
δ
ppm: 8.67 (1H, dd), 7.67 (1H, dd), 7.27-7.25 (1H, m), 6.99 (2H, s), 5.50 (1H, s), 3.33-3.29 (2H, m), 2.79-2.71 (2H, m), 2.51-2.24 (10H, m), 1.94-1.89 (2H, m), 1.07 (3H, t), 1.04 (3H, t)

Production of Compound Represented by Formula
1-155

1H NMR (CDCl$_3$)
δ
ppm: 9.02-9.01 (1H, m), 8.04 (1H, dd), 7.23 (1H, dd), 6.98 (2H, s), 5.53 (1H, s), 3.93 (3H, s), 3.32 (2H, t), 2.76 (2H, t), 2.51-2.23 (10H, m), 1.92 (2H, q), 1.05 (6H, q)

Production of Compound Represented by Formula
1-127

1H NMR (CDCl$_3$)
δ
ppm: 8.36 (1H, dd), 7.55 (1H, dd), 6.98-6.95 (3H, m), 5.46 (1H, s), 3.30 (2H, dt), 2.80-2.73 (2H, m), 2.52-2.25 (10H, m), 1.92 (2H, q), 1.07 (3H, t), 1.04 (3H, t)

Production of Compound Represented by Formula
1-160

1H NMR (CDCl$_3$)
δ
ppm: 6.98 (2H, s), 5.75 (1H, s), 5.55 (1H, s), 3.94 (6H, s), 3.29-3.18 (2H, m), 2.76-2.69 (2H, m), 2.47-2.26 (10H, m), 1.96 (2H, q), 1.07 (6H, q)

Production of Compound Represented by Formula
1-161

1H NMR (CDCl$_3$)
δ
ppm: 6.98 (2H, s), 6.84-6.78 (2H, m), 6.62 (1H, tt), 5.52 (1H, s), 3.03 (2H, ddd), 2.72 (2H, dt), 2.48-2.25 (10H, m), 1.87 (2H, dd), 1.07 (6H, dt)

Production of Compound Represented by Formula
1-70

1H NMR (CDCl$_3$)
δ
ppm: 7.61 (2H, d), 7.07 (2H, d), 6.97 (2H, s), 5.72 (1H, s), 3.04-2.92 (2H, m), 2.72-2.63 (2H, m), 2.45-2.21 (10H, m), 1.81 (2H, q), 1.08 (3H, t), 1.04 (3H, t)

Production of Compound Represented by Formula
1-75

1H NMR (CDCl$_3$)
δ
ppm: 7.34-7.28 (4H, m), 6.98 (2H, s), 5.46 (1H, s), 2.99 (2H, dt), 2.71-2.64 (2H, m), 2.43-2.23 (10H, m), 1.82 (2H, q), 1.31 (9H, s), 1.08 (3H, t), 1.04 (3H, t)

Production of Compound Represented by Formula
1-109

1H NMR (CDCl$_3$)
δ
ppm: 8.74 (2H, d), 6.98 (2H, s), 5.50 (1H, s), 3.28 (2H, dt), 2.79-2.73 (2H, m), 2.52-2.25 (10H, m), 1.96 (2H, q), 1.09-1.03 (6H, m)

Production of Compound Represented by Formula
1-112

1H NMR (CDCl$_3$)
δ
ppm: 8.62 (1H, d), 7.74 (1H, dd), 7.60 (1H, d), 6.98 (2H, s), 5.51 (1H, s), 3.15-3.07 (2H, m), 2.75-2.68 (2H, m), 2.47-2.24 (10H, m), 1.89 (2H, q), 1.09 (3H, t), 1.05 (3H, t)

Production of Compound Represented by Formula
1-115

1H NMR (CDCl$_3$)
δ
ppm: 8.70 (1H, s), 8.51 (1H, s), 6.98 (2H, s), 5.49 (1H, s), 3.33 (2H, dt), 2.79-2.72 (2H, m), 2.51-2.24 (10H, m), 1.93 (2H, q), 1.07 (3H, t), 1.04 (3H, t)

Production of Compound Represented by Formula
1-118

1H NMR (CDCl$_3$)
δ
ppm: 7.56 (1H, d), 7.49 (1H, d), 6.98 (2H, s), 5.48 (1H, s), 3.54-3.46 (2H, m), 2.79-2.70 (2H, m), 2.53-2.27 (10H, m), 2.06-1.99 (2H, m), 1.08 (3H, t), 1.06 (3H, t)

Production of Compound Represented by Formula
1-121

1H NMR (CDCl$_3$)
δ ppm: 8.61 (1H, d), 7.72 (1H, dd), 7.23 (1H, dd), 6.98 (2H, s), 3.29 (2H, ddd), 2.76 (2H, ddd), 2.52-2.23 (10H, m), 1.95-1.89 (2H, m), 1.06 (6H, dt)

Production of Compound Represented by Formula 1-169

1H NMR (CDCl$_3$)

δ ppm: 7.21-7.06 (3H, m), 6.95 (2H, s), 5.64 (1H, s), 2.97 (2H, ddd), 2.68 (2H, dt), 2.48-2.22 (10H, m), 1.83-1.74 (2H, m), 1.12-0.99 (6H, m)

Production of Compound Represented by Formula 1-172

1H NMR (CDCl$_3$)
δ
ppm: 6.95 (2H, s), 5.79 (1H, s), 4.07 (2H, t), 2.68 (2H, d), 2.37-2.16 (16H, m), 1.95 (2H, d), 1.09-0.98 (6H, m)

Production of Compound Represented by Formula 1-173

1H NMR (CDCl$_3$)
δ
ppm: 7.67 (2H, d), 7.32 (2H, d), 6.97 (2H, s), 6.30 (1H, s), 4.19-4.14 (2H, m), 2.79-2.66 (2H, m), 2.48-2.28 (13H, m), 2.08-1.98 (2H, m), 1.03 (6H, td)

Production Example 1-50

Production of Compound Represented by Formula (1-134)

Production of Compound Represented by Formula 35-1

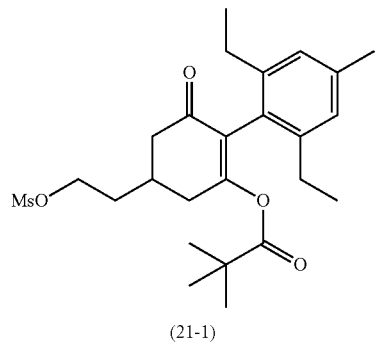

(21-1)

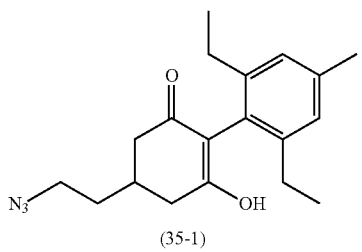

(35-1)

At room temperature, 360 mg of the compound represented by Formula (21-1) was dissolved in 4 ml of N,N-dimethylformamide, and 500 mg of sodium azide and 0.015 ml of 15-crown 5 ether were added thereto. The obtained mixed liquid was heated to 100° C., followed by stirring for about 4 hours. Next, the obtained reaction mixed liquid was concentrated under reduced pressure, and the resultant product was subjected to silica gel column chromatography (eluent, ethyl acetate:hexane=34:66), whereby 180 mg of the compound represented by Formula (35-1) was obtained.

1H NMR (CDCl$_3$)
δ
ppm: 6.98 (2H, s), 5.79 (1H, s), 3.44-3.40 (2H, m), 2.71-2.64 (2H, m), 2.44-2.24 (10H, m), 1.77 (2H, q), 1.07 (6H, td)

Production of Compound Represented by Formula 1-134

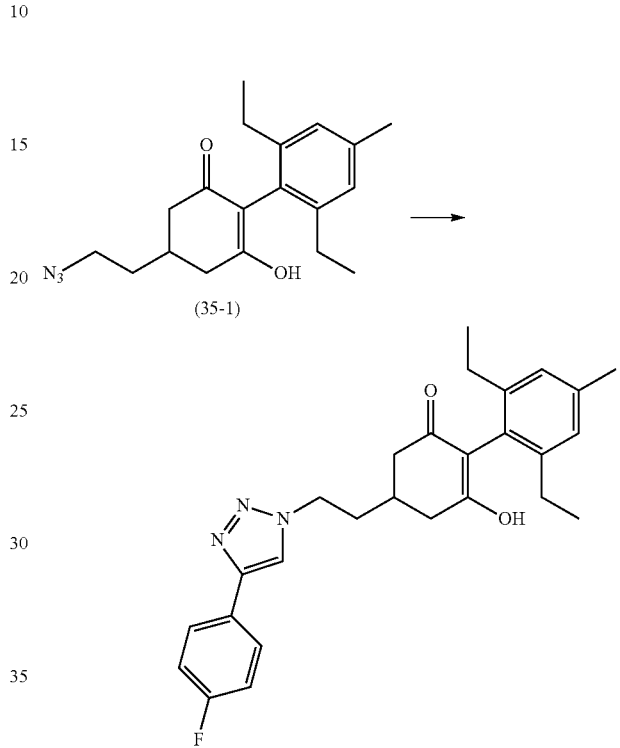

(1-134)

At room temperature, 100 mg of the compound represented by Formula (35-1) and 40 mg of 1-ethynyl-4-fluorobenzene were dissolved in a mixture of 4 ml of acetonitrile and 1 ml of dimethyl sulfoxide, and 7 mg of sodium ascorbate and 3 mg of copper sulfate were added to the obtained mixed liquid, followed by heating under reflux for about 5 hours. Next, the obtained reaction mixed liquid was concentrated under reduced pressure, and the resultant product was subjected to silica gel column chromatography (eluent, ethyl acetate:hexane=66:34), whereby 54.1 mg of the compound represented by Formula (1-134) was obtained.

1H NMR (CDCl$_3$)

δ ppm: 7.83-7.78 (2H, m), 7.75 (1H, s), 7.13 (2H, t), 6.98 (2H, s), 5.77 (1H, s), 4.57-4.46 (2H, m), 2.80-2.67 (2H, m), 2.52-2.12 (12H, m), 1.04 (6H, q)

The compound produced according to Production Example 1-50 is shown below.

Production of Compound Represented by Formula 1-135

1H NMR (CDCl$_3$)

δ ppm: 7.95 (2H, d), 7.88 (1H, s), 7.69 (2H, d), 6.97 (2H, s), 5.79 (1H, s), 4.60-4.48 (2H, m), 2.80-2.68 (2H, m), 2.53-2.12 (12H, m), 1.04 (6H, q)

Hereinafter, Formulation Examples are shown. The compounds are shown by the number of structural formula.

Formulation Example 1

Compound (1-1) 30% by weight
Benoxacor 1% by weight
Polyoxyethylene sorbitan monooleate 3% by weight
Carboxymethyl cellulose 3% by weight
Water 63% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Formulation Example 2

Compound (1-1) 20% by weight
Cloquintocet-mexyl 5% by weight
Sodium lignin sulfonate 5% by weight
Polyoxyethylene alkyl ether 5% by weight
White carbon 5% by weight
Clay 60% by weight The above materials are mixed and pulverized, whereby a wettable powder is obtained. The prepared formulation is diluted with water as appropriate, and used.

Each formulation is obtained in the same manner except for using any one of Compounds (1-2) to (1-156) or Compounds (1-158) to (1-200) instead of Compound (1-1).

Formulation Example 3

Compound (1-1) 20% by weight
Cyometronil 4% by weight
Polyoxyethylene sorbitan monooleate 3% by weight
Carboxymethyl cellulose 3% by weight
Water 70% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Formulation Example 4

Compound (1-1) 12% by weight
Dichlormid 2% by weight
Sodium lignin sulfonate 5% by weight
Polyoxyethylene alkyl ether 5% by weight
White carbon 5% by weight
Clay 71% by weight The above materials are mixed and pulverized, whereby a formulation is obtained. The prepared formulation is diluted as appropriate, and used.

Each formulation is obtained in the same manner except for using any one of Compounds (1-2) to (1-156) or Compounds (1-158) to (1-200) instead of Compound (1-1).

Formulation Example 5

Compound (1-1) 20% by weight
Fenchlorazole-ethyl 5% by weight
Polyoxyethylene sorbitan monooleate 3% by weight
Carboxymethyl cellulose 3% by weight
Water 69% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Formulation Example 6

Compound (1-1) 12% by weight
Fenclorim 4% by weight
Sodium lignin sulfonate 5% by weight
Polyoxyethylene alkyl ether 5% by weight
White carbon 5% by weight
Clay 69% by weight The above materials are mixed and pulverized, whereby a formulation is obtained. The prepared formulation is diluted as appropriate, and used.

Each formulation is obtained in the same manner except for using any one of Compounds (1-2) to (1-156) or Compounds (1-158) to (1-200) instead of Compound (1-1).

Formulation Example 7

Compound (1-1) 15% by weight
Flurazole 5% by weight
Polyoxyethylene sorbitan monooleate 3% by weight
Carboxymethyl cellulose 3% by weight
Water 74% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Formulation Example 8

Compound (1-1) 30% by weight
Furilazole 1% by weight
Sodium lignin sulfonate 5% by weight
Polyoxyethylene alkyl ether 5% by weight
White carbon 5% by weight
Clay 54% by weight The above materials are mixed and pulverized, whereby a formulation is obtained. The prepared formulation is diluted as appropriate, and used.

Each formulation is obtained in the same manner except for using any one of Compounds (1-2) to (1-156) or Compounds (1-158) to (1-200) instead of Compound (1-1).

Formulation Example 9

Compound (1-1) 16% by weight
Mefenpyr-diethyl 4% by weight
Polyoxyethylene sorbitan monooleate 3% by weight
Carboxymethyl cellulose 3% by weight
Water 74% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Formulation Example 10

Compound (1-1) 10% by weight
Oxabetrinil 5% by weight
Sodium lignin sulfonate 5% by weight
Polyoxyethylene alkyl ether 5% by weight
White carbon 5% by weight
Clay 70% by weight The above materials are mixed and pulverized, whereby a formulation is obtained. The prepared formulation is diluted with water as appropriate, and used.

Each formulation is obtained in the same manner except for using any one of Compounds (1-2) to (1-156) or Compounds (1-158) to (1-200) instead of Compound (1-1).

Formulation Example 11

Compound (1-1) 10% by weight
Isoxadifen 1% by weight
Polyoxyethylene sorbitan monooleate 5% by weight
Carboxymethyl cellulose 5% by weight
Water 79% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Formulation Example 12

Compound (1-1) 10% by weight
Cyprosulfamide 10% by weight
Sodium lignin sulfonate 5% by weight
Polyoxyethylene alkyl ether 5% by weight
White carbon 5% by weight
Clay 65% by weight The above materials are mixed and pulverized, whereby a formulation is obtained. The prepared formulation is diluted with water as appropriate, and used.

Each formulation is obtained in the same manner except for using any one of Compounds (1-2) to (1-156) or Compounds (1-158) to (1-200) instead of Compound (1-1).

Formulation Example 13

Compound (1-1) 10% by weight
Fluxofenim 3% by weight
Polyoxyethylene sorbitan monooleate 4% by weight
Carboxymethyl cellulose 6% by weight
Water 77% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Formulation Example 14

Compound (1-1) 14% by weight
1,8-Naphthalic anhydride 6% by weight
Sodium lignin sulfonate 6% by weight
Polyoxyethylene alkyl ether 3% by weight
White carbon 6% by weight
Clay 65% by weight The above materials are mixed and pulverized, whereby a formulation is obtained. The prepared formulation is diluted with water as appropriate, and used.

Each formulation is obtained in the same manner except for using any one of Compounds (1-2) to (1-156) or Compounds (1-158) to (1-200) instead of Compound (1-1).

Formulation Example 15

Compound (1-1) 20% by weight
AD-67 2% by weight
Polyoxyethylene sorbitan monooleate 4% by weight
Carboxymethyl cellulose 6% by weight
Water 68% by weight The above materials are mixed, and the resultant product is wet-pulverized until the particle size become equal to or less than 5 microns, whereby a formulation is obtained.

Each formulation is obtained in the same manner except for using any one of Compounds (1-2) to (1-156) or Compounds (1-158) to (1-200) instead of Compound (1-1).

Hereinafter, Test Examples are shown.

Test Example 1

Foliar Application Test to Weed

Commercially available soil was packed in a plastic cup, and a seed of barnyard grass (*Echinochloa crus-galli*) or wild oat (*Avena fatua*) was inoculated to this. The seed was covered with soil of about 0.5 cm, and cultivated in a greenhouse. When the plant was grown to a 1 to 2 leaf stage, the spray liquid of the herbicidal composition according to the invention was uniformly spayed throughout the plant so as to be a predetermined dosage. The spray liquid was prepared by dissolving a predetermined amount of each compound in a solution (2%) of Tween 20 (polyoxyethylene sorbitan fatty acid ester, manufactured by MP Biomedicals Inc.) in dimethyl formamide and diluting with water. After the drug treatment, the plant was placed for 3 weeks in a greenhouse. Herbicidal effect was evaluated in 101 stages from 0 (no effect) to 100 (complete death).

The results are shown in Tables 2 to 78.

TABLE 2

| Herbicidal composition of the invention | Dosage (gAI/ha) | Herbicidal effect (%) Barnyard grass |
|---|---|---|
| (Compound 1-1) + Cloquintocet-mexyl | 20 + 5 | 100 |
| (Compound 1-1) + Mefenpyr-diethyl | 200 + 50 | 100 |

TABLE 3

| Herbicidal composition of the invention | Dosage (gAI/ha) | Herbicidal effect (%) Barnyard grass |
|---|---|---|
| (Compound 1-4) + Cloquintocet-mexyl | 100 + 5 | 100 |
| (Compound 1-4) + Mefenpyr-diethyl | 10 + 50 | 100 |

TABLE 4

| Herbicidal composition of the invention | Dosage (gAI/ha) | Herbicidal effect (%) Barnyard grass |
|---|---|---|
| (Compound 1-3) + Mefenpyr-diethyl | 200 + 50 | 99 |

TABLE 5

| Herbicidal composition of the invention | Dosage (gAI/ha) | Herbicidal effect (%) Barnyard grass |
|---|---|---|
| (Compound 1-19) + Cloquintocet-mexyl | 200 + 50 | 100 |
| (Compound 1-19) + Mefenpyr-diethyl | 20 + 5 | 100 |

TABLE 6

| Herbicidal composition of the invention | Dosage (gAI/ha) | Herbicidal effect (%) Barnyard grass |
|---|---|---|
| (Compound 1-10) + Cloquintocet-mexyl | 10 + 5 | 100 |
| (Compound 1-10) + Mefenpyr-diethyl | 100 + 5 | 100 |

TABLE 7

| Herbicidal composition of the invention | Dosage (gAI/ha) | Herbicidal effect (%) Barnyard grass |
|---|---|---|
| (Compound 1-15) + Cloquintocet-mexyl | 40 + 5 | 100 |
| (Compound 1-15) + Mefenpyr-diethyl | 400 + 5 | 100 |

TABLE 8

| Herbicidal composition of the invention | Dosage (gAI/ha) | Herbicidal effect (%) Barnyard grass |
|---|---|---|
| (Compound 1-11) + Cloquintocet-mexyl | 20 + 5 | 100 |
| (Compound 1-11) + Mefenpyr-diethyl | 200 + 5 | 100 |

TABLE 9

| Herbicidal composition of the invention | Dosage (gAI/ha) | Herbicidal effect (%) Barnyard grass |
|---|---|---|
| (Compound 1-17) + Cloquintocet-mexyl | 200 + 50 | 100 |
| (Compound 1-17) + Mefenpyr-diethyl | 20 + 5 | 90 |

TABLE 10

| Herbicidal composition of the invention | Dosage (gAI/ha) | Herbicidal effect (%) Barnyard grass |
|---|---|---|
| (Compound 1-13) + Cloquintocet-mexyl | 10 + 5 | 100 |
| (Compound 1-13) + Cloquintocet-mexyl | 100 + 50 | 100 |
| (Compound 1-13) + Mefenpyr-diethyl | 10 + 50 | 100 |
| (Compound 1-13) + Mefenpyr-diethyl | 100 + 5 | 100 |

TABLE 11

| Herbicidal composition of the invention | Dosage (gAI/ha) | Herbicidal effect (%) Barnyard grass |
|---|---|---|
| (Compound 1-12) + Cloquintocet-mexyl | 40 + 5 | 100 |
| (Compound 1-12) + Cloquintocet-mexyl | 400 + 50 | 100 |
| (Compound 1-12) + Mefenpyr-diethyl | 40 + 50 | 100 |
| (Compound 1-12) + Mefenpyr-diethyl | 400 + 50 | 100 |

TABLE 12

| Herbicidal composition of the invention | Dosage (gAI/ha) | Herbicidal effect (%) Barnyard grass |
|---|---|---|
| (Compound 1-5) + Fenchlorazole-ethyl | 400 + 20 | 100 |
| (Compound 1-5) + Cloquintocet-mexyl | 400 + 20 | 100 |

TABLE 13

| Herbicidal composition of the invention | Dosage (gAI/ha) | Herbicidal effect (%) Barnyard grass |
|---|---|---|
| (Compound 1-6) + Mefenpyr-diethyl | 400 + 20 | 100 |
| (Compound 1-6) + Mefenpyr-diethyl | 400 + 100 | 100 |

TABLE 14

| Herbicidal composition of the invention | Dosage (gAI/ha) | Herbicidal effect (%) Barnyard grass |
|---|---|---|
| (Compound 1-7) + Fenchlorazole-ethyl | 400 + 20 | 100 |
| (Compound 1-7) + Cloquintocet-mexyl | 400 + 100 | 100 |

TABLE 15

| Herbicidal composition of the invention | Dosage (gAI/ha) | Herbicidal effect (%) Barnyard grass |
|---|---|---|
| (Compound 1-9) + Mefenpyr-diethyl | 400 + 20 | 100 |
| (Compound 1-9) + Cloquintocet-mexyl | 400 + 100 | 100 |

TABLE 16

| Herbicidal composition of the invention | Dosage (gAI/ha) | Herbicidal effect (%) Barnyard grass |
|---|---|---|
| (Compound 1-14) + Mefenpyr-diethyl | 400 + 100 | 100 |
| (Compound 1-14) + Cloquintocet-mexyl | 400 + 20 | 100 |

TABLE 17

| Herbicidal composition of the invention | Dosage (gAI/ha) | Herbicidal effect (%) Barnyard grass |
|---|---|---|
| (Compound 1-18) + Fenchlorazole-ethyl | 400 + 100 | 100 |
| (Compound 1-18) + Cloquintocet-mexyl | 400 + 20 | 100 |

TABLE 18

| Herbicidal composition of the invention | Dosage (gAI/ha) | Herbicidal effect (%) Barnyard grass |
|---|---|---|
| (Compound 1-20) + Fenchlorazole-ethyl | 400 + 100 | 100 |
| (Compound 1-20) + Cloquintocet-mexyl | 400 + 100 | 100 |

TABLE 19

| Herbicidal composition of the invention | Dosage (gAI/ha) | Herbicidal effect (%) Barnyard grass |
|---|---|---|
| (Compound 1-21) + Mefenpyr-diethyl | 400 + 100 | 100 |
| (Compound 1-21) + Cloquintocet-mexyl | 400 + 100 | 100 |

TABLE 20

| Herbicidal composition of the invention | Dosage (gAI/ha) | Herbicidal effect (%) Barnyard grass |
|---|---|---|
| (Compound 1-22) + Fenchlorazole-ethyl | 400 + 100 | 100 |
| (Compound 1-22) + Cloquintocet-mexyl | 400 + 100 | 100 |

TABLE 21

| Herbicidal composition of the invention | Dosage (gAI/ha) | Herbicidal effect (%) Barnyard grass |
|---|---|---|
| (Compound 1-23) + Fenchlorazole-ethyl | 400 + 20 | 99 |
| (Compound 1-23) + Cloquintocet-mexyl | 400 + 20 | 100 |

TABLE 22

| Herbicidal composition of the invention | Dosage (gAI/ha) | Herbicidal effect (%) Barnyard grass |
|---|---|---|
| (Compound 1-31) + Mefenpyr-diethyl | 400 + 20 | 100 |
| (Compound 1-31) + Cloquintocet-mexyl | 400 + 100 | 100 |

TABLE 23

| Herbicidal composition of the invention | Dosage (gAI/ha) | Herbicidal effect (%) Barnyard grass |
|---|---|---|
| (Compound 1-36) + Mefenpyr-diethyl | 400 + 20 | 100 |
| (Compound 1-36) + Cloquintocet-mexyl | 400 + 100 | 100 |

TABLE 24

| Herbicidal composition of the invention | Dosage (gAI/ha) | Herbicidal effect (%) Barnyard grass |
|---|---|---|
| (Compound 1-41) + Mefenpyr-diethyl | 400 + 100 | 100 |
| (Compound 1-41) + Cloquintocet-mexyl | 400 + 20 | 100 |

TABLE 25

| Herbicidal composition of the invention | Dosage (gAI/ha) | Herbicidal effect (%) Barnyard grass |
|---|---|---|
| (Compound 1-44) + Fenchlorazole-ethyl | 400 + 20 | 100 |

TABLE 25-continued

| Herbicidal composition of the invention | Dosage (gAI/ha) | Herbicidal effect (%) Barnyard grass |
|---|---|---|
| (Compound 1-44) + Fenchlorazole-ethyl | 400 + 100 | 100 |

TABLE 26

| Herbicidal composition of the invention | Dosage (gAI/ha) | Herbicidal effect (%) Barnyard grass |
|---|---|---|
| (Compound 1-58) + Mefenpyr-diethyl | 400 + 20 | 100 |
| (Compound 1-58) + Cloquintocet-mexyl | 400 + 100 | 100 |

TABLE 27

| Herbicidal composition of the invention | Dosage (gAI/ha) | Herbicidal effect (%) Barnyard grass |
|---|---|---|
| (Compound 1-59) + Fenchlorazole-ethyl | 400 + 20 | 100 |
| (Compound 1-59) + Mefenpyr-diethyl | 400 + 20 | 100 |

TABLE 28

| Herbicidal composition of the invention | Dosage (gAI/ha) | Herbicidal effect (%) Barnyard grass |
|---|---|---|
| (Compound 1-62) Mefenpyr-diethyl | 400 + 100 | 100 |
| (Compound 1-62) Cloquintocet-mexyl | 400 + 20 | 100 |

TABLE 29

| Herbicidal composition of the invention | Dosage (gAI/ha) | Herbicidal effect (%) Barnyard grass |
|---|---|---|
| (Compound 1-64) + Fenchlorazole-ethyl | 400 + 100 | 100 |
| (Compound 1-64) + Mefenpyr-diethyl | 400 + 100 | 100 |

TABLE 30

| Herbicidal composition of the invention | Dosage (gAI/ha) | Herbicidal effect (%) Barnyard grass |
|---|---|---|
| (Compound 1-69) + Cloquintocet-mexyl | 400 + 20 | 100 |
| (Compound 1-69) + Cloquintocet-mexyl | 400 + 100 | 100 |

TABLE 31

| Herbicidal composition of the invention | Dosage (gAI/ha) | Herbicidal effect (%) Barnyard grass |
|---|---|---|
| (Compound 1-71) + Fenchlorazole-ethyl | 400 + 100 | 100 |
| (Compound 1-71) + Mefenpyr-diethyl | 400 + 20 | 100 |

TABLE 32

| Herbicidal composition of the invention | Dosage (gAI/ha) | Herbicidal effect (%) Barnyard grass |
|---|---|---|
| (Compound 1-74) + Fenchlorazole-ethyl | 400 + 20 | 99 |
| (Compound 1-74) + Fenchlorazole-ethyl | 400 + 100 | 99 |

TABLE 33

| Herbicidal composition of the invention | Dosage (gAI/ha) | Herbicidal effect (%) Barnyard grass |
|---|---|---|
| (Compound 1-75) + Fenchlorazole-ethyl | 400 + 20 | 100 |
| (Compound 1-75) + Fenchlorazole-ethyl | 400 + 100 | 100 |

TABLE 34

| Herbicidal composition of the invention | Dosage (gAI/ha) | Herbicidal effect (%) Barnyard grass |
|---|---|---|
| (Compound 1-78) + Fenchlorazole-ethyl | 400 + 100 | 100 |
| (Compound 1-78) + Mefenpyr-diethyl | 400 + 20 | 100 |

TABLE 35

| Herbicidal composition of the invention | Dosage (gAI/ha) | Herbicidal effect (%) Barnyard grass |
|---|---|---|
| (Compound 1-91) + Fenchlorazole-ethyl | 400 + 100 | 100 |
| (Compound 1-91) + Cloquintocet-mexyl | 400 + 20 | 100 |

TABLE 36

| Herbicidal composition of the invention | Dosage (gAI/ha) | Herbicidal effect (%) Barnyard grass |
|---|---|---|
| (Compound 1-94) + Cloguintocet-mexyl | 400 + 20 | 95 |

TABLE 37

| Herbicidal composition of the invention | Dosage (gAI/ha) | Herbicidal effect (%) Barnyard grass |
|---|---|---|
| (Compound 1-95) + Fenchlorazole-ethyl | 400 + 100 | 100 |
| (Compound 1-95) + Mefenpyr-diethyl | 400 + 100 | 100 |

TABLE 38

| Herbicidal composition of the invention | Dosage (gAI/ha) | Herbicidal effect (%) Barnyard grass |
|---|---|---|
| (Compound 1-97) + Fenchlorazole-ethyl | 400 + 100 | 100 |
| (Compound 1-97) + Mefenpyr-diethyl | 400 + 20 | 100 |

TABLE 39

| Herbicidal composition of the invention | Dosage (gAI/ha) | Herbicidal effect (%) Barnyard grass |
|---|---|---|
| (Compound 1-100) + Mefenpyr-diethyl | 400 + 20 | 100 |
| (Compound 1-100) + Cloquintocet-mexyl | 400 + 20 | 100 |

TABLE 40

| Herbicidal composition of the invention | Dosage (gAI/ha) | Herbicidal effect (%) Barnyard grass |
|---|---|---|
| (Compound 1-102) + Fenchlorazole-ethyl | 400 + 20 | 98 |
| (Compound 1-102) + Cloquintocet-mexyl | 400 + 20 | 99 |

TABLE 41

| Herbicidal composition of the invention | Dosage (gAI/ha) | Herbicidal effect (%) Barnyard grass |
|---|---|---|
| (Compound 1-103) + Fenchlorazole-ethyl | 400 + 20 | 100 |
| (Compound 1-103) + Mefenpyr-diethyl | 400 + 100 | 100 |

TABLE 42

| Herbicidal composition of the invention | Dosage (gAI/ha) | Herbicidal effect (%) Barnyard grass |
|---|---|---|
| (Compound 1-104) + Fenchlorazole-ethyl | 400 + 20 | 100 |

TABLE 42-continued

| Herbicidal composition of the invention | Dosage (gAI/ha) | Herbicidal effect (%) Barnyard grass |
|---|---|---|
| (Compound 1-104) + Mefenpyr-diethyl | 400 + 100 | 100 |

TABLE 43

| Herbicidal composition of the invention | Dosage (gAI/ha) | Herbicidal effect (%) Barnyard grass |
|---|---|---|
| (Compound 1-107) + Fenchlorazole-ethyl | 400 + 20 | 100 |
| (Compound 1-107) + Mefenpyr-diethyl | 400 + 20 | 100 |

TABLE 44

| Herbicidal composition of the invention | Dosage (gAI/ha) | Herbicidal effect (%) Barnyard grass |
|---|---|---|
| (Compound 1-127) + Cloquintocet-mexyl | 400 + 20 | 100 |
| (Compound 1-127) + Cloquintocet-mexyl | 400 + 100 | 100 |

TABLE 45

| Herbicidal composition of the invention | Dosage (gAI/ha) | Herbicidal effect (%) Barnyard grass |
|---|---|---|
| (Compound 1-135) + Fenchlorazole-ethyl | 400 + 20 | 98 |
| (Compound 1-135) + Cloquintocet-mexyl | 400 + 100 | 100 |

TABLE 46

| Herbicidal composition of the invention | Dosage (gAI/ha) | Herbicidal effect (%) Barnyard grass |
|---|---|---|
| (Compound 1-136) + Fenchlorazole-ethyl | 400 + 20 | 100 |
| (Compound 1-136) + Mefenpyr-diethyl | 400 + 20 | 100 |

TABLE 47

| Herbicidal composition of the invention | Dosage (gAI/ha) | Herbicidal effect (%) Barnyard grass |
|---|---|---|
| (Compound 1-139) + Fenchlorazole-ethyl | 400 + 100 | 100 |
| (Compound 1-139) + Cloquintocet-mexyl | 400 + 100 | 100 |

TABLE 48

| Herbicidal composition of the invention | Dosage (gAI/ha) | Herbicidal effect (%) Barnyard grass |
|---|---|---|
| (Compound 1-143) + Fenchlorazole-ethyl | 400 + 20 | 100 |
| (Compound 1-143) + Cloquintocet-mexyl | 400 + 100 | 100 |

TABLE 49

| Herbicidal composition of the invention | Dosage (gAI/ha) | Herbicidal effect (%) Barnyard grass |
|---|---|---|
| (Compound 1-144) + Cloquintocet-mexyl | 400 + 20 | 100 |
| (Compound 1-144) + Cloquintocet-mexyl | 400 + 100 | 100 |

TABLE 50

| Herbicidal composition of the invention | Dosage (gAI/ha) | Herbicidal effect (%) Barnyard grass |
|---|---|---|
| (Compound 1-145) + Mefenpyr-diethyl | 400 + 20 | 100 |
| (Compound 1-145) + Cloquintocet-mexyl | 400 + 20 | 100 |

TABLE 51

| Herbicidal composition of the invention | Dosage (gAI/ha) | Herbicidal effect (%) Barnyard grass |
|---|---|---|
| (Compound 1-146) + Mefenpyr-diethyl | 400 + 20 | 100 |
| (Compound 1-146) + Mefenpyr-diethyl | 400 + 100 | 100 |

TABLE 52

| Herbicidal composition of the invention | Dosage (gAI/ha) | Herbicidal effect (%) Barnyard grass |
|---|---|---|
| (Compound 1-147) + Mefenpyr-diethyl | 400 + 100 | 100 |
| (Compound 1-147) + Cloquintocet-mexyl | 400 + 100 | 100 |

TABLE 53

| Herbicidal composition of the invention | Dosage (gAI/ha) | Herbicidal effect (%) Barnyard grass |
|---|---|---|
| (Compound 1-148) + Mefenpyr-diethyl | 400 + 20 | 100 |
| (Compound 1-148) + Cloquintocet-mexyl | 400 + 20 | 100 |

TABLE 54

| Herbicidal composition of the invention | Dosage (gAI/ha) | Herbicidal effect (%) Barnyard grass |
|---|---|---|
| (Compound 1-149) + Fenchlorazole-ethyl | 400 + 20 | 100 |
| (Compound 1-149) + Cloquintocet-mexyl | 400 + 100 | 100 |

TABLE 55

| Herbicidal composition of the invention | Dosage (gAI/ha) | Herbicidal effect (%) Barnyard grass |
|---|---|---|
| (Compound 1-151) + Mefenpyr-diethyl | 400 + 100 | 100 |
| (Compound 1-151) + Cloquintocet-mexyl | 400 + 20 | 100 |

TABLE 56

| Herbicidal composition of the invention | Dosage (gAI/ha) | Herbicidal effect (%) Barnyard grass |
|---|---|---|
| (Compound 1-160) + Fenchlorazole-ethyl | 400 + 100 | 98 |
| (Compound 1-160) + Mefenpyr-diethyl | 400 + 100 | 98 |

TABLE 57

| Herbicidal composition of the invention | Dosage (gAI/ha) | Herbicidal effect (%) Barnyard grass |
|---|---|---|
| (Compound 1-161) + Fenchlorazole-ethyl | 400 + 20 | 100 |
| (Compound 1-161) + Mefenpyr-diethyl | 400 + 100 | 100 |

TABLE 58

| Herbicidal composition of the invention | Dosage (gAI/ha) | Herbicidal effect (%) Barnyard grass |
|---|---|---|
| (Compound 1-162) + Mefenpyr-diethyl | 400 + 20 | 100 |
| (Compound 1-162) + Cloquintocet-mexyl | 400 + 100 | 100 |

TABLE 59

| Herbicidal composition of the invention | Dosage (gAI/ha) | Herbicidal effect (%) Barnyard grass |
|---|---|---|
| (Compound 1-167) + Mefenpyr-diethyl | 400 + 20 | 98 |
| (Compound 1-167) + Cloquintocet-mexyl | 400 + 20 | 99 |

TABLE 60

| Herbicidal composition of the invention | Dosage (gAI/ha) | Herbicidal effect (%) Barnyard grass |
|---|---|---|
| (Compound 1-171) + Fenchlorazole-ethyl | 400 + 100 | 95 |
| (Compound 1-171) + Cloquintocet-mexyl | 400 + 100 | 95 |

TABLE 61

| Herbicidal composition of the invention | Dosage (gAI/ha) | Herbicidal effect (%) Barnyard grass |
|---|---|---|
| (Compound 1-174) + Mefenpyr-diethyl | 400 + 20 | 100 |
| (Compound 1-174) + Cloquintocet-mexyl | 400 + 20 | 100 |

TABLE 62

| Herbicidal composition of the invention | Dosage (gAI/ha) | Herbicidal effect (%) Wild oat |
|---|---|---|
| (Compound 1-176) + Cloquintocet-mexyl | 32 + 32 | 100 |
| (Compound 1-176) Cloquintocet-mexyl + | 16 + 32 | 100 |

TABLE 63

| Herbicidal composition of the invention | Dosage (gAI/ha) | Herbicidal effect (%) Barnyard grass |
|---|---|---|
| (Compound 1-178) + Fenchlorazole-ethyl | 400 + 20 | 100 |
| (Compound 1-178) + Cloquintocet-mexyl | 400 + 100 | 100 |

TABLE 64

| Herbicidal composition of the invention | Dosage (gAI/ha) | Herbicidal effect (%) Barnyard grass |
|---|---|---|
| (Compound 1-179) + Fenchlorazole-ethyl | 400 + 20 | 98 |
| (Compound 1-179) + Cloquintocet-mexyl | 400 + 20 | 100 |

TABLE 65

| Herbicidal composition of the invention | Dosage (gAI/ha) | Herbicidal effect (%) Barnyard grass |
|---|---|---|
| (Compound 1-180) + Fenchlorazole-ethyl | 400 + 100 | 100 |
| (Compound 1-180) + Cloquintocet-mexyl | 400 + 20 | 100 |

TABLE 66

| Herbicidal composition of the invention | Dosage (gAI/ha) | Herbicidal effect (%) Barnyard grass |
|---|---|---|
| (Compound 1-181) + Fenchlorazole-ethyl | 400 + 20 | 100 |
| (Compound 1-181) + Cloquintocet-mexyl | 400 + 100 | 100 |

TABLE 67

| Herbicidal composition of the invention | Dosage (gAI/ha) | Herbicidal effect (%) Barnyard grass |
|---|---|---|
| (Compound 1-183) + Mefenpyr-diethyl | 400 + 100 | 100 |
| (Compound 1-183) + Fenchlorazole-ethyl | 400 + 20 | 100 |

TABLE 68

| Herbicidal composition of the invention | Dosage (gAI/ha) | Herbicidal effect (%) Barnyard grass |
|---|---|---|
| (Compound 1-184) + Mefenpyr-diethyl | 400 + 20 | 100 |
| (Compound 1-184) + Cloquintocet-mexyl | 400 + 100 | 100 |

TABLE 69

| Herbicidal composition of the invention | Dosage (gAI/ha) | Herbicidal effect (%) Barnyard grass |
|---|---|---|
| (Compound 1-186) + Fenchlorazole-ethyl | 400 + 20 | 100 |
| (Compound 1-186) + Cloquintocet-mexyl | 400 + 20 | 98 |

TABLE 70

| Herbicidal composition of the invention | Dosage (gAI/ha) | Herbicidal effect (%) Wild oat |
|---|---|---|
| (Compound 1-187) + Cloquintocet-mexyl | 32 + 32 | 100 |
| (Compound 1-187) + Cloquintocet-mexyl | 16 + 32 | 100 |

TABLE 71

| Herbicidal composition of the invention | Dosage (gAI/ha) | Herbicidal effect (%) Wild oat |
|---|---|---|
| (Compound 1-188) + Fenchlorazole-ethyl | 32 + 32 | 100 |
| (Compound 1-188) + Cloquintocet-mexyl | 16 + 32 | 100 |

TABLE 72

| Herbicidal composition of the invention | Dosage (gAI/ha) | Herbicidal effect (%) Barnyard grass |
|---|---|---|
| (Compound 1-189) + Mefenpyr-diethyl | 400 + 20 | 100 |
| (Compound 1-189) + Mefenpyr-diethyl | 400 + 100 | 99 |

TABLE 73

| Herbicidal composition of the invention | Dosage (gAI/ha) | Herbicidal effect (%) Barnyard grass |
|---|---|---|
| (Compound 1-190) + Mefenpyr-diethyl | 400 + 100 | 100 |
| (Compound 1-190) + Cloquintocet-mexyl | 400 + 20 | 100 |

TABLE 74

| Herbicidal composition of the invention | Dosage (gAI/ha) | Herbicidal effect (%) Barnyard grass |
|---|---|---|
| (Compound 1-191) + Fenchlorazole-ethyl | 400 + 100 | 100 |
| (Compound 1-191) + Cloquintocet-mexyl | 400 + 100 | 100 |

TABLE 75

| Herbicidal composition of the invention | Dosage (gAI/ha) | Herbicidal effect (%) Barnyard grass |
|---|---|---|
| (Compound 1-192) + Fenchlorazole-ethyl | 400 + 100 | 100 |
| (Compound 1-192) + Mefenpyr-diethyl | 400 + 100 | 100 |

TABLE 76

| Herbicidal composition of the invention | Dosage (gAI/ha) | Herbicidal effect (%) Barnyard grass |
|---|---|---|
| (Compound 1-193) + Cloquintocet-mexyl | 400 + 100 | 100 |
| (Compound 1-193) + Mefenpyr-diethyl | 400 + 20 | 100 |

TABLE 77

| Herbicidal composition of the invention | Dosage (gAI/ha) | Herbicidal effect (%) Barnyard grass |
|---|---|---|
| (Compound 1-194) + Cloquintocet-mexyl | 400 + 20 | 100 |
| (Compound 1-194) + Fenchlorazole-ethyl | 400 + 20 | 100 |

TABLE 78

| Herbicidal composition of the invention | Dosage (gAI/ha) | Herbicidal effect (%) Barnyard grass |
|---|---|---|
| (Compound 1-195) + Cloquintocet-mexyl | 400 + 100 | 98 |
| (Compound 1-195) + Mefenpyr-diethyl | 400 + 100 | 95 |

INDUSTRIAL APPLICABILITY

According to the invention, it is possible to provide a herbicidal composition having an excellent weed-controlling effect.

The herbicidal composition according to the invention is useful for weed-controlling.

The invention claimed is:
1. A herbicidal composition, comprising:
a cyclohexanone compound represented by Formula (I); and
at least one compound selected from Group A,

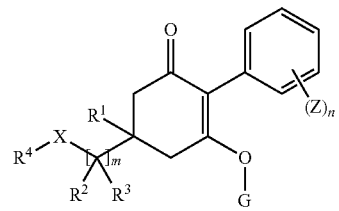

(I)

in the formula,
m represents 1, 2, or 3,
n represents an integer of 1 to 5,
X represents $CH_2$, O, $NR^9$, S, S(O), or $S(O)_2$,
$R^1$ represents hydrogen or a methyl group,
$R^2$ and $R^3$ each independently represent hydrogen, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl) $C_{3-8}$ cycloalkyl group, a ($C_{3-8}$ cycloalkyl) $C_{1-6}$ alkyl group, a ($C_{3-8}$ cycloalkyl) $C_{3-8}$ cycloalkyl group, a ($C_{3-8}$ halocycloalkyl) $C_{1-6}$ alkyl group, a {($C_{1-6}$ alkyl) $C_{3-8}$ cycloalkyl} $C_{1-6}$ alkyl group, or $R^2$ and $R^3$ are bonded to form a $C_{2-5}$ alkylene chain, or $R^2$ and $R^3$ together represent a $C_{1-3}$ alkylidene group optionally having a halogen, and when m is 2 or 3, two or three $R^2$'s are the same or different, and two or three $R^3$'s are the same or different, $R^4$ represents a $C_{6-10}$ aryl group or a 5- or 6-membered heteroaryl group, wherein the $C_{6-10}$ aryl group and the 5- or 6-membered heteroaryl group optionally have one or more substituents selected from the group consisting of a halogen, a cyano group, a nitro group, an amino group, a ($C_{1-6}$ alkyl)amino group, a ($C_{1-6}$ alkyl)($C_{1-6}$ alkyl)amino group, a benzoylamino group, an aminocarbonyl group, a ($C_{1-6}$ alkyl)amino carbonyl group, a ($C_{1-6}$ alkyl)($C_{1-6}$ alkyl)amino carbonyl group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group, a $C_{6-10}$ aryl group, a $C_{6-10}$ aryloxy group, a $C_{1-6}$ alkylsulfinyl group, a $C_{1-6}$ alkylsulfonyl group, a hydroxyl group, a ($C_{1-6}$ alkyl)carbonyl group, a hydroxycarbonyl group, a ($C_{1-6}$ alkoxy)carbonyl group, and a ($C_{6-10}$ aryl) $C_{1-6}$ alkoxy group, and when two or more substituents are present, the substituents are the same or different, and wherein the ($C_{1-6}$ alkyl) amino group, the ($C_{1-6}$ alkyl) ($C_{1-6}$ alkyl)amino group, the benzoylamino group, the ($C_{1-6}$ alkyl) amino carbonyl group, the ($C_{1-6}$ alkyl) ($C_{1-6}$ alkyl) amino carbonyl group, the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy)carbonyl group, and the ($C_{6-10}$ aryl) $C_{1-6}$ alkoxy group optionally have one or more halogens or $C_{1-3}$ haloalkyl groups, and when two or more halogens or $C_{1-3}$ haloalkyl groups are present, the halogens or $C_{1-3}$ haloalkyl groups are the same or different, G represents hydrogen or any one group of the following formulae:

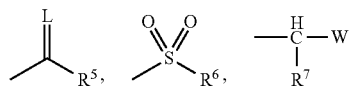

in the formulae, L represents oxygen or sulfur, $R^5$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl) $C_{1-6}$ alkoxy group, a ($C_{1-6}$ alkyl) ($C_{1-6}$ alkyl) amino group, a ($C_{3-6}$ alkenyl) ($C_{3-6}$ alkenyl) amino group, a ($C_{1-6}$ alkyl) ($C_{6-10}$ aryl) amino group, or a 5- or 6-membered heteroaryl group, wherein all of the groups representing $R^5$ optionally have one or more halogens, and when two or more halogens are present, the halogens are the same or different, and wherein all of the $C_{3-8}$ cycloalkyl group, the $C_{6-10}$ aryl group, an aryl moiety of the ($C_{6-10}$ aryl) $C_{1-6}$ alkyl group, the $C_{3-8}$ cycloalkoxy group, the $C_{6-10}$ aryloxy group, an aryl moiety of the ($C_{6-10}$ aryl) $C_{1-6}$ alkoxy group, an aryl moiety of a ($C_{1-6}$ alkyl) ($C_{6-10}$ aryl) amino group, and the 5- or 6-membered heteroaryl group optionally have one or more $C_{1-6}$ alkyl groups, and when two or more $C_{1-6}$ alkyl groups are present, the alkyl groups are the same or different, $R^6$ represents a $C_{1-6}$ alkyl group, a $C_{6-10}$ aryl group, or a ($C_{1-6}$ alkyl) ($C_{1-6}$ alkyl) amino group, wherein all of the groups representing $R^6$ optionally have one or more halogens, and when two or more halogens are present, the halogens are the same or different, and wherein the $C_{6-10}$ aryl group optionally has one or more $C_{1-6}$ alkyl groups, and when two or more $C_{1-6}$ alkyl groups are present, the $C_{1-6}$ alkyl groups are the same or different, $R^7$ represents hydrogen or a $C_{1-6}$ alkyl group, and W represents a $C_{1-6}$ alkoxy group, a $C_{1-6}$ alkylthio group, a $C_{1-6}$ alkylsulfinyl group, or a $C_{1-6}$ alkylsulfonyl group, wherein all of the groups representing W optionally have one or more halogens, and when two or more halogens are present, the halogens are the same or different, $R^9$ represents hydrogen, a $C_{1-6}$ alkyl group, a $C_{6-10}$ aryl group, a $C_{6-10}$ arylthio group, a $C_{6-10}$ arylsulfinyl group, or a $C_{6-10}$ arylsulfonyl group, wherein the $C_{1-6}$ alkyl group optionally has one or more halogens, and when two or more halogens are present, the halogens are the same or different, and wherein the $C_{6-10}$ aryl group, the $C_{6-10}$ arylthio group, the $C_{6-10}$ arylsulfinyl group, and the $C_{6-10}$ arylsulfonyl group optionally have one or more substituents selected from the group consisting of a halogen, a cyano group, a nitro group, and an amino group, and Z represents a halogen, a cyano group, a nitro group, a $C_{1-6}$ alkyl group, a $C_{2-6}$ alkenyl group, a $C_{2-6}$ alkynyl group, a $C_{1-6}$ alkoxy group, a ($C_{1-6}$ alkyl)carbonyl group, a $C_{1-6}$ alkylthio group, a $C_{6-10}$ aryloxy group, a 5- or 6-membered heteroaryloxy group, a $C_{3-8}$ cycloalkyl group, a $C_{6-10}$ aryl group, or a 5- or 6-membered heteroaryl group, wherein the $C_{1-6}$ alkyl group, the $C_{2-6}$ alkenyl group, the $C_{2-6}$ alkynyl group, the $C_{1-6}$ alkoxy group, the ($C_{1-6}$ alkyl) carbonyl group, and the $C_{1-6}$ alkylthio group optionally have one or more halogens, and when the two or more halogens are present, the halogens are the same or different, and wherein the $C_{6-10}$ aryl group, the 5- or 6-membered heteroaryl group, the $C_{6-10}$ aryloxy group, and the 5- or 6-membered heteroaryloxy group optionally have one or more substituents selected from the group consisting of a halogen, a $C_{1-6}$ alkyl group, and $C_{1-6}$ haloalkyl group, and when two or more substituents are present, the substituents are the same or different, and wherein the $C_{3-8}$ cycloalkyl group optionally has one or more substituents selected from the group consisting of a halogen and a $C_{1-6}$ alkyl group, and when two or more substituents are present, the substituents are the same or different, and when n represents an integer of equal to or greater than 2, Z's are the same or different, Group A: consisting of benoxacor, cloquintocet-mexyl, cyometrinil, dichlormid, fenchlorazole-ethyl, fenclorim, flurazole, furilazole, mefenpyr-diethyl, oxabetrinil, isoxadifen-ethyl, cyprosulfamide, fluxofenim, 1,8-naphthalic anhydride, and AD-67.

2. The herbicidal composition according to claim 1,
wherein n is an integer of 1 to 3,
$R^1$ is hydrogen,
$R^2$ and $R^3$ each independently are hydrogen, a $C_{1-3}$ alkyl group, or $R^2$ and $R^3$ are bonded to form a $C_{2-5}$ alkylene chain, and when m is 2 or 3, two or three $R^2$'s are the same or different, and two or three $R^3$'s are the same or different,
$R^4$ represents a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group,
wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and the 2-thiazolyl group optionally have one or more substituents selected from the group consisting of a halogen, a $C_{1-3}$ alkyl group, a hydroxyl group, a ($C_{1-3}$ alkyl)carbonyl group, a ($C_{1-3}$ alkoxy)carbonyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group, and a $C_{1-3}$ haloalkoxy group, and when two or more substituents are present, the substituents are the same or different, and
wherein the 1,2,3-triazolyl group and the 1-pyrazolyl group optionally have one or more substituents selected from the group consisting of a $C_{1-3}$ alkyl group and a $C_{6-10}$ aryl group, the $C_{1-3}$ alkyl group and the $C_{6-10}$ aryl group optionally have one or more halogens or one or more $C_{1-3}$ haloalkyl groups, and when two or more halogens or two or more $C_{1-3}$ haloalkyl groups are present, the halogens or the $C_{1-3}$ haloalkyl groups are the same or different,
G is hydrogen or any one group of the following formulae:

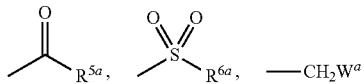

in the formulae, $R^{5a}$ represents a $C_{1-6}$ alkyl group, a $C_{1-6}$ alkoxy group, a $C_{3-6}$ alkenyloxy group, or a $C_{6-10}$ aryloxy group,
$R^{6a}$ represents a $C_{1-6}$ alkyl group, and
$W^a$ represents a $C_{1-3}$ alkoxy group,
$R^9$ is hydrogen, a $C_{1-6}$ alkyl group, or a $C_{6-10}$ arylsulfonyl group, wherein the $C_{1-6}$ alkyl group optionally has one or more halogens, and when the two or more halogens, the halogens are the same or different, and the $C_{6-10}$ arylsulfonyl group optionally has one or more substituents selected from the group consisting of a halogen and a nitro group, and when two or more substituents are present, the substituents are the same or different, and
Z is a halogen, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group, or a 5- or 6-membered heteroaryloxy group,
wherein the $C_{1-3}$ alkyl group, the $C_{2-6}$ alkenyl group, the $C_{2-6}$ alkynyl group, the $C_{1-3}$ alkoxy group, the phenyl group, and the 5- or 6-membered heteroaryloxy group optionally have one or more halogens, and when two or more halogens are present, the halogens are the same or different.

3. The herbicidal composition according to claim 2,
wherein $R^2$ and $R^3$ each independently are hydrogen, a methyl group, an ethyl group, or $R^2$ and $R^3$ are bonded to form an ethylene chain, and two $R^2$'s may be the same or different, and two $R^3$'s may be the same or different,
$R^4$ is a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group, a 1,2,3-triazolyl group, or a 1-pyrazolyl group,
wherein the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group, and 2-thiazolyl group have one or more substituents selected from the group consisting of chlorine, bromine, iodine, fluorine, a methyl group, an ethyl group, an isopropyl group, a t-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group, and a trifluoromethyl group, and
wherein the 1,2,3-triazolyl group and 1-pyrazolyl group optionally have one or more substituents selected from the group consisting of a methyl group and a phenyl group, and
wherein the phenyl group optionally has one or more substituents selected from the group consisting of chlorine, bromine, iodine, fluorine, and a trifluoromethyl group,
G is hydrogen, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group, or an ethoxymethyl group,
$R^9$ is hydrogen, a 2-nitrophenylsulfonyl group, or a methyl group, and
Z represents a methyl group, an ethyl group, a phenyl group, a vinyl group, a cyclopropyl group, a nitro group, fluorine, chlorine, bromine, a methoxy group, a trifluoromethyl group, a 5-trifluoromethyl-2-chloropyridyloxy group, or an ethynyl group.

4. The herbicidal composition according to claim 1,
wherein G is hydrogen.

5. A herbicide comprising:
the herbicidal composition according to claim 1, and a liquid or a solid carrier.

6. A method for controlling weeds, comprising applying effective amounts of cyclohexanone compound of Formula (I) and at least one compound selected from the following Group A to weeds or soil where the weeds grow,
Formula (I):
in the formula,

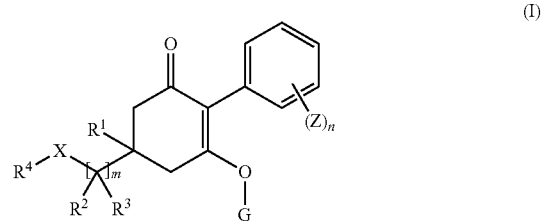

m represents 1, 2, or 3, n represents an integer of 1 to 5,

X represents $CH_2$, O, $NR^9$, S, S(O), or $S(O)_2$, $R^1$ represents hydrogen or a methyl group, $R^2$ and $R^3$ each independently represent hydrogen, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl) $C_{3-8}$ cycloalkyl group, a ($C_{3-8}$ cycloalkyl) $C_{1-6}$ alkyl group, a ($C_{3-8}$ cycloalkyl) $C_{3-8}$ cycloalkyl group, a ($C_{3-8}$ halocycloalkyl) $C_{1-6}$ alkyl group, a {($C_{1-6}$ alkyl) $C_{3-8}$ cycloalkyl} $C_{1-6}$ alkyl group, or $R^2$ and $R^3$ are bonded to form a $C_{2-5}$ alkylene chain, or $R^2$ and $R^3$ together represent a $C_{1-3}$ alkylidene group optionally having a halogen, and when m is 2 or 3, two or three $R^2$'s are the same or different, and two or three $R^3$'s are the same or different, $R^4$ represents a $C_{6-10}$ aryl group or a 5- or 6-membered heteroaryl group, wherein the $C_{6-10}$ aryl group and the 5- or 6-membered heteroaryl group optionally have one or more substituents selected from the group consisting of a halogen, a cyano group, a nitro group, an amino group, a ($C_{1-6}$ alkyl)amino group, a ($C_{1-6}$ alkyl) ($C_{1-6}$ alkyl)amino group, a benzoylamino group, an aminocarbonyl group, a ($C_{1-6}$ alkyl)amino carbonyl group, a ($C_{1-6}$ alkyl)($C_{1-6}$ alkyl)amino carbonyl group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group, a $C_{6-10}$ aryl group, a $C_{6-10}$ aryloxy group, a $C_{1-6}$ alkylsulfinyl group, a $C_{1-6}$ alkylsulfonyl group, a hydroxyl group, a ($C_{1-6}$ alkyl)carbonyl group, a hydroxycarbonyl group, a ($C_{1-6}$ alkoxy)carbonyl group, and a ($C_{6-10}$ aryl) $C_{1-6}$ alkoxy group, and when two or more substituents are present, the substituents are the same or different, and wherein the ($C_{1-6}$ alkyl) amino group, the ($C_{1-6}$ alkyl) ($C_{1-6}$ alkyl)amino group, the benzoylamino group, the ($C_{1-6}$ alkyl) amino carbonyl group, the ($C_{1-6}$ alkyl) ($C_{1-6}$ alkyl) amino carbonyl group, the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy)carbonyl group, and the ($C_{6-10}$ aryl) $C_{1-6}$ alkoxy group optionally have one or more halogens or $C_{1-3}$ haloalkyl groups, and when two or more halogens or $C_{1-3}$ haloalkyl groups are present, the halogens or $C_{1-3}$ haloalkyl groups are the same or different, G represents hydrogen or any one group of the following formulae:

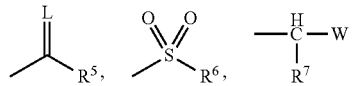

in the formulae, L represents oxygen or sulfur, $R^5$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl) $C_{1-6}$ alkoxy group, a ($C_{1-6}$ alkyl) ($C_{1-6}$ alkyl) amino group, a ($C_{3-6}$ alkenyl) ($C_{3-6}$ alkenyl) amino group, a ($C_{1-6}$ alkyl) ($C_{6-10}$ aryl) amino group, or a 5- or 6-membered heteroaryl group, wherein all of the groups representing $R^5$ optionally have one or more halogens, and when two or more halogens are present, the halogens are the same or different, and wherein all of the $C_{3-8}$ cycloalkyl group, the $C_{6-10}$ aryl group, an aryl moiety of the ($C_{6-10}$ aryl) $C_{1-6}$ alkyl group, the $C_{3-8}$ cycloalkoxy group, the $C_{6-10}$ aryloxy group, an aryl moiety of the ($C_{6-10}$ aryl) $C_{1-6}$ alkoxy group, an aryl moiety of a ($C_{1-6}$ alkyl) ($C_{6-10}$ aryl) amino group, and the 5- or 6-membered heteroaryl group optionally have one or more $C_{1-6}$ alkyl groups, and when two or more $C_{1-6}$ alkyl groups are present, the alkyl groups are the same or different, $R^6$ represents a $C_{1-6}$ alkyl group, a $C_{6-10}$ aryl group, or a ($C_{1-6}$ alkyl) ($C_{1-6}$ alkyl) amino group, wherein all of the groups representing $R^6$ optionally have one or more halogens, and when two or more halogens are present, the halogens are the same or different, and wherein the $C_{6-10}$ aryl group optionally has one or more $C_{1-6}$ alkyl groups, and when two or more $C_{1-6}$ alkyl groups are present, the $C_{1-6}$ alkyl groups are the same or different, $R^7$ represents hydrogen or a $C_{1-6}$ alkyl group, and W represents a $C_{1-6}$ alkoxy group, a $C_{1-6}$ alkylthio group, a $C_{1-6}$ alkylsulfinyl group, or a $C_{1-6}$ alkylsulfonyl group, wherein all of the groups representing W optionally have one or more halogens, and when two or more halogens are present, the halogens are the same or different, $R^9$ represents hydrogen, a $C_{1-6}$ alkyl group, a $C_{6-10}$ aryl group, a $C_{6-10}$ arylthio group, a $C_{6-10}$ arylsulfinyl group, or a $C_{6-10}$ arylsulfonyl group, wherein the $C_{1-6}$ alkyl group optionally has one or more halogens, and when two or more halogens are present, the halogens are the same or different, and wherein the $C_{6-10}$ aryl group, the $C_{6-10}$ arylthio group, the $C_{6-10}$ arylsulfinyl group, and the $C_{6-10}$ arylsulfonyl group optionally have one or more substituents selected from the group consisting of a halogen, a cyano group, a nitro group, and an amino group, and Z represents a halogen, a cyano group, a nitro group, a $C_{1-6}$ alkyl group, a $C_{2-6}$ alkenyl group, a $C_{2-6}$ alkynyl group, a $C_{1-6}$ alkoxy group, a ($C_{1-6}$ alkyl)carbonyl group, a $C_{1-6}$ alkylthio group, a $C_{6-10}$ aryloxy group, a 5- or 6-membered heteroaryloxy group, a $C_{3-8}$ cycloalkyl group, a $C_{6-10}$ aryl group, or a 5- or 6-membered heteroaryl group, wherein the $C_{1-6}$ alkyl group, the $C_{2-6}$ alkenyl group, the $C_{2-6}$ alkynyl group, the $C_{1-6}$ alkoxy group, the ($C_{1-6}$ alkyl) carbonyl group, and the $C_{1-6}$ alkylthio group optionally have one or more halogens, and when the two or more halogens are present, the halogens are the same or different, and wherein the $C_{6-10}$ aryl group, the 5- or 6-membered heteroaryl group, the $C_{6-10}$ aryloxy group, and the 5- or 6-membered heteroaryloxy group optionally have one or more substituents selected from the group consisting of a halogen, a $C_{1-6}$ alkyl group, and $C_{1-6}$ haloalkyl group, and when two or more substituents are present, the substituents are the same or different, and wherein the $C_{3-8}$ cycloalkyl group optionally has one or more substituents selected from the group consisting of a halogen and a $C_{1-6}$ alkyl group, and when two or more substituents are present, the substituents are the same or different, and when n represents an integer of equal to or greater than 2, Z's are the same or different, and Group A: consisting of benoxacor, cloquintocet-mexyl, cyometrinil, dichlormid, fenchlorazole-ethyl, fenclorim, flurazole, furilazole, mefenpyr-diethyl, oxabetrinil, isoxadifen-ethyl, cyprosulfamide, fluxofenim, 1,8-naphthalic anhydride, and AD-67.

* * * * *